(12) United States Patent
Shoshtaev

(10) Patent No.: US 10,507,116 B2
(45) Date of Patent: Dec. 17, 2019

(54) EXPANDABLE INTERVERTEBRAL FUSION DEVICE

(71) Applicant: INTEGRITY IMPLANTS INC., Jupiter, FL (US)

(72) Inventor: Eugene Shoshtaev, Del Mar, CA (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 0 days.

(21) Appl. No.: 16/219,814

(22) Filed: Dec. 13, 2018

(65) Prior Publication Data

US 2019/0117409 A1    Apr. 25, 2019

Related U.S. Application Data

(63) Continuation of application No. PCT/US2018/013207, filed on Jan. 10, 2018.

(60) Provisional application No. 62/481,565, filed on Apr. 4, 2017, provisional application No. 62/471,206, filed on Mar. 14, 2017, provisional application No. 62/444,663, filed on Jan. 10, 2017.

(51) Int. Cl.
*A61F 2/44* (2006.01)
*A61F 2/46* (2006.01)
*A61F 2/30* (2006.01)

(52) U.S. Cl.
CPC ............ *A61F 2/4425* (2013.01); *A61F 2/447* (2013.01); *A61F 2/4455* (2013.01); *A61F 2/4611* (2013.01); *A61F 2002/30476* (2013.01); *A61F 2002/30518* (2013.01); *A61F 2002/30537* (2013.01); *A61F 2002/30579* (2013.01); *A61F 2002/443* (2013.01)

(58) Field of Classification Search
CPC .......... A61F 2/44; A61F 2/4425; A61F 2/447; A61F 2/46
See application file for complete search history.

(56) References Cited

U.S. PATENT DOCUMENTS

| 4,309,777 A | 1/1982 | Patil |
| 4,733,665 A | 3/1988 | Palmaz |
| 4,759,766 A | 7/1988 | Buettner-Janz et al. |

(Continued)

FOREIGN PATENT DOCUMENTS

| CN | 101909548 | 7/2014 |
| EP | 1011503 | 2/1998 |

(Continued)

OTHER PUBLICATIONS

U.S. Appl. No. 16/290,428, Shoshtaev—owned by Applicant, filed Mar. 1, 2018.

(Continued)

*Primary Examiner* — Christopher J Beccia
(74) *Attorney, Agent, or Firm* — Brian S. Boyer; Syndicated Law, PC

(57) ABSTRACT

The present invention provides an expandable fusion device capable of being installed inside an intervertebral disc space to maintain normal disc spacing and restore spinal stability, thereby facilitating an intervertebral fusion. The fusion device described herein is capable of being installed inside an intervertebral disc space at a minimum to no distraction height and for a fusion device capable of maintaining a normal distance between adjacent vertebral bodies when implanted.

7 Claims, 152 Drawing Sheets

(56) References Cited

U.S. PATENT DOCUMENTS

| | | |
|---|---|---|
| 4,820,305 A | 4/1989 | Harms et al. |
| 4,997,432 A | 3/1991 | Keller |
| 5,192,327 A | 3/1993 | Brantigan |
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr. et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 | 5/2007 | Branch |
| 7,544,208 B1 | 6/2009 | Mueller et al. |
| 7,621,950 B1 | 11/2009 | Globerman et al. |
| 7,643,884 B2 | 1/2010 | Pond et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 4/2011 | Hamada |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O'Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 | 9/2012 | Cipoletti et al. |
| 8,353,961 B2 | 1/2013 | McClintock |
| 8,353,963 B2 | 1/2013 | Glerum |
| 8,491,659 B2 | 7/2013 | Weiman et al. |
| 8,551,173 B2 | 10/2013 | Lechmann et al. |
| 8,628,578 B2 | 1/2014 | Miller et al. |
| 8,632,595 B2 | 1/2014 | Weiman |
| 8,663,332 B1 | 3/2014 | To |
| 8,845,731 B2 | 9/2014 | Weiman |
| 8,852,279 B2 | 10/2014 | Weiman et al. |
| 8,926,704 B2 | 1/2015 | Glerum et al. |
| 8,936,641 B2 | 1/2015 | Cain |
| 8,940,048 B2 | 1/2015 | Butler et al. |
| 8,940,052 B2 | 1/2015 | Lechmann et al. |
| 9,060,876 B1 | 1/2015 | To |
| 8,986,387 B1 | 3/2015 | To |
| 9,034,041 B2 | 5/2015 | Wolters |
| 9,039,771 B2 | 5/2015 | Glerum et al. |
| 9,138,328 B2 | 9/2015 | Butler et al. |
| 9,186,259 B2 | 11/2015 | To |
| 9,216,095 B2 | 12/2015 | Glerum et al. |
| 9,278,008 B2 | 3/2016 | Perloff et al. |
| 9,320,610 B2 | 4/2016 | Alheidt et al. |
| 9,333,092 B2 | 5/2016 | To |
| 9,351,848 B2 | 5/2016 | Glerum et al. |
| 9,402,733 B1 | 8/2016 | To |
| 9,402,739 B2 | 8/2016 | Weiman et al. |
| 9,445,918 B1 | 9/2016 | Lin et al. |
| 9,463,052 B2 | 10/2016 | Geist |
| 9,474,625 B2 | 10/2016 | Weiman |
| 9,480,574 B2 | 11/2016 | Lee et al. |
| 9,545,316 B2 | 1/2017 | Ashley et al. |
| 9,561,116 B2 | 2/2017 | Weiman et al. |
| 9,566,168 B2 | 2/2017 | Glerum et al. |
| 9,655,744 B1 | 5/2017 | Pimenta |
| 9,675,469 B2 | 6/2017 | Landry et al. |
| 9,717,601 B2 | 8/2017 | Miller |
| 9,737,411 B2 | 8/2017 | Loebl et al. |
| 9,795,493 B1 | 10/2017 | Bannigan |
| 9,801,640 B2 | 10/2017 | O'Neil et al. |
| 9,801,733 B2 | 10/2017 | Wolters et al. |
| 9,801,734 B1 | 10/2017 | Stein et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 | 3/2018 | Thommen et al. |
| 9,913,736 B2 | 3/2018 | To |
| 9,987,143 B2 | 6/2018 | Robinson et al. |
| 9,999,517 B2 | 6/2018 | To |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 | 10/2018 | Koch et al. |
| 10,143,569 B2 | 12/2018 | Weiman et al. |
| 10,149,773 B2 | 12/2018 | To |
| 10,154,911 B2 | 12/2018 | Predick et al. |
| 2002/0040243 A1 | 4/2002 | Attali |
| 2003/0074075 A1 | 4/2003 | Thomas et al. |
| 2003/0083746 A1 | 5/2003 | Kuslich |
| 2004/0010315 A1 | 1/2004 | Song |
| 2004/0024463 A1 | 2/2004 | Thomas et al. |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0222043 A1 | 9/2009 | Altarac |
| 2009/0234389 A1 | 9/2009 | Chuang |
| 2009/0281551 A1 | 11/2009 | Frey |
| 2010/0010542 A1 | 1/2010 | Jackson |
| 2010/0010633 A1 | 1/2010 | Kohm |
| 2010/0042218 A1 | 2/2010 | Nebosky et al. |

(56) References Cited

U.S. PATENT DOCUMENTS

| | | |
|---|---|---|
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1* | 11/2010 | Lechmann ............ A61F 2/3094 623/17.12 |
| 2010/0292796 A1 | 11/2010 | Greenhalgh |
| 2011/0022090 A1 | 1/2011 | Gordon |
| 2011/0029082 A1 | 2/2011 | Hall |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1 | 12/2011 | Glerum |
| 2012/0029636 A1 | 2/2012 | Ragab |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0184822 A1 | 7/2013 | Kleiner |
| 2014/0039625 A1 | 2/2014 | To |
| 2014/0243981 A1 | 8/2014 | Davenport et al. |
| 2015/0073555 A1* | 3/2015 | To ........................ A61F 2/4611 623/17.16 |
| 2015/0100128 A1 | 4/2015 | Glerum et al. |
| 2015/0190242 A1 | 7/2015 | Blain et al. |
| 2015/0374508 A1 | 12/2015 | Sandul |
| 2016/0015530 A1 | 1/2016 | To |
| 2016/0256291 A1 | 9/2016 | Miller |
| 2016/0317315 A1 | 11/2016 | Weiman |
| 2016/0338854 A1 | 11/2016 | Serhan et al. |
| 2016/0361176 A1* | 12/2016 | Weiman .................. A61F 2/447 |
| 2017/0119540 A1 | 5/2017 | Greenhalgh |
| 2017/0209282 A1 | 7/2017 | Aghayev et al. |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0098860 A1 | 4/2018 | To |
| 2018/0193164 A1 | 7/2018 | Shoshtaev |
| 2018/0221175 A1 | 8/2018 | To |
| 2018/0256357 A1 | 9/2018 | To |
| 2018/0296361 A1 | 10/2018 | Butler et al. |
| 2018/0360489 A1 | 12/2018 | Geist |
| 2019/0053913 A1 | 2/2019 | To |
| 2019/0060085 A1 | 2/2019 | Geist |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| WO | WO 1996/040015 | 6/1996 |
| WO | WO 2000/044319 | 1/2000 |
| WO | WO 2001/066047 | 7/2001 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | PCT/US2013/052799 | 7/2012 |
| WO | WO 2012/135764 | 10/2012 |
| WO | PCT/US2013/073435 | 12/2013 |
| WO | PCT/US2014/054437 | 2/2014 |
| WO | PCT/US2016/014100 | 12/2015 |
| WO | PCT/US2017/52708 | 9/2017 |
| WO | PCT/US2019/20354 | 3/2018 |
| WO | PCT/US2018/43517 | 7/2018 |

OTHER PUBLICATIONS

U.S. Appl. No. 16/334,486, To—owned by Applicant, filed Sep. 21, 2016.
U.S. Appl. No. 60/666,945 (priority for U.S. Pat. No. 7,731,751, cited herein), Butler, et al., filed Mar. 31, 2005.
U.S. Appl. No. 61/585,724 (priority for U.S. Pat. No. 9,463,052, cited herein), Geist—owned by Applicant, filed Jan. 12, 2012.
U.S. Appl. No. 61/737,054 (priority for U.S. Pat. No. 8,663,332, cited herein), To—owned by Applicant, filed Dec. 15, 2013.
U.S. Appl. No. 61/875,688 (priority for U.S. Pat. No. 9,186,259, cited herein), To—owned by Applicant, filed Oct. 4, 2013.
U.S. Appl. No. 62/232,021 (priority for U.S. Pat. No. 10,058,350, cited herein), Geist—owned by Applicant, filed Sep. 24, 2015.
U.S. Appl. No. 62/444,663 (priority for U.S. 2018/0193164, cited herein), Shoshtaev—owned by Applicant, filed Jan. 10, 2017.
U.S. Appl. No. 62/471,206 (priority for U.S. 2018/0193164, cited herein), Shoshtaev—owned by Applicant, filed Jan. 10, 2017.
U.S. Appl. No. 62/481,565 (priority for U.S. 2018/0193164, cited herein), Shoshtaev—owned by Applicant, filed Jan. 10, 2017.
U.S. Appl. No. 62/536,335 (priority for PCT/US2018/43517, cited herein), To—owned by Applicant, filed Jul. 24, 2017.
U.S. Appl. No. 62/550,557 (priority for U.S Appl. No. 16/113,040, cited herein), Geist—owned by Applicant, filed Aug. 25, 2017.
Written opinion and search report for PCT/US2013/052799, To—owned by Applicant, dated Dec. 2, 2012.
Written opinion and search report for PCT/US2013/073435, To—owned by Applicant, dated Apr. 30, 2012.
Written opinion and search report for PCT/US2014/054437, To—owned by Applicant, Jan. 6, 2015.
Written opinion and search report for PCT/US2016/014100, To—owned by Applicant, Jan. 6, 2015.
Written opinion and search report for PCT/US2017/52708, To—owned by Applicant, Sep. 21, 2017.
PCT/US2016/053467 Published as WO 2017/053813, Geist—owned by Applicant, Sep. 24, 2015.
Written opinion and search report for PCT/US2016/053467, Geist—owned by Applicant, Sep. 24, 2015.
PCT/US2018/13207 Published as WO 2018/132502, Shoshtaev—owned by Applicant, Jan. 10, 2018.
Written opinion and search report for PCT/US2018/13207, Shoshtaev—owned by Applicant, Jan. 10, 2018.
Written opinion and search report for PCT/US2018/43517, To—owned by Applicant, Jul. 24, 2018.
European search report for EP 13862126, Dec. 5, 2013, To—owned by Applicant.
European search report for EP 14842880, Jun. 22, 2016, To—owned by Applicant.
European search report for EP 16740662, Nov. 29, 2017, To—owned by Applicant.
JP 2009/505686 Cumulative of WO/2007/009107, Jul. 14, 2005, Greenhalgh, et al.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].

(56) References Cited

OTHER PUBLICATIONS

CAPSTONE® PEEK spinal system PLIF anf TLIF surgical technique. Medtronic Sofamor Danek 1-36 (2009).
Coalign. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage__Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].
Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system. [online] URL: http://www.spineology.com/fb/intl/products/products/optimesh 1500e.html (retrieved Jun. 3, 2013).
STAXX XD, www.spinewave.com. [online] URL: http://www.spinewave.com/products/xd_us.html [retrieved on Jan. 27, 2013].
Synfix-LR System. Instruments and implants for stand-alone anterior lumbar interbody fusion (ALIF). Synthes SynFix-LR system technique guide 52 pages (2010).
Transforaminal Lumbar Interbody Fusion (TLIF). Virgina spine institute, Reston Virgina. [online] URL: http://www.spinemd.com/operative-treatments/tlif- transforaminal-lumbat-interbody-fusion.com 1-6 (2013). [retrieved on Jun. 16, 2013].
Uchida, K. et al. Anterior expandable strut cage replacement for osteoporotic thoracolumbar vertebral collapse. J Neurosurg Spine 4(6): 454-462 (Jun. 2006).
Xenos. Cage mesh system for spine. Biotek Chetan Meditech Pvt. Ltd. [online] URL: http://www.biotekortho.net/spine-treatment.html [retrieved on Feb. 13, 2013].
Zeus-O, [online] URL: http://www.amendia.com/zeuso.html [retrieved on Jan. 27, 2013].
U.S. Appl. No. 16/403,576, To—owned by Applicant, filed Sep. 9, 2013.
U.S. Appl. No. 16/444,888, To—owned by Applicant, filed Dec. 13, 2012.
U.S. Appl. No. 16/527,294, To—owned by Applicant, filed Dec. 13, 2012.
Written opinion and search report for PCT/US2019/20354, Shoshtaev—owned by Applicant, dated Mar. 1, 2018.

* cited by examiner

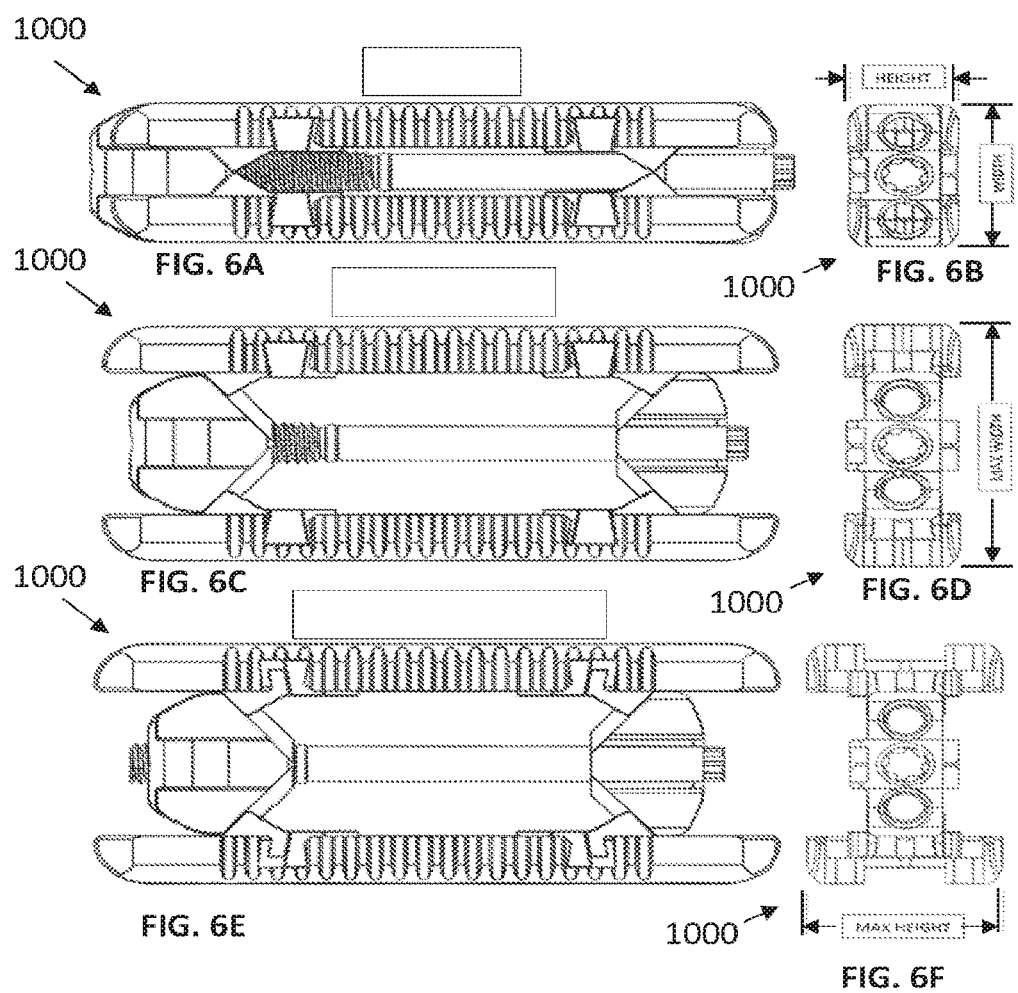

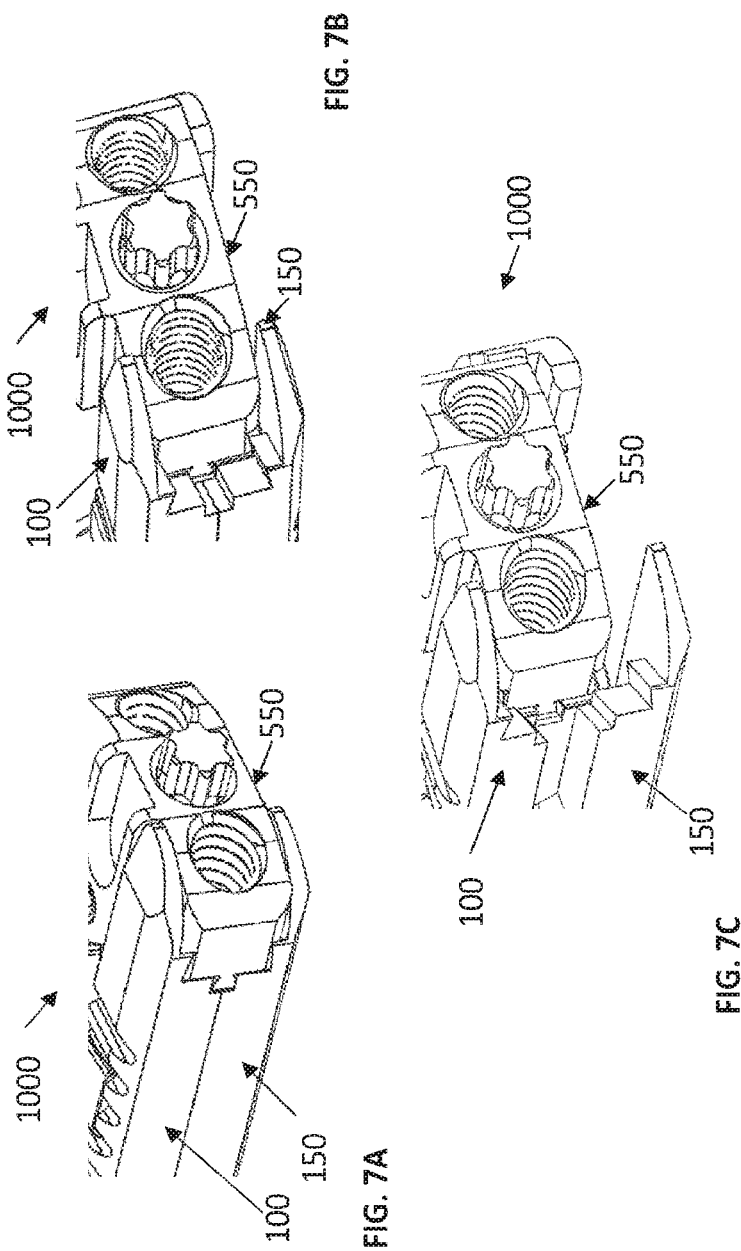

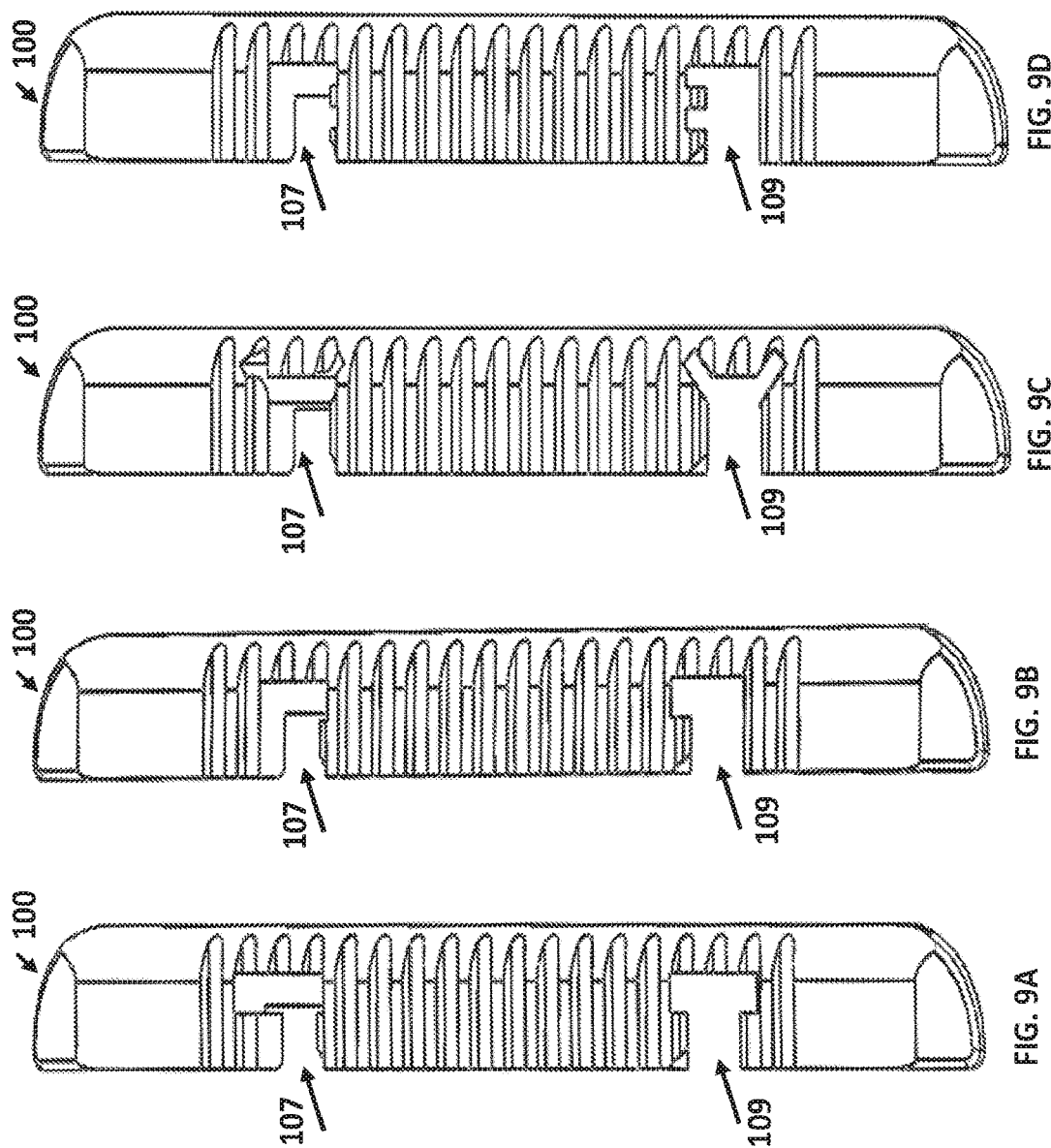

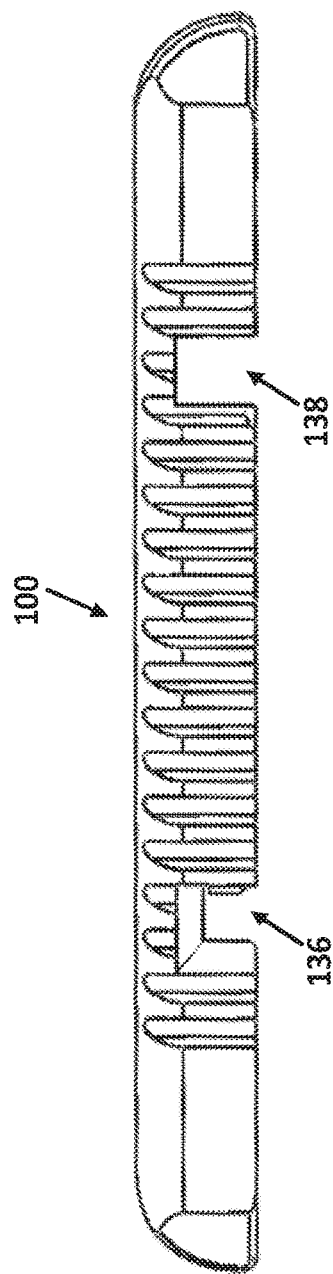

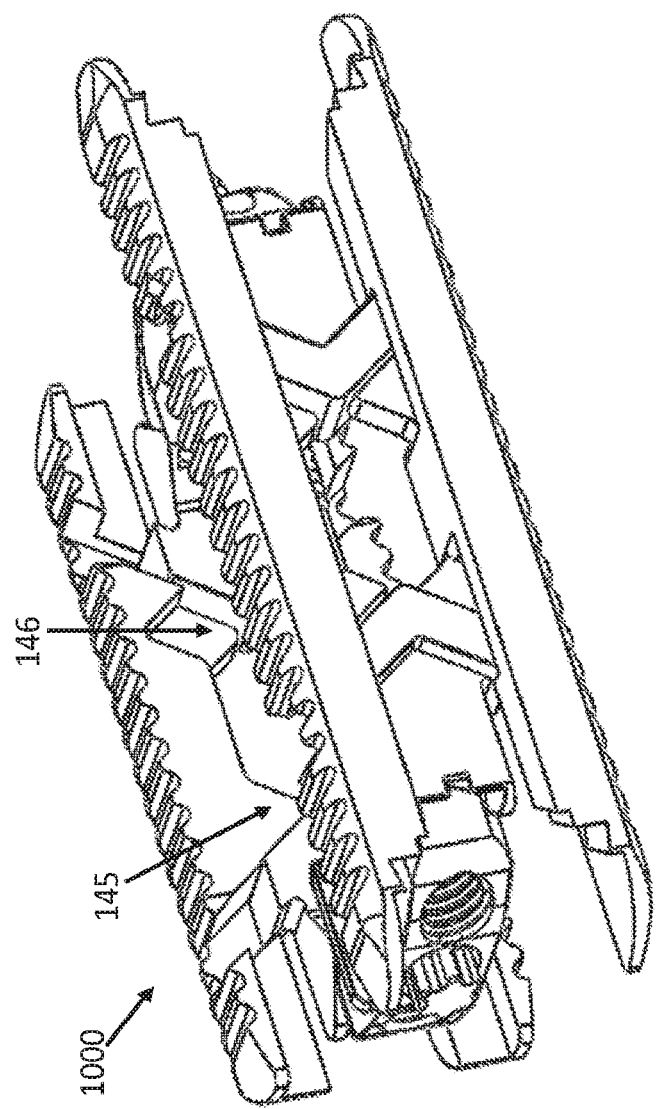

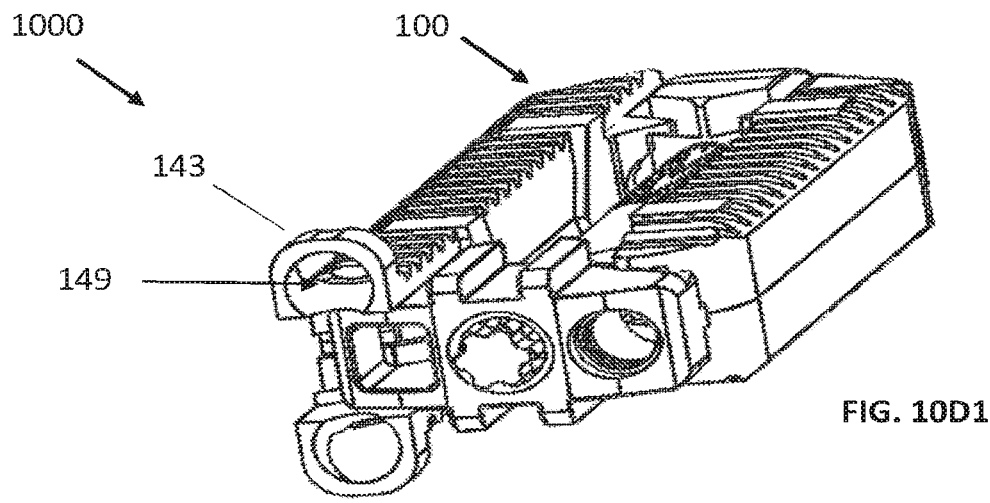
FIG. 10D1
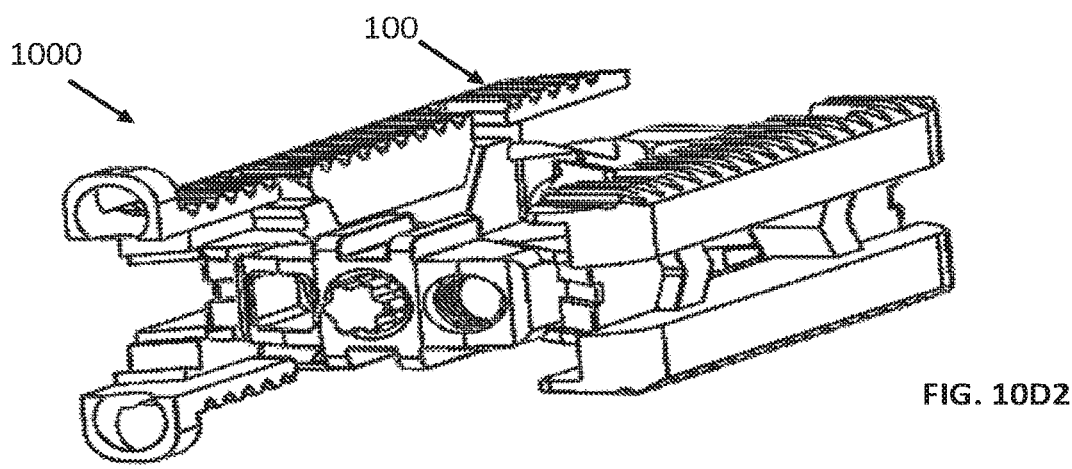
FIG. 10D2
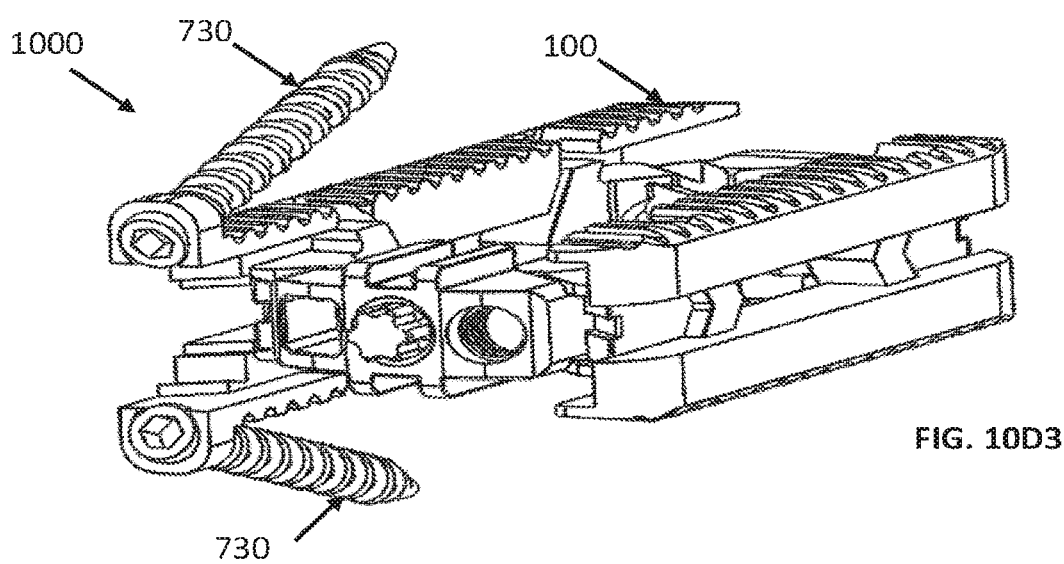
FIG. 10D3

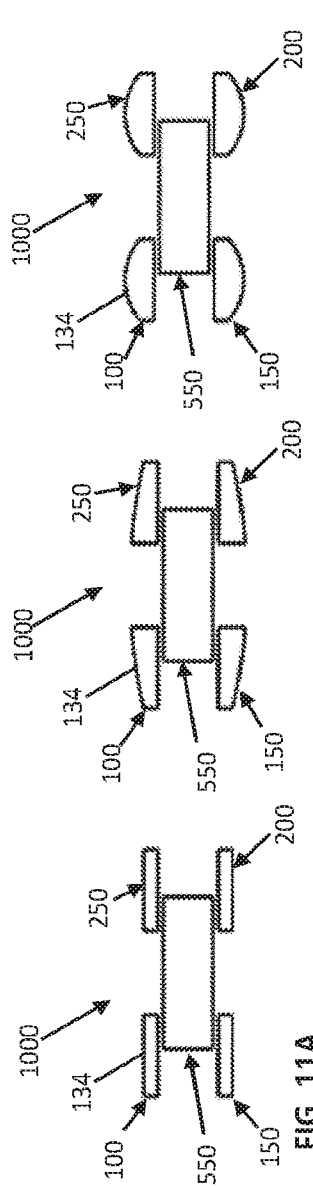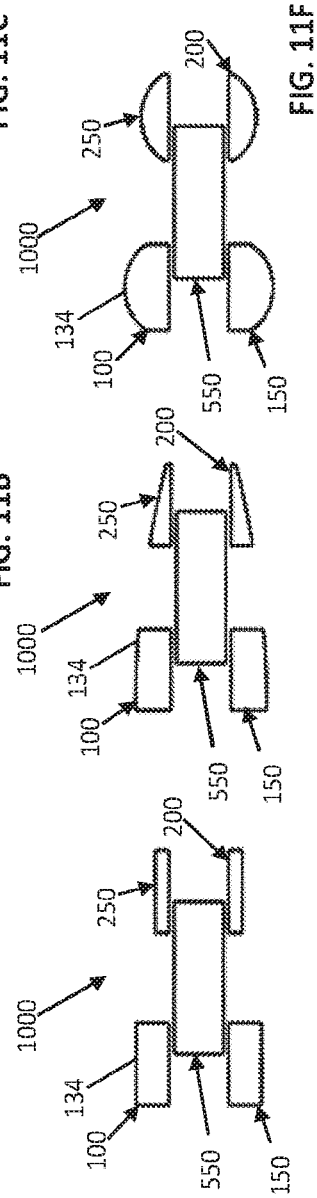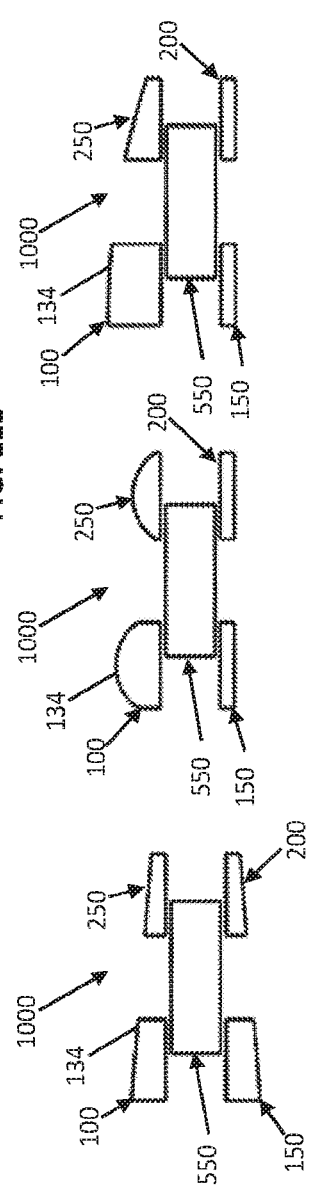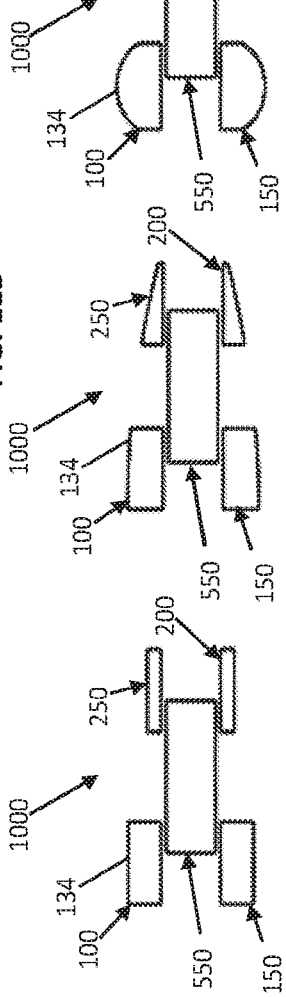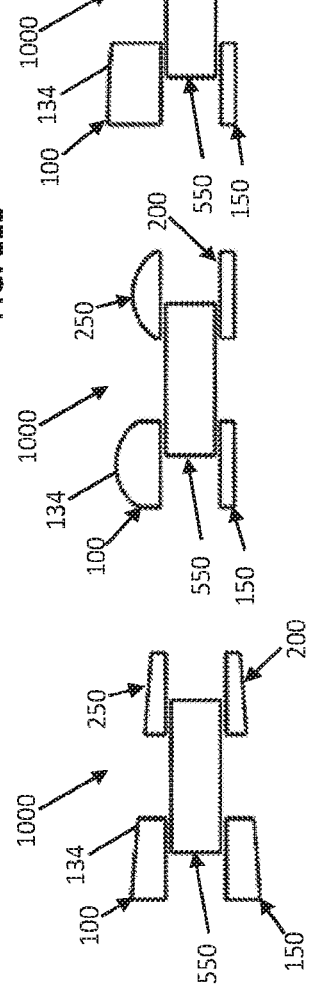

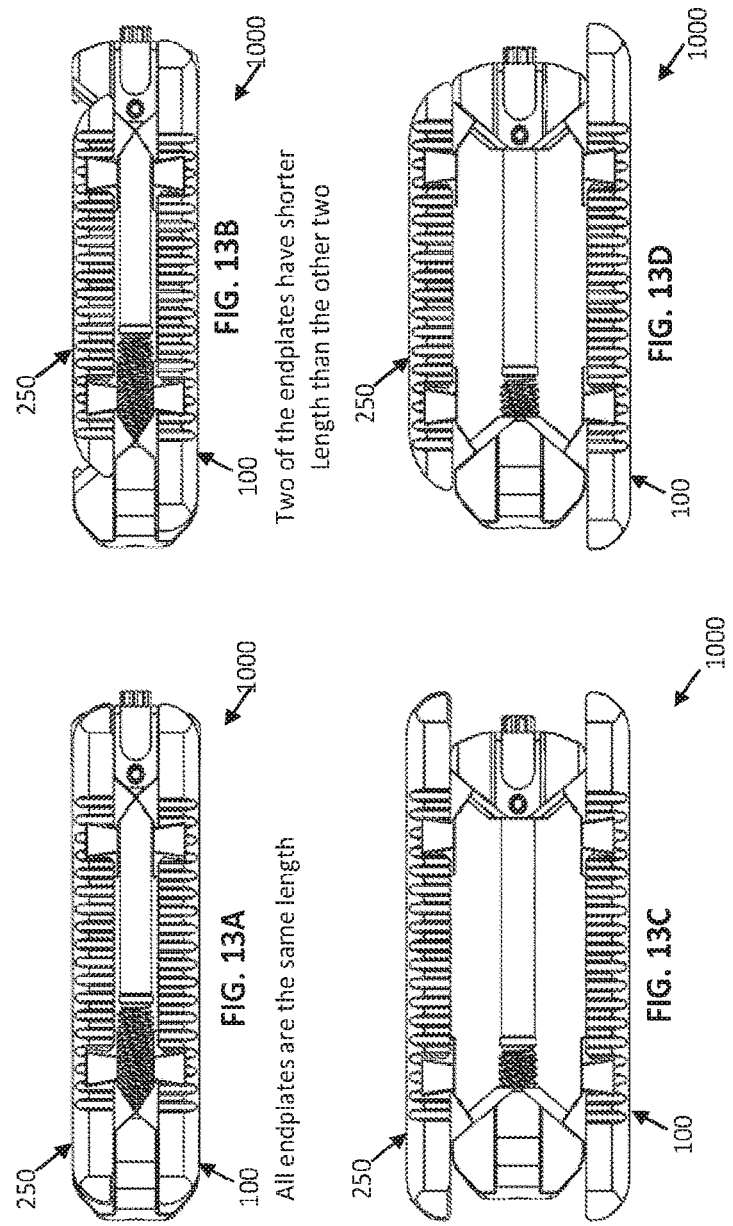

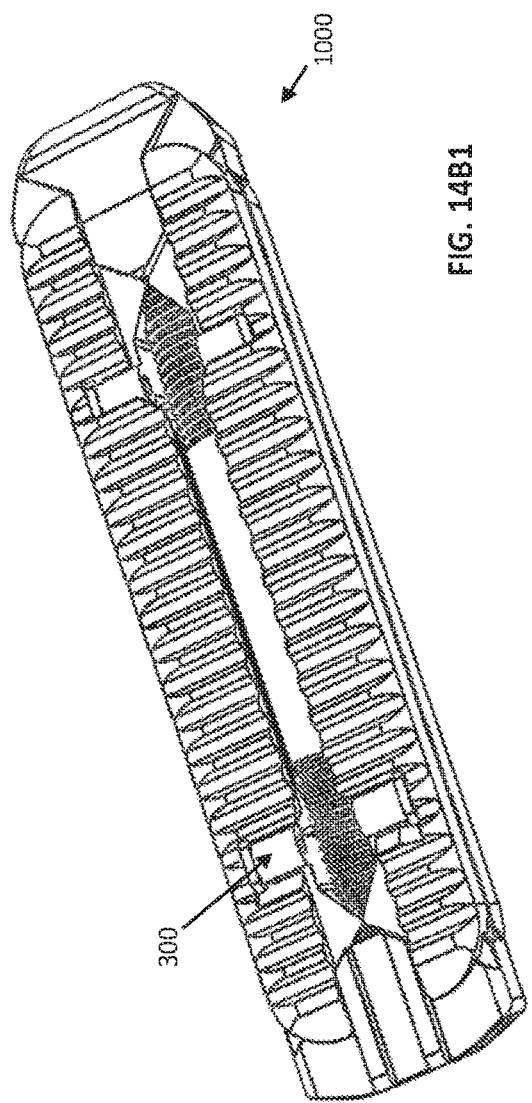
FIG. 14B1

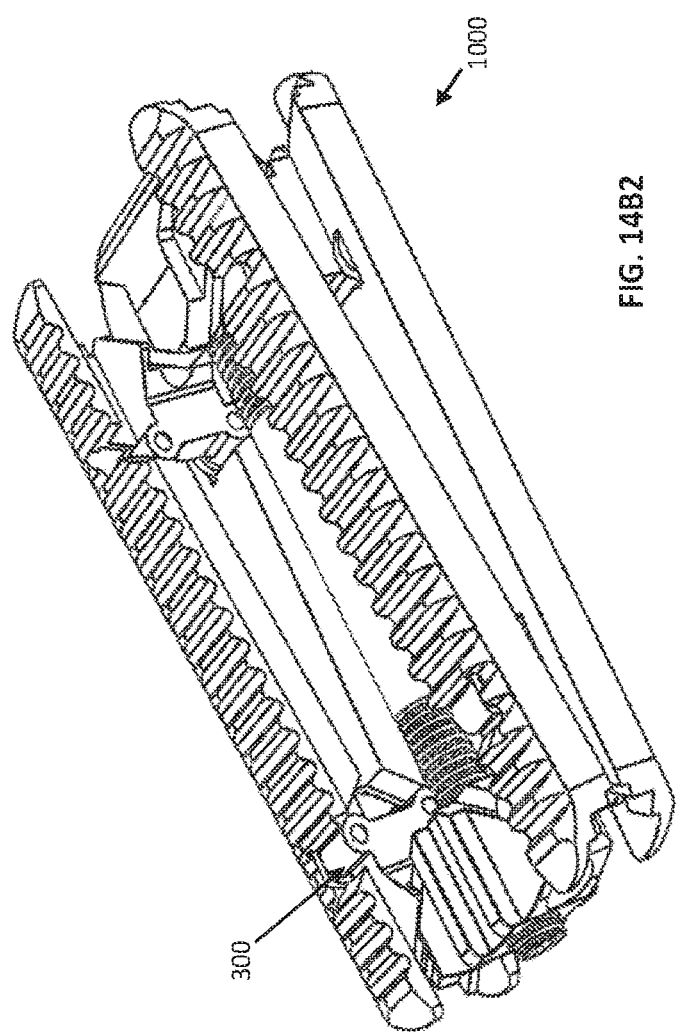
FIG. 14B2

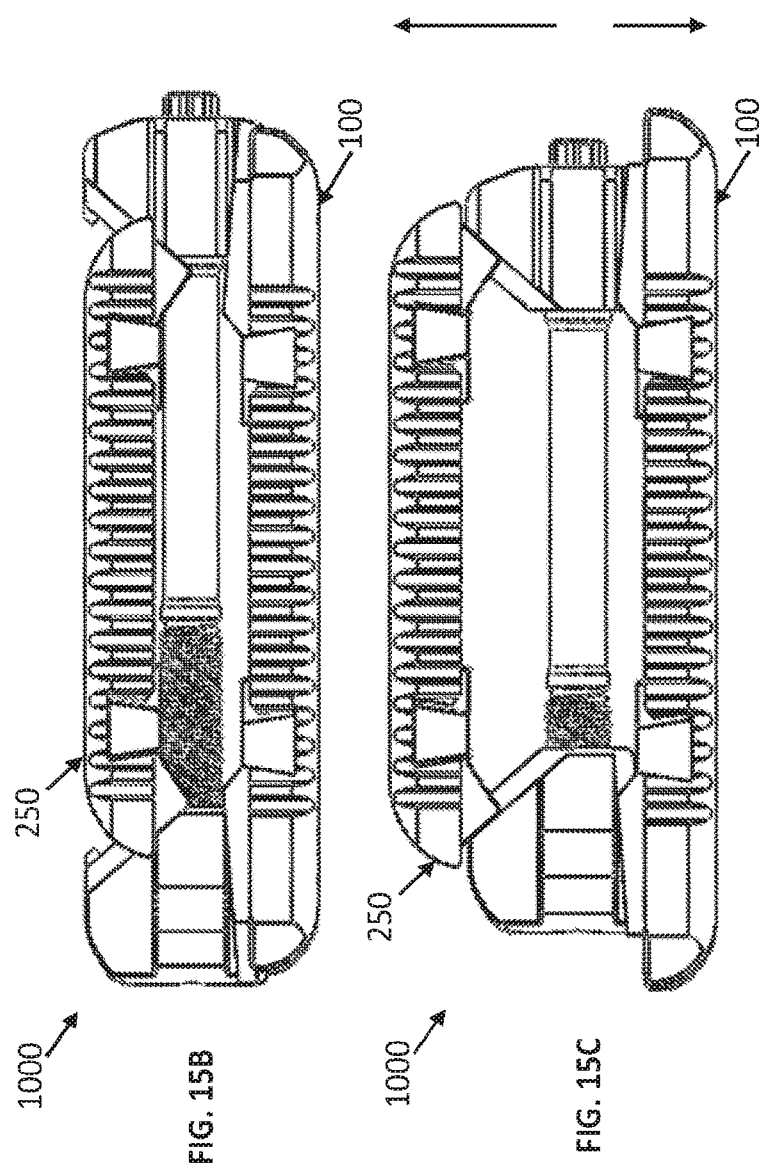

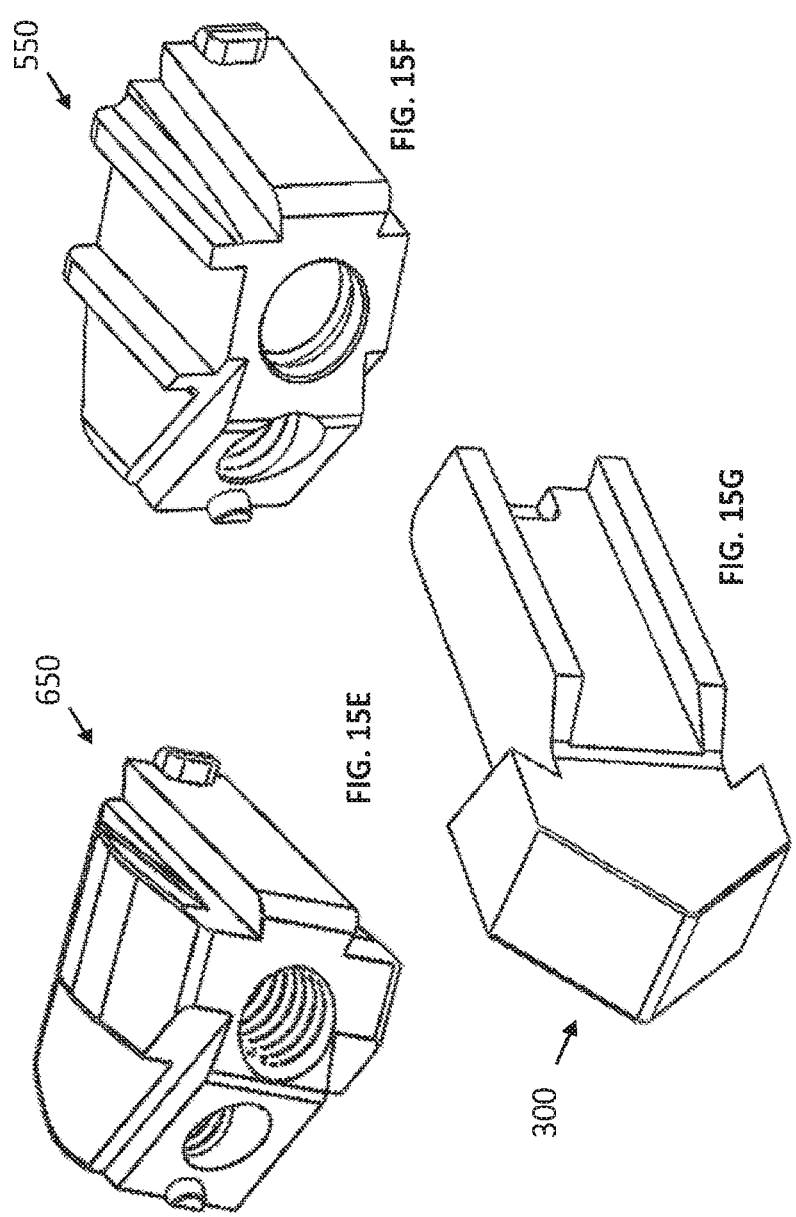

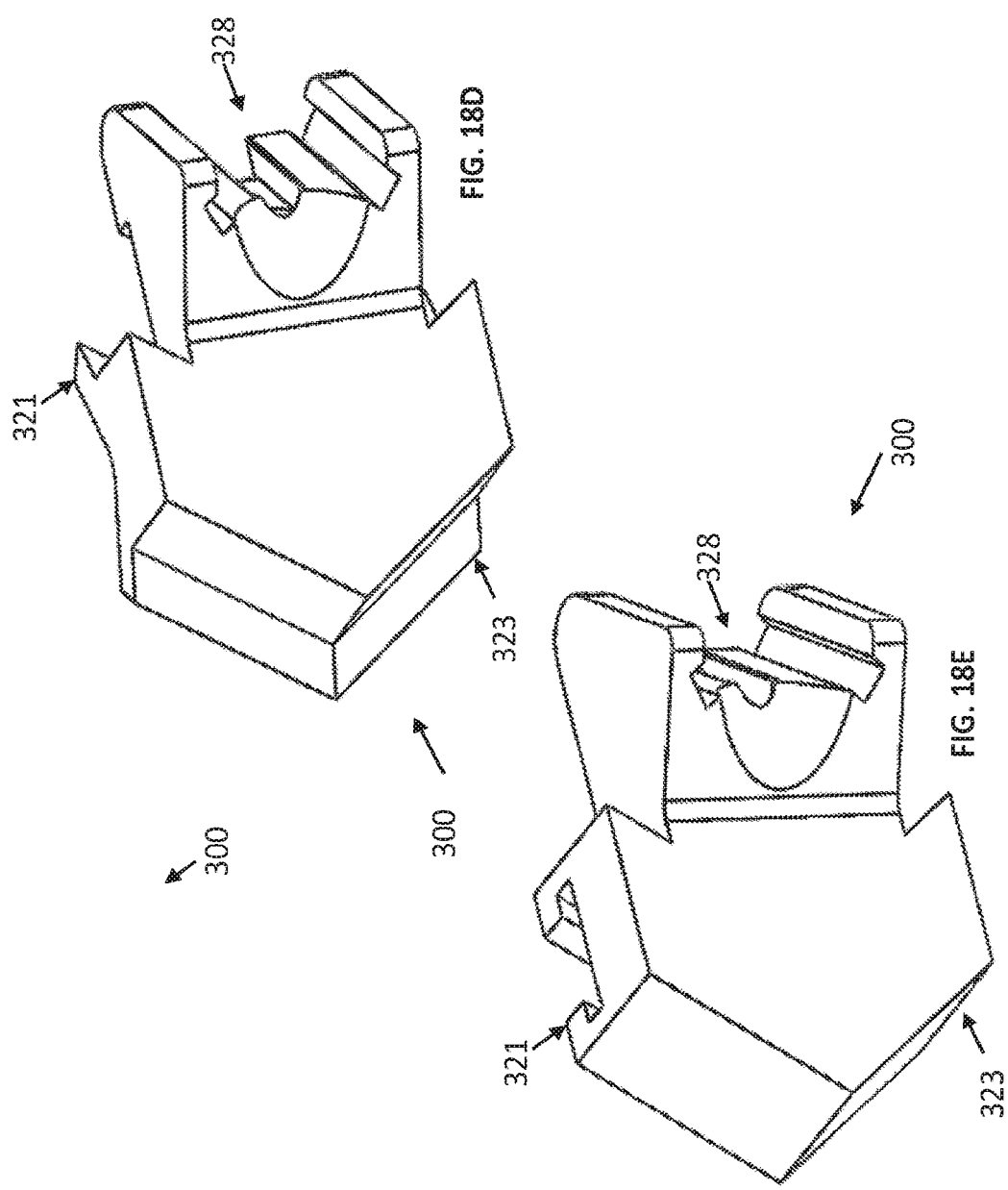

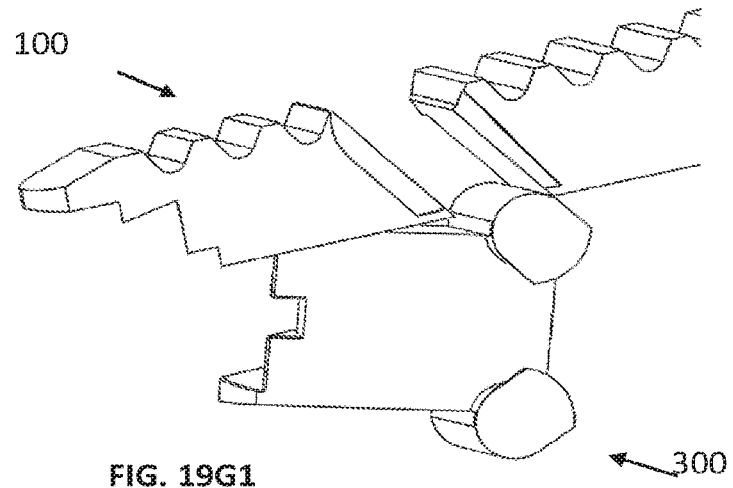
FIG. 19G1
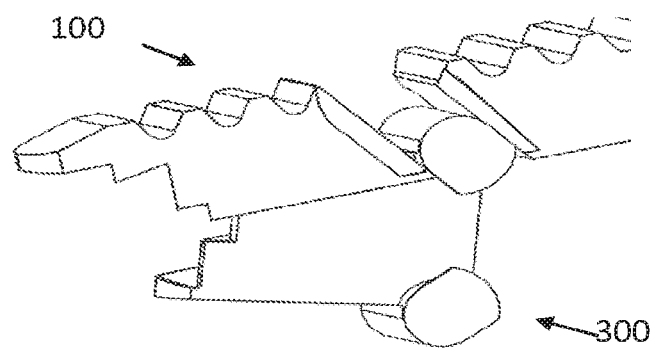
FIG. 19G2
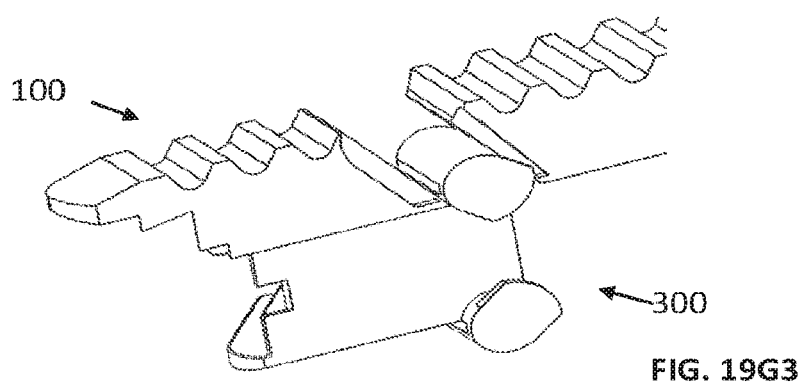
FIG. 19G3

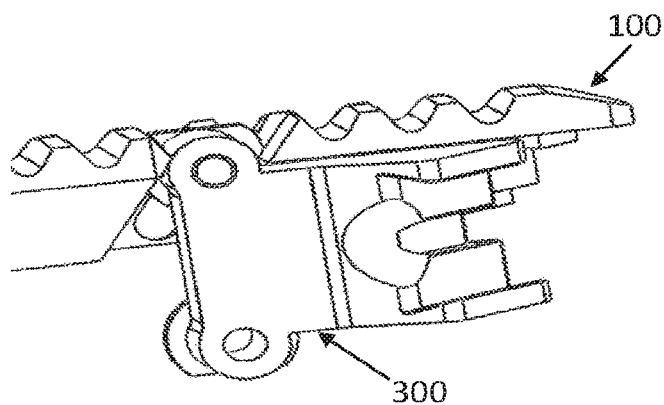
FIG. 19H1
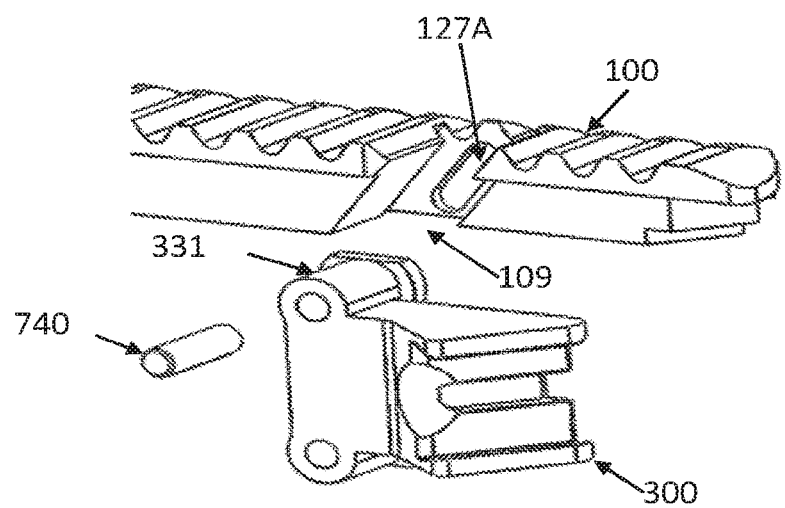
FIG. 19H2

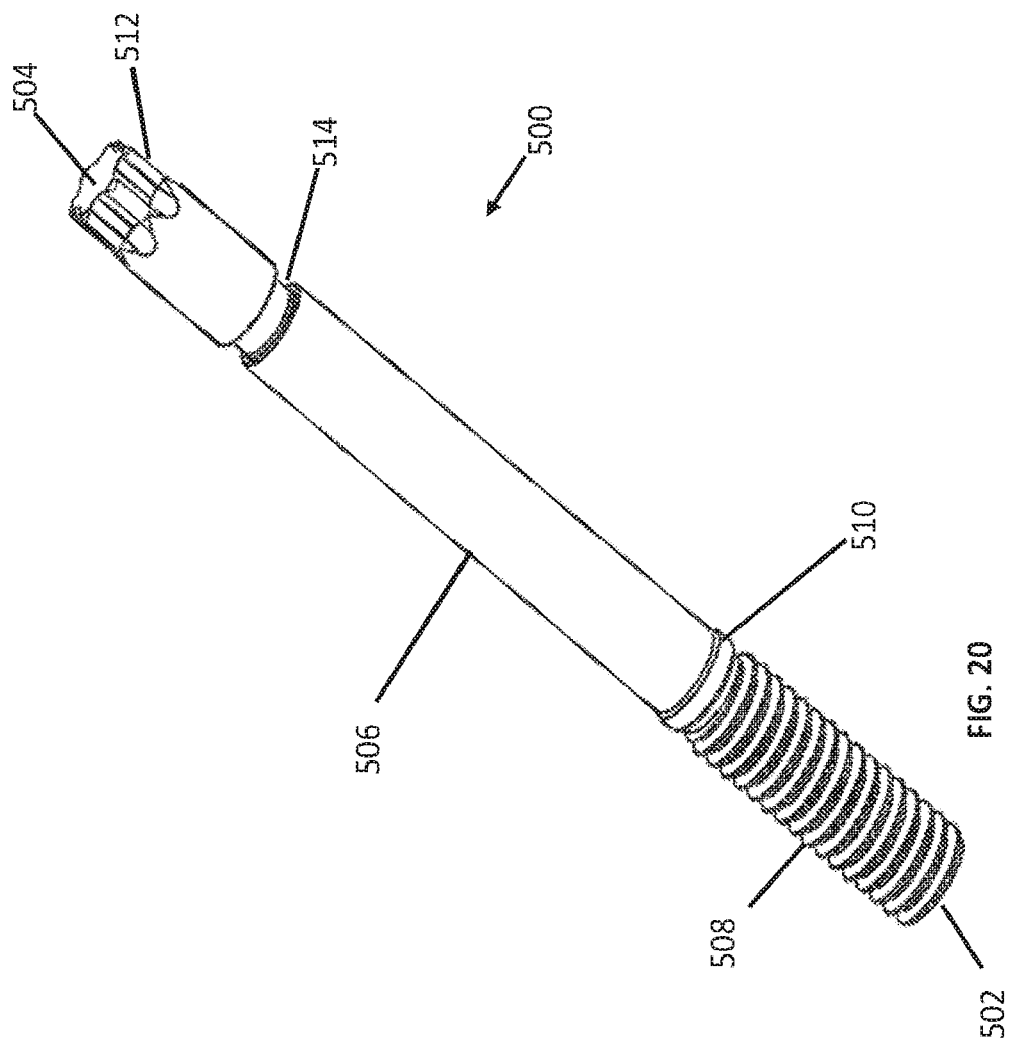

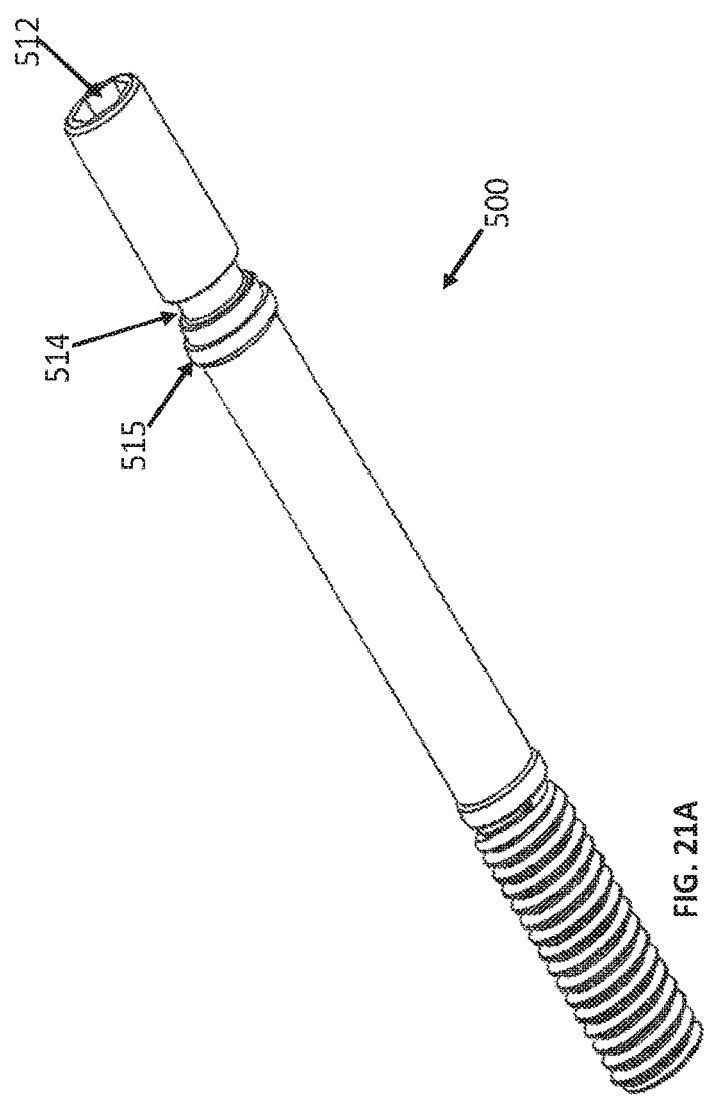

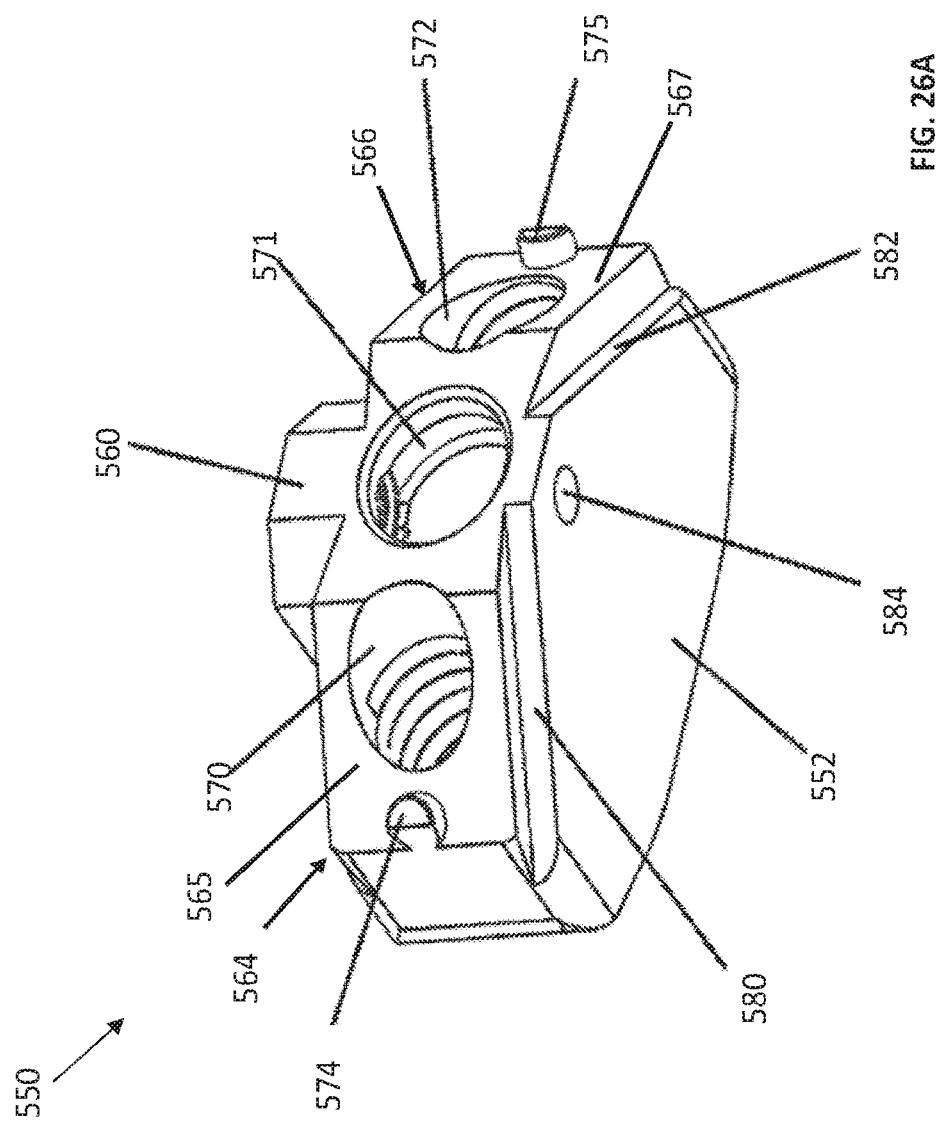

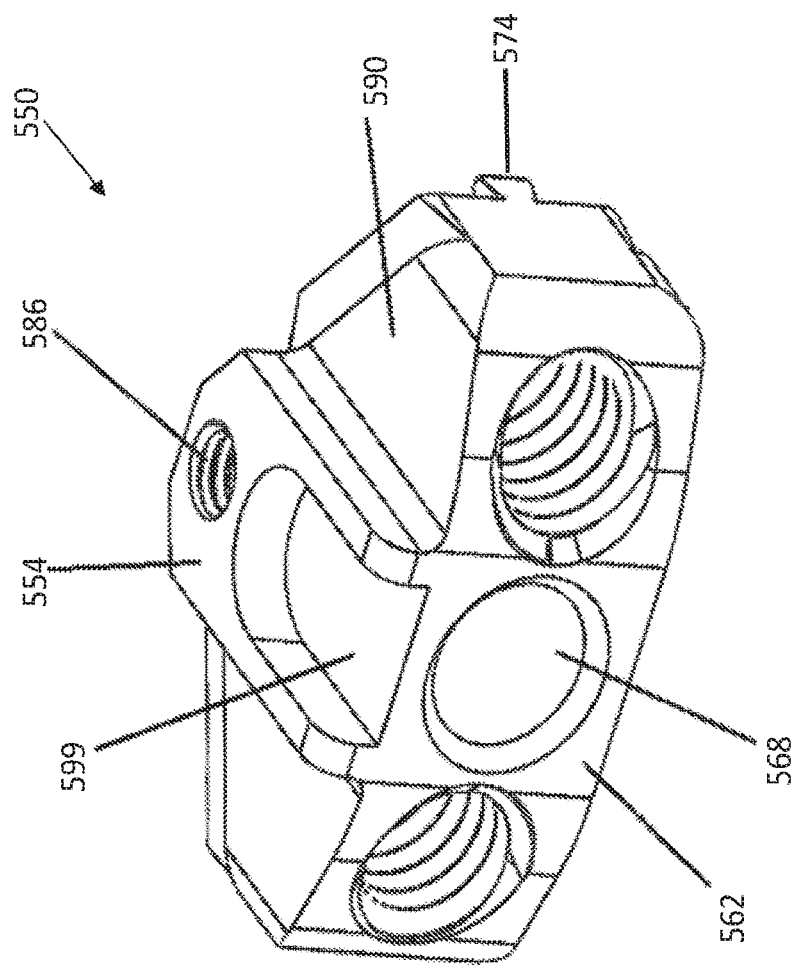

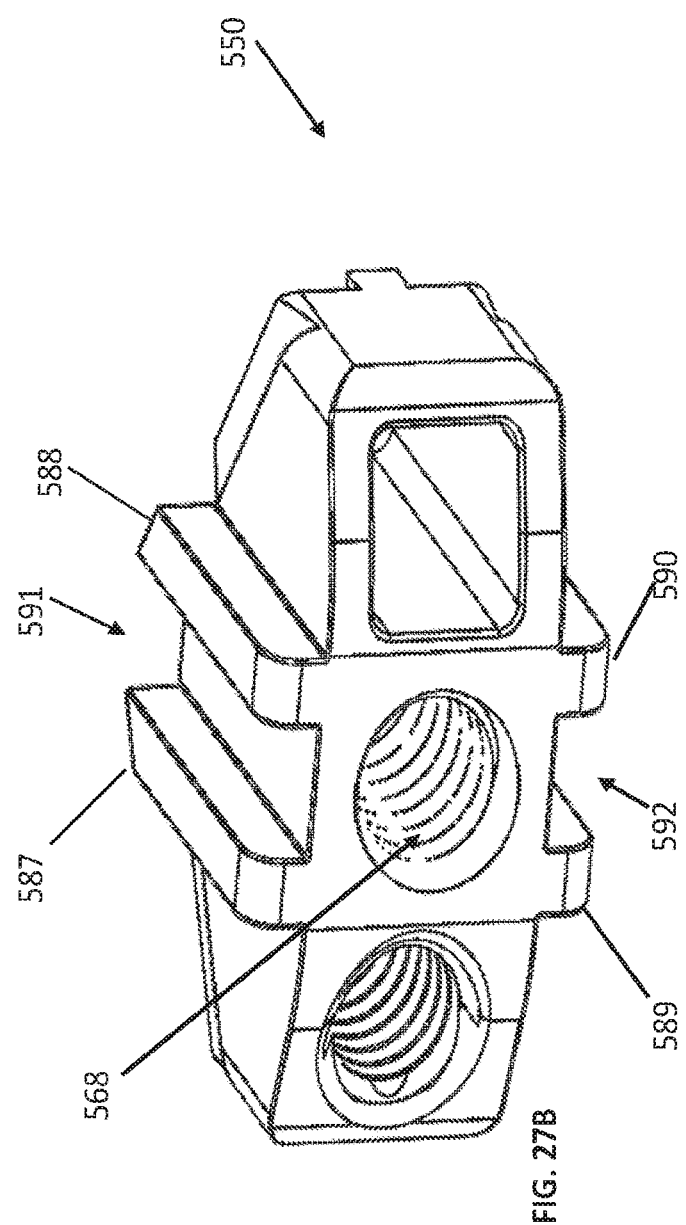

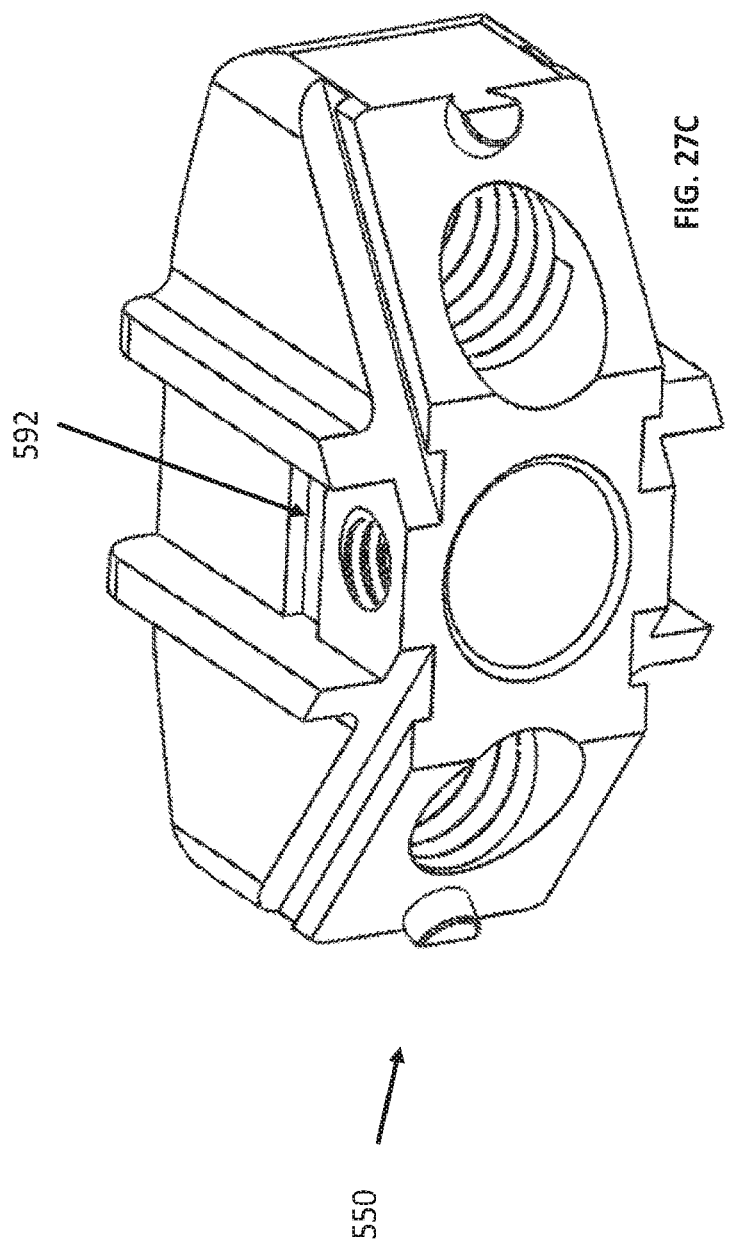

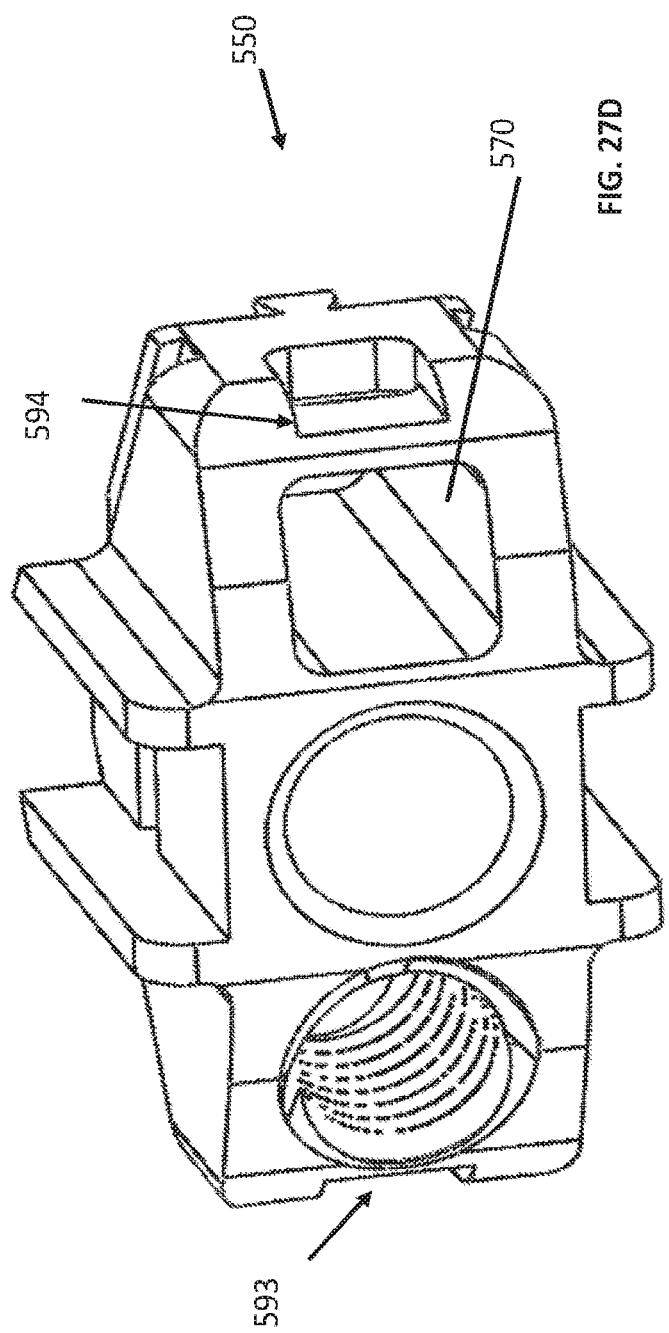

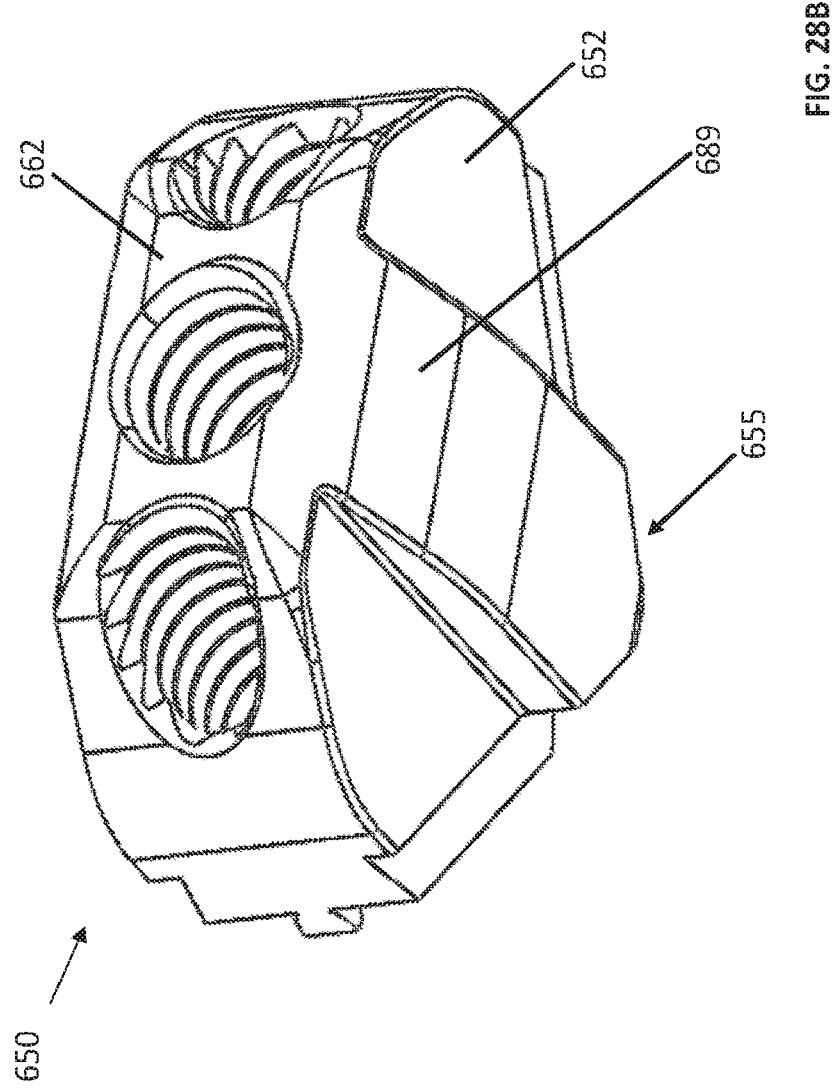

650

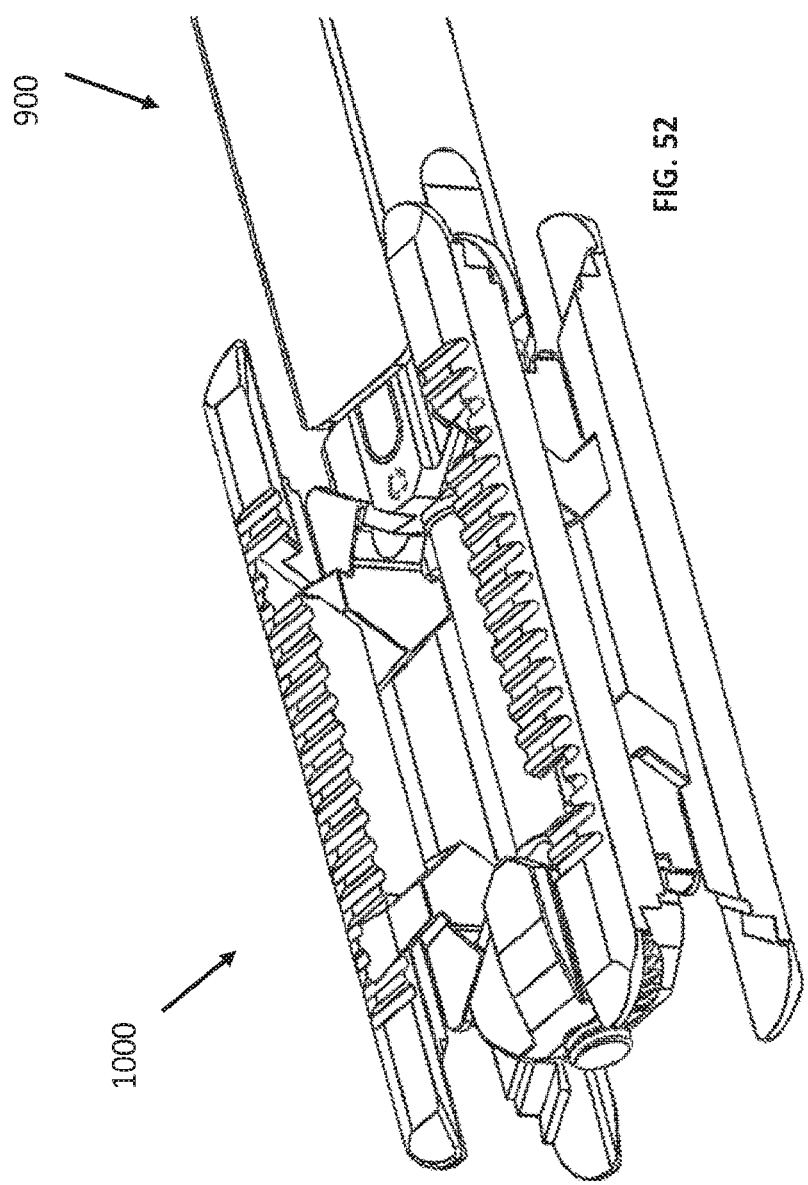

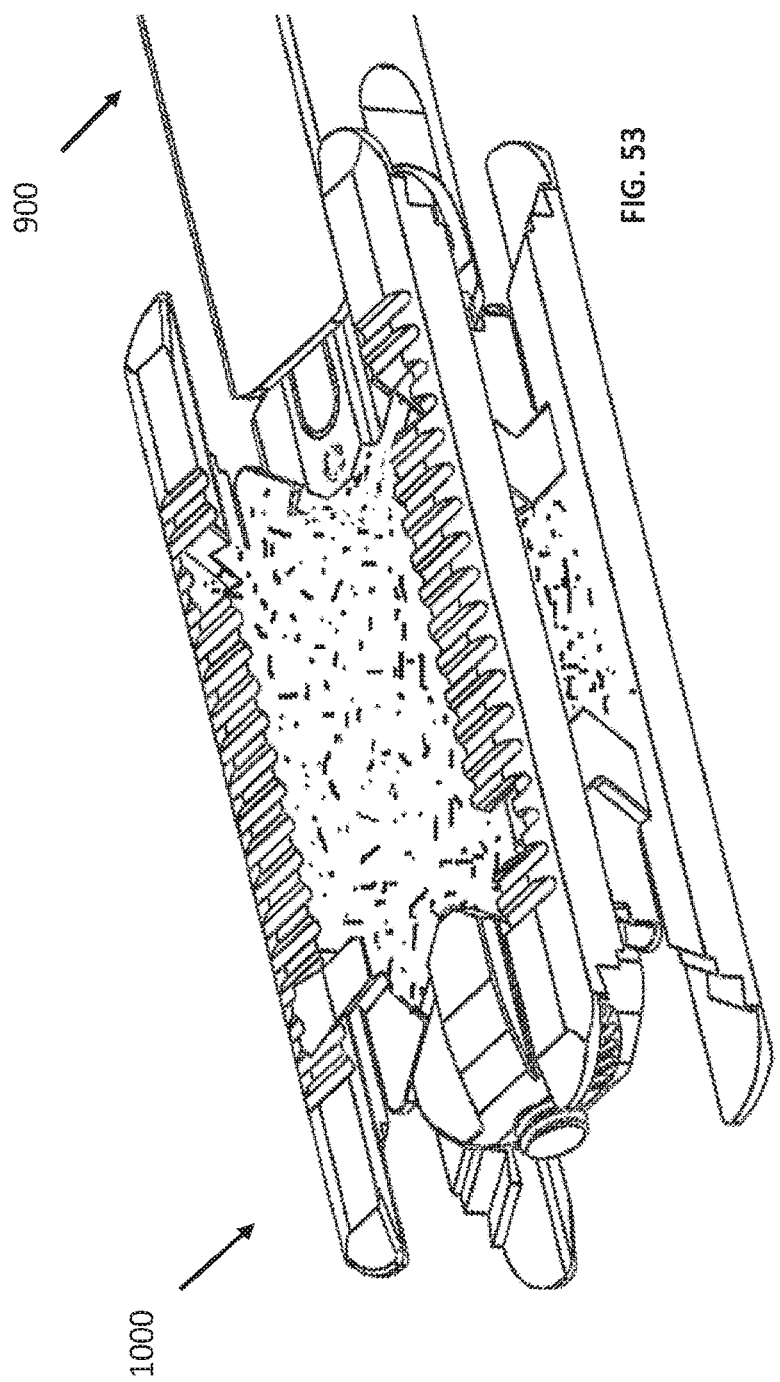

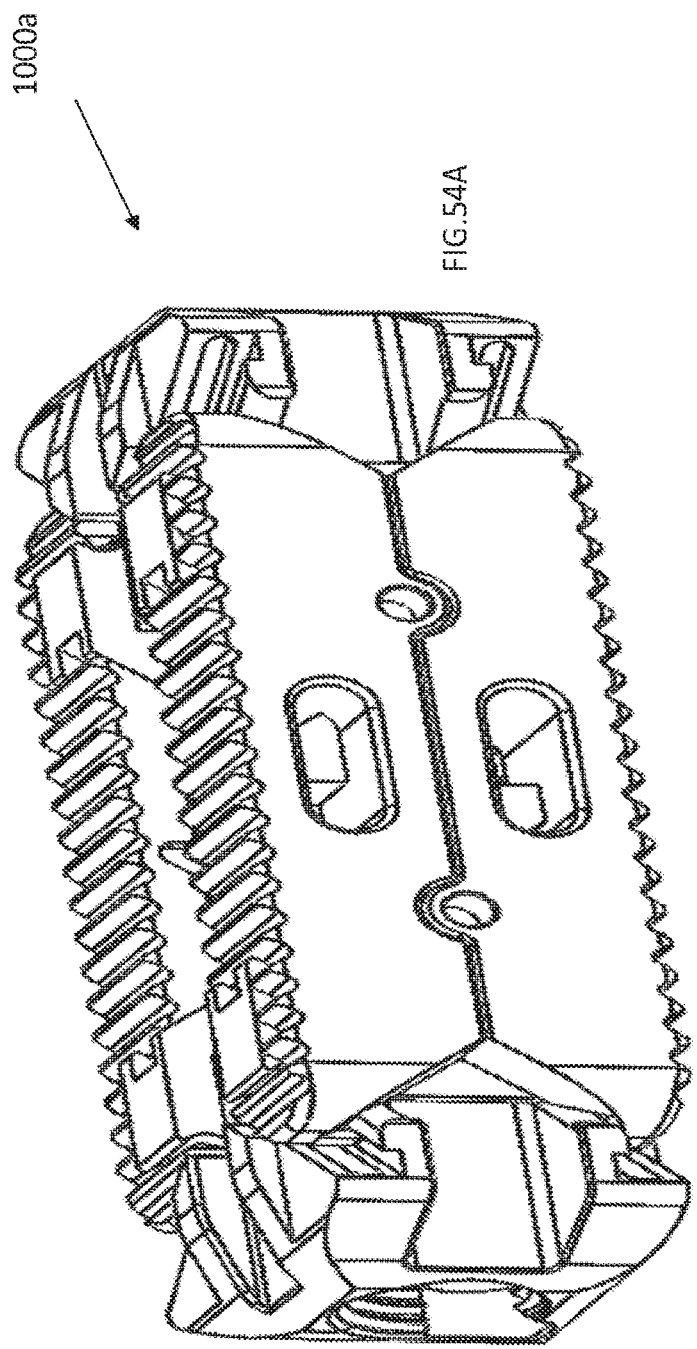

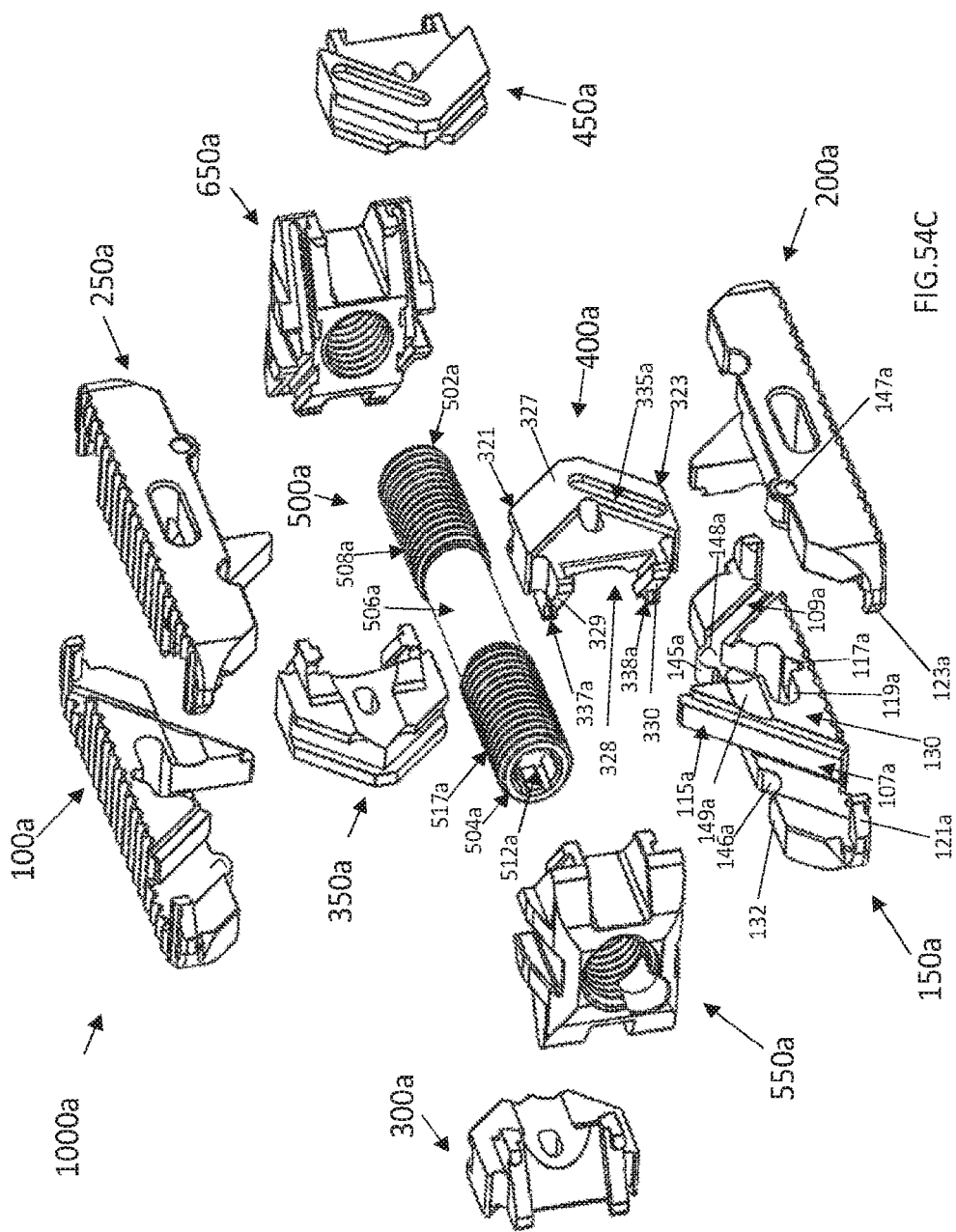

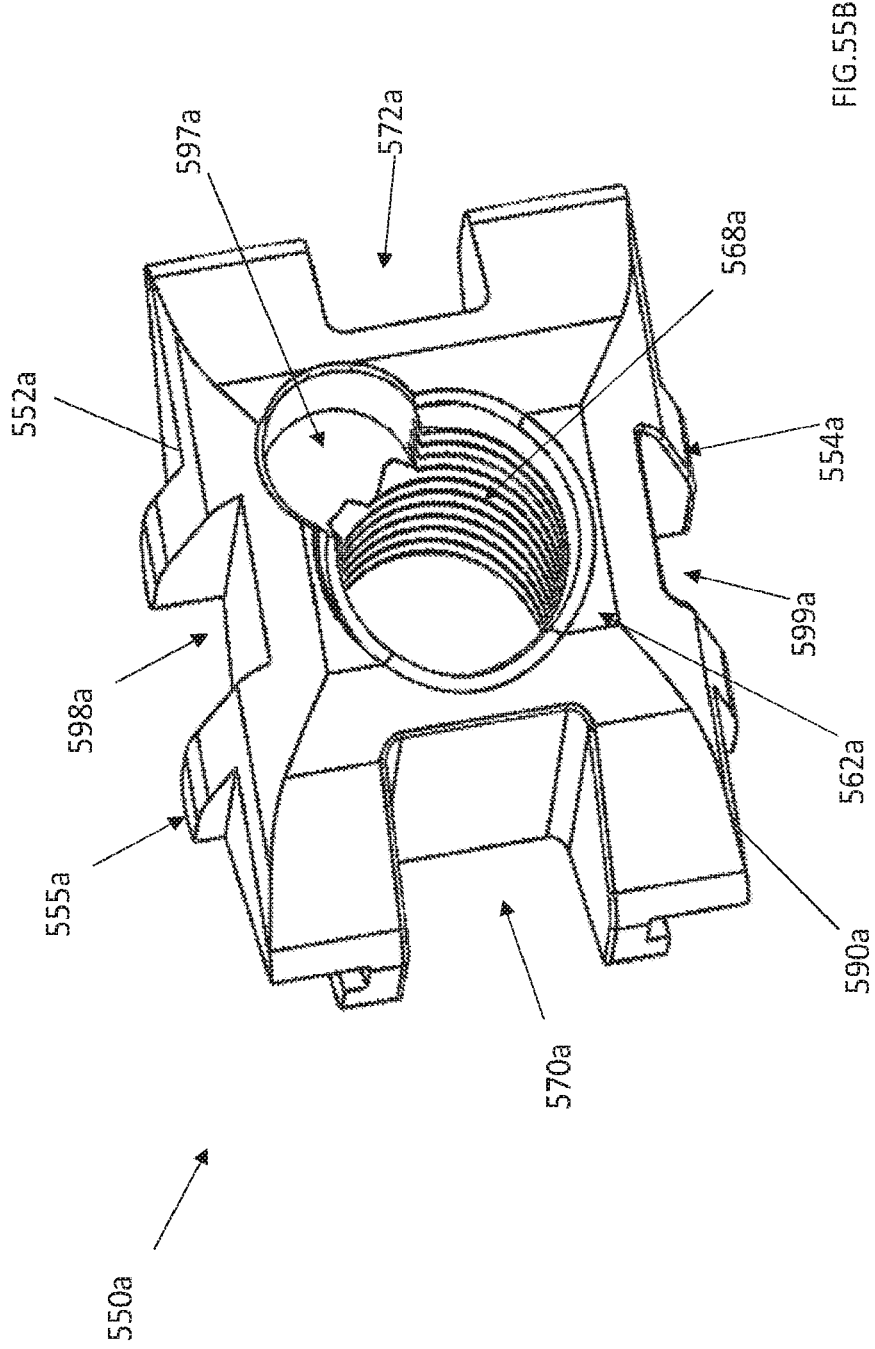

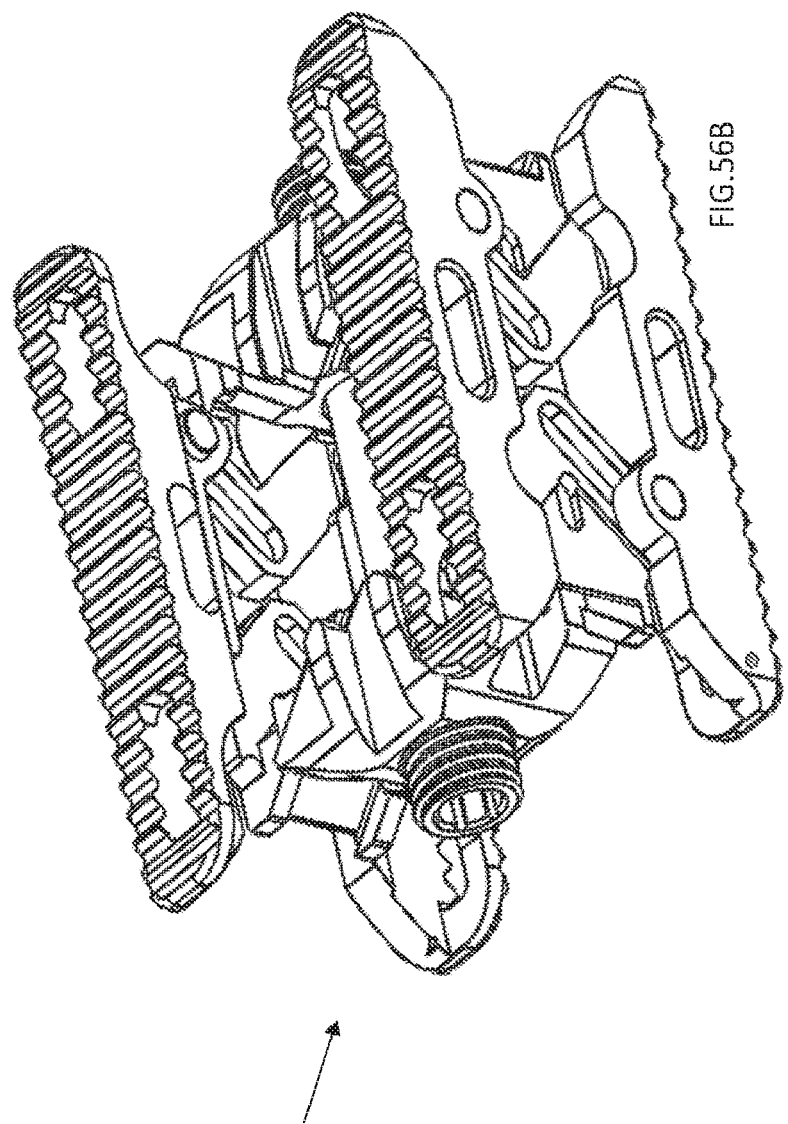

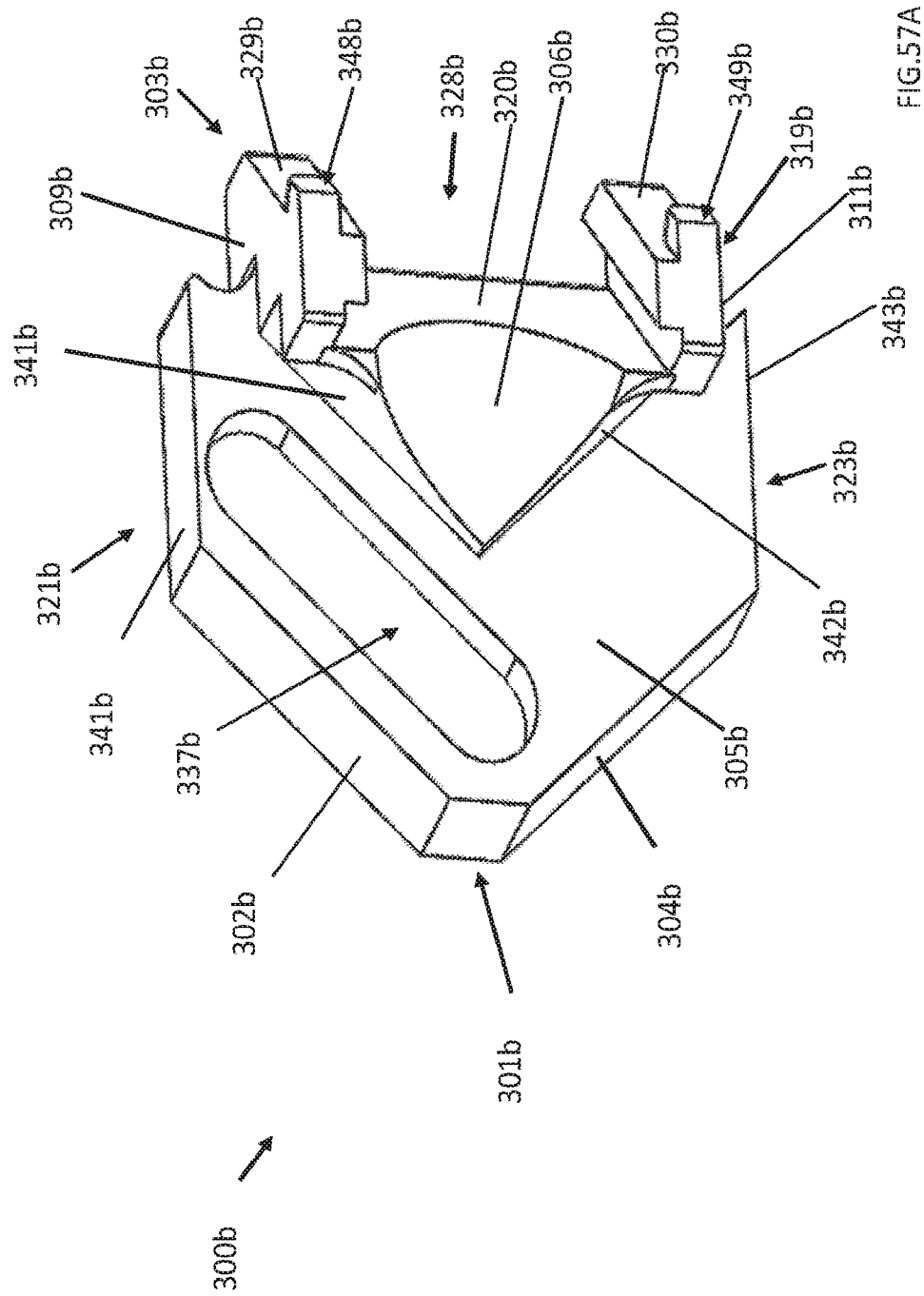

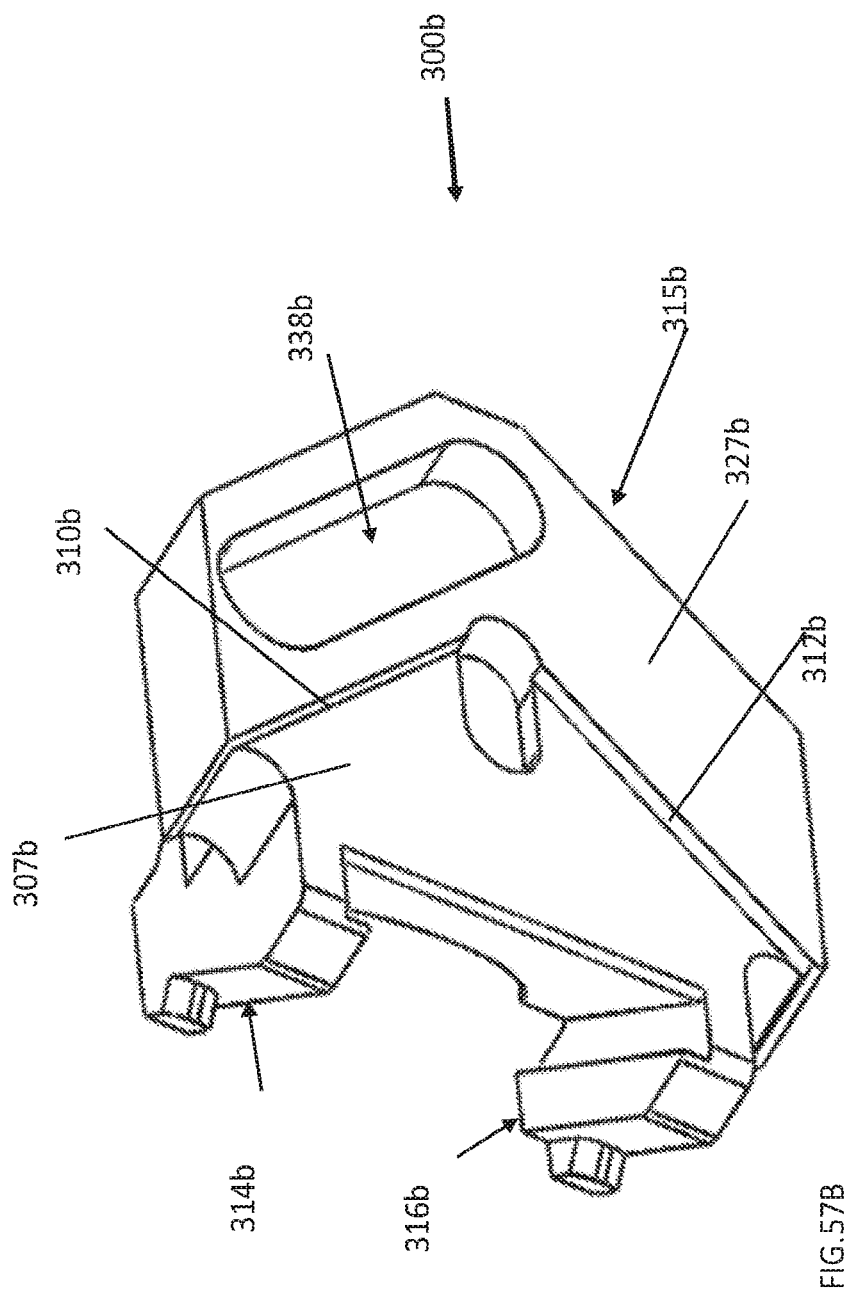

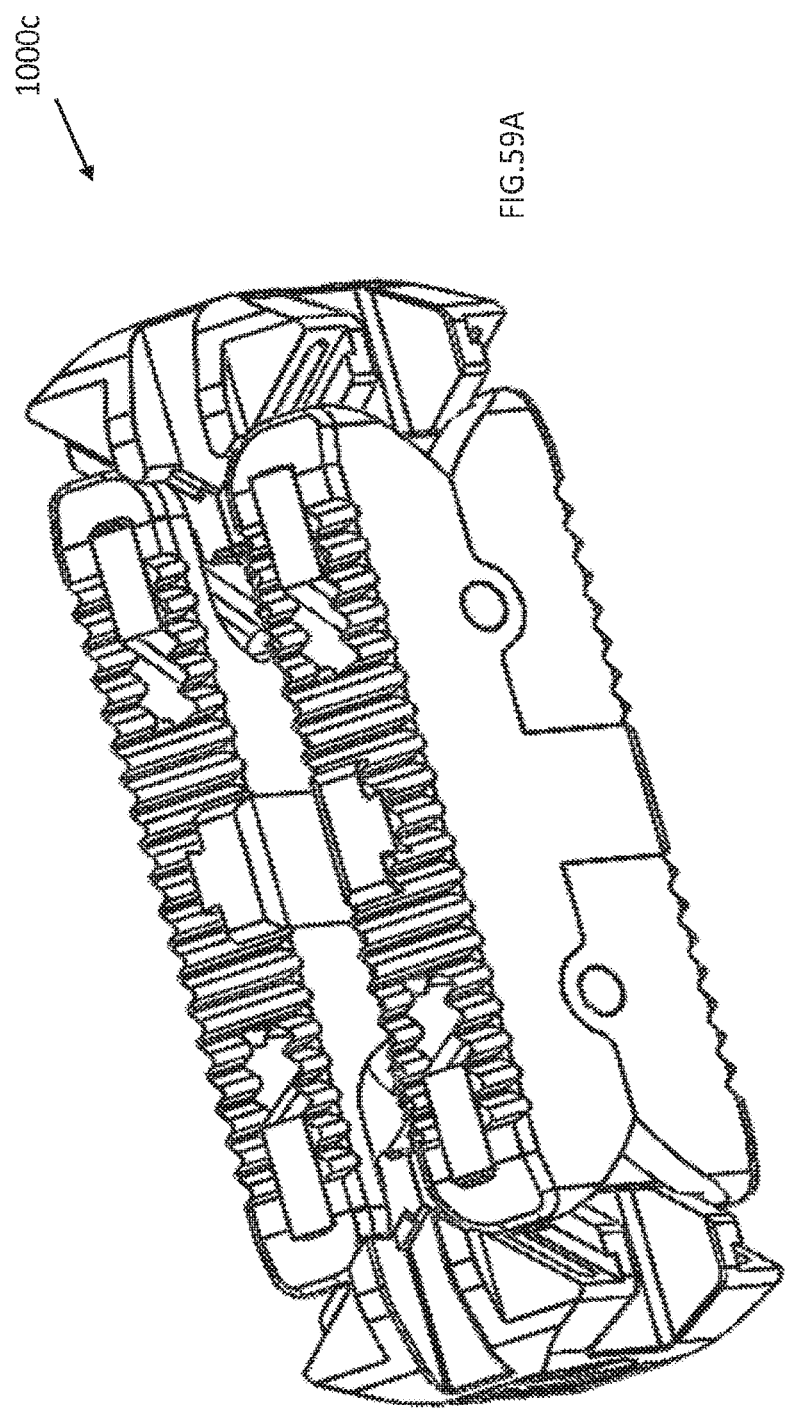

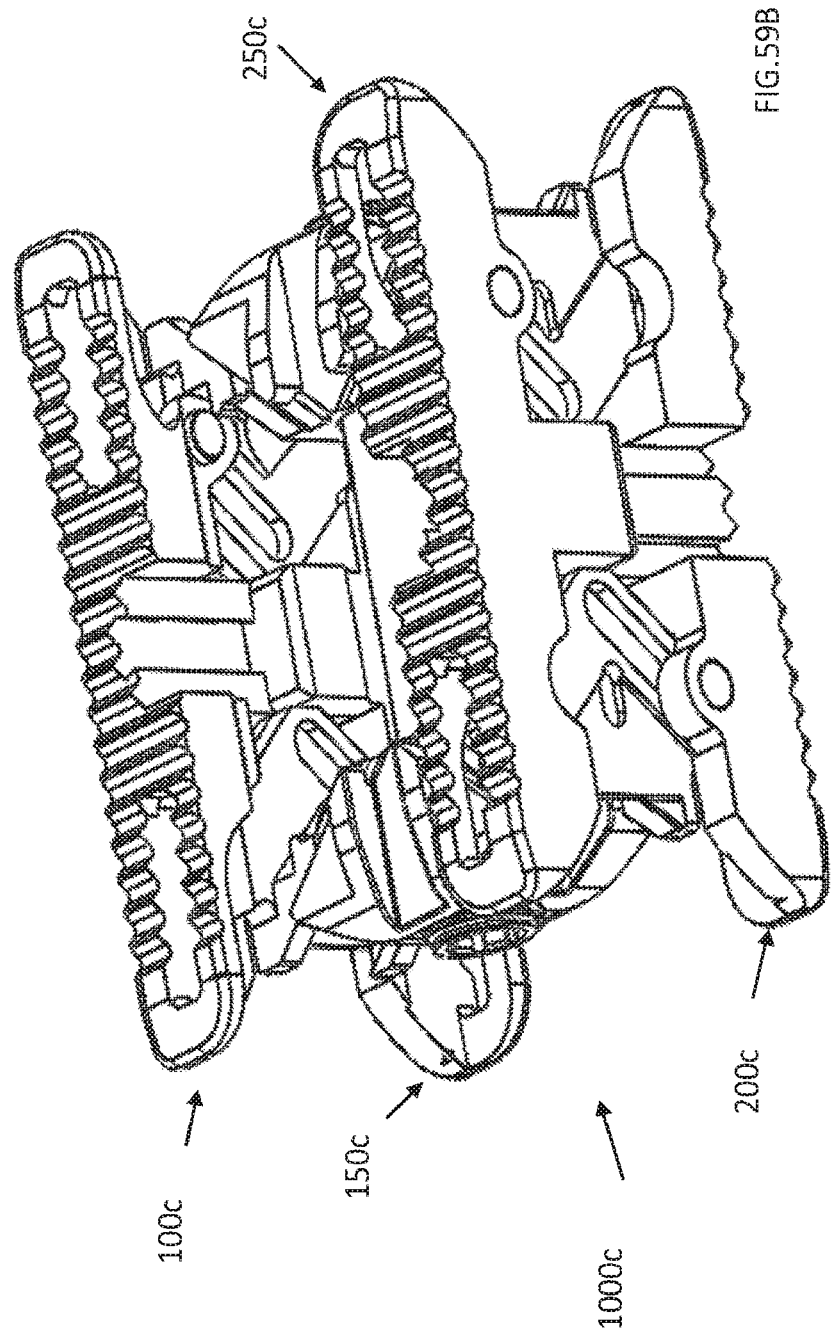

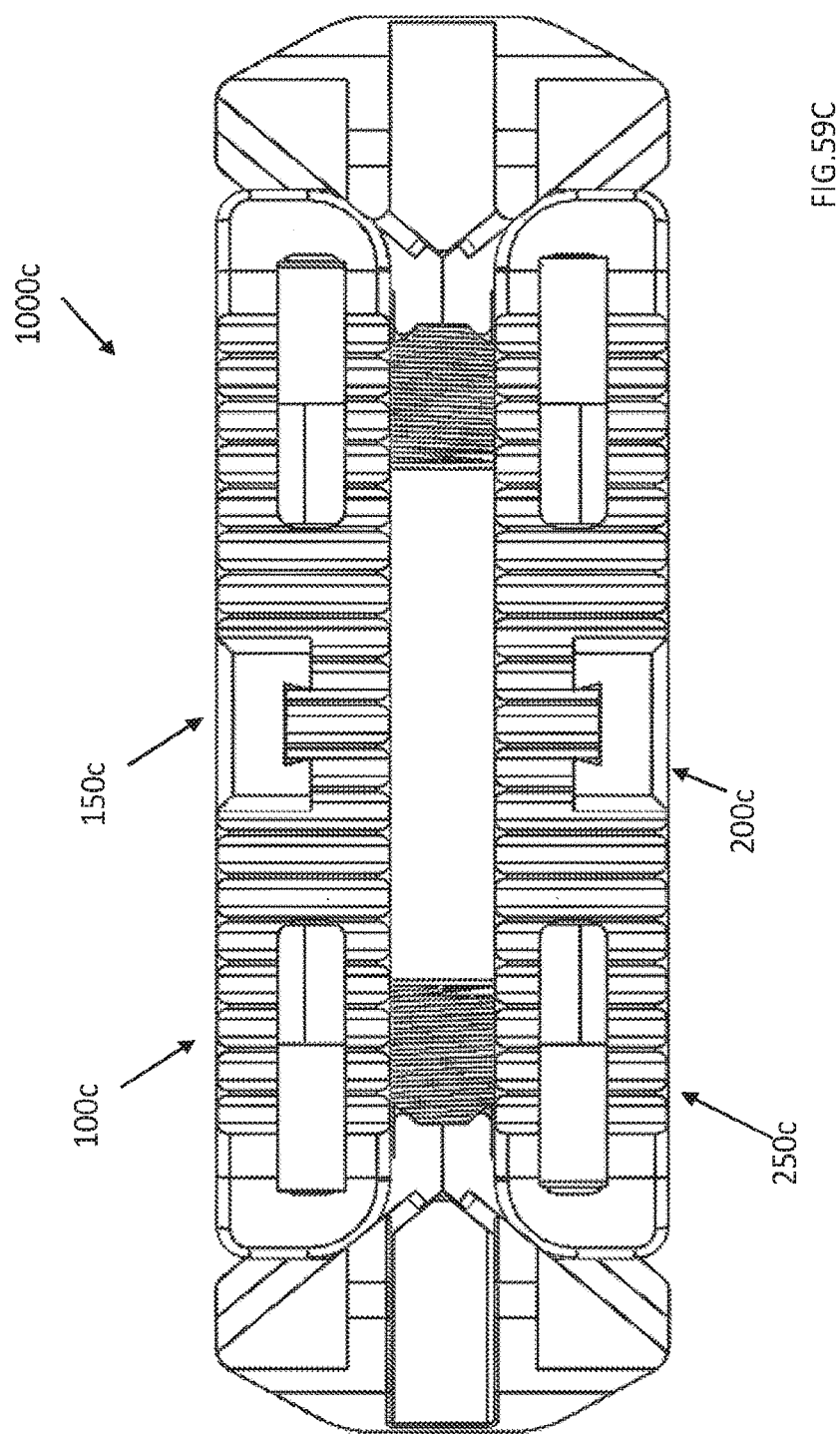

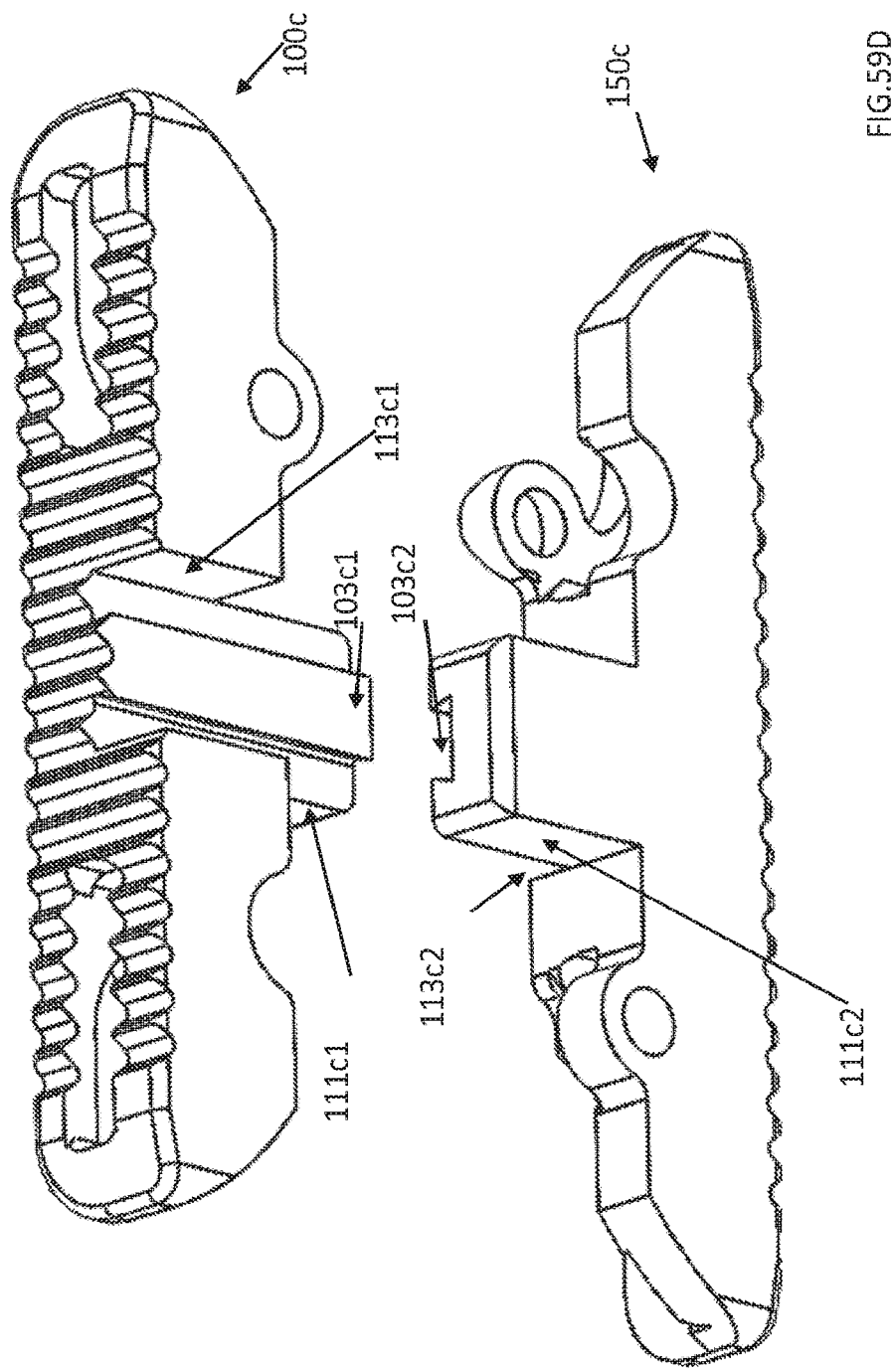

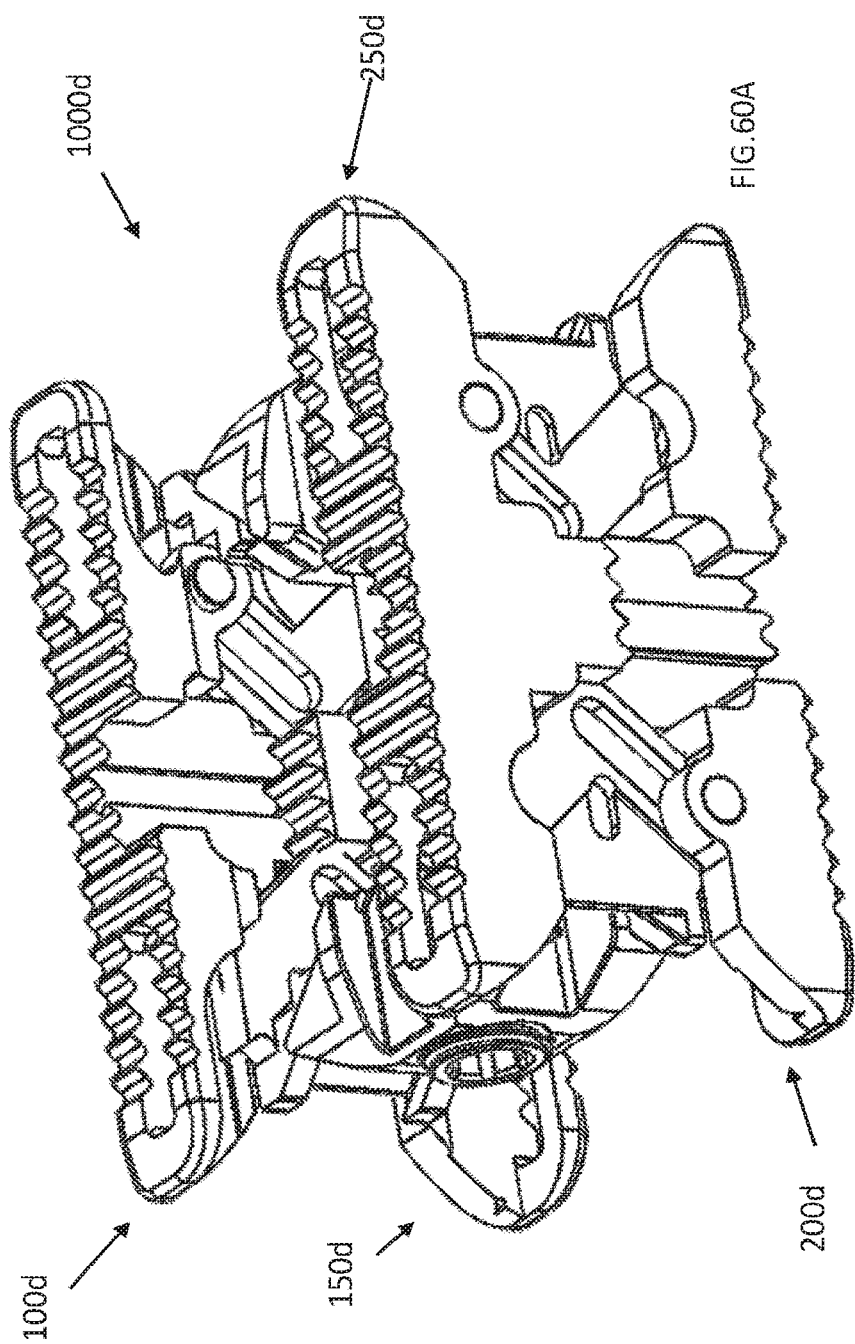

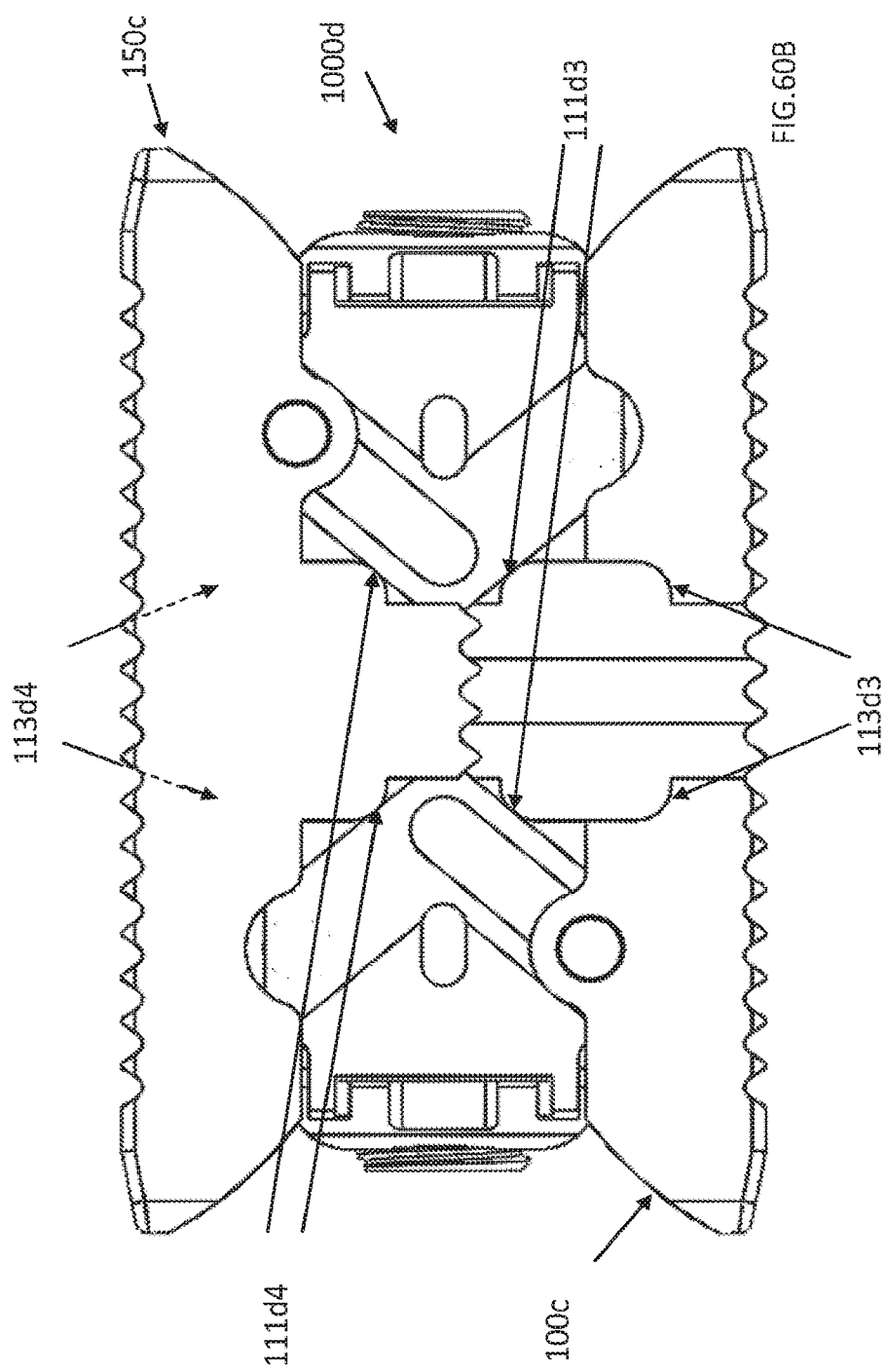

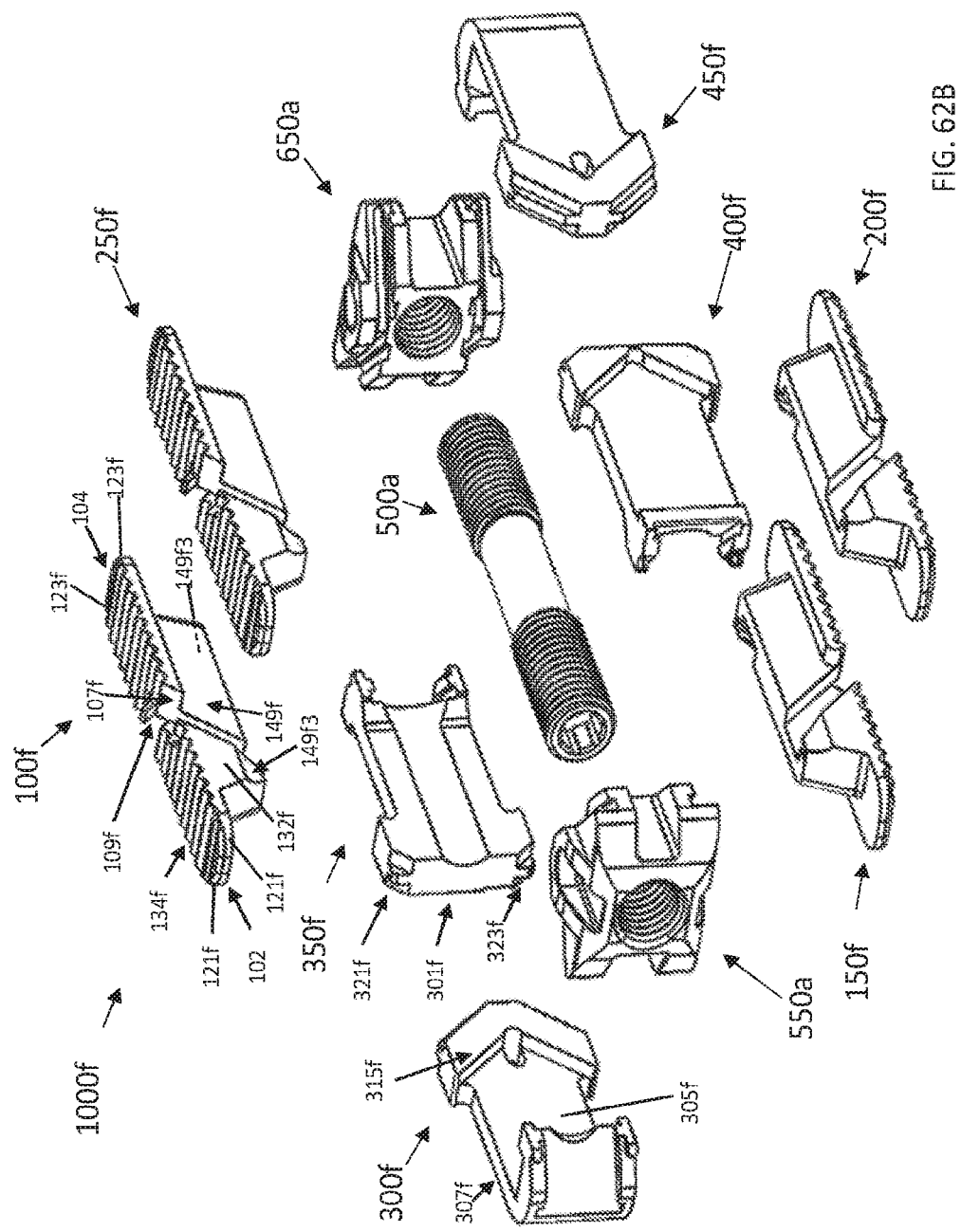

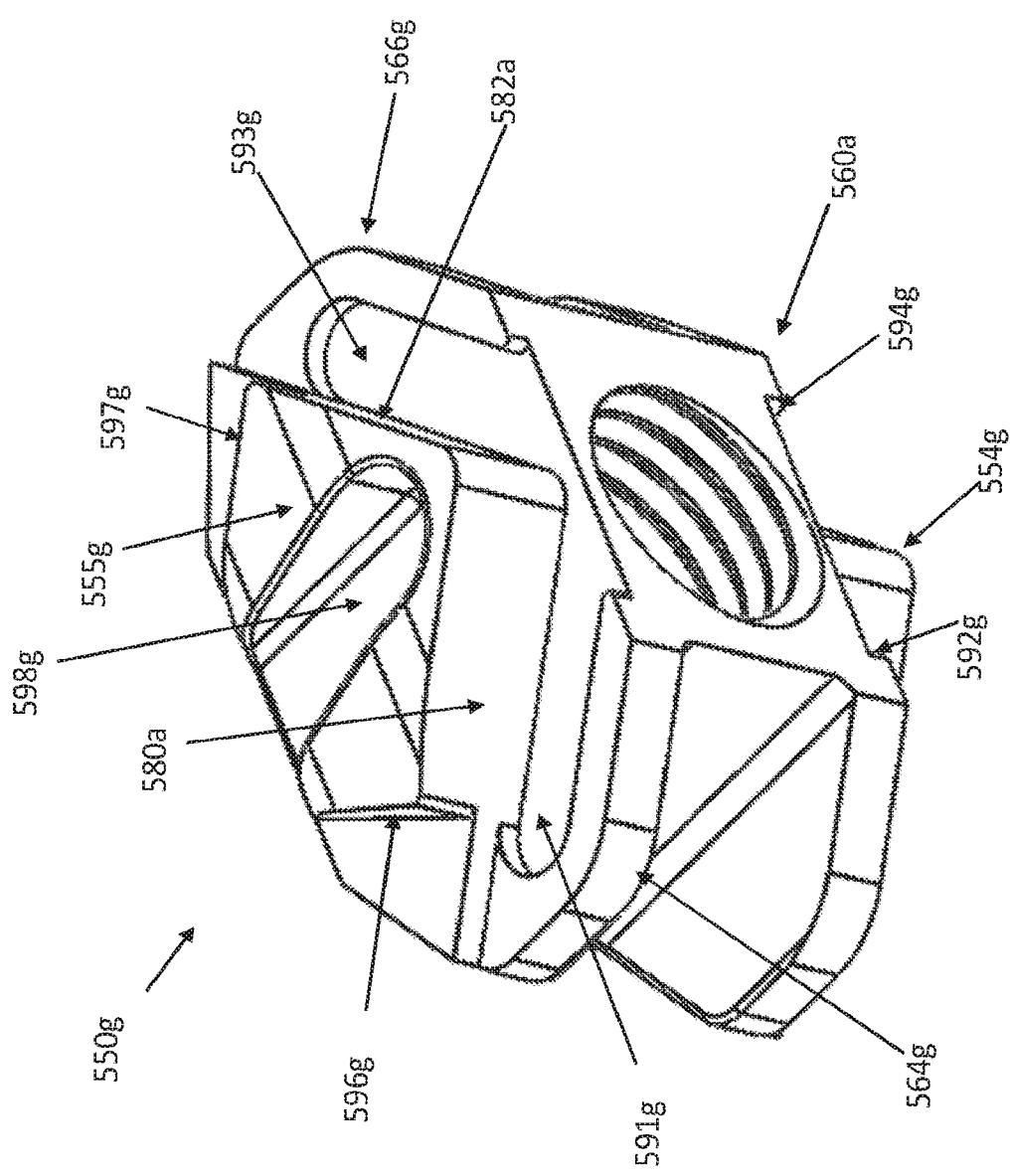

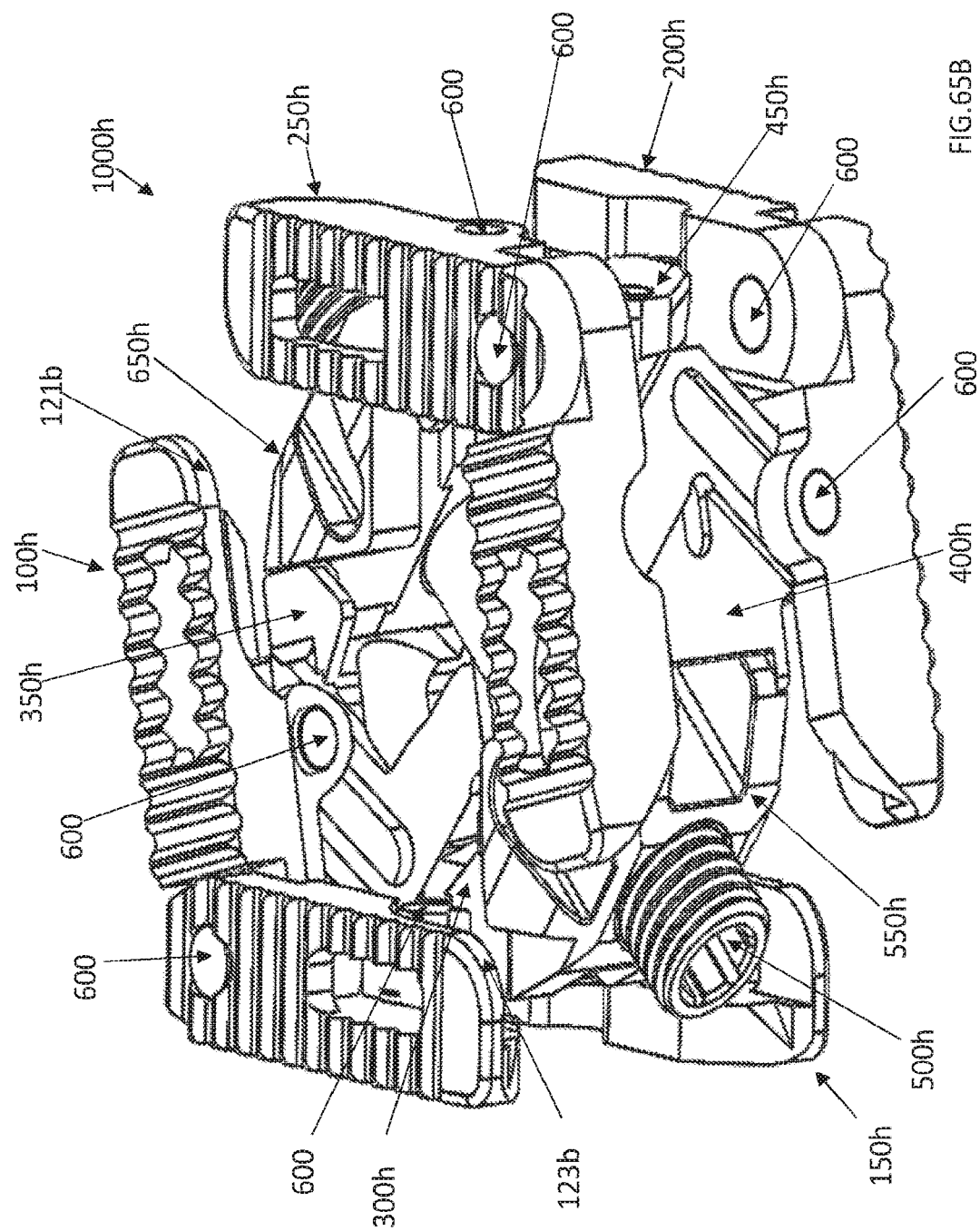

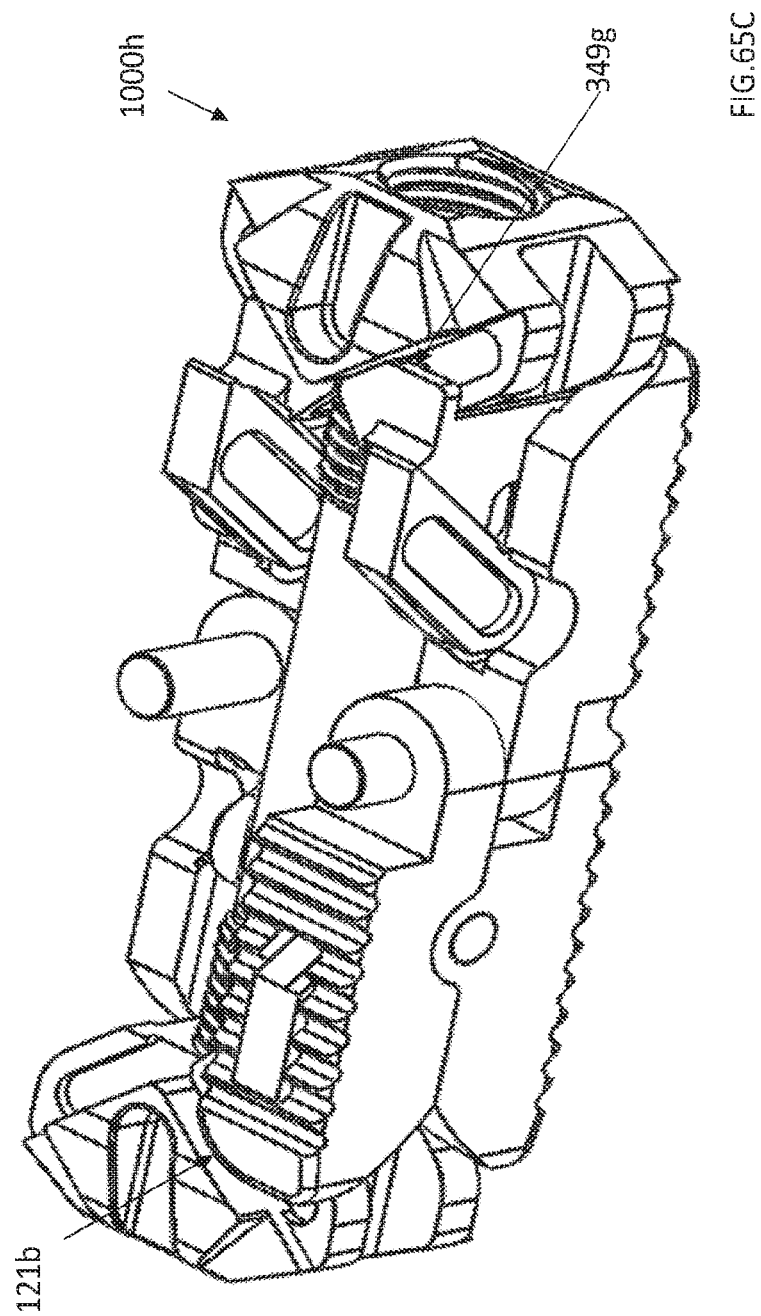

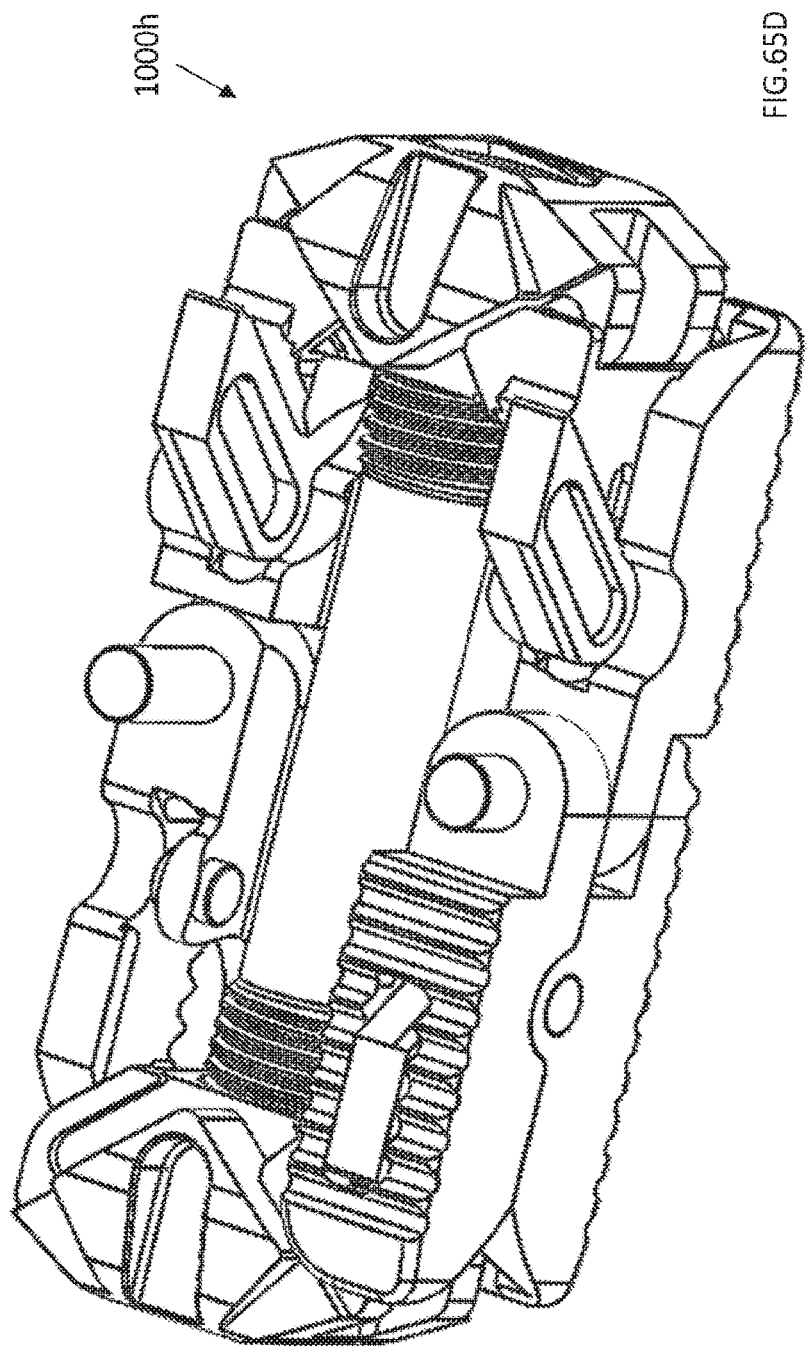

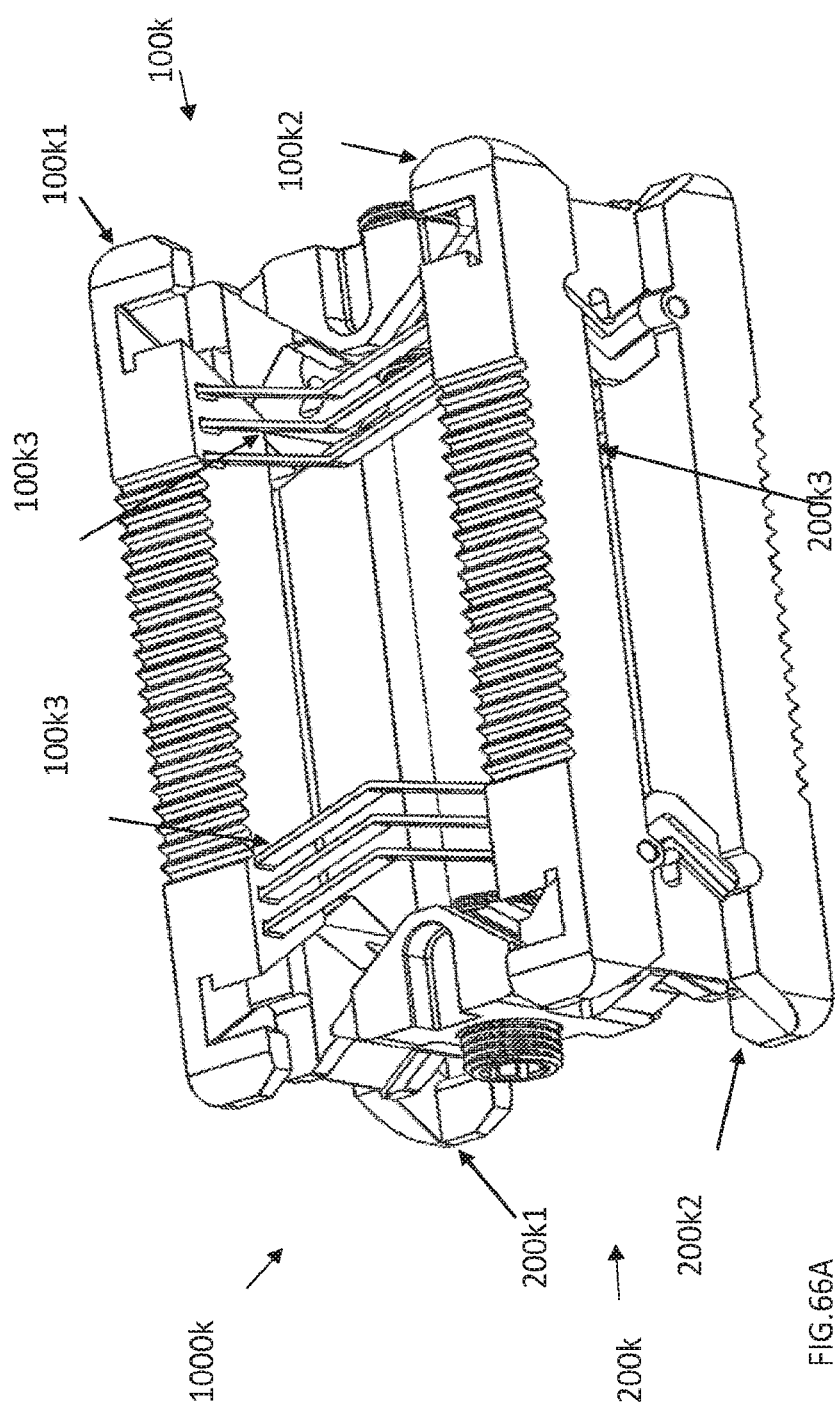

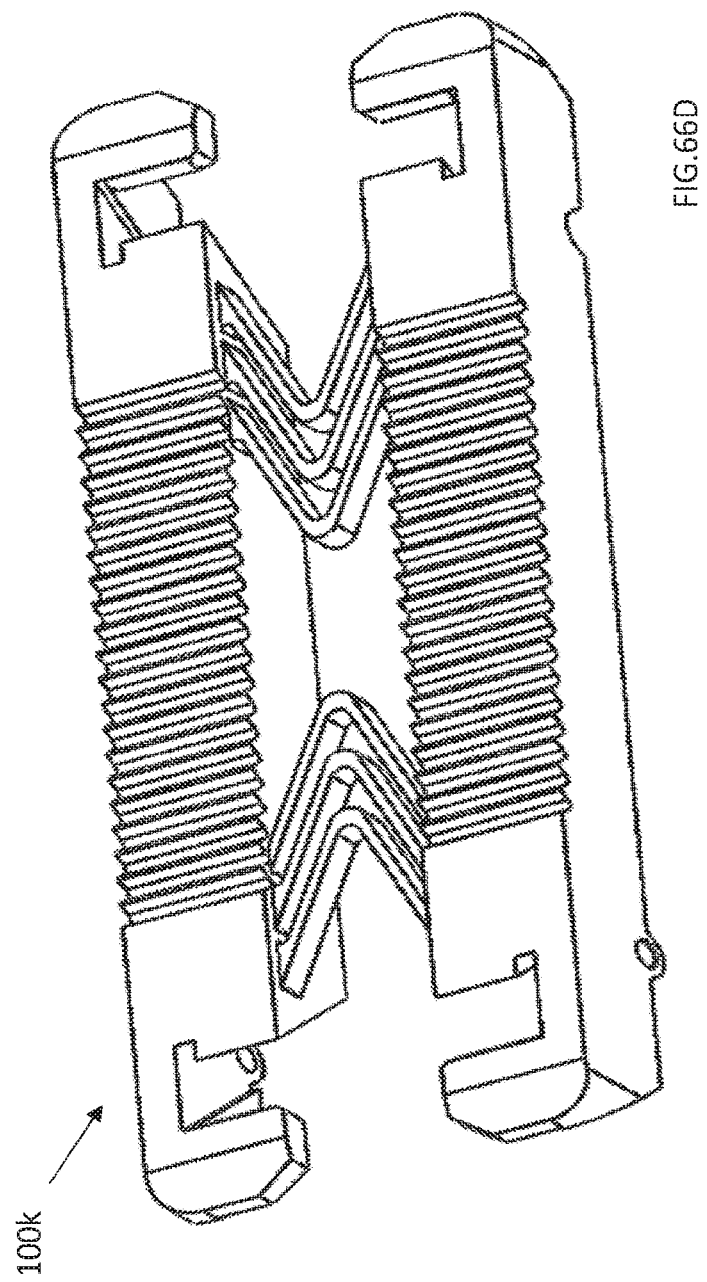

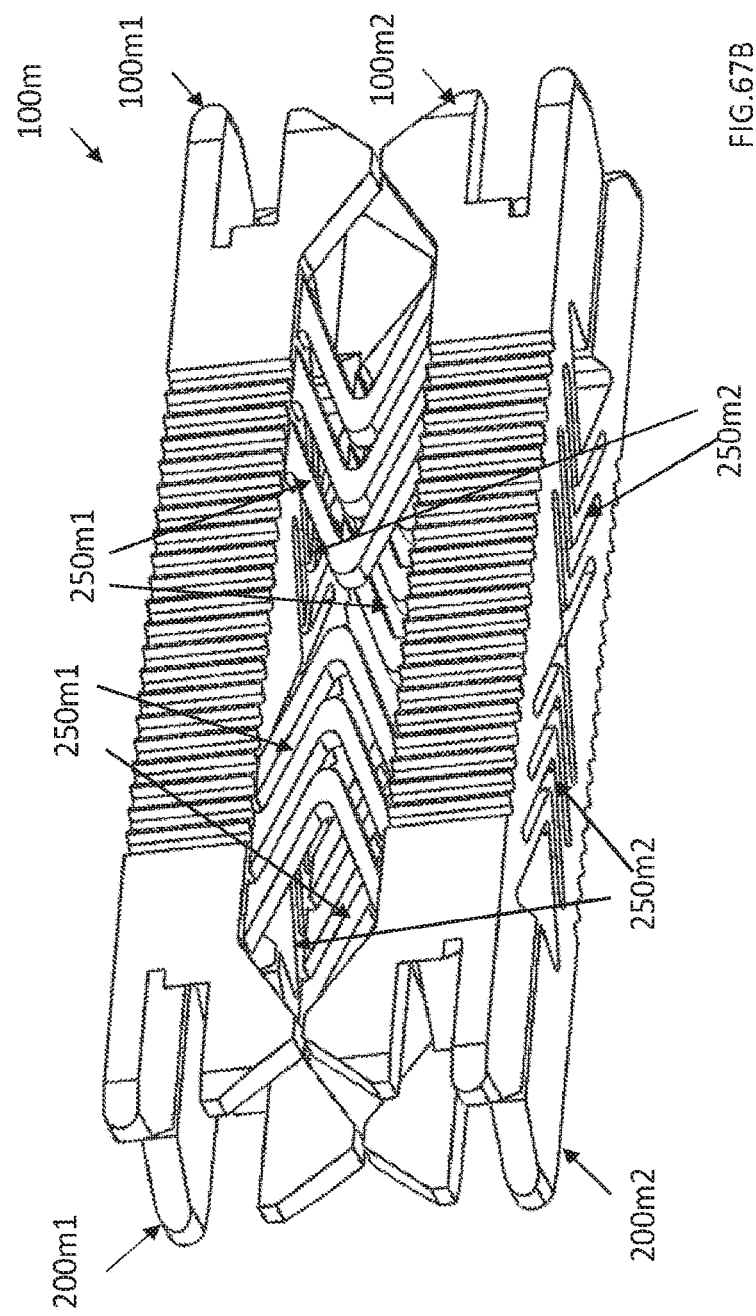

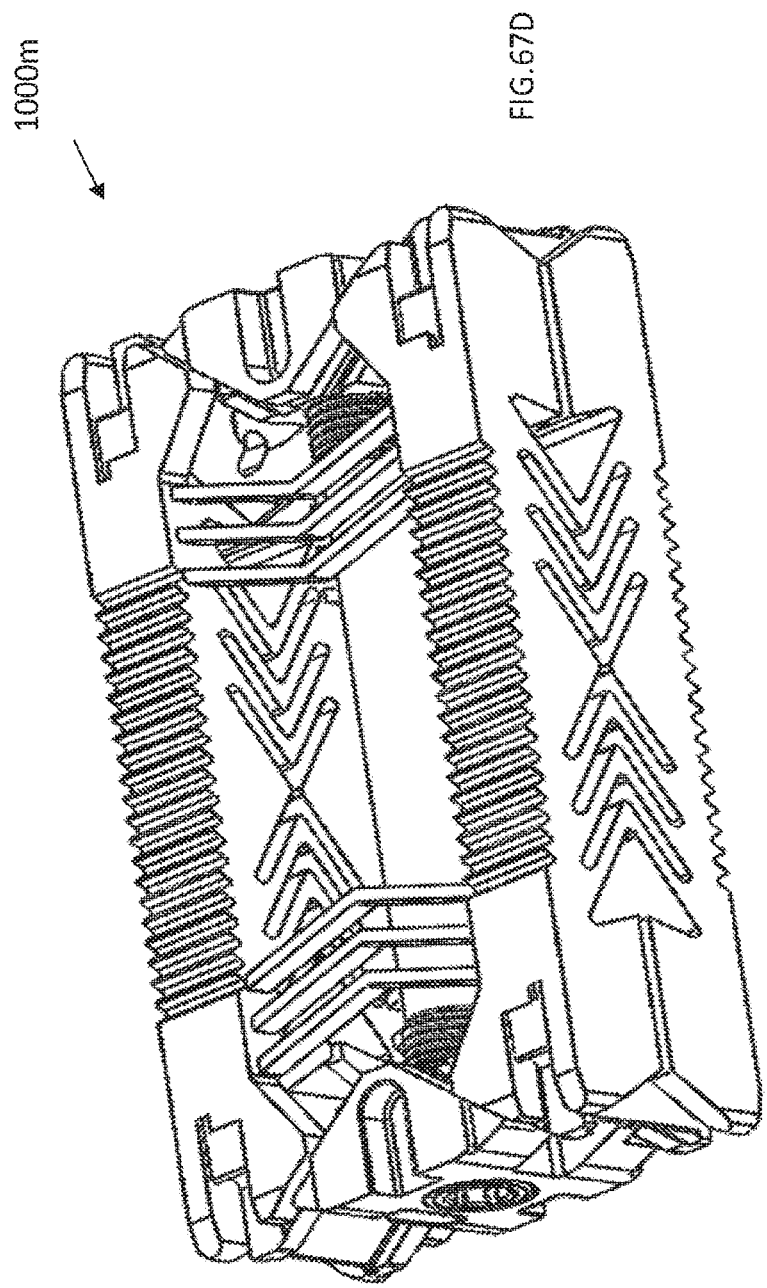

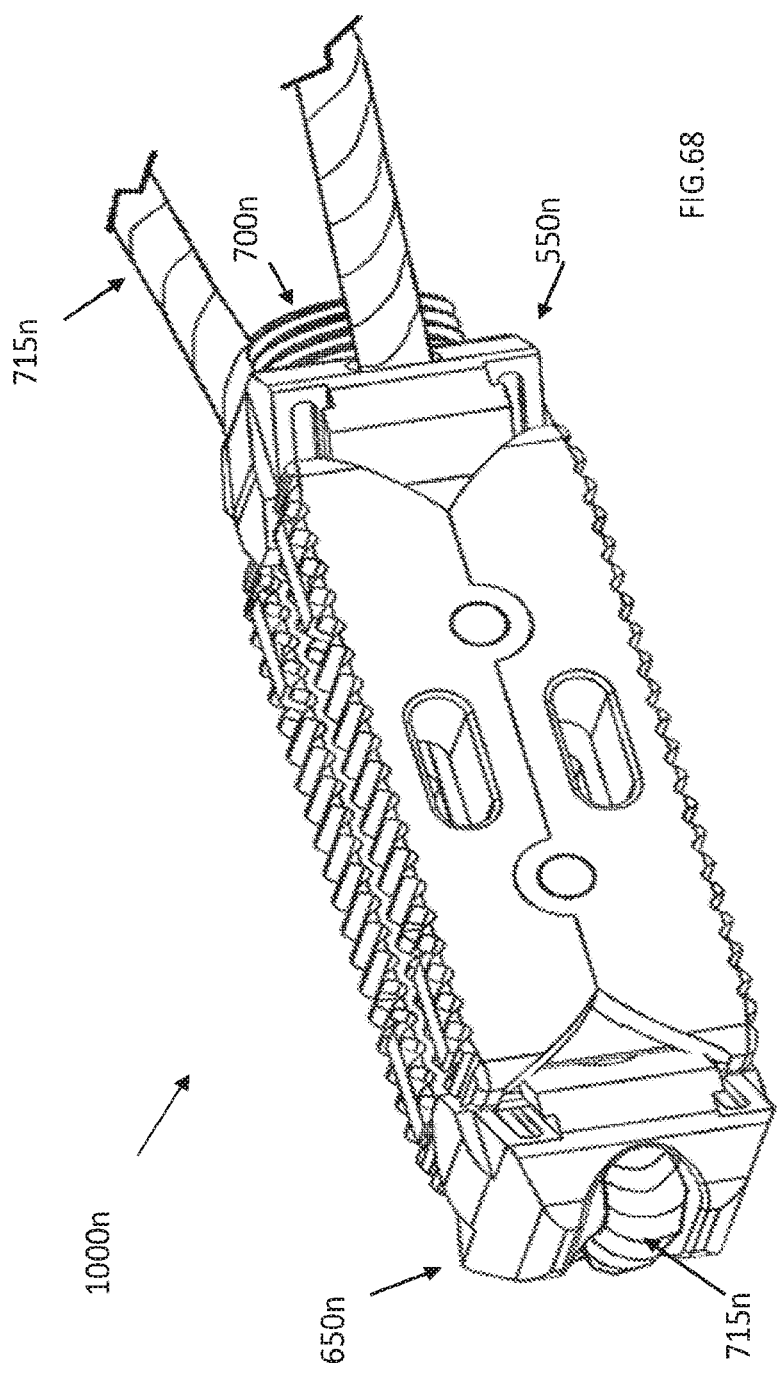

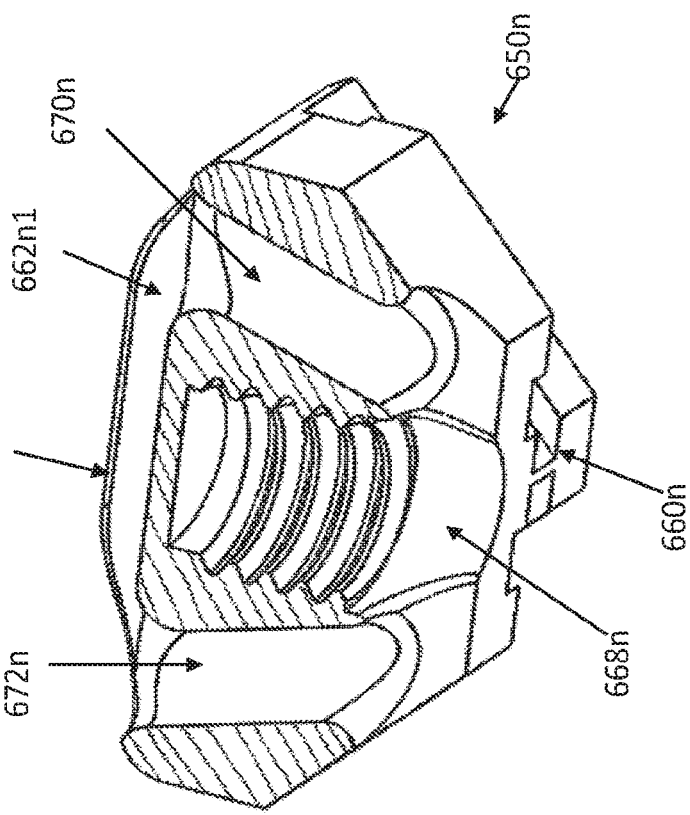
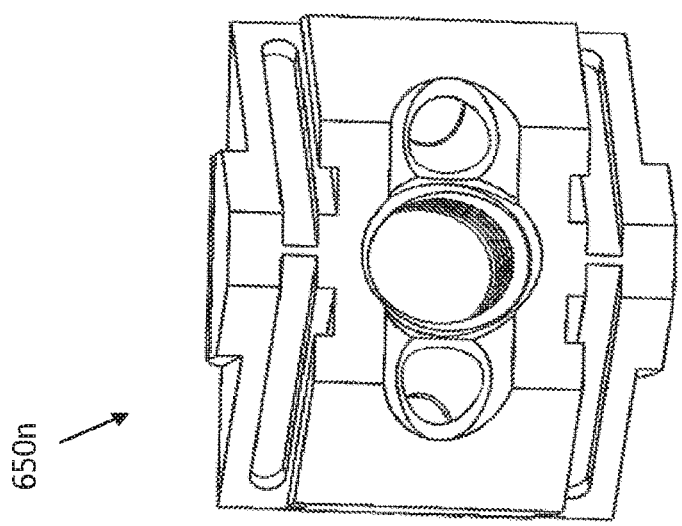

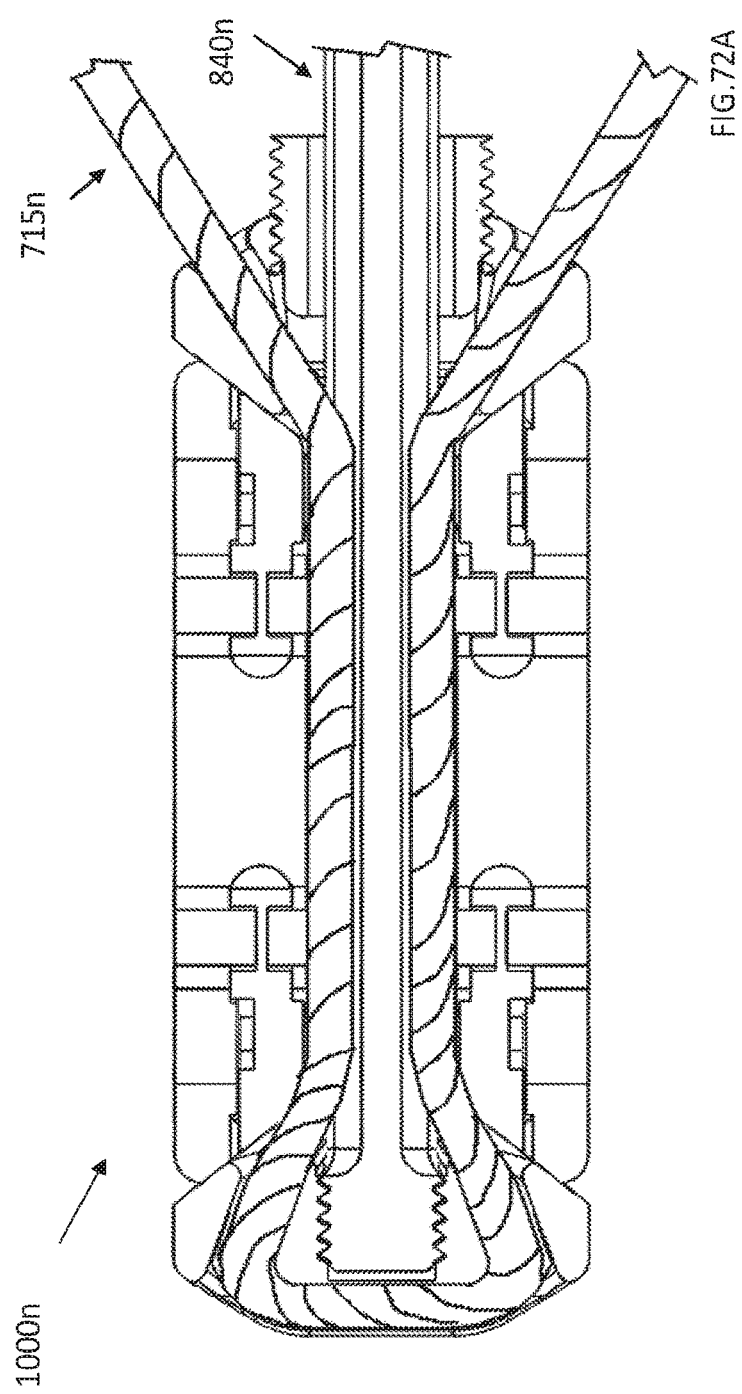

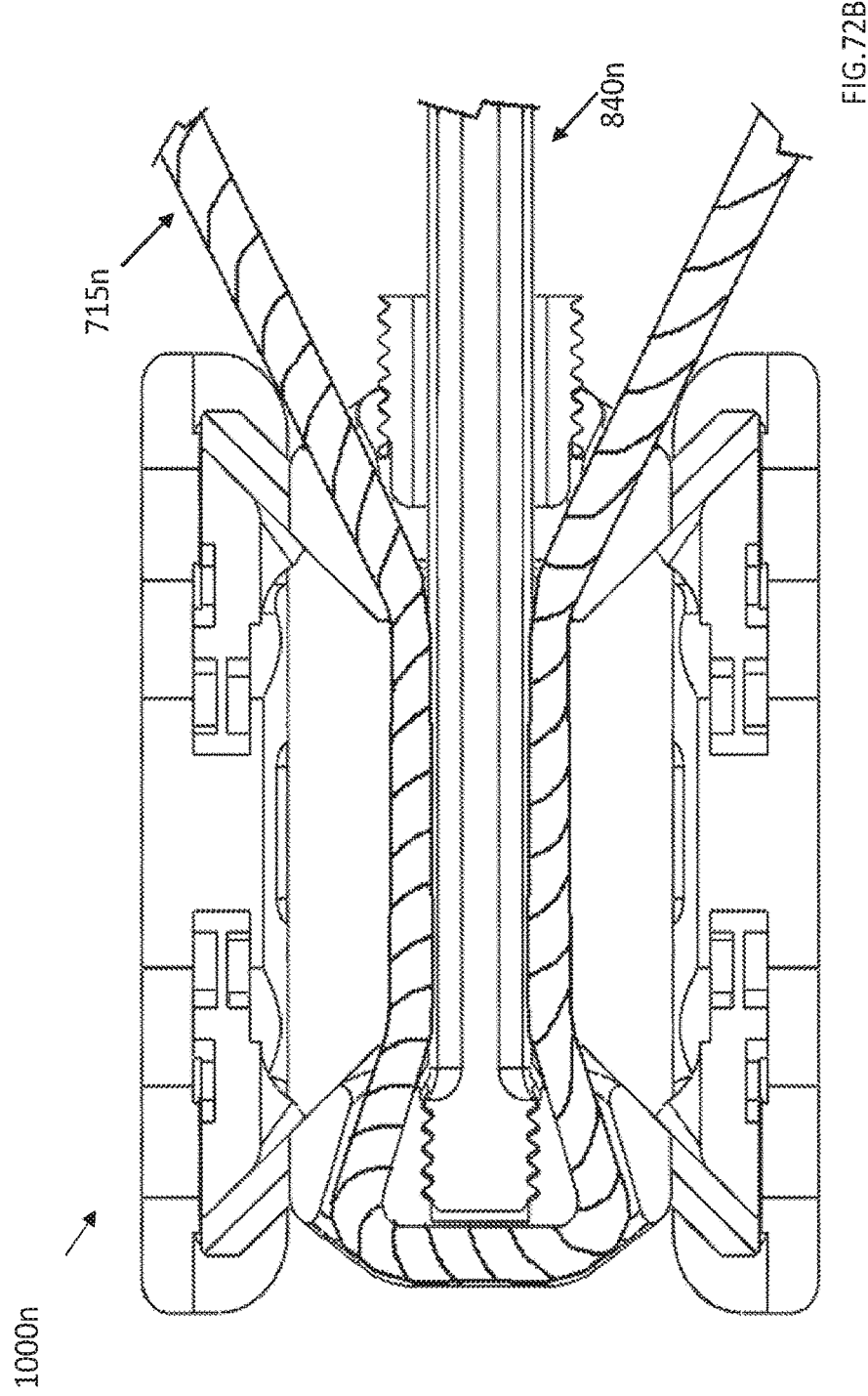

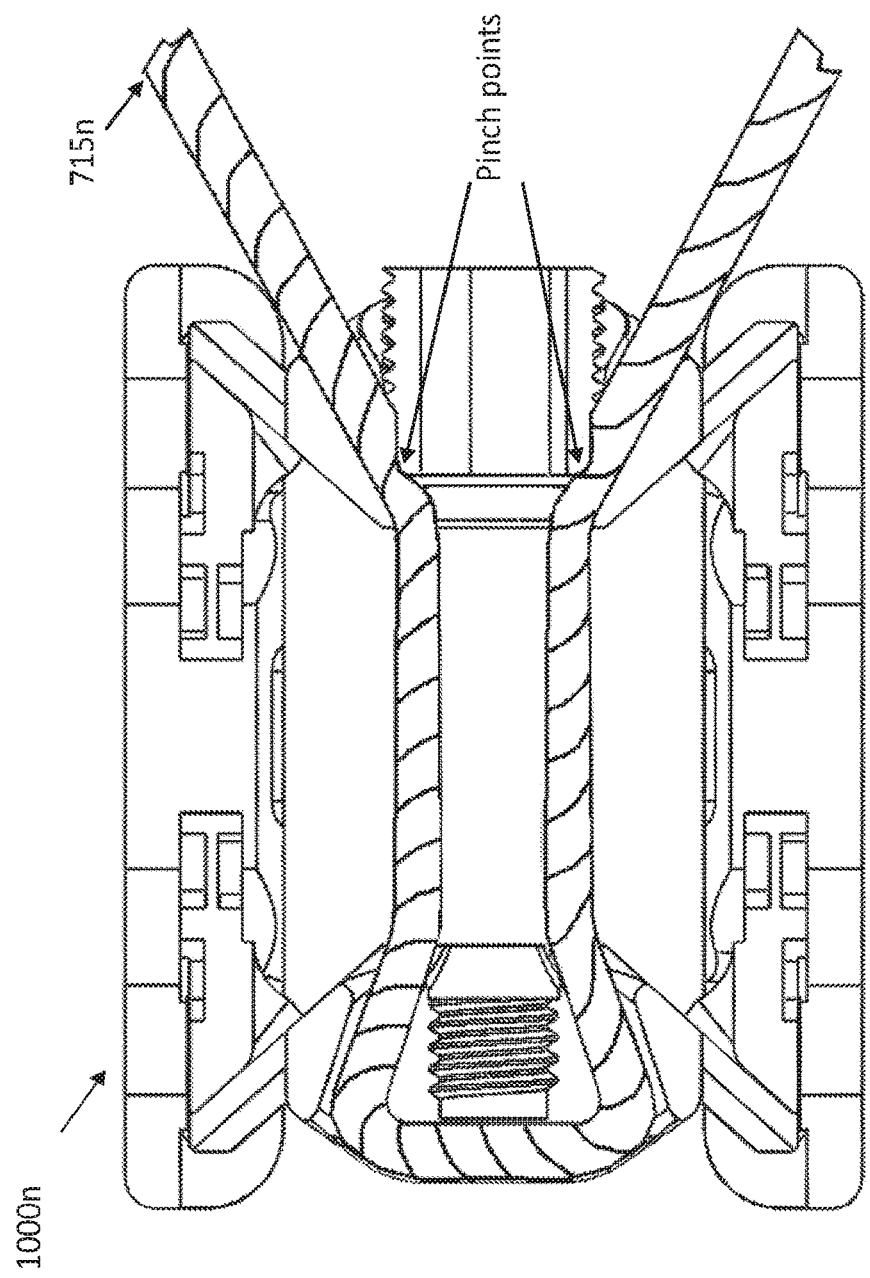

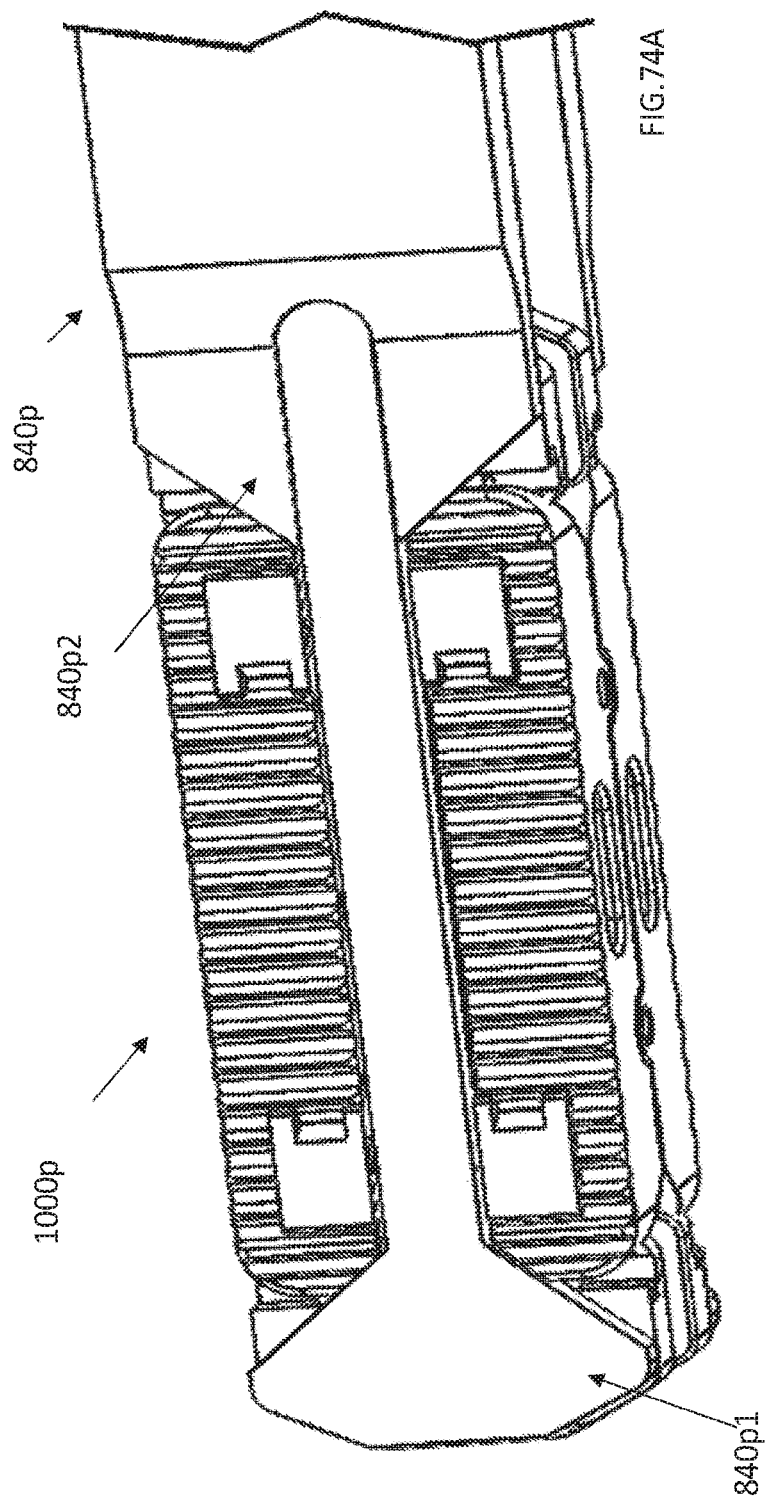

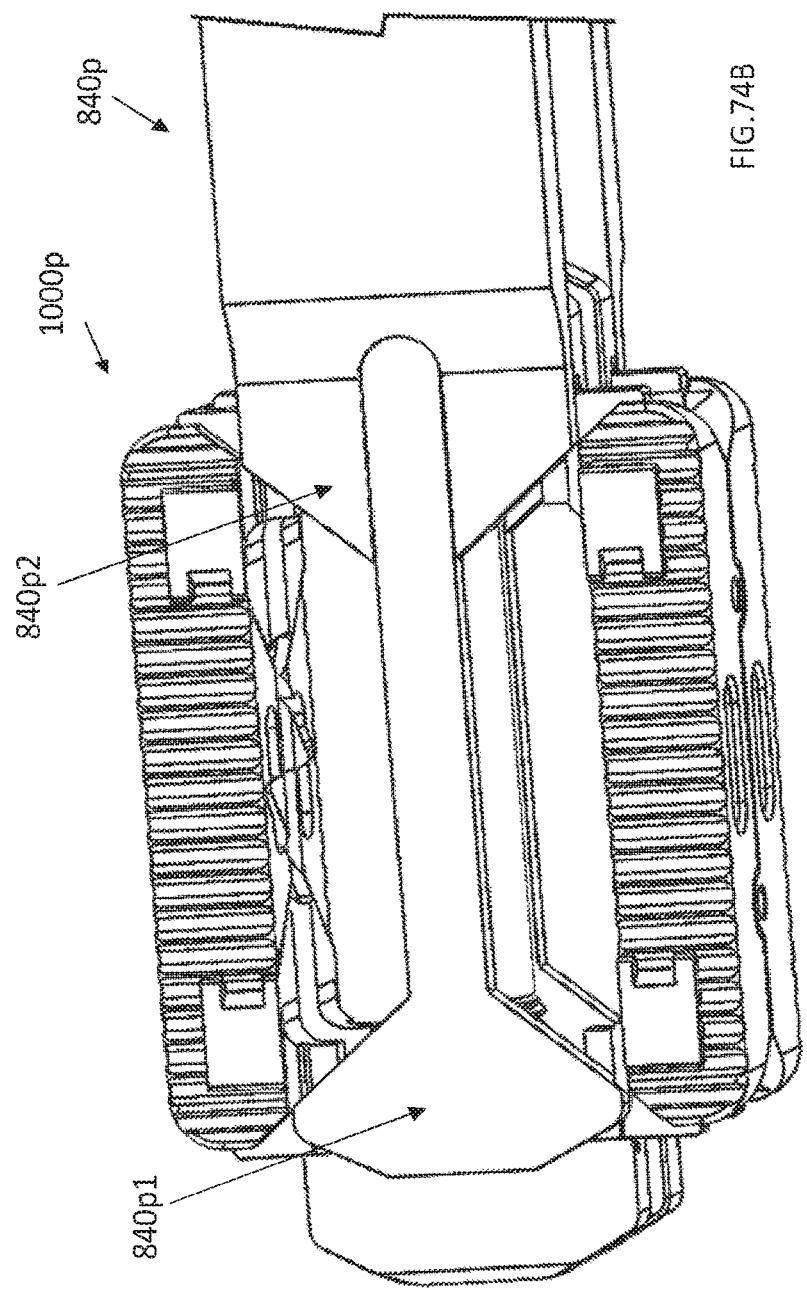

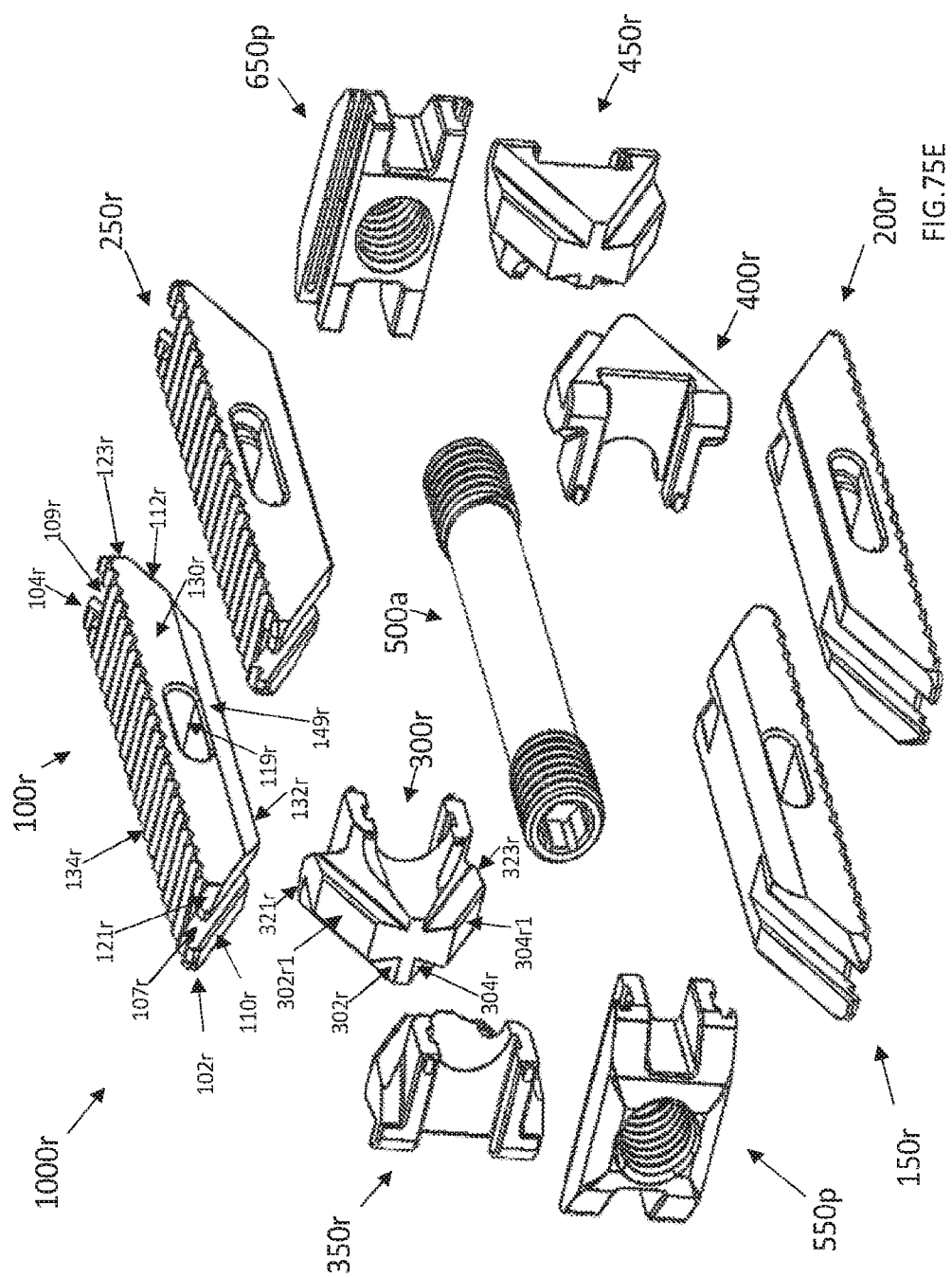

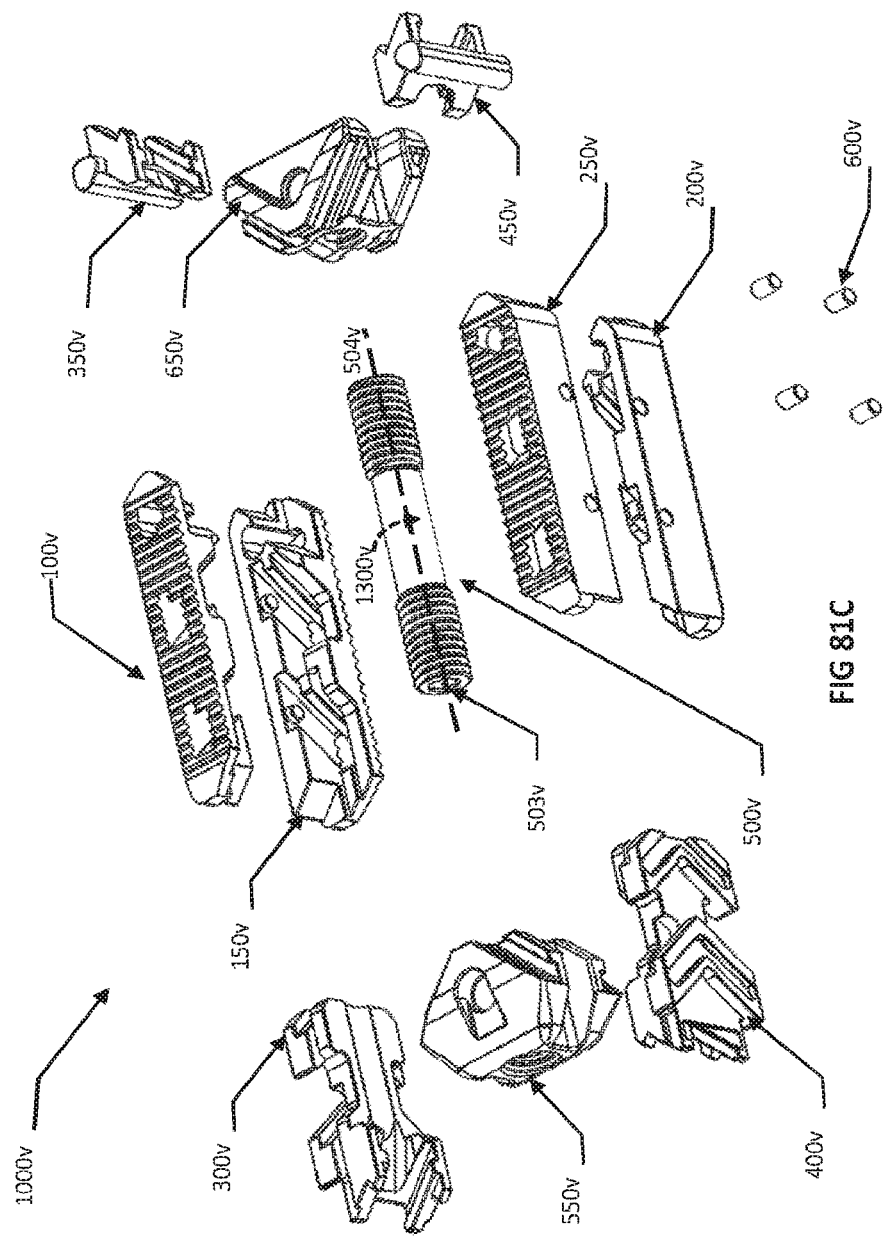

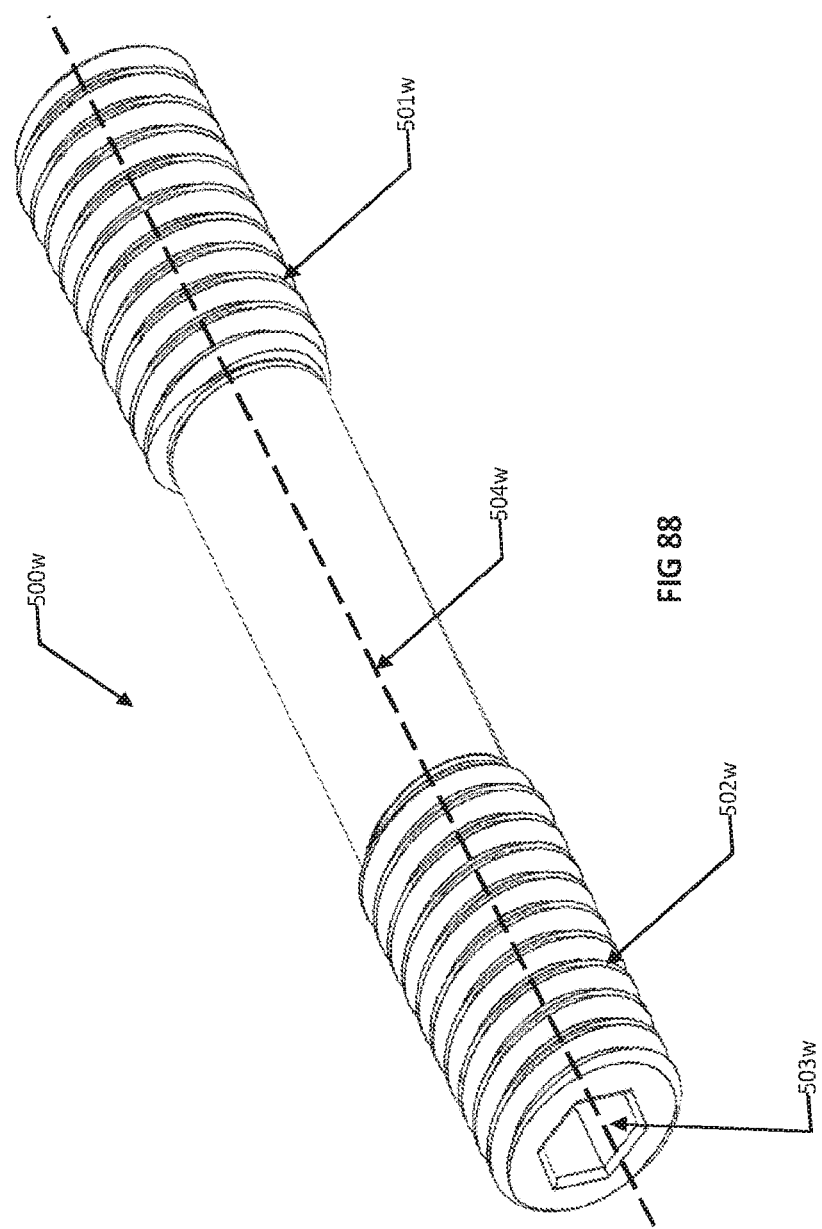

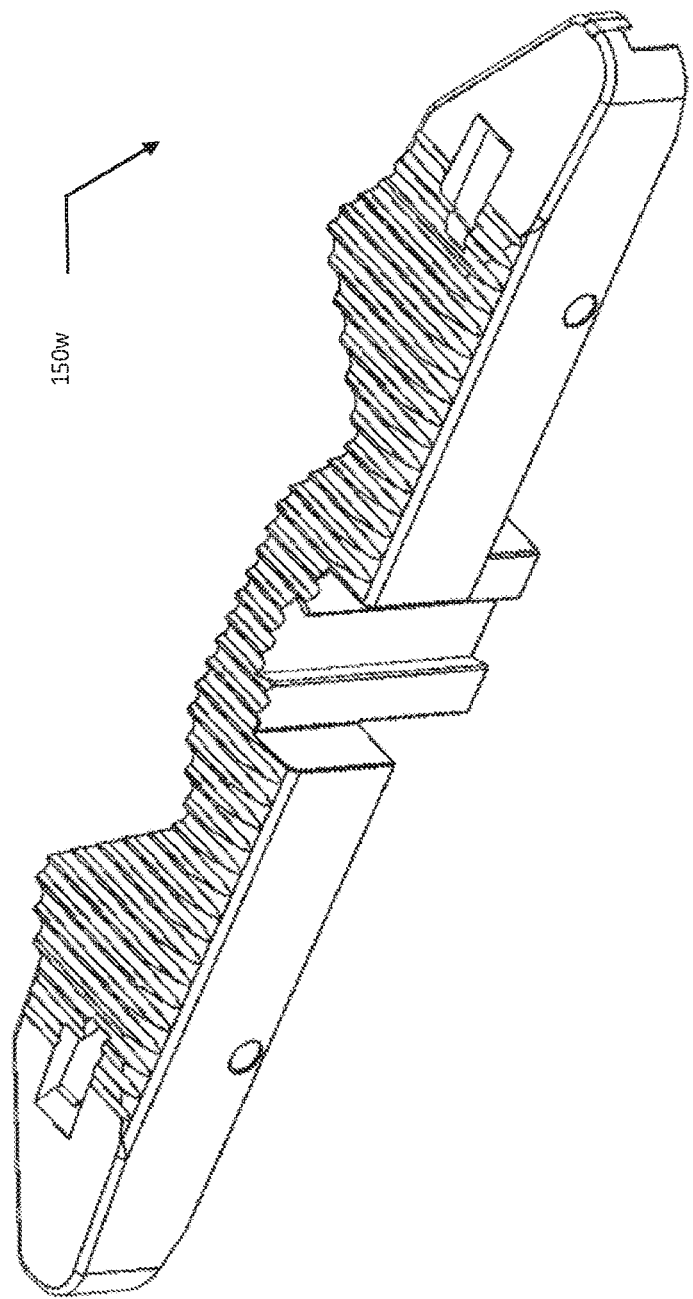

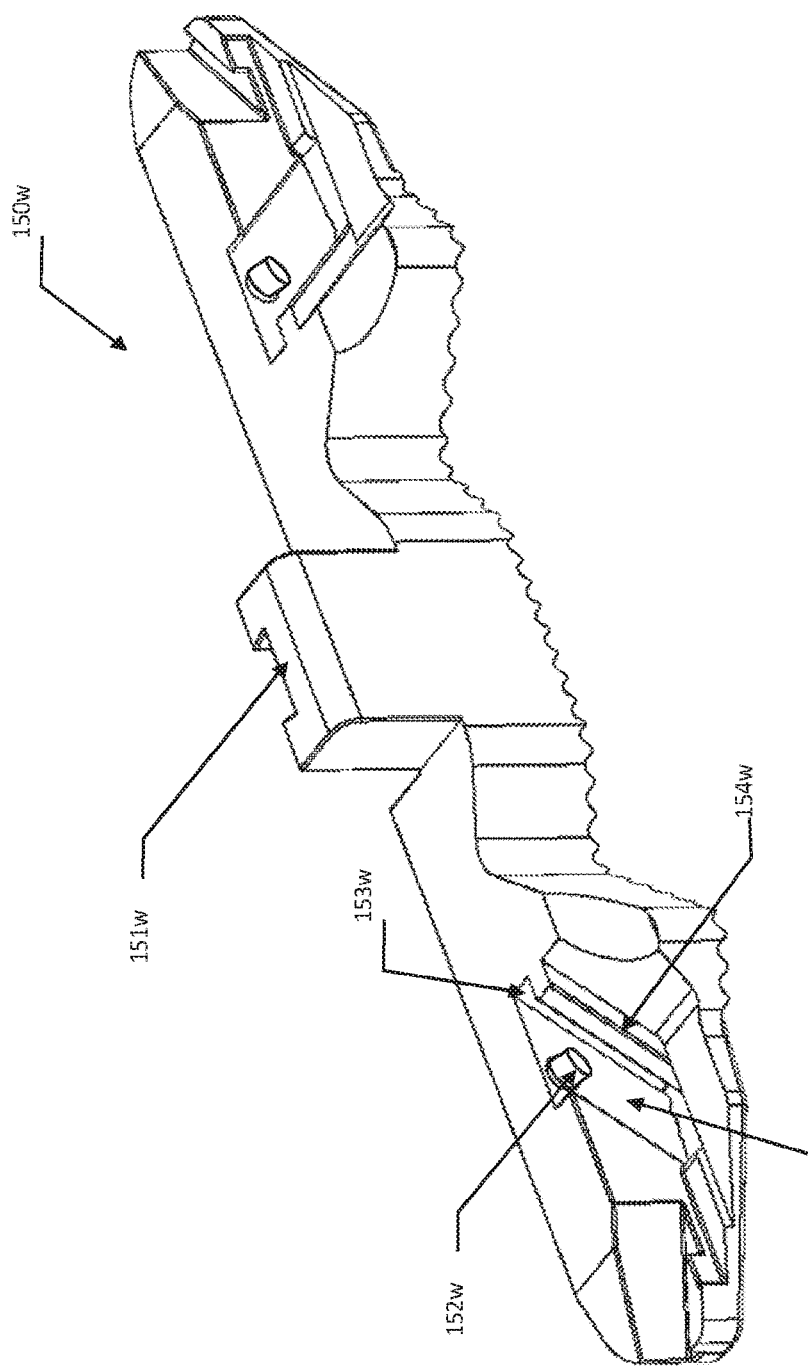

EXPANDABLE INTERVERTEBRAL FUSION DEVICE

CROSS-REFERENCE

This is a bypass application which is a continuation of PCT/US18/13207, filed Jan. 10, 2018, which claims the benefit of U.S. Provisional Application Nos. 62/444,663, filed Jan. 10, 2017, 62/471,206, filed Mar. 14, 2017, 62/481,565, filed Apr. 4, 2017; each application of which is hereby incorporated herein by reference in its entirety.

BACKGROUND

The present disclosure relates to medical devices and methods, and more preferably relates to the apparatus and method for promoting an intervertebral fusion, and more particularly relates to an expandable fusion device capable of being inserted between adjacent vertebrae to facilitate the fusion process.

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are challenges associated with the known conventional fusion devices and methodologies. For example, present methods for installing a conventional fusion device may require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height may make it difficult for a surgeon to install the fusion device in the distracted intervertebral space.

As such, there exists a need for a fusion device capable of being installed inside an intervertebral disc space at a minimum to no distraction height and for a fusion device capable of maintaining a normal distance between adjacent vertebral bodies when implanted.

One of the most common post-operative complications of intervertebral fusion surgery is intervertebral graft or cage subsidence which are minimized or mitigated by using an intervertebral cage or graft of a larger footprint. This is often difficult because to minimize the trauma and morbidity associated with spine surgery, it is often advantageous to utilize the smallest surgical access corridor possible to achieve the goals of surgery. As such there exists a need for a fusion device capable of being inserted through a relatively small surgical corridor and capable to then be expanded to a larger footprint suitable to resist subsidence.

The present device preferably is capable of meeting both of these criteria—being able to be inserted at a minimum to minimal or no intervertebral distraction and at a minimum width through a relatively small surgical corridor to then be expanded and maintained at a larger footprint suitable for resisting subsidence and at a greater height suitable for the goal of decompressing the neural elements and maintaining the intervertebral height as well as desirable alignment of the adjacent vertebral bodies. At least some of these objectives will be met by the exemplary embodiments disclosed herein.

DESCRIPTION OF THE BACKGROUND ART

U.S. Pat. Nos. 8,568,481; 8,926,704; 9,474,625; 9,138,328; 9,445,918; 2016/0317315; 2016/0324654; US20170056200A1; U.S. Pat. Nos. 9,801,734; 9,795,493; 9,717,601; 6,821,298; US20110035011A1; U.S. Pat. Nos. 9,445,918; 9,480,574; 6,176,882; 8,105,382; 8,568,481; US20160302940; U.S. Pat. Nos. 9,561,116; 9,278,008.

SUMMARY

Optionally, in any embodiment, the present disclosure provides an expandable fusion device capable of being inserted at a minimum to no intervertebral distraction and at a minimum width through a relatively small surgical corridor to then be expanded and maintained at a larger footprint suitable for resisting subsidence and at a greater height suitable for the goal of decompressing the neural elements and maintaining the intervertebral height as well as desirable alignment of the adjacent vertebral bodies.

In one embodiment, the fusion device includes a proximal wedge, a distal wedge, a first ramp, a second ramp, a third ramp, a forth ramp, a first endplate, a second endplate, a third endplate, a fourth endplate, an actuator and a retention member designed to constrain the linear motion of the actuator relative to the proximal wedge. The actuator capable of drawing the proximal wedge and the distal wedge together or apart from each other, forcing the first ramp away from the fourth ramp and forcing the second ramp away from the third ramp and also forcing the first ramp away from or toward the second ramp and forcing the third ramp away from or toward the fourth ramp, to result in moving the first endplate, the second endplate, the third endplate and the fourth endplate outwardly from each other and into an expanded configuration.

A first aspect provided herein is an expandable fusion device for implantation between two adjacent vertebrae, the device comprising: an actuator comprising a drive feature and an longitudinal axis; a wedge assembly coupled to the actuator; a ramp assembly slidably coupled with the wedge assembly, an upper endplate assembly slidably coupled with the ramp assembly; and a lower endplate assembly slidably coupled with the ramp assembly.

Optionally, in any embodiment, the device has a width comprising an external width of at least one of the upper endplate assembly and the lower endplate assembly. Optionally, in any embodiment, the device has a height comprising an external distance between the upper endplate assembly and the lower endplate assembly. Optionally, in any embodiment, actuation of the drive feature by a first number of actuations in a first actuation direction increases the width without increasing the height. Optionally, in any embodiment, actuation of the drive feature by a second number of actuations beyond the first number of actuations in the first actuation direction increases at least one of the height and the width.

Optionally, in any embodiment, the first number of actuations is about 0.5 actuations to about 10 actuations. Optionally, in any embodiment, the first number of actuations is at least about 0.5 actuations. Optionally, in any embodiment, the first number of actuations is at most about 10 actuations. Optionally, in any embodiment, the first number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the first number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, the second number of actuations is about 0.5 actuations to about 10 actuations. Optionally, in any embodiment, the second number of actuations is at least about 0.5 actuations. Optionally, in any embodiment, the second number of actuations is at most about 10 actuations. Optionally, in any embodiment, the second number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the second number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, actuation of the drive feature by a second number of actuations beyond the first number of actuations in the first actuation direction increases both the height and the width. Optionally, in any embodiment, actuation of the drive feature by a second number of actuations beyond the first number of actuations in the first actuation direction increases the height without increasing the width.

Optionally, in any embodiment, the width of the device reaches an apex once the drive feature is actuated by at least the first number of actuations. Optionally, in any embodiment, the height of the device reaches an apex once the drive feature is actuated by at least the first and second number of actuations.

Optionally, in any embodiment, actuation of the drive feature in the first actuation direction by at least the first number of actuations increases the height of the device by about 30% to about 400%. Optionally, in any embodiment, actuation of the drive feature in the first actuation direction by at least the first number of actuations increases the height of the device by at least about 30%. Optionally, in any embodiment, actuation of the drive feature in the first actuation direction by at least the first number of actuations increases the height of the device by at most about 400%. Optionally, in any embodiment, actuation of the drive feature in the first actuation direction by at least the first number of actuations increases the height of the device by about 30% to about 50%, about 30% to about 75%, about 30% to about 100%, about 30% to about 125%, about 30% to about 150%, about 30% to about 175%, about 30% to about 200%, about 30% to about 250%, about 30% to about 300%, about 30% to about 350%, about 30% to about 400%, about 50% to about 75%, about 50% to about 100%, about 50% to about 125%, about 50% to about 150%, about 50% to about 175%, about 50% to about 200%, about 50% a to about 250%, about 50% to about 300%, about 50% to about 350%, about 50% to about 400%, about 75% to about 100%, about 75% to about 125%, about 75% to about 150%, about 75% to about 175%, about 75% to about 200%, about 75% to about 250%, about 75% to about 300%, about 75% to about 350%, about 75% to about 400%, about 100% to about 125%, about 100% to about 150%, about 100% to about 175%, about 100% to about 200%, about 100% to about 250%, about 100% to about 300%, about 100% to about 350%, about 100% to about 400%, about 125% to about 150%, about 125% to about 175%, about 125% to about 200%, about 125% to about 250%, about 125% to about 300%, about 125% to about 350%, about 125% to about 400%, about 150% to about 175%, about 150% to about 200%, about 150% to about 250%, about 150% to about 300%, about 150% to about 350%, about 150% to about 400%, about 175% to about 200%, about 175% to about 250%, about 175% to about 300%, about 175% to about 350%, about 175% to about 400%, about 200% to about 250%, about 200% to about 300%, about 200% to about 350%, about 200% to about 400%, about 250% to about 300%, about 250% to about 350%, about 250% to about 400%, about 300% to about 350%, about 300% to about 400%, or about 350% to about 400%. Optionally, in any embodiment, actuation of the drive feature in the first actuation direction by at least the first number of actuations increases the height of the device by about 30%, about 50%, about 75%, about 100%, about 125%, about 150%, about 175%, about 200%, about 250%, about 300%, about 350%, or about 400%.

Optionally, in any embodiment, actuation of the drive feature in the first actuation direction by at least the first and the second number of actuations increases the width of the device by about 14% to about 150%. Optionally, in any embodiment, actuation of the drive feature in the first actuation direction by at least the first and the second number of actuations increases the width of the device by at least about 14%. Optionally, in any embodiment, actuation of the drive feature in the first actuation direction by at least the first and the second number of actuations increases the width of the device by at most about 150%. Optionally, in any embodiment, actuation of the drive feature in the first actuation direction by at least the first and the second number of actuations increases the width of the device by about 14% to about 20%, about 14% to about 30%, about 14% to about 40%, about 14% to about 50%, about 14% to about 60%, about 14% to about 70%, about 14% to about 80%, about 14% to about 100%, about 14% to about 120%, about 14% to about 140%, about 14% to about 150%, about 20% to about 30%, about 20% to about 40%, about 20% to about 50%, about 20% to about 60%, about 20% to about 70%, about 20% to about 80%, about 20% to about 100%, about 20% to about 120%, about 20% to about 140%, about 20% to about 150%, about 30% to about 40%, about 30% to about 50%, about 30% to about 60%, about 30% to about 70%, about 30% to about 80%, about 30% to about 100%, about 30% to about 120%, about 30% to about 140%, about 30% to about 150%, about 40% to about 50%, about 40% to about 60%, about 40% to about 70%, about 40% to about 80%, about 40% to about 100%, about 40% to about 120%, about 40% to about 140%, about 40% to about 150%, about 50% to about 60%, about 50% to about 70%, about 50% to about 80%, about 50% to about 100%, about 50% to about 120%, about 50% to about 140%, about 50% to about 150%, about 60% to about 70%, about 60% to about 80%, about 60% to about 100%, about 60% to about 120%, about 60% to about 140%, about 60% to about 150%, about 70% to about 80%, about 70% to about 100%, about 70% to about 120%, about 70% to about 140%, about 70% to about 150%, about 80% to about 100%, about 80% to about 120%, about 80% to about 140%, about 80% to about 150%, about 100% to about 120%, about 100% to about 140%, about 100% to about 150%, about 120% to about 140%, about 120% to about 150%, or about 140% to about 150%. Optionally, in any embodiment, actuation of the drive feature in the first actuation direction by at least the first and the second number of actuations increases the width of the device by about 14%, about 20%, about 30%, about 40%, about 50%, about 60%, about 70%, about 80%, about 100%, about 120%, about 140%, or about 150%.

Optionally, in any embodiment, the actuator has a distal end and a proximal end. Optionally, in any embodiment, at least a portion of the distal end comprises a first thread feature. Optionally, in any embodiment, at least a portion of the proximal end comprises a second thread feature. Optionally, in any embodiment, the proximal end comprises the drive feature. Optionally, in any embodiment, at least one of the first thread feature and the second thread feature comprise a thread disposed externally around the actuator. Optionally, in any embodiment, at least one of the first thread feature and the second thread feature has an opposite threading direction.

Optionally, in any embodiment, the wedge assembly comprises a distal wedge and a proximal wedge. Optionally, in any embodiment, actuation of the drive feature in the first direction converges the distal wedge and the proximal wedge toward one another. Optionally, in any embodiment, the distal wedge comprises a third thread feature, and wherein the third thread feature is threadably coupled to the first thread feature. Optionally, in any embodiment, the proximal wedge comprises a fourth thread feature, and wherein the fourth thread feature is threadably coupled to the second thread feature. Optionally, in any embodiment, the third thread feature comprises a thread disposed internally within the distal wedge. Optionally, in any embodiment, the fourth thread feature comprises a thread disposed internally within the proximal wedge.

Optionally, in any embodiment, the ramp assembly comprises a first distal ramp, a second distal ramp, a first proximal ramp, and a second proximal ramp. Optionally, in any embodiment, the slideable coupling between at least one of the wedge assembly and the ramp assembly, the ramp assembly and the upper endplate, assembly, and the ramp assembly and the lower endplate assembly is at a transverse angle from the longitudinal axis.

Optionally, in any embodiment, the transverse angle is about 0 degrees to about 90 degrees. Optionally, in any embodiment, the transverse angle is at least about 0 degrees. Optionally, in any embodiment, the transverse angle is at most about 90 degrees. Optionally, in any embodiment, the transverse angle is about 0 degrees to about 1 degrees, about 0 degrees to about 5 degrees, about 0 degrees to about 10 degrees, about 0 degrees to about 20 degrees, about 0 degrees to about 30 degrees, about 0 degrees to about 40 degrees, about 0 degrees to about 50 degrees, about 0 degrees to about 60 degrees, about 0 degrees to about 70 degrees, about 0 degrees to about 80 degrees, about 0 degrees to about 90 degrees, about 1 degrees to about 5 degrees, about 1 degrees to about 10 degrees, about 1 degrees to about 20 degrees, about 1 degrees to about 30 degrees, about 1 degrees to about 40 degrees, about 1 degrees to about 50 degrees, about 1 degrees to about 60 degrees, about 1 degrees to about 70 degrees, about 1 degrees to about 80 degrees, about 1 degrees to about 90 degrees, about 5 degrees to about 10 degrees, about 5 degrees to about 20 degrees, about 5 degrees to about 30 degrees, about 5 degrees to about 40 degrees, about 5 degrees to about 50 degrees, about 5 degrees to about 60 degrees, about 5 degrees to about 70 degrees, about 5 degrees to about 80 degrees, about 5 degrees to about 90 degrees, about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 40 degrees to about 50 degrees, about 40 degrees to about 60 degrees, about 40 degrees to about 70 degrees, about 40 degrees to about 80 degrees, about 40 degrees to about 90 degrees, about 50 degrees to about 60 degrees, about 50 degrees to about 70 degrees, about 50 degrees to about 80 degrees, about 50 degrees to about 90 degrees, about 60 degrees to about 70 degrees, about 60 degrees to about 80 degrees, about 60 degrees to about 90 degrees, about 70 degrees to about 80 degrees, about 70 degrees to about 90 degrees, or about 80 degrees to about 90 degrees. Optionally, in any embodiment, the transverse angle is about 0 degrees, about 1 degrees, about 5 degrees, about 10 degrees, about 20 degrees, about 30 degrees, about 40 degrees, about 50 degrees, about 60 degrees, about 70 degrees, about 80 degrees, or about 90 degrees.

Optionally, in any embodiment, the slideable coupling between at least one of the wedge assembly and the ramp assembly, the ramp assembly and the upper endplate, assembly, and the ramp assembly and the lower endplate assembly comprises a protrusion and a slot. Optionally, in any embodiment, the protrusion extends from at least one of the wedge assembly, the ramp assembly, the upper endplate assembly, and the lower endplate assembly, and wherein the slot is disposed in at least one of the upper endplate assembly, and the lower endplate assembly. Optionally, in any embodiment, the protrusion comprises a pin, a ridge, a dimple, a bolt, a screw, a bearing, or any combination thereof. Optionally, in any embodiment, the slot comprises a through slot, a blind slot, a t-slot, a v-slot, a groove, or any combination thereof.

Optionally, in any embodiment, the drive feature comprises a recessed region configured to receive a driving instrument. Optionally, in any embodiment, the recessed region comprises a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, a thread, a friction fit, or a pentalobe recess. Optionally, in any embodiment, the driving feature comprises a protuberance extending therefrom and configured to be coupled to a driving instrument. Optionally, in any embodiment, the protuberance comprises a hex, a hexalobular, a threaded, or a square protuberance.

Optionally, in any embodiment, the upper endplate assembly comprises a first endplate and a second endplate, and wherein the lower endplate assembly comprises a third endplate and a fourth endplate. Optionally, in any embodiment, at least one of the first endplate and the second endplate, the third endplate and the fourth endplate, the first proximal ramp and the second proximal ramp, and the first distal ramp and the second distal ramp have mirrored equivalence. Optionally, in any embodiment, at least one of the second endplate and the fourth endplate is larger than at least one of the first endplate and the third endplate. Optionally, in any embodiment, at least one of the exterior faces of the first end plate, the second endplate, the third endplate, and the fourth endplate comprise a texture configured to grip the vertebrae. Optionally, in any embodiment, the texturing comprises a tooth, a ridge, a roughened area, a metallic coating, a ceramic coating, a keel, a spike, a projection, a groove, or any combination thereof.

Optionally, in any embodiment, at least one of the actuator, the wedge assembly, the ramp assembly, the upper endplate assembly, and the lower endplate assembly comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

A second aspect provided herein is an expandable fusion system for implantation between two adjacent vertebrae, the system comprising an inserter and an expandable fusion device comprising: an actuator comprising a drive feature and an longitudinal axis; a wedge assembly; a ramp assembly; an upper endplate assembly; and a lower endplate assembly; wherein the device has a width comprising an external distance between at least one of the first endplate and the third endplate, and the second endplate and the fourth endplate; wherein the device has a height comprising an external distance between at least one of the first endplate and the second endplate, and the third endplate and the fourth endplate; wherein actuation of the drive feature by a first number of actuations in a first actuation direction increases the width without increasing the height; and wherein actuation of the drive feature by a second number of actuations beyond the first number of actuations in the first actuation direction increases at least one of the height and the width.

Optionally, in any embodiment, actuation of the drive feature by a second number of actuations beyond the first number of actuations in the first actuation direction increases both the height and the width. Optionally, in any embodiment, actuation of the drive feature by a second number of actuations beyond the first number of actuations in the first actuation direction increases the height without increasing the width.

Optionally, in any embodiment, the width of the device reaches an apex once the drive feature is actuated by at least the first number of actuations. Optionally, in any embodiment, the height of the device reaches an apex once the drive feature is actuated by at least the first and second number of actuations.

Optionally, in any embodiment, the first number of actuations is about 0.5 actuations to about 10 actuations. Optionally, in any embodiment, the first number of actuations is at least about 0.5 actuations. Optionally, in any embodiment, the first number of actuations is at most about 10 actuations. Optionally, in any embodiment, the first number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the first number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, the second number of actuations is about 0.5 actuations to about 10 actuations. Optionally, in any embodiment, the second number of actuations is at least about 0.5 actuations. Optionally, in any embodiment, the second number of actuations is at most about 10 actuations. Optionally, in any embodiment, the second number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the second number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, actuation of the drive feature in the first actuation direction by at least the first number of actuations increases the height of the device by about 30% to about 400%. Optionally, in any embodiment, actuation of the drive feature in the first actuation direction by at least the first number of actuations increases the height of the device by at least about 30%. Optionally, in any embodiment, actuation of the drive feature in the first actuation direction by at least the first number of actuations increases the height of the device by at most about 400%. Optionally, in any embodiment, actuation of the drive feature in the first actuation direction by at least the first number of actuations increases the height of the device by about 30% to about 50%, about 30% to about 75%, about 30% to about 100%, about 30% to about 125%, about 30% to about 150%, about 30% to about 175%, about 30% to about 200%, about 30% to about 250%, about 30% to about 300%, about 30% to about 350%, about 30% to about 400%, about 50% to about 75%, about 50% to about 100%, about 50% to about 125%, about 50% to about 150%, about 50% to about 175%, about 50% to about 200%, about 50% to about 250%, about 50% to about 300%, about 50% to about 350%, about 50% to about 400%, about 75% to about 100%, about 75% to about 125%, about 75% to about 150%, about 75% to about 175%, about 75% to about 200%, about 75% to about 250%, about 75% to about 300%, about 75% to about 350%, about 75% to about 400%, about 100% to about 125%, about 100% to about 150%, about 100% to about 175%, about 100% to about 200%, about 100% to about 250%, about 100% to about 300%, about 100% to about 350%, about 100% to about 400%, about 125% to about 150%, about 125% to about 175%, about 125% to about 200%, about 125% to about 250%, about 125% to about 300%, about 125% to about 350%, about 125% to about 400%, about 150% to about 175%, about 150% to about 200%, about 150% to about 250%, about 150% to about 300%, about 150% to about 350%, about 150% to about 400%, about 175% to about 200%, about 175% to about 250%, about 175% to about 300%, about 175% to about 350%, about 175% to about 400%, about 200% to about 250%, about 200% to about 300%, about 200% to about 350%, about 200% to about 400%, about 250% to about 300%, about 250% to about 350%, about 250% to about 400%, about 300% to about 350%, about 300%, to about 400%, or about 350% to about 400%. Optionally, in any embodiment, actuation of the drive feature in the first actuation direction by at least the first number of actuations increases the height of the device by about 30%, about 50%, about 75%, about 100%, about 125%, about 150%, about 175%, about 200%, about 250%, about 300%, about 350%, or about 400%.

Optionally, in any embodiment, actuation of the drive feature in the first actuation direction by at least the first and the second number of actuations increases the width of the device by about 14% to about 150%. Optionally, in any embodiment, actuation of the drive feature in the first actuation direction by at least the first and the second number of actuations increases the width of the device by at least about 14%. Optionally, in any embodiment, actuation of the drive feature in the first actuation direction by at least the first and the second number of actuations increases the width of the device by at most about 150%. Optionally, in any embodiment, actuation of the drive feature in the first actuation direction by at least the first and the second number of actuations increases the width of the device by about 14% to about 20%, about 14% to about 30%, about 14% to about 40%, about 14% to about 50%, about 14/to about 60%, about 14% to about 70%, about 14% to about 80%, about 14% to about 90%, about 14% to about 100%, about 14% to about 120%, about 14% to about 150%, about 20% to about 30%, about 20% to about 40%, about 20% to about 50%, about 20% to about 60%, about 20% to about 70%, about 20% to about 80%, about 20% to about 90%, about 20% to about 100%, about 20%, to about 120%, about 20% to about 150%, about 30% to about 40%, about 30% to about 50%, about 30% to about 60%, about 30% to about 70%, about 30% to about 80%, about 30% to about 90%, about 30% to about 100%, about 30% to about 120%, about 30% to about 150%, about 40% to about 50%, about 40% to about 60%, about 40% to about 70%, about 40% to about 80%, about 40% to about 90%, about 40% to about 100%, about 40% to about 120%, about 40% to about 150%, about 50% to about 60%, about 50% to about 70%, about 50% to about 80%, about 50% to about 90%, about 50% to about 100%, about 50% to about 120%, about 50%, to about 150%, about 60% to about 70%, about 60% to about 80%, about 60% to about 90%, about 60% to about 100%, about 60% to about 120%, about 60% to about 150%, about 70% to about 80%, about 70% to about 90%, about 70% to about 100%, about 70% to about 120%, about 70% to about 150%, about 80% to about 90%, about 80% to about 100%, about 80% to about 120%, about 80% to about 150%, about 90% to about 100%, about 90% to about 120%, about 90% to about 150%, about 100% to about 120%, about 100% to about 150%, or about 120% to about 150%. Optionally, in any embodiment, actuation of the drive feature in the first actuation direction by at least the first and the second number of actuations increases the width of the device by about 14%, about 20%, about 30%, about 40%, about 50%, about 60%, about 70%, about 80%, about 90%, about 100%, about 120%, or about 150%.

Optionally, in any embodiment, the actuator has a distal end and a proximal end. Optionally, in any embodiment, at least a portion of the distal end comprises a first thread feature. Optionally, in any embodiment, at least a portion of the proximal end comprises a second thread feature, and wherein the proximal end comprises the drive feature. Optionally, in any embodiment, at least one of the first thread feature and the second thread feature comprise a thread disposed externally around the actuator. Optionally, in any embodiment, the first thread feature and the second thread feature have an opposite threading direction.

Optionally, in any embodiment, the wedge assembly comprises a distal wedge and a proximal wedge. Optionally, in any embodiment, actuation of the drive feature in the first direction converges the distal wedge and the proximal wedge toward one another. Optionally, in any embodiment, the distal wedge comprises a third thread feature, and wherein the third thread feature is threadably coupled to the first thread feature. Optionally, in any embodiment, the proximal wedge comprises a fourth thread feature, and wherein the fourth thread feature is threadably coupled to the second thread feature. Optionally, in any embodiment, the third thread feature comprises a thread disposed internally within the distal wedge. Optionally, in any embodiment, the fourth thread feature comprises a thread disposed internally within the proximal wedge.

Optionally, in any embodiment, the ramp assembly comprises a first distal ramp, a second distal ramp, a first proximal ramp, and a second proximal ramp. Optionally, in any embodiment, the slideable coupling between at least one of the wedge assembly and the ramp assembly, the ramp assembly and the upper endplate, assembly, and the ramp assembly and the lower endplate assembly is at a transverse angle from the longitudinal axis. Optionally, in any embodiment, the transverse angle is about 0 degrees to about 90 degrees. Optionally, in any embodiment, the slideable coupling between at least one of the wedge assembly and the ramp assembly, the ramp assembly and the upper endplate, assembly, and the ramp assembly and the lower endplate assembly comprises a protrusion and a slot. Optionally, in any embodiment, the protrusion extends from at least one of the wedge assembly, the ramp assembly, the upper endplate assembly, and the lower endplate assembly, and wherein the slot is disposed in at least one of the upper endplate assembly, and the lower endplate assembly. Optionally, in any embodiment, the protrusion comprises a pin, a ridge, a dimple, a bolt, a screw, a bearing, or any combination thereof. Optionally, in any embodiment, the slot comprises a through slot, a blind slot, a t-slot, a v-slot, a groove, or any combination thereof.

Optionally, in any embodiment, the drive feature comprises a recessed region configured to receive a driving instrument. Optionally, in any embodiment, the recessed region comprises a slot, Phillips, pozidrive, frearson, robertson, 12-point flange, hex socket, security hex socket, star drive, hexalobe, security torx, ta, tri-point, tri-wing, spanner head, clutch, one-way, double-square, triple-square, polydrive, spline drive, double hex, bristol, a thread, a friction fit, or a pentalobe recess or any other shaped recess. Optionally, in any embodiment, the driving feature comprises a protuberance extending therefrom and configured to be coupled to a driving instrument. Optionally, in any embodiment, the protuberance comprises a hex, a hexalobular, a threaded, or a square protuberance or any other shape protuberance.

Optionally, in any embodiment, the upper endplate assembly comprises a first endplate and a second endplate, and wherein the lower endplate assembly comprises a third endplate and a fourth endplate. Optionally, in any embodiment, at least one of the first endplate and the second endplate, the third endplate and the fourth endplate, the first proximal ramp and the second proximal ramp, and the first distal ramp and the second distal ramp have mirrored equivalence. Optionally, in any embodiment, at least one of the second endplate and the fourth endplate is larger than at least one of the first endplate and the third endplate. Optionally, in any embodiment, at least one of the exterior faces of the first end plate, the second endplate, the third endplate, and the fourth endplate comprise a texture configured to grip the vertebrae. Optionally, in any embodiment, the texturing comprises a tooth, a ridge, a roughened area, a metallic coating, a ceramic coating, a keel, a spike, a projection, a groove, or any combination thereof.

Optionally, in any embodiment, at least one of the actuator, the wedge assembly, the upper endplate assembly, and the lower endplate assembly comprise titanium, cobalt, stainless steel, tantalum, platinum, PEEK, PEKK, PEI, PET, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

A third aspect provided herein is a method for implanting an expandable fusion device between two adjacent vertebrae comprising: inserting the device, having a width and a height, between two adjacent vertebrae; actuating a drive feature by a first number of actuations in a first actuation to increase the width without increasing the height; and actuating the drive feature by the second number of actuations beyond the first number of actuations in the first actuation direction to increase at least one of the height and the width; attaching an inserter to the expandable fusion device, the device having a width and a height and comprising a drive feature.

Optionally, in any embodiment, actuation of the drive feature by a second number of actuations beyond the first number of actuations in the first actuation direction increases both the height and the width. Optionally, in any embodiment, actuation of the drive feature by a second number of actuations beyond the first number of actuations in the first actuation direction increases the height without increasing the width.

Optionally, in any embodiment, the width of the device reaches an apex once the drive feature is actuated by at least the first number of actuations. Optionally, in any embodiment, the height of the device reaches an apex once the drive feature is actuated by at least the first and second number of actuations.

Optionally, in any embodiment, the first number of actuations is about 0.5 actuations to about 10 actuations. Optionally, in any embodiment, the first number of actuations is at least about 0.5 actuations. Optionally, in any embodiment, the first number of actuations is at most about 10 actuations. Optionally, in any embodiment, the first number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the first number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, the second number of actuations is about 0.5 actuations to about 10 actuations. Optionally, in any embodiment, the second number of actuations is at least about 0.5 actuations. Optionally, in any embodiment, the second number of actuations is at most about 10 actuations. Optionally, in any embodiment, the second number of actuations is about 0.5 actuations to about 1 actuations, about 0.5 actuations to about 1.5 actuations, about 0.5 actuations to about 2 actuations, about 0.5 actuations to about 2.5 actuations, about 0.5 actuations to about 3 actuations, about 0.5 actuations to about 3.5 actuations, about 0.5 actuations to about 4 actuations, about 0.5 actuations to about 5 actuations, about 0.5 actuations to about 6 actuations, about 0.5 actuations to about 8 actuations, about 0.5 actuations to about 10 actuations, about 1 actuations to about 1.5 actuations, about 1 actuations to about 2 actuations, about 1 actuations to about 2.5 actuations, about 1 actuations to about 3 actuations, about 1 actuations to about 3.5 actuations, about 1 actuations to about 4 actuations, about 1 actuations to about 5 actuations, about 1 actuations to about 6 actuations, about 1 actuations to about 8 actuations, about 1 actuations to about 10 actuations, about 1.5 actuations to about 2 actuations, about 1.5 actuations to about 2.5 actuations, about 1.5 actuations to about 3 actuations, about 1.5 actuations to about 3.5 actuations, about 1.5 actuations to about 4 actuations, about 1.5 actuations to about 5 actuations, about 1.5 actuations to about 6 actuations, about 1.5 actuations to about 8 actuations, about 1.5 actuations to about 10 actuations, about 2 actuations to about 2.5 actuations, about 2 actuations to about 3 actuations, about 2 actuations to about 3.5 actuations, about 2 actuations to about 4 actuations, about 2 actuations to about 5 actuations, about 2 actuations to about 6 actuations, about 2 actuations to about 8 actuations, about 2 actuations to about 10 actuations, about 2.5 actuations to about 3 actuations, about 2.5 actuations to about 3.5 actuations, about 2.5 actuations to about 4 actuations, about 2.5 actuations to about 5 actuations, about 2.5 actuations to about 6 actuations, about 2.5 actuations to about 8 actuations, about 2.5 actuations to about 10 actuations, about 3 actuations to about 3.5 actuations, about 3 actuations to about 4 actuations, about 3 actuations to about 5 actuations, about 3 actuations to about 6 actuations, about 3 actuations to about 8 actuations, about 3 actuations to about 10 actuations, about 3.5 actuations to about 4 actuations, about 3.5 actuations to about 5 actuations, about 3.5 actuations to about 6 actuations, about 3.5 actuations to about 8 actuations, about 3.5 actuations to about 10 actuations, about 4 actuations to about 5 actuations, about 4 actuations to about 6 actuations, about 4 actuations to about 8 actuations, about 4 actuations to about 10 actuations, about 5 actuations to about 6 actuations, about 5 actuations to about 8 actuations, about 5 actuations to about 10 actuations, about 6 actuations to about 8 actuations, about 6 actuations to about 10 actuations, or about 8 actuations to about 10 actuations. Optionally, in any embodiment, the second number of actuations is about 0.5 actuations, about 1 actuations, about 1.5 actuations, about 2 actuations, about 2.5 actuations, about 3 actuations, about 3.5 actuations, about 4 actuations, about 5 actuations, about 6 actuations, about 8 actuations, or about 10 actuations.

Optionally, in any embodiment, actuation of the drive feature in the first actuation direction by at least the first number of actuations increases the height of the device by about 30% to about 400%. Optionally, in any embodiment, actuation of the drive feature in the first actuation direction by at least the first number of actuations increases the height of the device by at least about 30%. Optionally, in any embodiment, actuation of the drive feature in the first actuation direction by at least the first number of actuations increases the height of the device by at most about 400%. Optionally, in any embodiment, actuation of the drive feature in the first actuation direction by at least the first number of actuations increases the height of the device by about 30% to about 50%, about 30% to about 75%, about 30% to about 100%, about 30% to about 125%, about 30% to about 150%, about 30% to about 175%, about 30% to about 200%, about 30% to about 250%, about 30% to about 300%, about 30% to about 350%, about 30% to about 400%, about 50% to about 75%, about 50% to about 100%, about 50% to about 125%, about 50% to about 150%, about 50% to about 175%, about 50% to about 200%, about 50% to about 250%, about 50% to about 300%, about 50% to about 350%, about 50% to about 400%, about 75% to about 100%, about 75% to about 125%, about 75% to about 150%, about 75% to about 175%, about 75% to about 200%, about 75% to about 250%, about 75% to about 300%, about 75% to about 350%, about 75% to about 400%, about 100% to about 125%, about 100% to about 150%, about 100% to about 175%, about 100% to about 200%, about 100% to about 250%, about 100% to about 300%, about 100% to about 350%, about 100% to about 400%, about 125% to about 150%, about 125% to about 175%, about 125% to about 200%, about 125% to about 250%, about 125% to about 300%, about 125% to about 350%, about 125% to about 400%, about 150% to about 175%, about 150% to about 200%, about 150% to about 250%, about 150% to about 300%, about 150% to about 350%, about 150% to about 400%, about 175% to about 200%, about 175% to about 250%, about 175% to about 300%, about 175% to about 350%, about 175% to about 400%, about 200% to about 250%, about 200% to about 300%, about 200% to about 350%, about 200% to about 400%, about 250% to about 300%, about 250% to about 350%, about 250% to about 400%, about 300% to about 350%, about 300% to about 400%, or about 350% to about 400%. Optionally, in any embodiment, actuation of the drive feature in the first actuation direction by at least the first number of actuations increases the height of the device by about 30%, about 50%, about 75%, about 100%, about 125%, about 150%, about 175%, about 200%, about 250%, about 300%, about 350%, or about 400%.

Optionally, in any embodiment, actuation of the drive feature in the first actuation direction by at least the first and the second number of actuations increases the width of the device by about 14% to about 150%. Optionally, in any embodiment, actuation of the drive feature in the first actuation direction by at least the first and the second number of actuations increases the width of the device by at least about 14%. Optionally, in any embodiment, actuation of the drive feature in the first actuation direction by at least the first and the second number of actuations increases the width of the device by at most about 150%. Optionally, in any embodiment, actuation of the drive feature in the first actuation direction by at least the first and the second number of actuations increases the width of the device by about 14% to about 20%, about 14% to about 30%, about 14% to about 40%, about 14% to about 50%, about 14% to about 60%, about 14% to about 70%, about 14% to about 80%, about 14% to about 100%, about 14% to about 120%, about 14% to about 140%, about 14% to about 150%, about 20% to about 30%, about 20% to about 40%, about 20% to about 50%, about 20% to about 60%, about 20% to about 70%, about 20% to about 80%, about 20% to about 100%, about 20% to about 120%, about 20% to about 140%, about 20% to about 150%, about 30% to about 40%, about 30% to about 50%, about 30% to about 60%, about 30% to about 70%, about 30% to about 80%, about 30% to about 100%, about 30% to about 120%, about 30% to about 140%, about 30% to about 150%, about 40% to about 50%, about 40% to about 60%, about 40% to about 70%, about 40% to about 80%, about 40% to about 100%, about 40% to about 120%, about 40% to about 140%, about 40% to about 150%, about 50% to about 60%, about 50% to about 70%, about 50% to about 80%, about 50% to about 100%, about 50% to about 120%, about 50% to about 140%, about 50% to about 150%, about 60% to about 70%, about 60% to about 80%, about 60% to about 100%, about 60% to about 120%, about 60% to about 140%, about 60% to about 150%, about 70% to about 80%, about 70% to about 100%, about 70% to about 120%, about 70% to about 140%, about 70% to about 150%, about 80% to about 100%, about 80% to about 120%, about 80% to about 140%, about 80% to about 150%, about 100% to about 120%, about 100% to about 140%, about 100% to about 150%, about 120% to about 140%, about 120% to about 150%, or about 140% to about 150%. Optionally, in any embodiment, actuation of the drive feature in the first actuation direction by at least the first and the second number of actuations increases the width of the device by about 14%, about 20%, about 30%, about 40%, about 50%, about 60%, about 70%, about 80%, about 100%, about 120%, about 140%, or about 150%.

Optionally, in any embodiment, the actuator has a distal end and a proximal end. Optionally, in any embodiment, at least a portion of the distal end comprises a first thread feature. Optionally, in any embodiment, at least a portion of the proximal end comprises a second thread feature, and wherein the proximal end comprises the drive feature. Optionally, in any embodiment, at least one of the first thread feature and the second thread feature comprise a thread disposed externally around the actuator. Optionally, in any embodiment, the first thread feature and the second thread feature have an opposite threading direction.

Optionally, in any embodiment, the wedge assembly comprises a distal wedge and a proximal wedge. Optionally, in any embodiment, actuation of the drive feature in the first direction converges the distal wedge and the proximal wedge toward one another. Optionally, in any embodiment, the distal wedge comprises a third thread feature, and wherein the third thread feature is threadably coupled to the first thread feature. Optionally, in any embodiment, the proximal wedge comprises a fourth thread feature, and wherein the fourth thread feature is threadably coupled to the second thread feature. Optionally, in any embodiment, the third thread feature comprises a thread disposed internally within the distal wedge. Optionally, in any embodiment, the fourth thread feature comprises a thread disposed internally within the proximal wedge.

Optionally, in any embodiment, the ramp assembly comprises a first distal ramp, a second distal ramp, a first proximal ramp, and a second proximal ramp. Optionally, in any embodiment, the slideable coupling between at least one of the wedge assembly and the ramp assembly, the ramp assembly and the upper endplate, assembly, and the ramp assembly and the lower endplate assembly is at a transverse angle from the longitudinal axis. Optionally, in any embodiment, the transverse angle is about 30 degrees to about 90 degrees. Optionally, in any embodiment, the slideable coupling between at least one of the wedge assembly and the ramp assembly, the ramp assembly and the upper endplate, assembly, and the ramp assembly and the lower endplate assembly comprises a protrusion and a slot. Optionally, in any embodiment, the protrusion extends from at least one of the wedge assembly, the ramp assembly, the upper endplate assembly, and the lower endplate assembly, and wherein the slot is disposed in at least one of the upper endplate assembly, and the lower endplate assembly. Optionally, in any embodiment, the protrusion comprises a pin, a ridge, a dimple, a bolt, a screw, a bearing, or any combination thereof. Optionally, in any embodiment, the slot comprises a through slot, a blind slot, a t-slot, a v-slot, a groove, or any combination thereof.

Optionally, in any embodiment, the drive feature comprises a recessed region configured to receive a driving instrument. Optionally, in any embodiment, the recessed region comprises a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, a thread, a friction fit, or a pentalobe recess. Optionally, in any embodiment, the driving feature comprises a protuberance extending therefrom and configured to be coupled to a driving instrument. Optionally, in any embodiment, the protuberance comprises a hex, a hexalobular, a threaded a square protuberance.

Optionally, in any embodiment, the upper endplate assembly comprises a first endplate and a second endplate, and wherein the lower endplate assembly comprises a third endplate and a fourth endplate. Optionally, in any embodiment, at least one of the first endplate and the second endplate, the third endplate and the fourth endplate, the first proximal ramp and the second proximal ramp, and the first distal ramp and the second distal ramp have mirrored equivalence. Optionally, in any embodiment, at least one of the second endplate and the fourth endplate is larger than at least one of the first endplate and the third endplate. Optionally, in any embodiment, at least one of the exterior faces of the first end plate, the second endplate, the third endplate, and the fourth endplate comprise a texture configured to grip the vertebrae. Optionally, in any embodiment, the texturing comprises a tooth, a ridge, a roughened area, a metallic coating, a ceramic coating, a keel, a spike, a projection, a groove, or any combination thereof.

Optionally, in any embodiment, at least one of the actuator, the wedge assembly, the upper endplate assembly, and the lower endplate assembly comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Further areas of applicability of the present disclosure will become apparent from the detailed description provided hereinafter. It should be understood that the detailed description and specific examples, while indicating the preferred or exemplary embodiments of the disclosure, are intended for purposes of illustration only and are not intended to limit the scope of the disclosure.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 6A depicts a planar top view of an exemplary first expandable fusion device in initial collapsed state.

FIG. 6B depicts a planar end view of an exemplary first expandable fusion device in initial collapsed state.

FIG. 6C depicts a planar top view of an exemplary first expandable fusion device fully expanded in width.

FIG. 6D depicts a planar end view of an exemplary first expandable fusion device fully expanded in width.

FIG. 6E depicts a planar top view of an exemplary first expandable fusion device fully expanded in both width and height.

FIG. 6F depicts a planar end view of an exemplary first expandable fusion device fully expanded in both width and height.

FIG. 7A depicts a detailed view of an exemplary first expandable fusion device in its initial collapsed state and illustrates the articulation responsible for delay in height expansion.

FIG. 7B depicts a detailed view of an exemplary first expandable fusion device in a partially width expanded state.

FIG. 7C depicts a detailed view of an exemplary first expandable fusion device in a partially width and height expanded state.

FIG. 9A depicts an exemplary endplate with T-shaped slots.

FIG. 9B depicts an exemplary endplate with L-shaped slots.

FIG. 9C depicts an exemplary endplate with Y-shaped slots.

FIG. 9D depicts an exemplary endplate with F-shaped slots.

FIG. 9E depicts an exemplary endplate with rectilinear slots.

FIG. 10C depicts a perspective view of an exemplary first expandable fusion device in fully expanded state.

FIG. 10D1 depicts a perspective view of an exemplary first expandable fusion device in initial collapsed state.

FIG. 10D2 depicts a perspective view of an exemplary first expandable fusion device in fully expanded state.

FIG. 10D3 depicts a perspective view of an exemplary first expandable fusion device in fully expanded state and assembled with bone fasteners.

FIG. 1A depicts end view of an exemplary first expandable fusion device with all planar endplates.

FIG. 11B depicts end view of an exemplary first expandable fusion device with all convex endplates.

FIG. 11C depicts end view of an exemplary first expandable fusion device with all individually convex endplates.

FIG. 11D depicts end view of an exemplary first expandable fusion device with all planar endplates, with some of the endplates having different heights.

FIG. 11E depicts end view of an exemplary first expandable fusion device with the top and bottom plates generally convex and lordotic.

FIG. 11F depicts end view of an exemplary first expandable fusion device with all convex endplates, with some of the endplates having different heights.

FIG. 11G depicts end view of an exemplary first expandable fusion device with flat and lordotic endplates.

FIG. 11H depicts end view of an exemplary first expandable fusion device with flat bottom endplates, individually convex top endplates having different lengths.

FIG. 11I depicts end view of an exemplary first expandable fusion device with two generally convex top endplates and two flat bottom endplates.

FIG. 13A depicts top view of an exemplary first expandable fusion device with all endplates of same length in initial collapsed state.

FIG. 13B depicts top view of an exemplary first expandable fusion device with endplates of different lengths in initial collapsed state.

FIG. 13C depicts top view of an exemplary first expandable fusion device with all endplates of same length in fully width expanded state.

FIG. 13D depicts top view of an exemplary first expandable fusion device with endplates of different lengths in fully width expanded state.

FIG. 14B1 depicts a top view of the collapsed state of an exemplary first expandable fusion device configured to expand unevenly on both ends.

FIG. 14B2 depicts a top view of a fully expanded state of an exemplary first expandable fusion device with an alternative expansion mechanism and designed to expand unevenly on both ends.

FIG. 15B depicts a top view of an initial collapsed state of an exemplary first expandable fusion device with different length endplates designed to achieve more width expansion on one side than on the other.

FIG. 15C depicts a top view of a fully width expanded state of an exemplary first expandable fusion device with different length endplates designed to achieve more width expansion on one side than on the other.

FIG. 15E depicts a perspective view of an exemplary distal wedge with uneven ramps.

FIG. 15F depicts a perspective view of an exemplary proximal wedge with uneven ramps.

FIG. 15G depicts a perspective view of an exemplary ramp.

FIG. 18D depicts an inside perspective view of an exemplary ramp with Y-shaped branches and Y-shaped channel.

FIG. 18E depicts an inside perspective view of an exemplary ramp with an inside T-shaped branches and Y-shaped channel.

FIG. 19G1 depicts a detailed section view of articulation between an exemplary ramp and of an exemplary endplate in unassembled state.

FIG. 19G2 depicts a detailed section view of articulation an exemplary ramp and an exemplary endplate in a partially assembled state.

FIG. 19G3 depicts a detailed section view of articulation between an exemplary ramp and of an exemplary endplate in a fully assembled state, in which the travel range of a ramp is limited.

FIG. 19H1 depicts detailed view of articulation between an exemplary ramp, an exemplary endplate, and an exemplary fastener in which the travel range of a ramp is limited.

FIG. 19H2 depicts detailed exploded view of articulation between an exemplary ramp, an exemplary endplate, and an exemplary fastener in which the travel range of a ramp is limited.

FIG. 20 depicts a perspective view of an embodiment of an exemplary actuator.

FIG. 21A depicts a perspective view of an exemplary actuator.

FIG. 26A depicts a rear perspective view of an exemplary proximal wedge.

FIG. 26B depicts a front perspective view of an exemplary proximal wedge.

FIG. 27B depicts a perspective view of an exemplary proximal wedge with threaded central aperture and alternative instrument attachment features.

FIG. 27C depicts a perspective view of an exemplary proximal wedge with T-shaped projections and alternative instrument attachment features.

FIG. 27D depicts a perspective view of an exemplary proximal wedge with T-shaped projections, alternative instrument attachment features and an alternative side aperture shape.

FIG. 28B depicts a rear perspective view of an exemplary distal wedge.

FIG. 52 depicts a perspective view of an exemplary first expandable fusion device in a fully width and height expanded state and attached to an exemplary inserter instrument.

FIG. 53 depicts a perspective view of an exemplary first expandable fusion device in a fully width and height expanded state filled with graft material and attached to an exemplary inserter instrument.

FIG. 54A depicts a perspective view of an exemplary second expandable fusion device in an initial collapsed state.

FIG. 54C depicts an exploded view of an exemplary second expandable fusion device.

FIG. 55B depicts a rear view of an exemplary proximal wedge, used in an exemplary second expandable fusion device of FIGS. 54A-54C.

FIG. 56A depicts a perspective view of an exemplary third expandable fusion device in an initial collapsed state.

FIG. 56B depicts a perspective view of an exemplary third expandable fusion in a fully expanded state.

FIG. 56C depicts an exploded view of an exemplary third expandable fusion device.

FIG. 57A depicts a right view of an exemplary ramp of an exemplary third expandable fusion device.

FIG. 57B depicts a left view of an exemplary ramp of an exemplary third expandable fusion device.

FIG. 58 depicts a bottom view of an exemplary endplate of an exemplary third expandable fusion device.

FIG. 59A depicts a perspective view of an exemplary fourth expandable fusion device in an initial collapsed state.

FIG. 59B depicts a perspective view of an exemplary fourth expandable fusion device of FIG. 59A in a fully expanded state.

FIG. 59C depicts a top view of an exemplary fourth expandable fusion device of FIG. 59A in an initial fully collapsed state.

FIG. 59D depicts a perspective view of partial assembly of an exemplary fourth expandable fusion device comprising two opposing endplates.

FIG. 60A depicts a perspective view of an exemplary fifth expandable fusion device in a fully expanded state.

FIG. 60B depicts a side view of an exemplary fifth expandable fusion device of FIG. 60A in a fully expanded state.

Figure 61A:
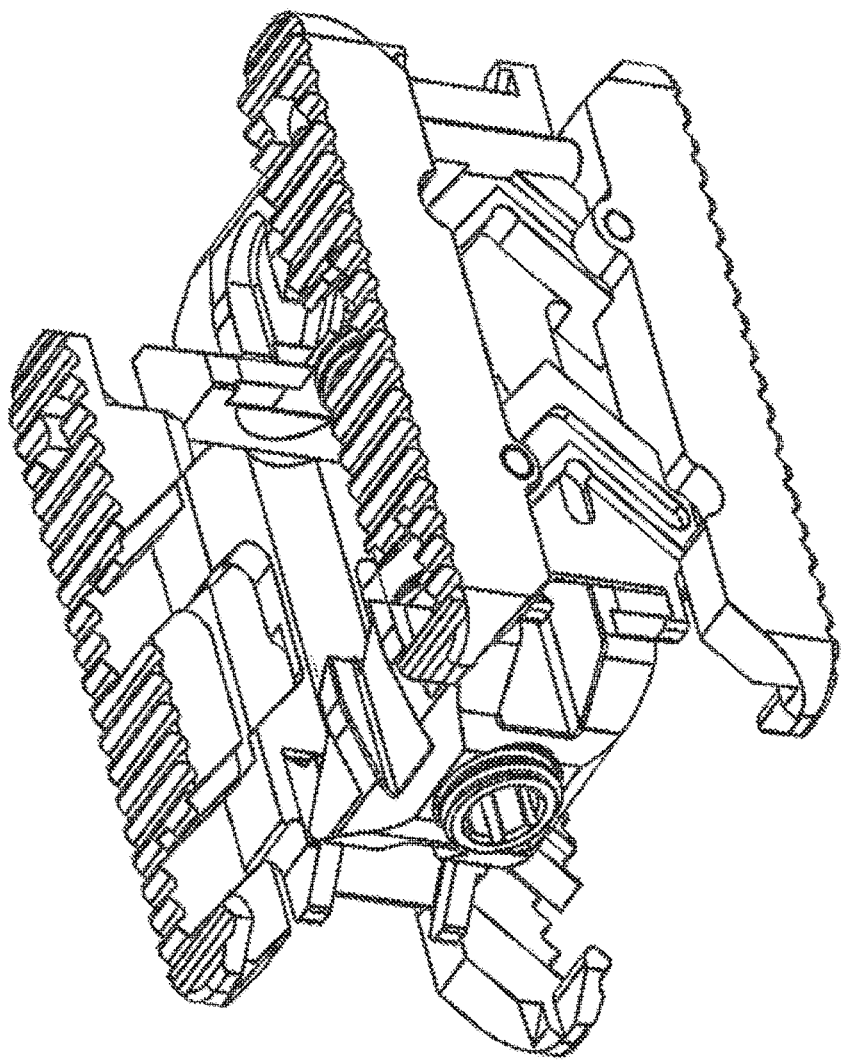

FIG. 61A depicts a perspective view of an exemplary sixth expandable fusion device in a fully expanded state.

Figure 61B:
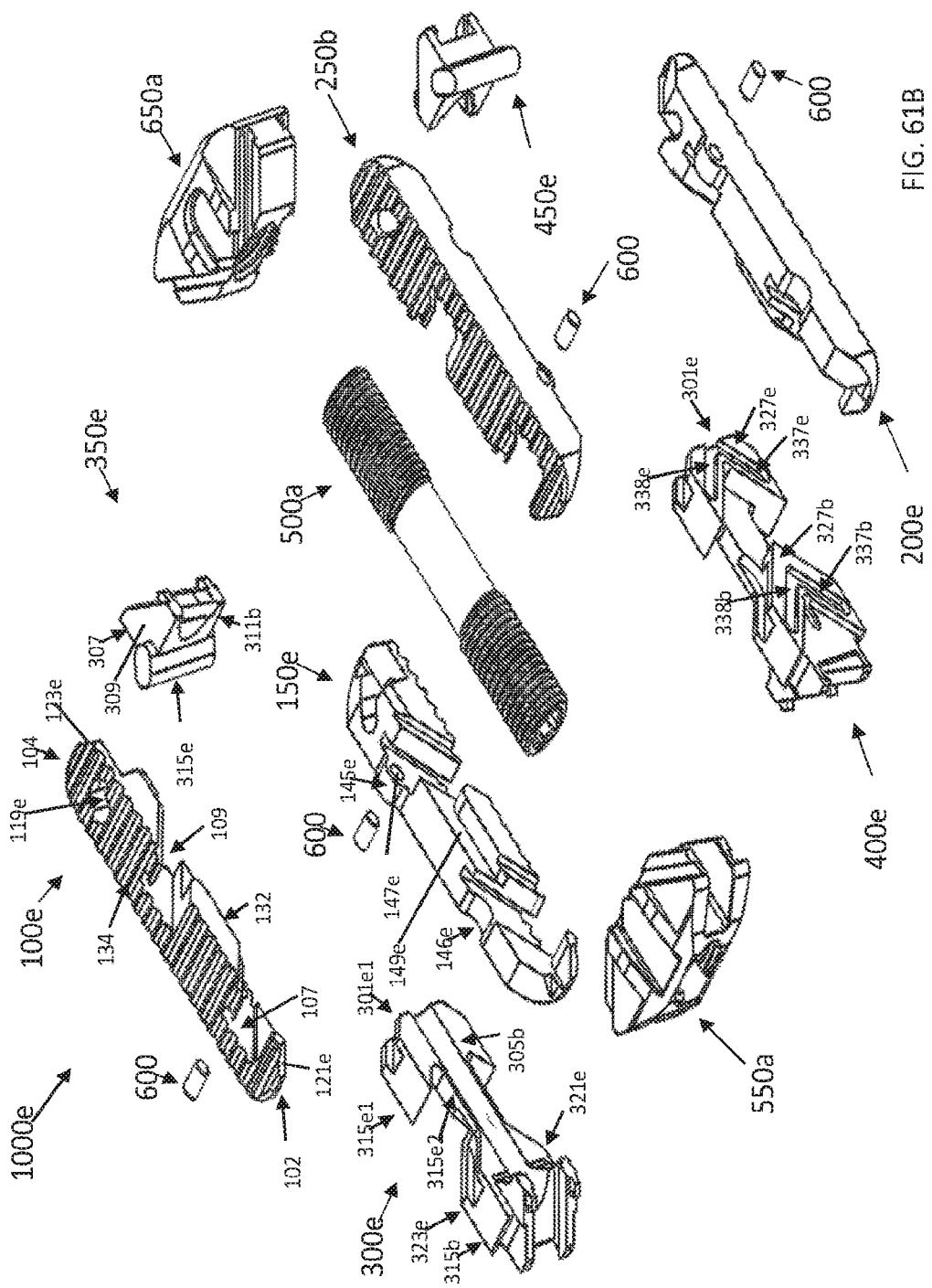

FIG. 61B depicts an exploded view of an exemplary sixth expandable fusion device.

Figure 62A:
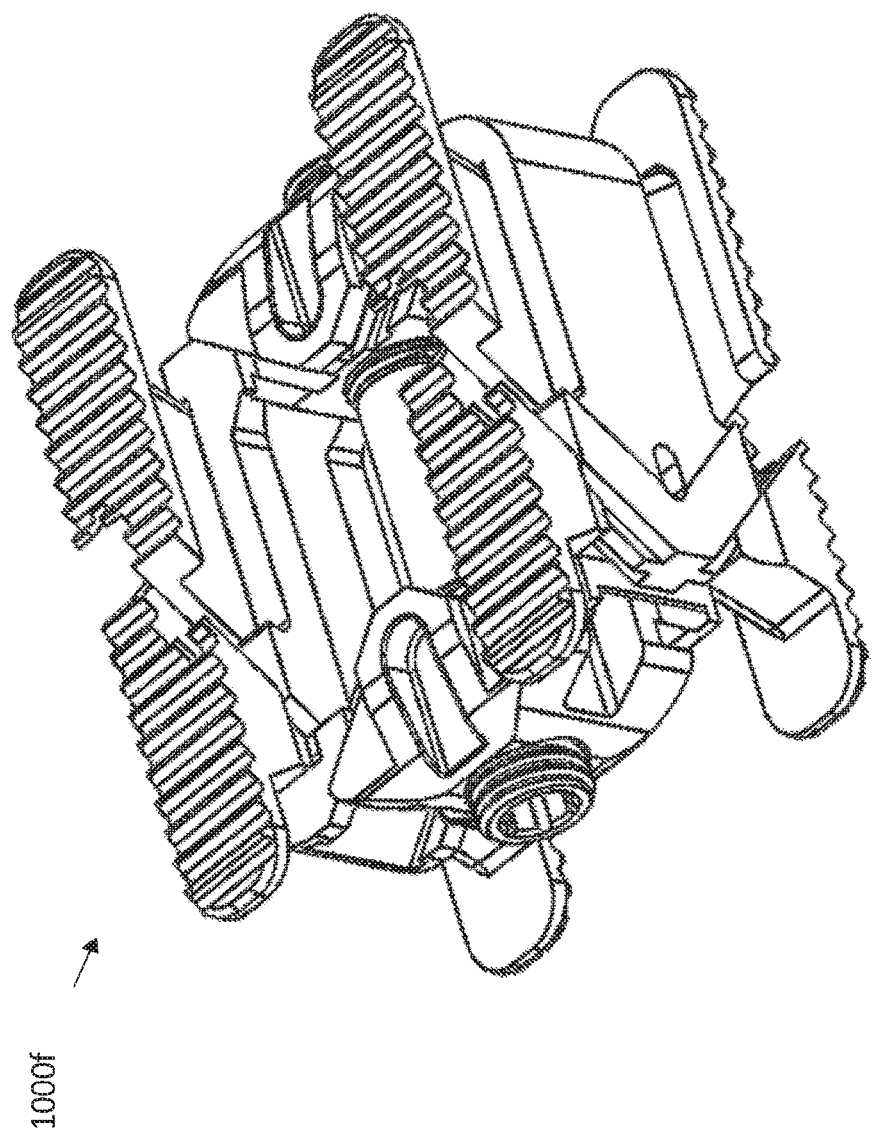

FIG. 62A depicts a perspective view of an exemplary seventh expandable fusion device in a fully expanded state.

FIG. 62B depicts an exploded view of an exemplary seventh expandable fusion device.

Figure 63A:
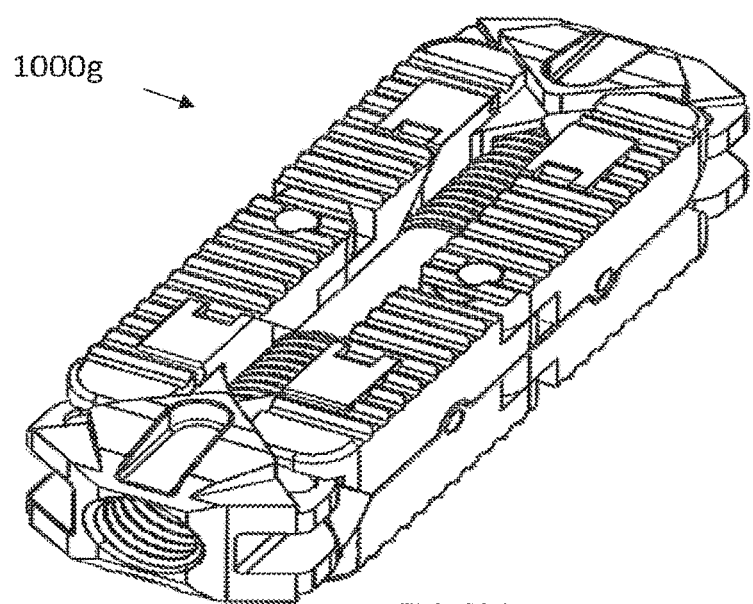

FIG. 63A depicts a perspective view of an exemplary eighth expandable fusion device in an initial collapsed state.

Figure 63B:
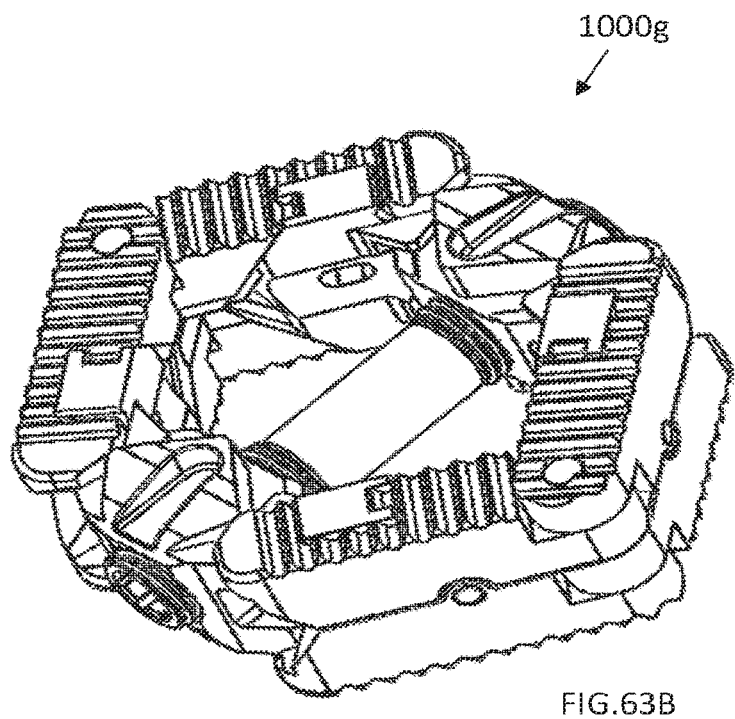

FIG. 63B depicts a perspective view of an exemplary eighth expandable fusion device in a fully width expanded state.

Figure 63C:
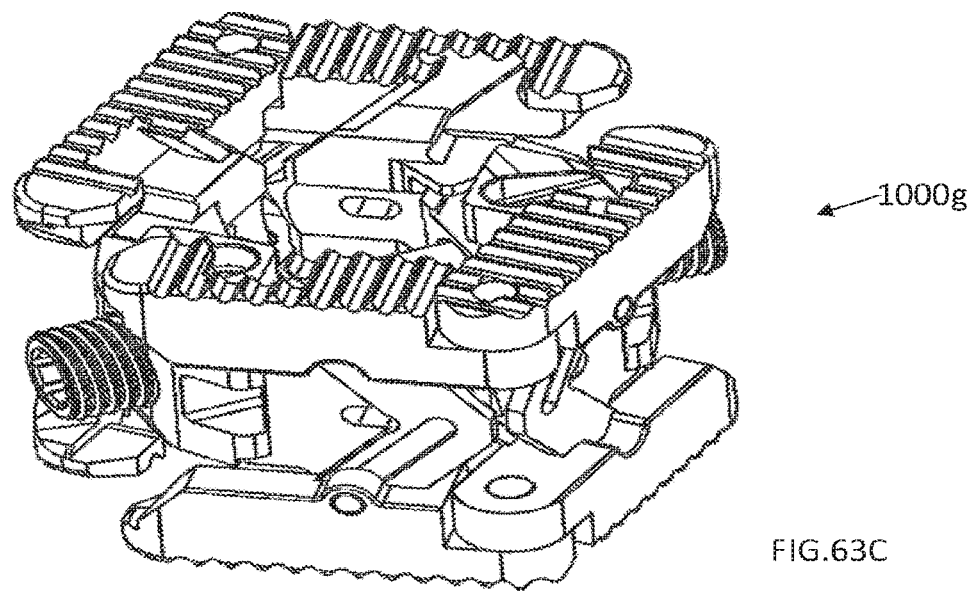

FIG. 63C depicts a perspective view of an exemplary eighth expandable fusion device in a fully expanded state.

Figure 63D:
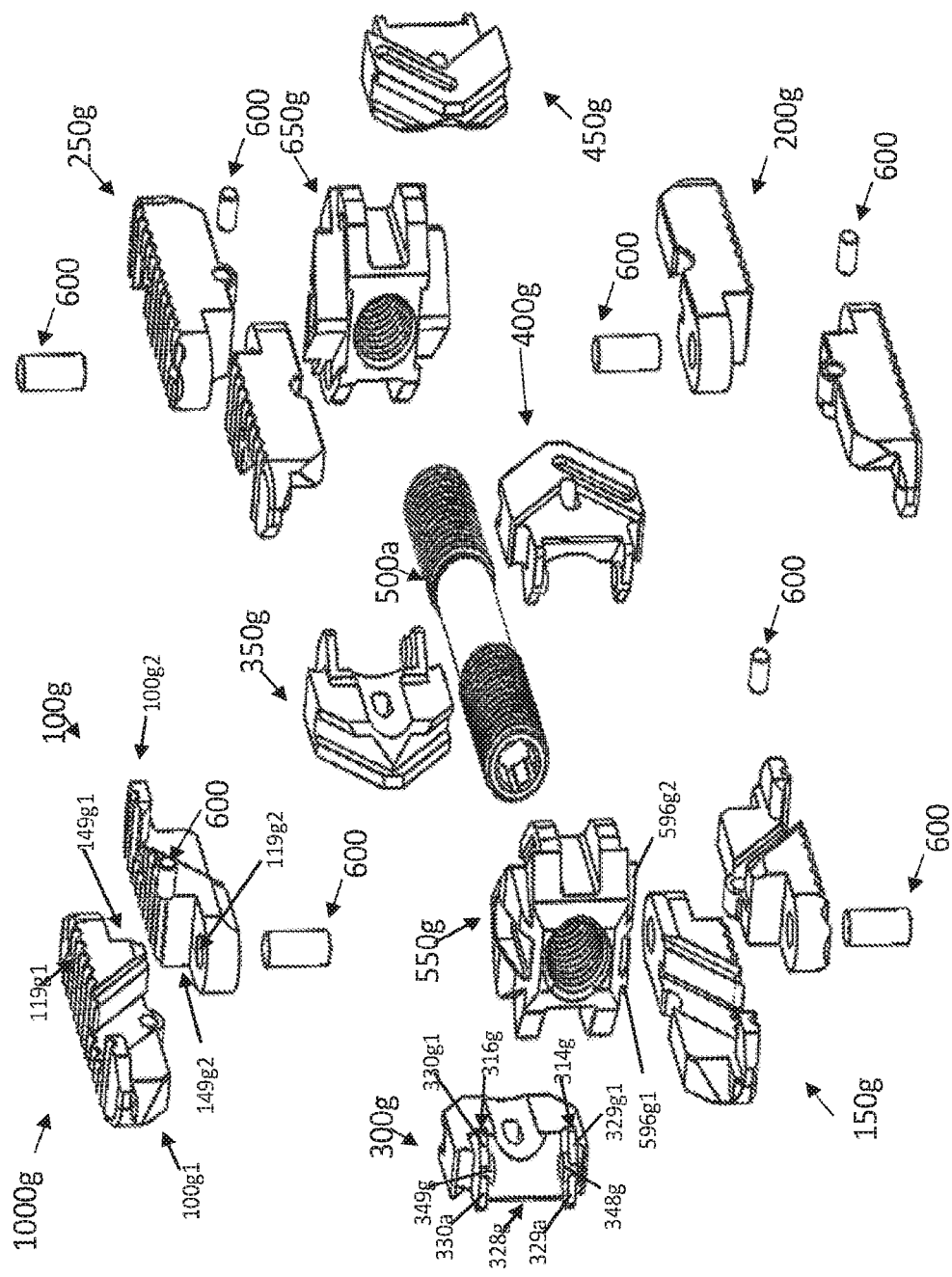

FIG. 63D depicts an exploded view of an exemplary eighth expandable fusion.

FIG. 64 depicts a perspective view of an exemplary eighth proximal wedge, used in an exemplary expandable fusion device.

Figure 65A:
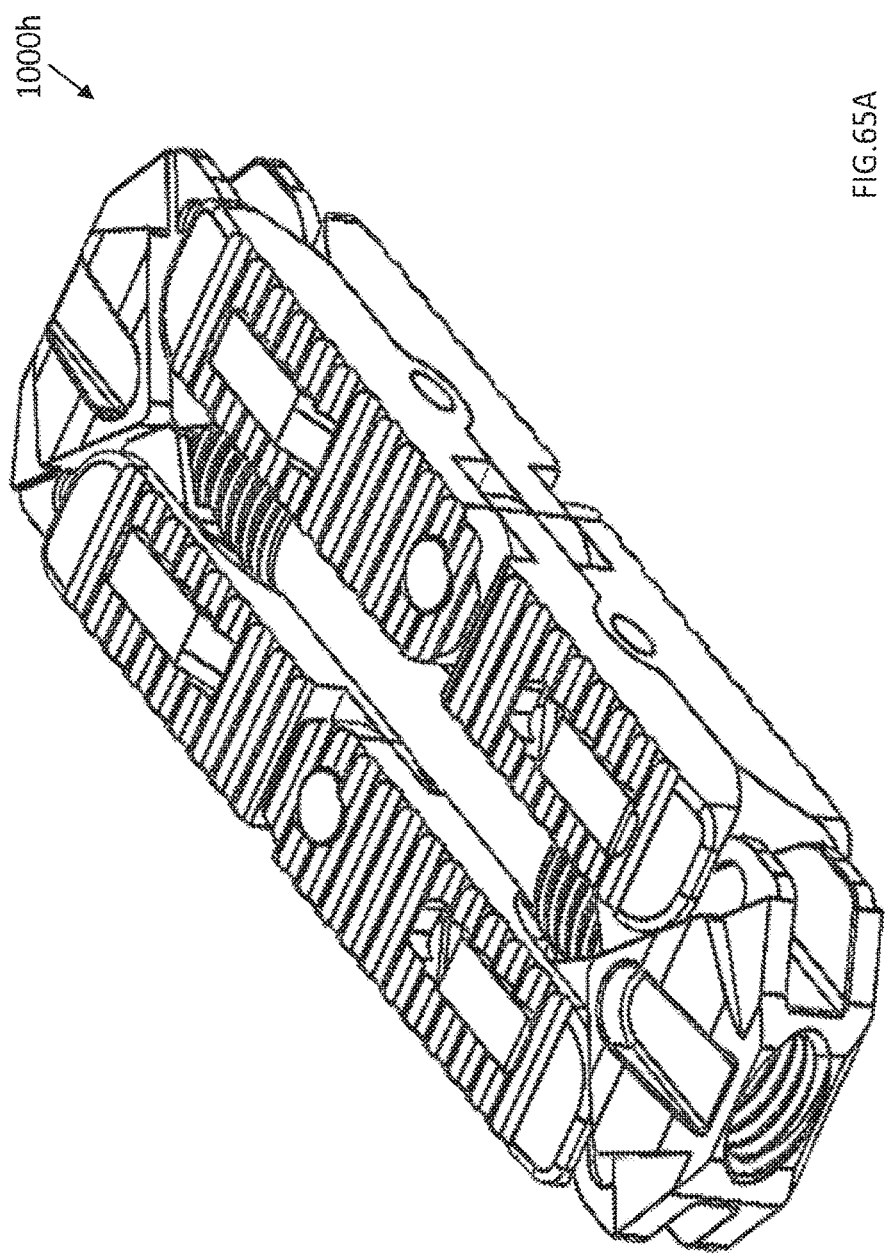

FIG. 65A depicts a perspective view of an exemplary ninth expandable fusion device in an initial collapsed state.

FIG. 65B depicts a perspective view of an exemplary ninth expandable fusion device in a fully expanded state.

FIG. 65C depicts a partially assembled perspective view of an exemplary ninth expandable fusion device in an initial collapsed state.

FIG. 65D depicts a partially assembled perspective view of an exemplary ninth expandable fusion device in a partially width expanded state (linear width expansion only).

Figure 65E:
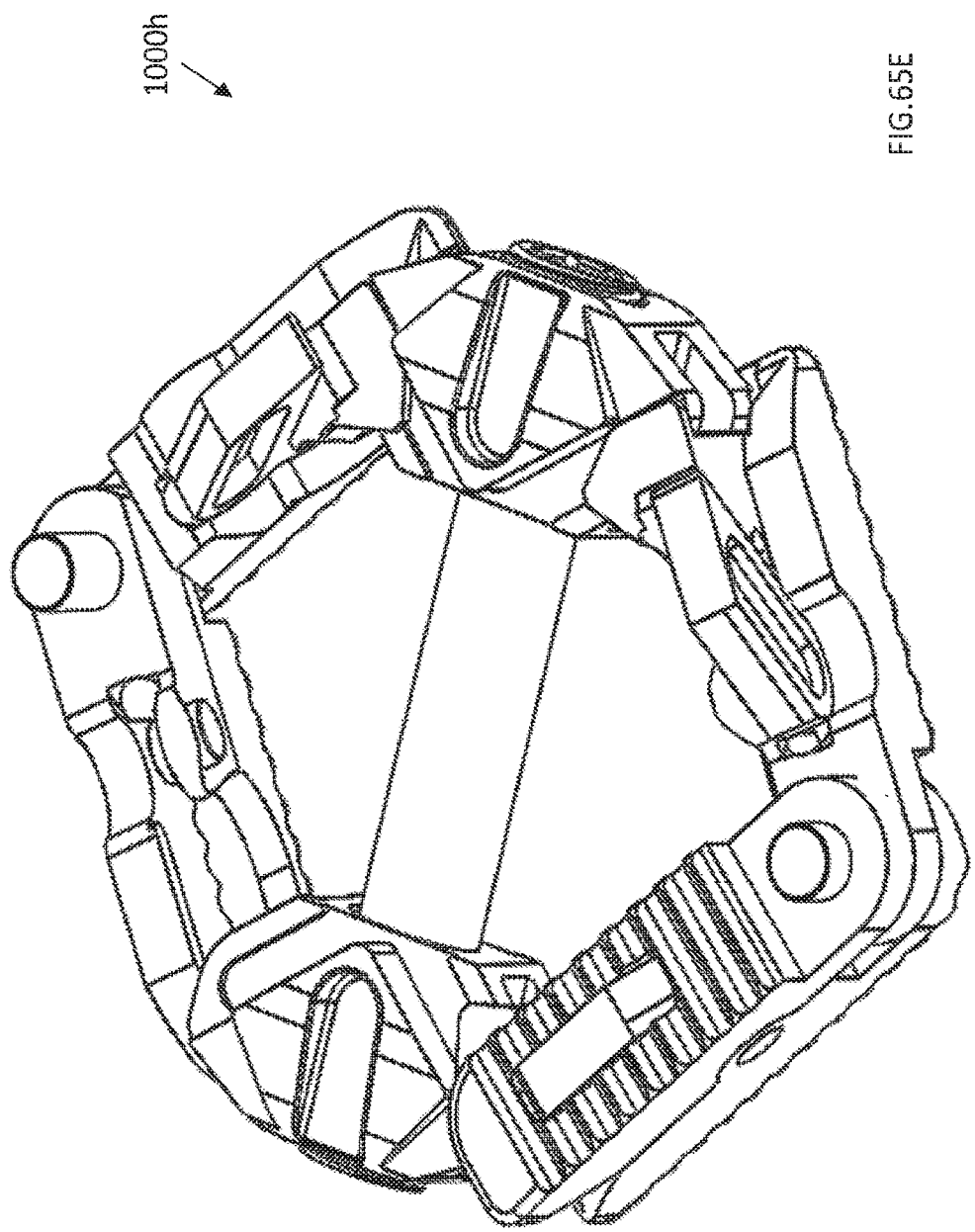

FIG. 65E depicts a partially assembled perspective view of an exemplary ninth expandable fusion device in a fully width expanded state (both linear and angular expansion completed).

FIG. 66A depicts a perspective view of an exemplary tenth expandable fusion device in a fully expanded state.

Figure 66B:
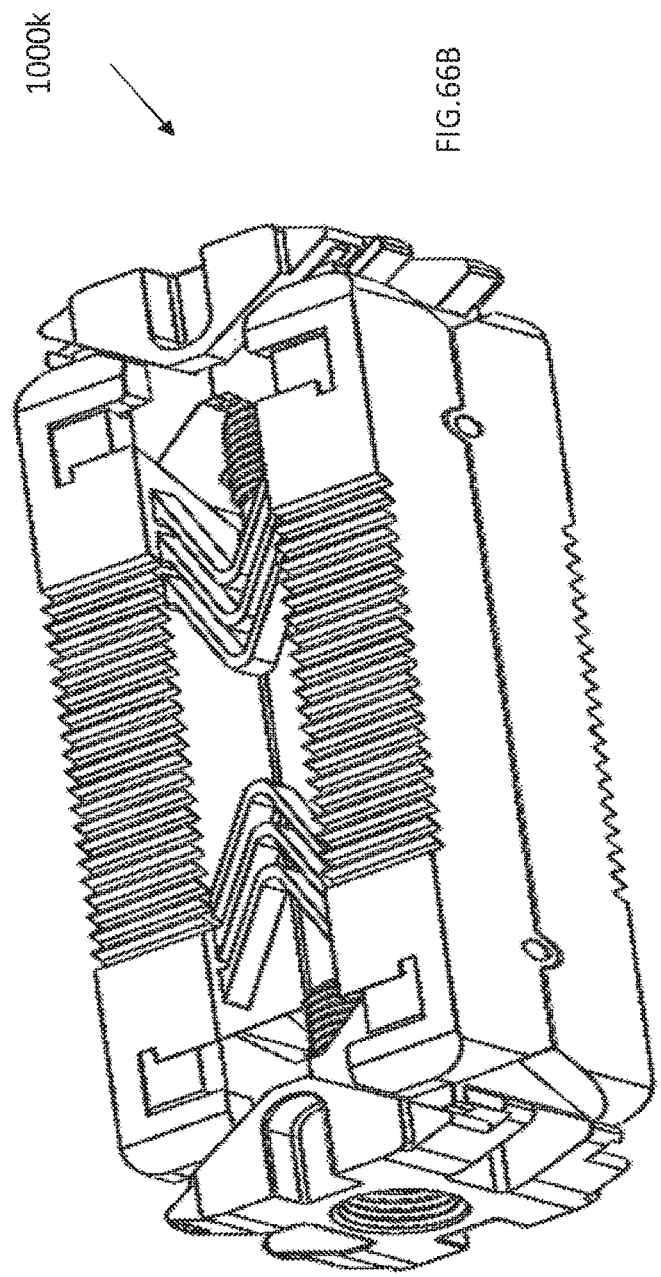

FIG. 66B depicts a perspective view of an exemplary tenth expandable fusion device in an initial collapsed state.

Figure 66C:
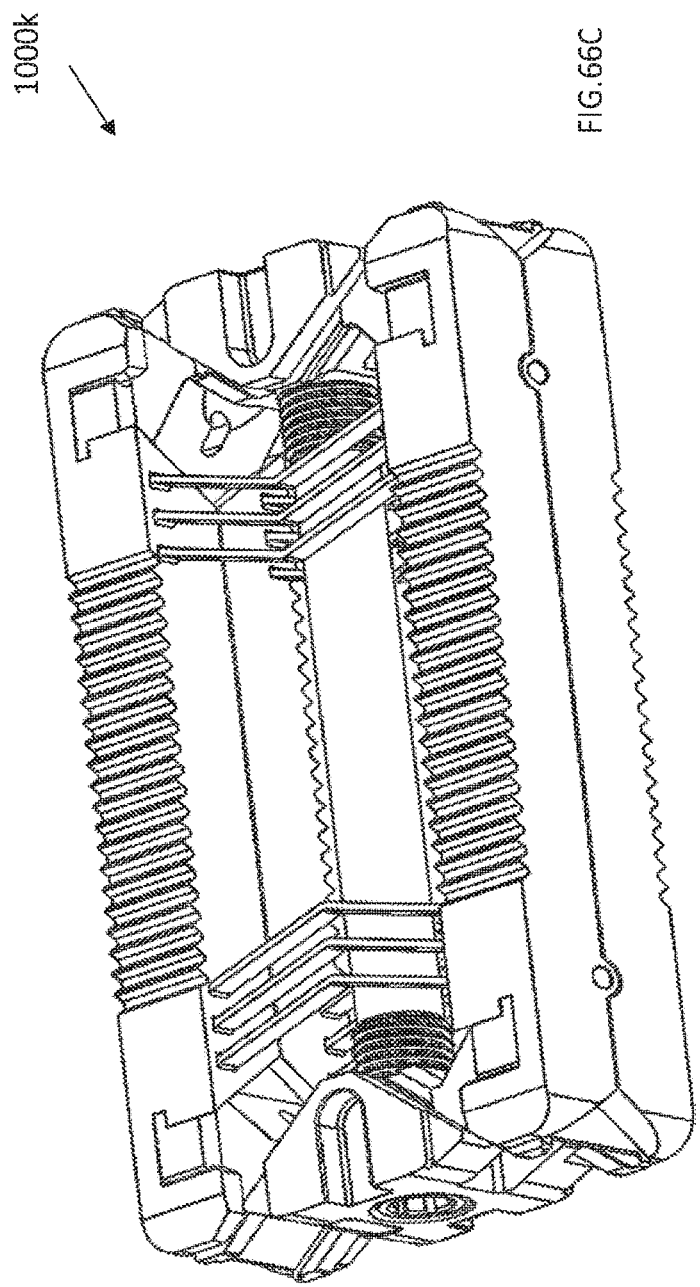

FIG. 66C depicts a perspective view of an exemplary tenth expandable fusion device in a fully width expanded state.

FIG. 66D depicts a top perspective view of an exemplary tenth compound endplate, used in an exemplary expandable fusion device.

Figure 67A:
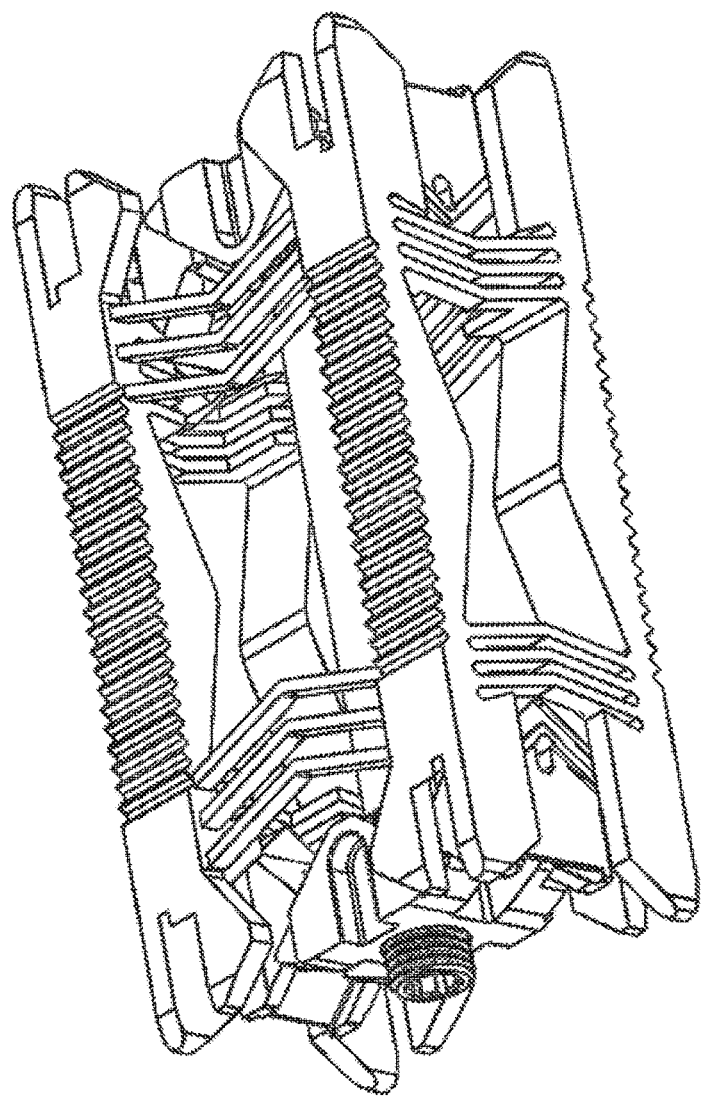

FIG. 67A depicts a perspective view of an exemplary eleventh expandable fusion device in a fully expanded state.

FIG. 67B depicts a perspective view of an exemplary eleventh endplate complex, used in an exemplary expandable fusion device.

Figure 67C:
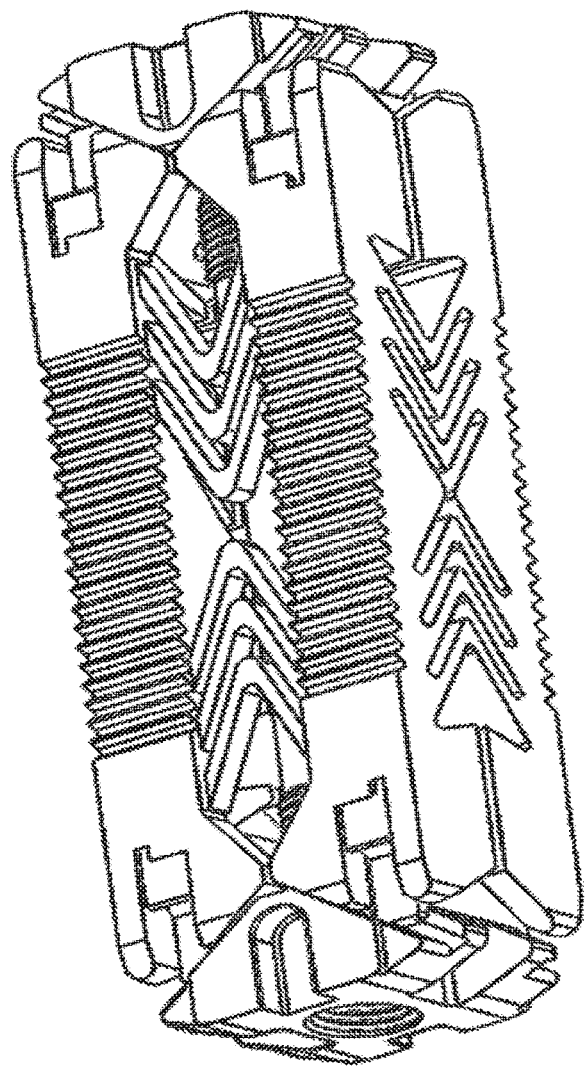

FIG. 67C depicts a perspective view of an exemplary eleventh expandable fusion device of FIG. 67A in an initial collapsed state.

FIG. 67D depicts a perspective view of an exemplary eleventh expandable fusion device of FIG. 67A in a fully width expanded state.

FIG. 68 depicts a perspective view of an exemplary twelfth expandable fusion device in an initial collapsed state.

Figure 69B:
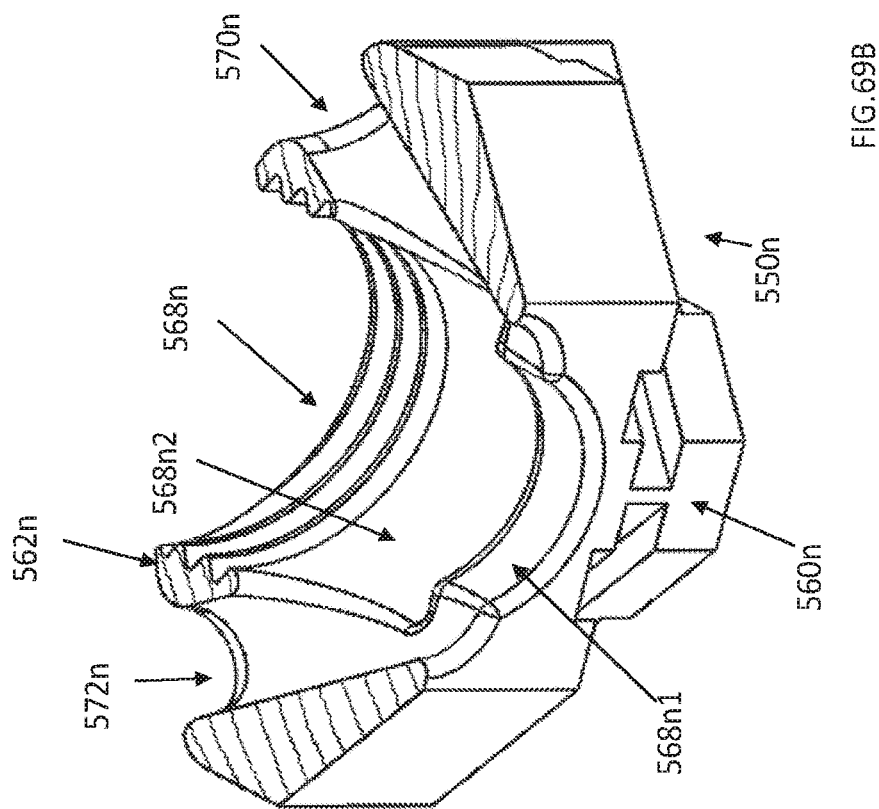
Figure 69A:
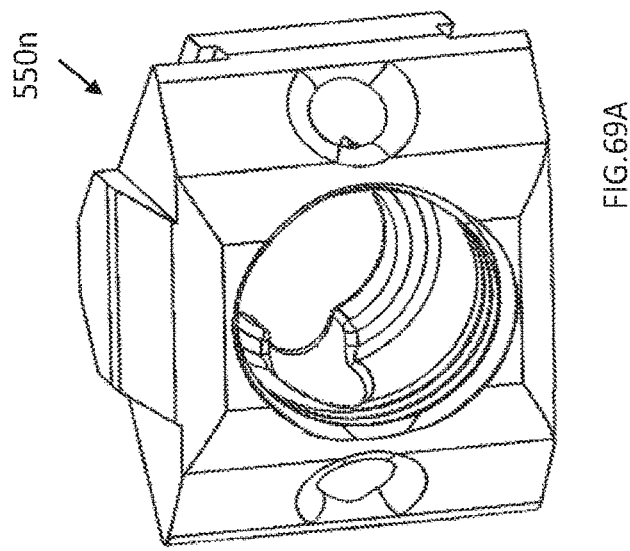

FIG. 69A depicts a rear perspective view of an exemplary twelfth proximal wedge used in an exemplary expandable fusion device.

FIG. 69B depicts a section view of an exemplary twelfth proximal wedge used in an exemplary expandable fusion device.

FIG. 70A depicts a front view of an exemplary twelfth distal wedge used in an exemplary expandable fusion device.

FIG. 70B depicts a section view of an exemplary twelfth distal wedge used in an exemplary expandable fusion device.

Figure 71:
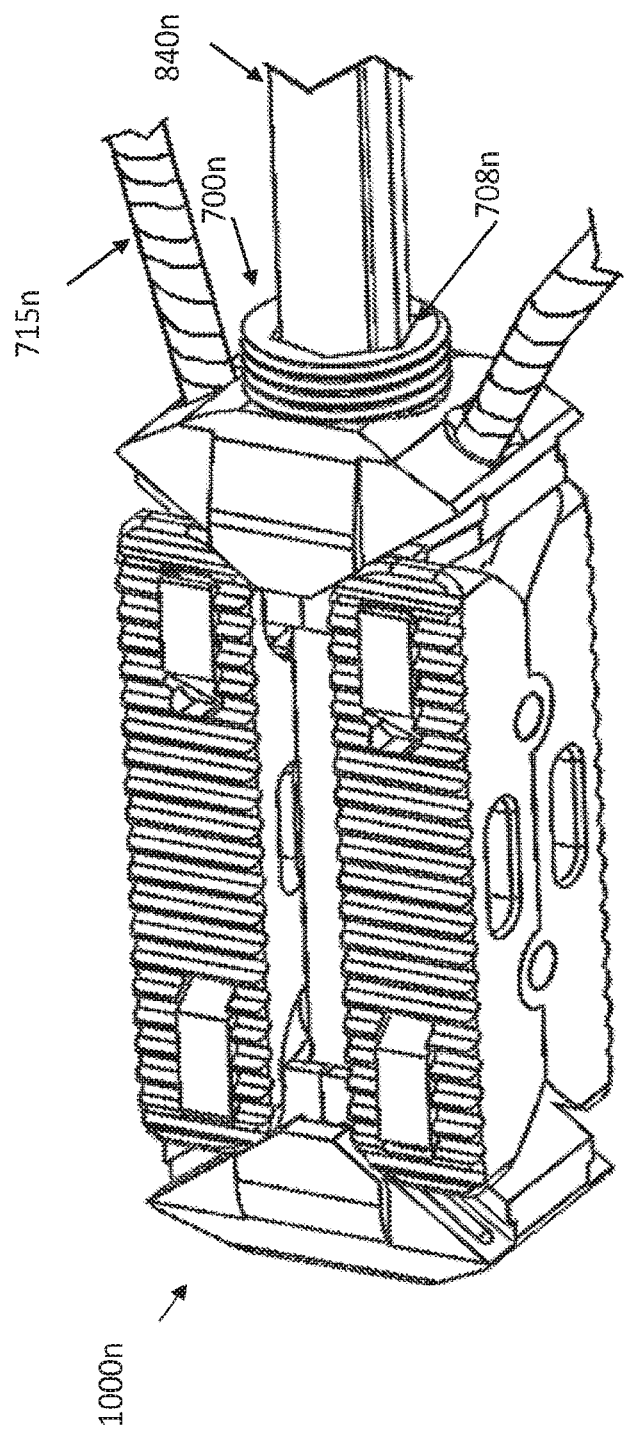

FIG. 71 depicts a perspective view of an exemplary twelfth expandable fusion device in an initial collapsed state and assembled with a tensioner instrument.

FIG. 72A Depicts a section view of an exemplary twelfth expandable fusion device in an initial collapsed state assembled with tensioner instrument.

FIG. 72B Depicts a section view of an exemplary twelfth expandable fusion device in an expanded state assembled with tensioner instrument.

FIG. 72C Depicts a section view of an exemplary twelfth expandable fusion device in an expanded state with tension member locked in place.

Figure 73A:
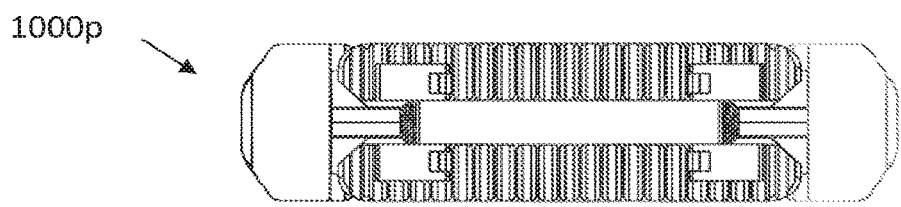

FIG. 73A depicts a top view of an exemplary thirteenth expandable fusion device in the initial collapsed state.

Figure 73B:
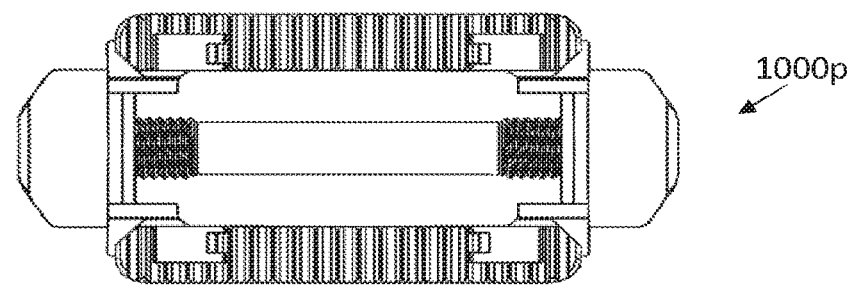

FIG. 73B depicts a top view of an exemplary thirteenth exemplary expandable fusion device in a fully width expanded state.

Figure 73C:
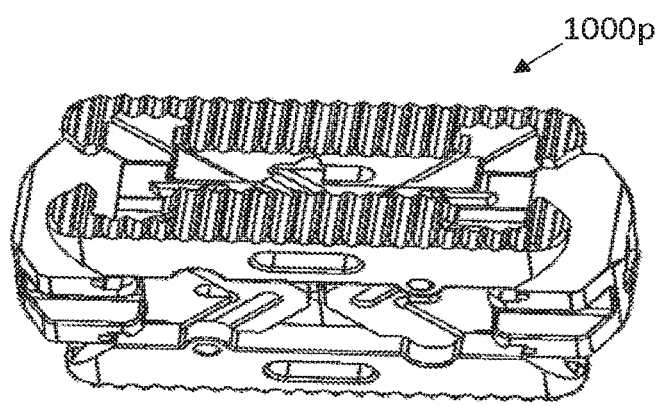

FIG. 73C depicts a perspective view an exemplary thirteenth expandable fusion device in the fully height expanded state.

Figure 73D:
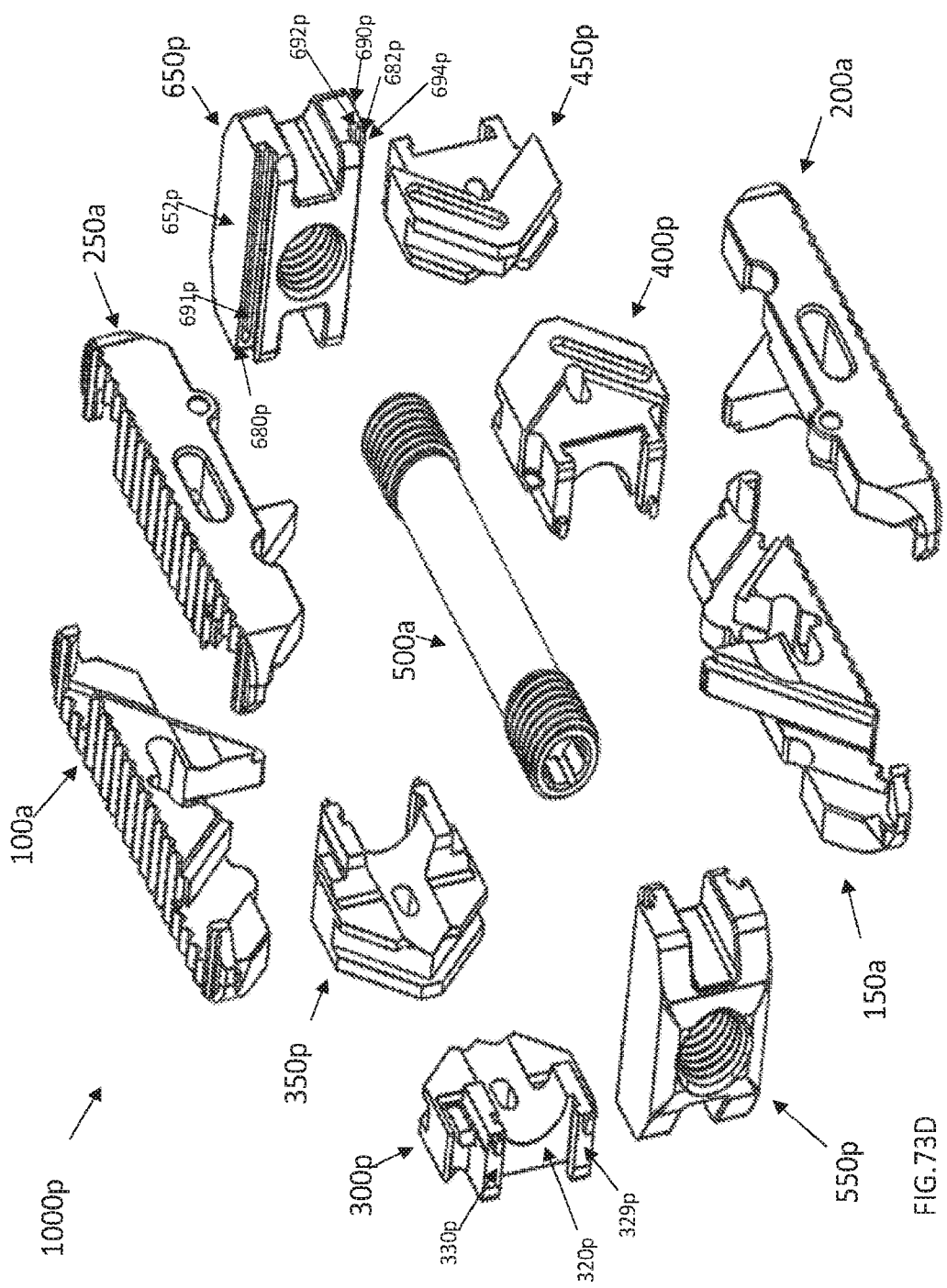

FIG. 73D depicts an exploded view of an exemplary thirteenth expandable fusion device.

FIG. 74A depicts a perspective view of an exemplary thirteenth expandable fusion device attached to an exemplary inserter-expander instrument in the initial collapsed state.

FIG. 74B depicts a perspective view of an exemplary thirteenth expandable fusion device attached to an exemplary inserter-expander instrument in the fully width expanded state.

Figure 75A:
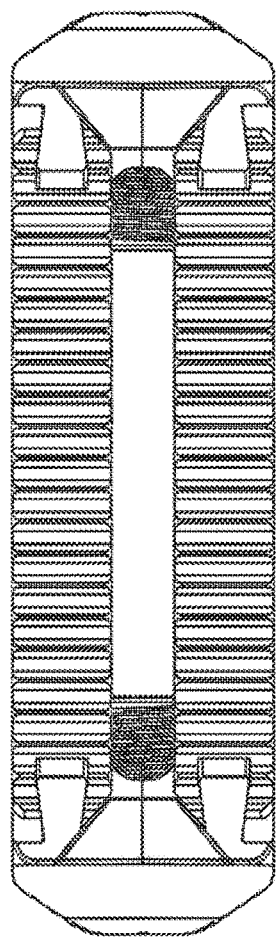

FIG. 75A depicts a top view of an exemplary fourteenth expandable fusion device in the initial collapsed state.

Figure 75B:
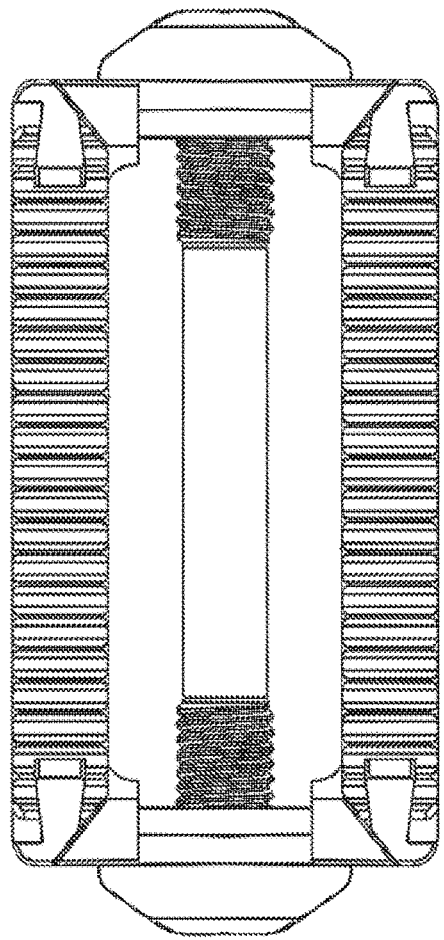

FIG. 75B depicts a top view of an exemplary fourteenth expandable fusion device in the fully width expanded state.

Figure 75C:
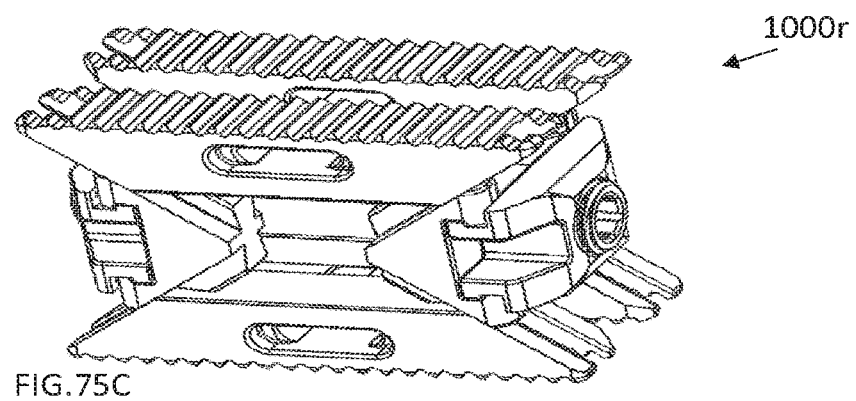

FIG. 75C depicts a perspective view of an exemplary fourteenth expandable fusion device in the fully height expanded state.

Figure 75D:
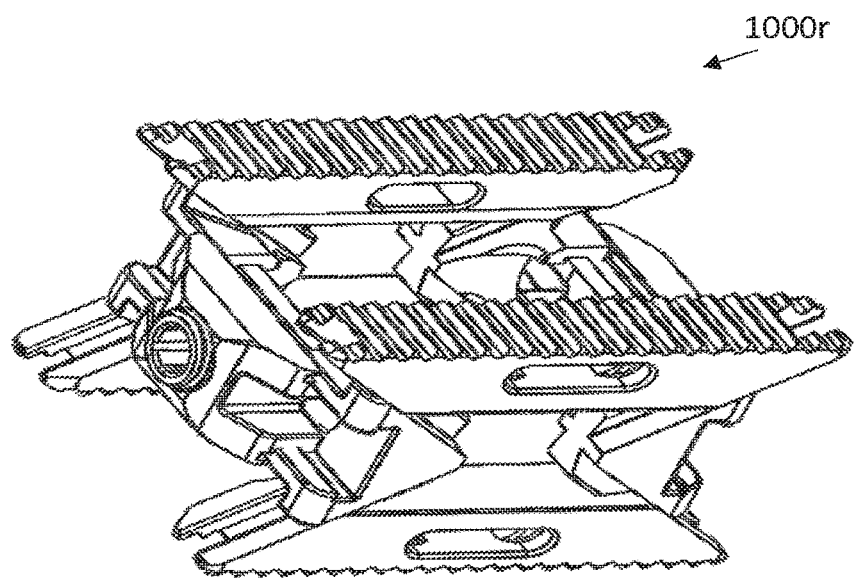

FIG. 75D depicts a perspective view of an exemplary fourteenth expandable fusion device in the fully width and height expanded state.

FIG. 75E depicts an exploded view of an exemplary fourteenth expandable fusion device.

Figure 76A:
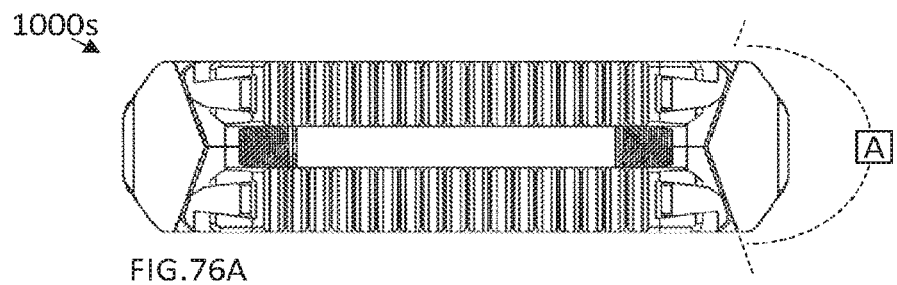

FIG. 76A depicts a top view of an exemplary fifteenth expandable fusion device in the initial collapsed state.

Figure 76B:
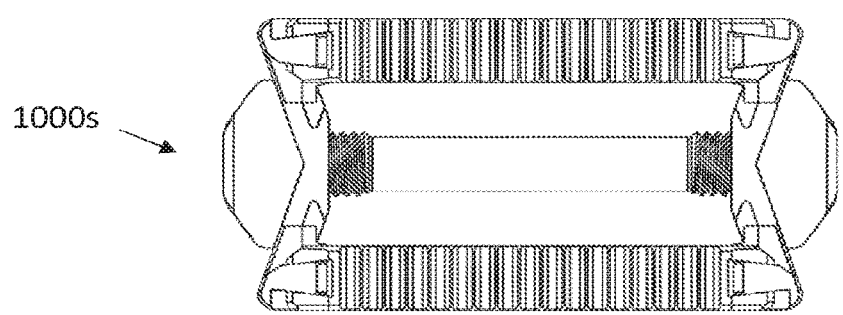

FIG. 76B depicts a top view of an exemplary fifteenth expandable fusion device in the fully width expanded state.

Figure 76C:
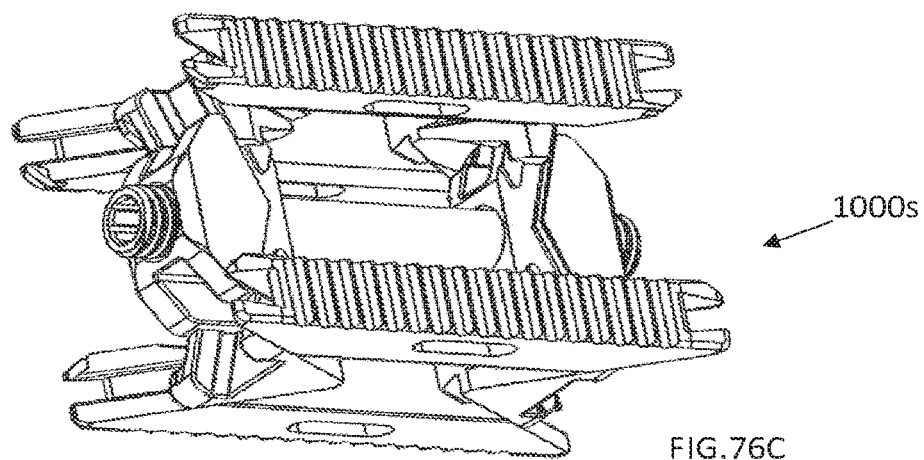

FIG. 76C depicts a perspective view of an exemplary fifteenth expandable fusion device in a fully width and height expanded state.

Figure 76D:
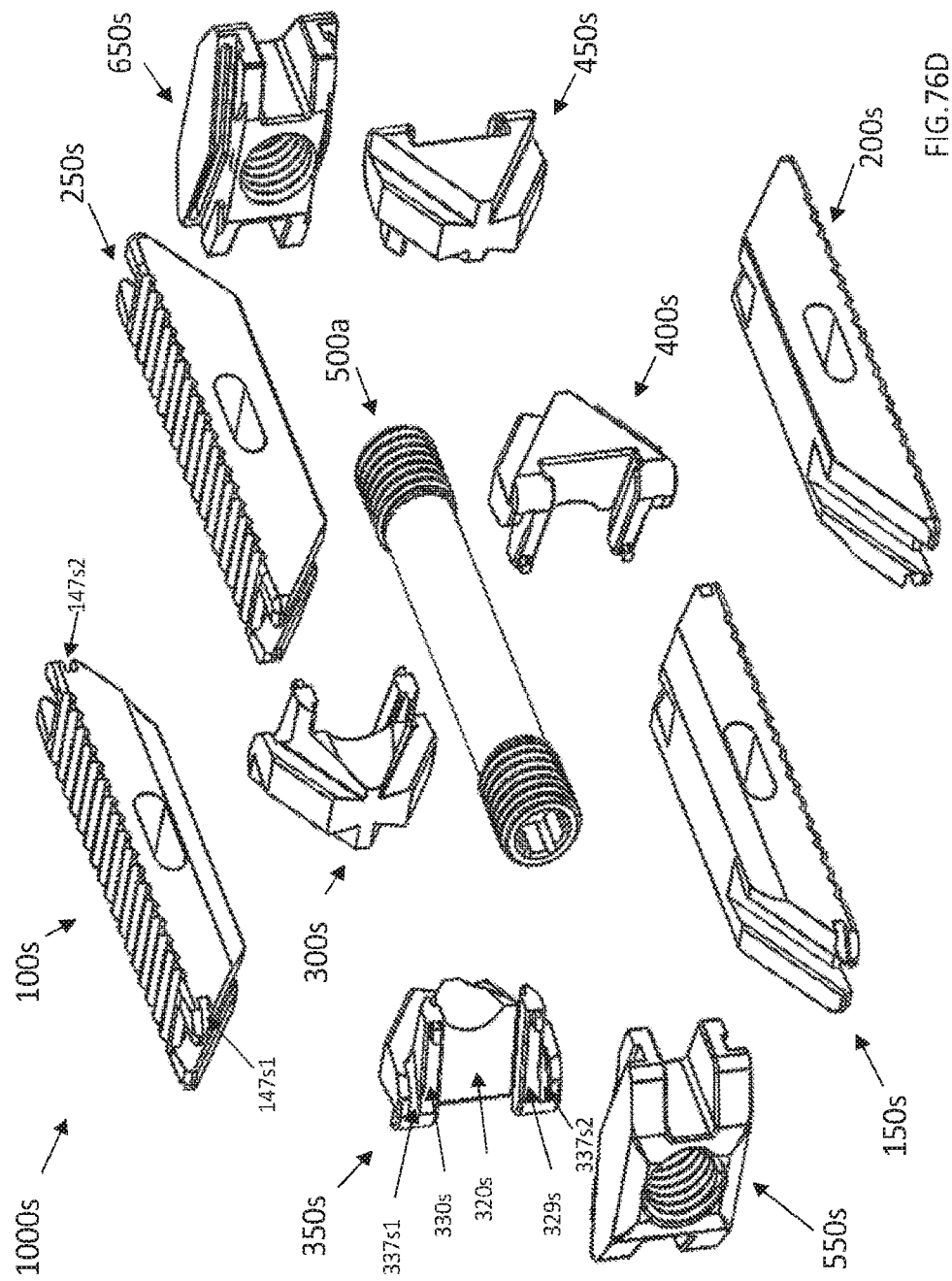

FIG. 76D depicts an exploded view of an exemplary fifteenth expandable fusion device.

Figure 77A:
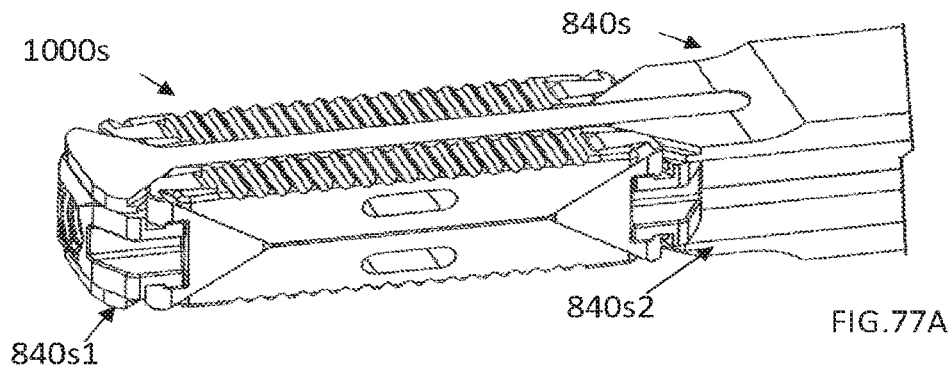

FIG. 77A depicts a perspective view of an exemplary fifteenth expandable fusion device attached to the inserter-expander instrument in the initial collapsed state.

Figure 77B:
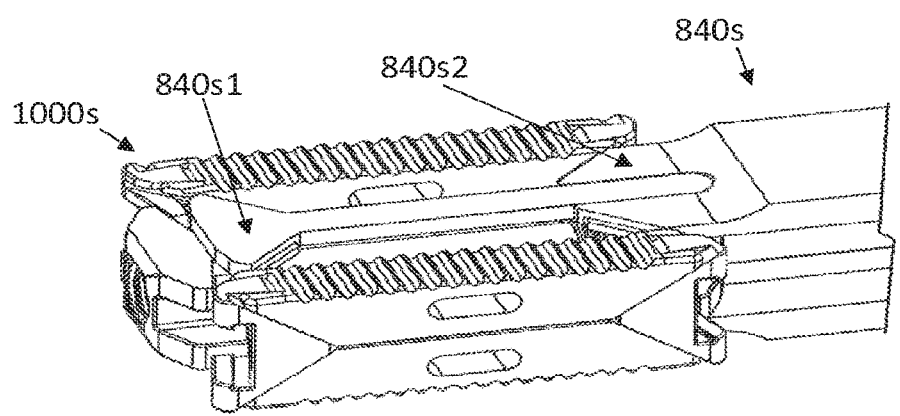

FIG. 77B depicts a perspective view of an exemplary fifteenth expandable fusion device attached to the inserter-expander instrument in the fully width expanded state.

Figure 78:
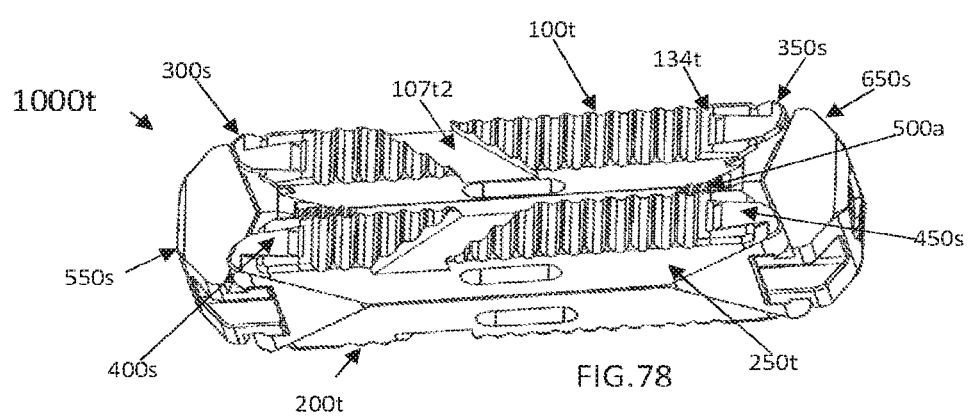

FIG. 78 depicts a perspective view of an exemplary sixteenth expandable fusion device in the initial collapsed state.

Figure 79A:
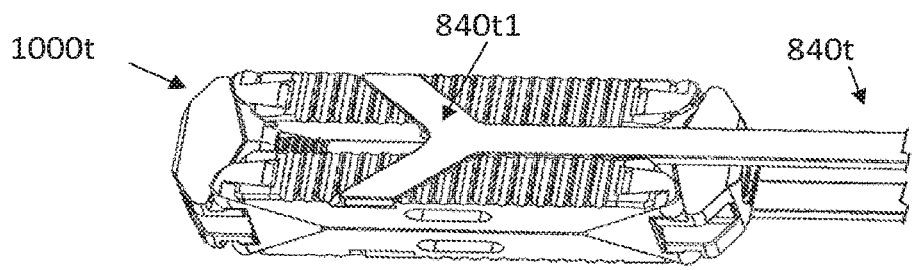

FIG. 79A depicts a perspective view of an exemplary sixteenth expandable fusion device attached to the inserter-expander instrument in the initial collapsed state.

Figure 79B:
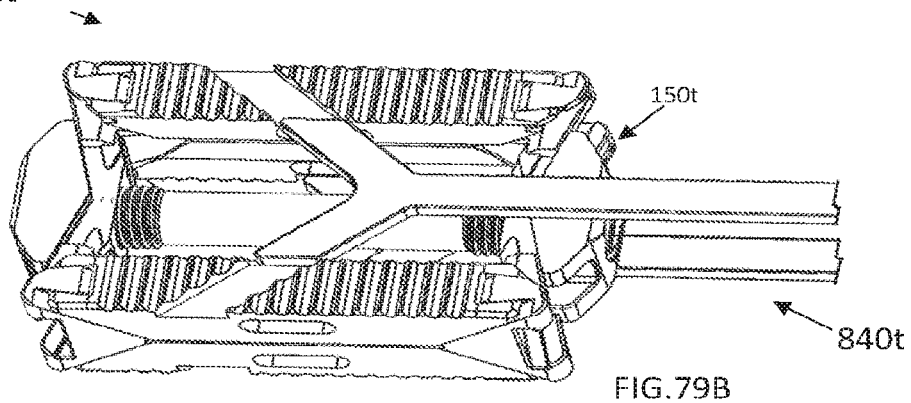

FIG. 79B depicts a perspective view of an exemplary sixteenth expandable fusion device attached to the inserter-expander instrument in the fully width expanded state.

Figure 80:
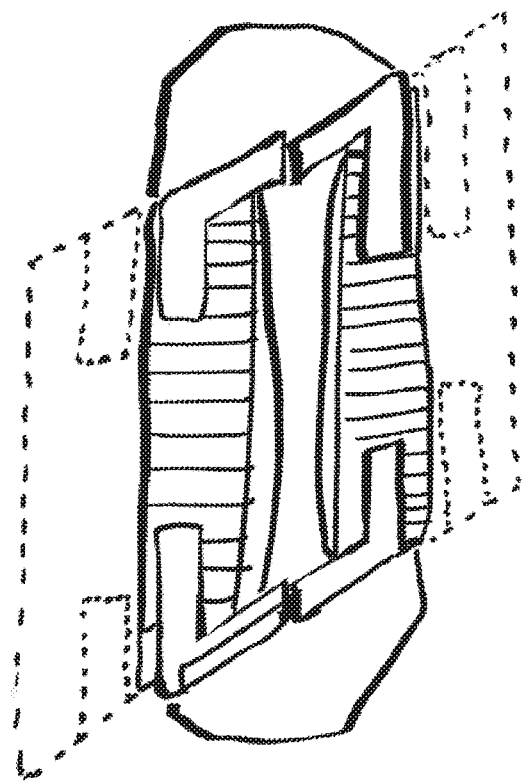

FIG. 80 depicts a top schematic view of an exemplary seventeenth expandable fusion device outlining its initial and width expanded configurations.

Figure 81A:
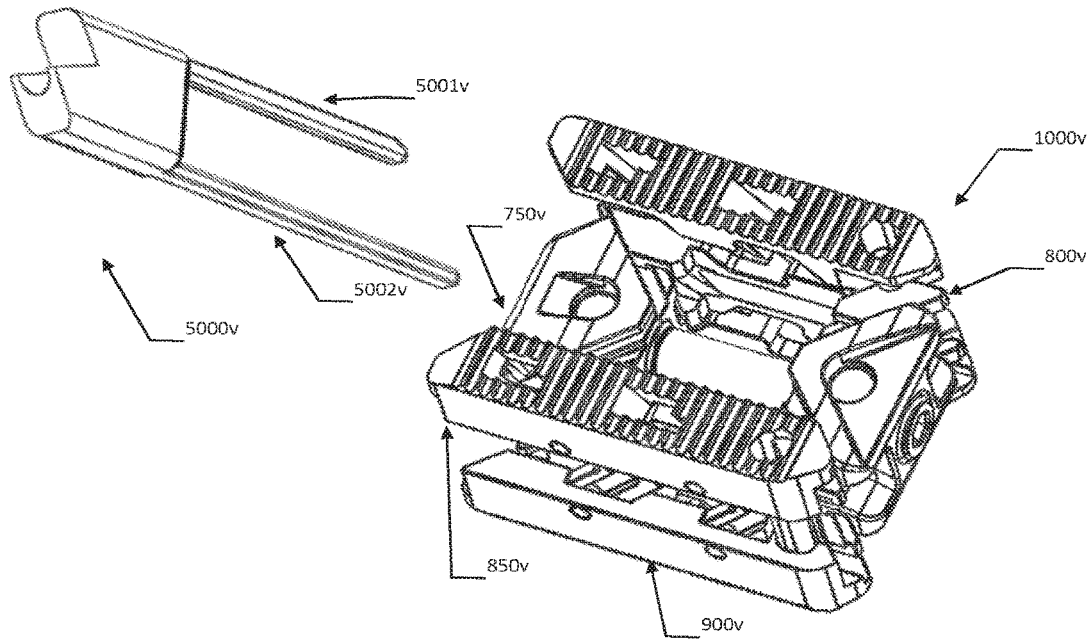

FIG. 81A depicts a perspective view of an exemplary eighteenth expandable fusion device in its expanded state.

Figure 81B:
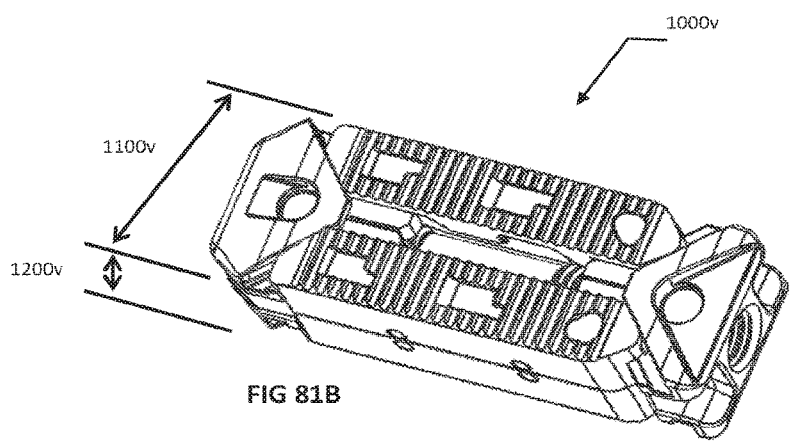

FIG. 81B depicts a perspective view of an exemplary eighteenth expandable fusion device in its collapsed state.

FIG. 81C depicts a perspective view of an exemplary eighteenth expandable fusion device in an exploded state.

Figure 82:
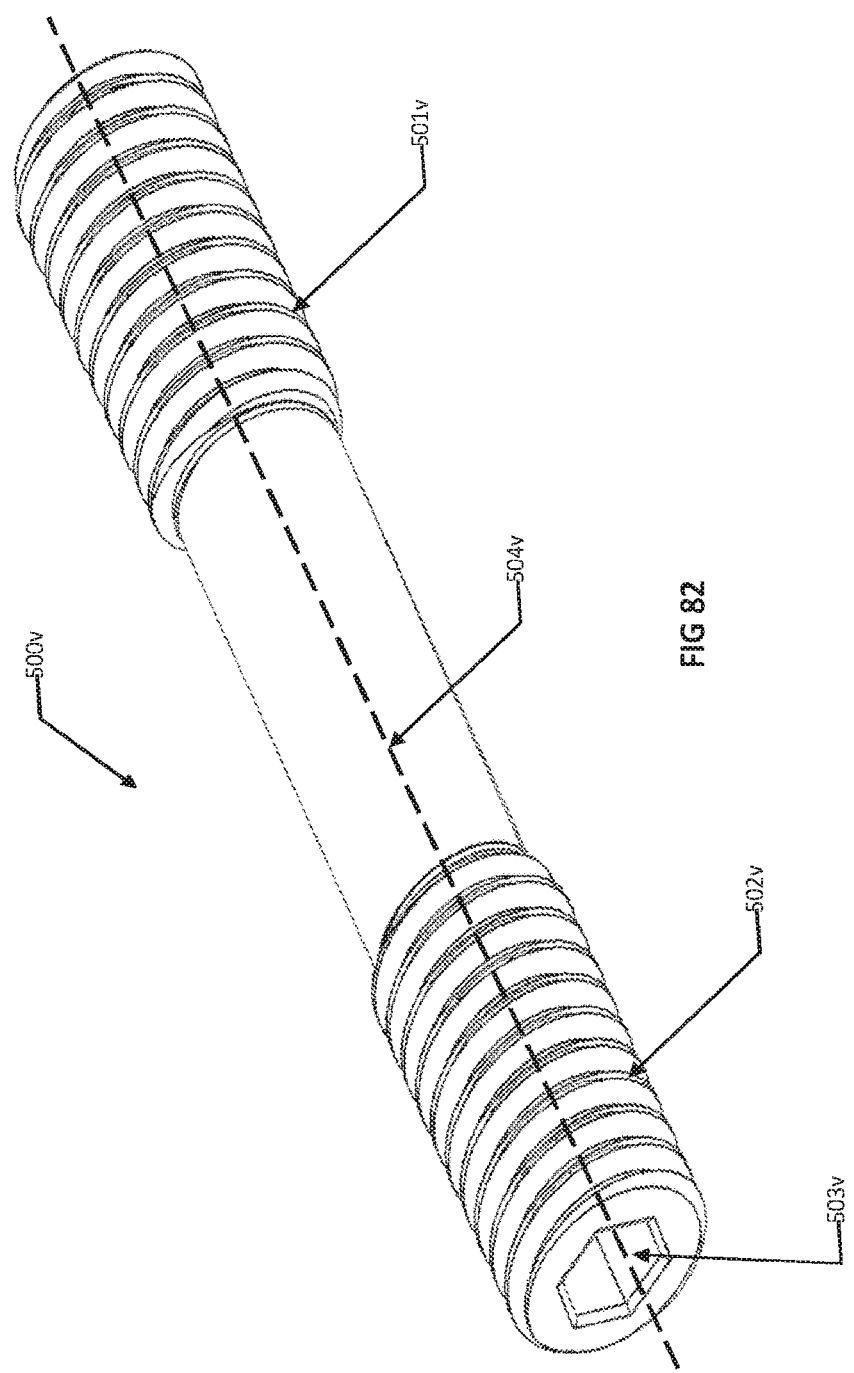

FIG. 82 depicts a perspective view of an exemplary actuator of the eighteenth expandable fusion device.

Figure 83A:
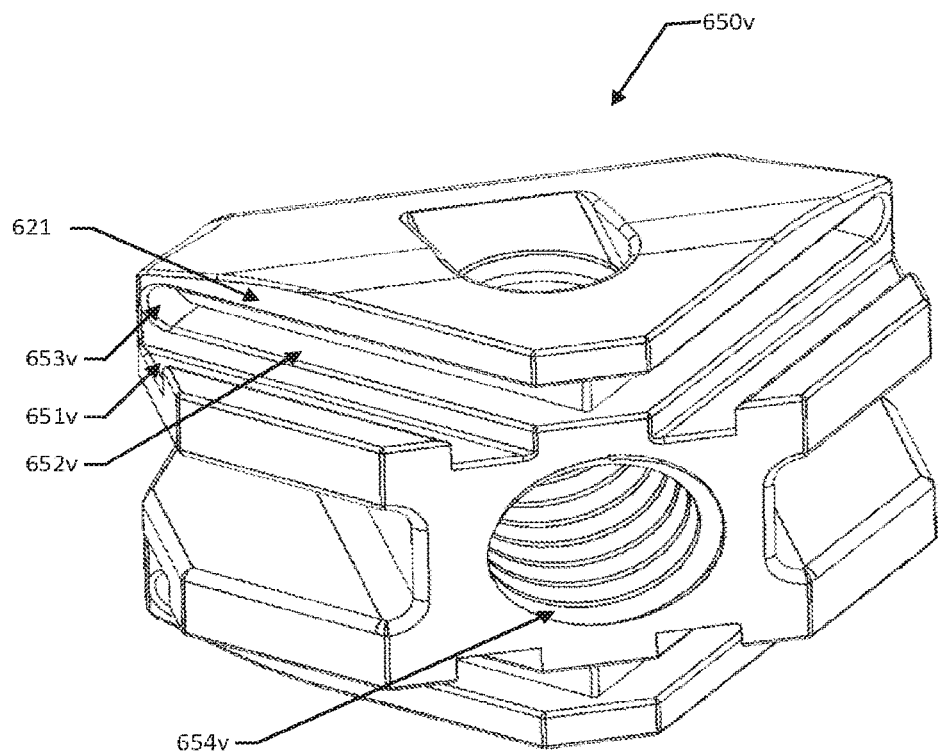

FIG. 83A depicts a perspective view of an exemplary proximal wedge of the eighteenth expandable fusion device.

Figure 83B:
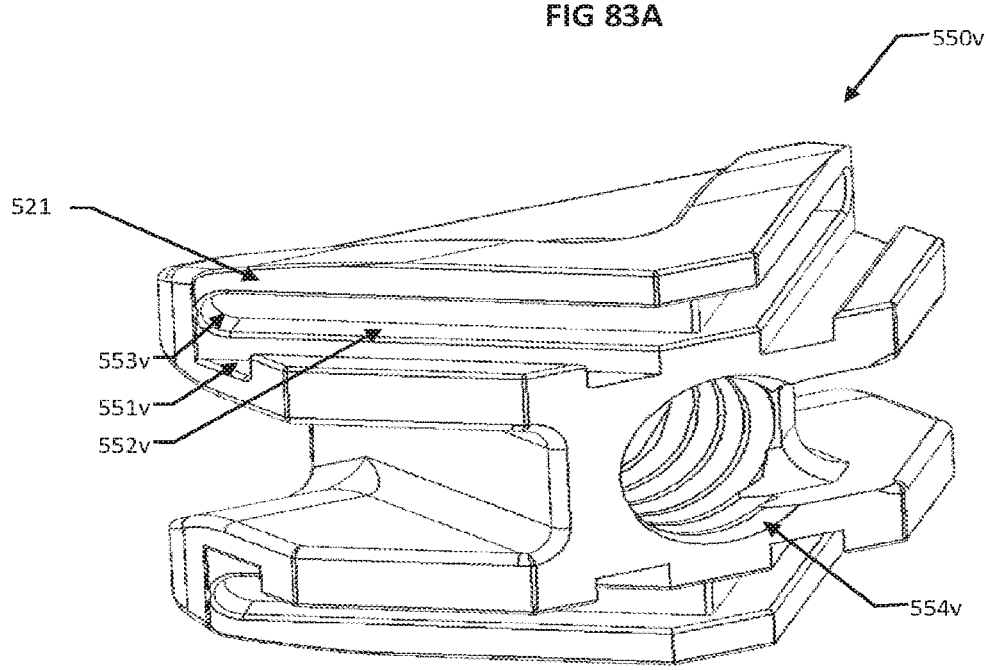

FIG. 83B depicts a perspective view of an exemplary distal wedge of the eighteenth expandable fusion device.

Figure 84A:
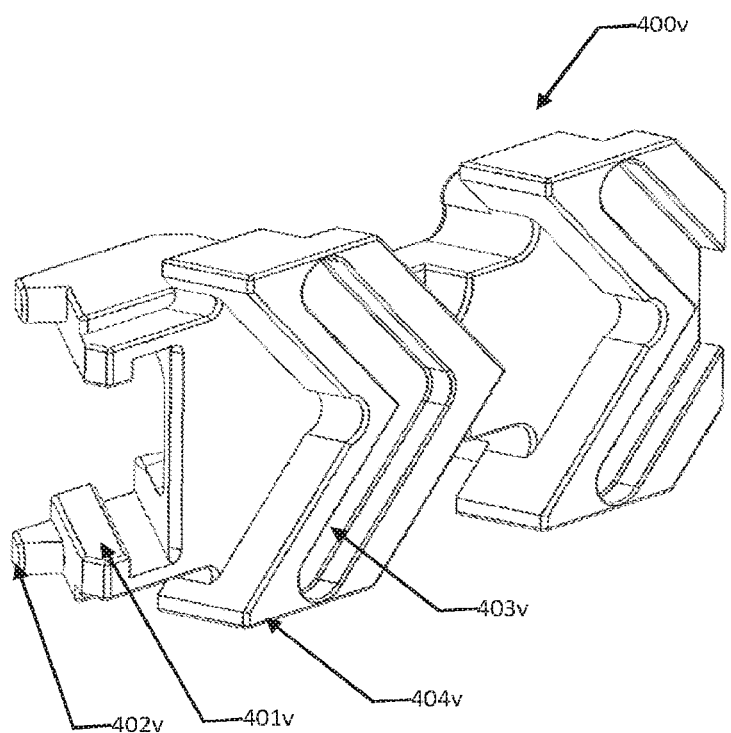

FIG. 84A depicts a first perspective view of an exemplary proximal ramp of the eighteenth expandable fusion device.

Figure 84B:
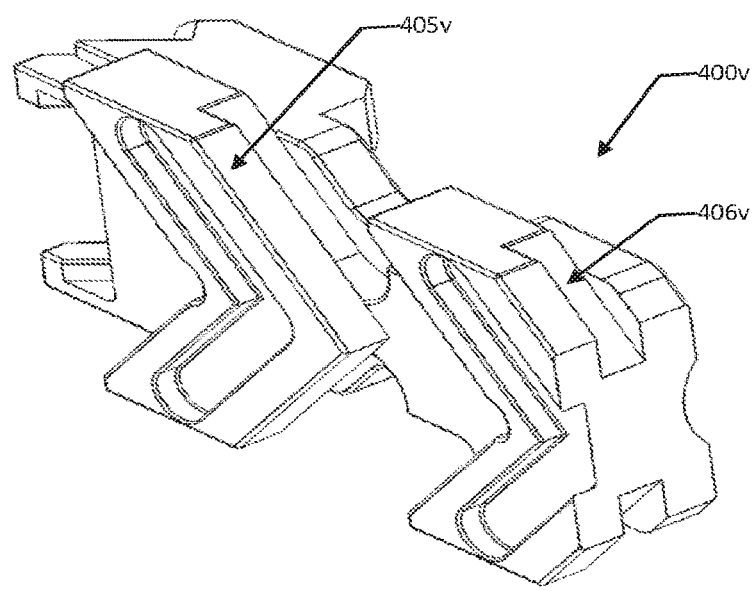

FIG. 84B depicts a second perspective view of an exemplary proximal ramp of the eighteenth expandable fusion device.

Figure 85:
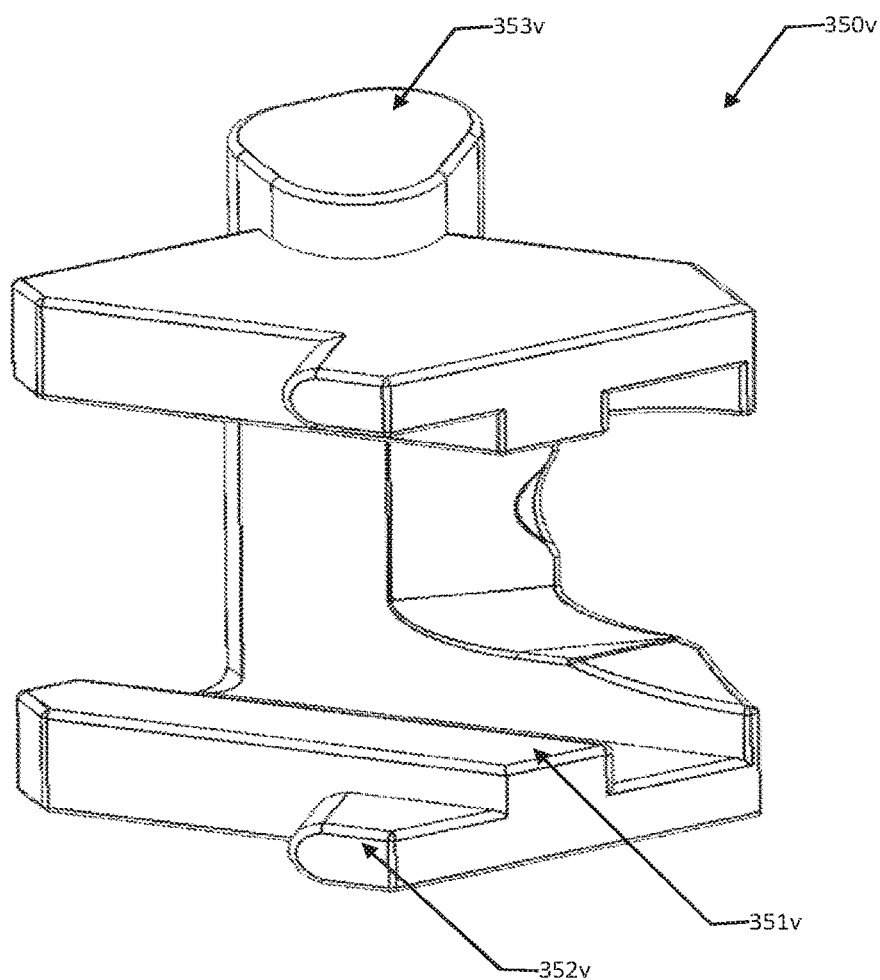

FIG. 85 depicts a perspective view of an exemplary distal ramp of the eighteenth expandable fusion device.

Figure 86:
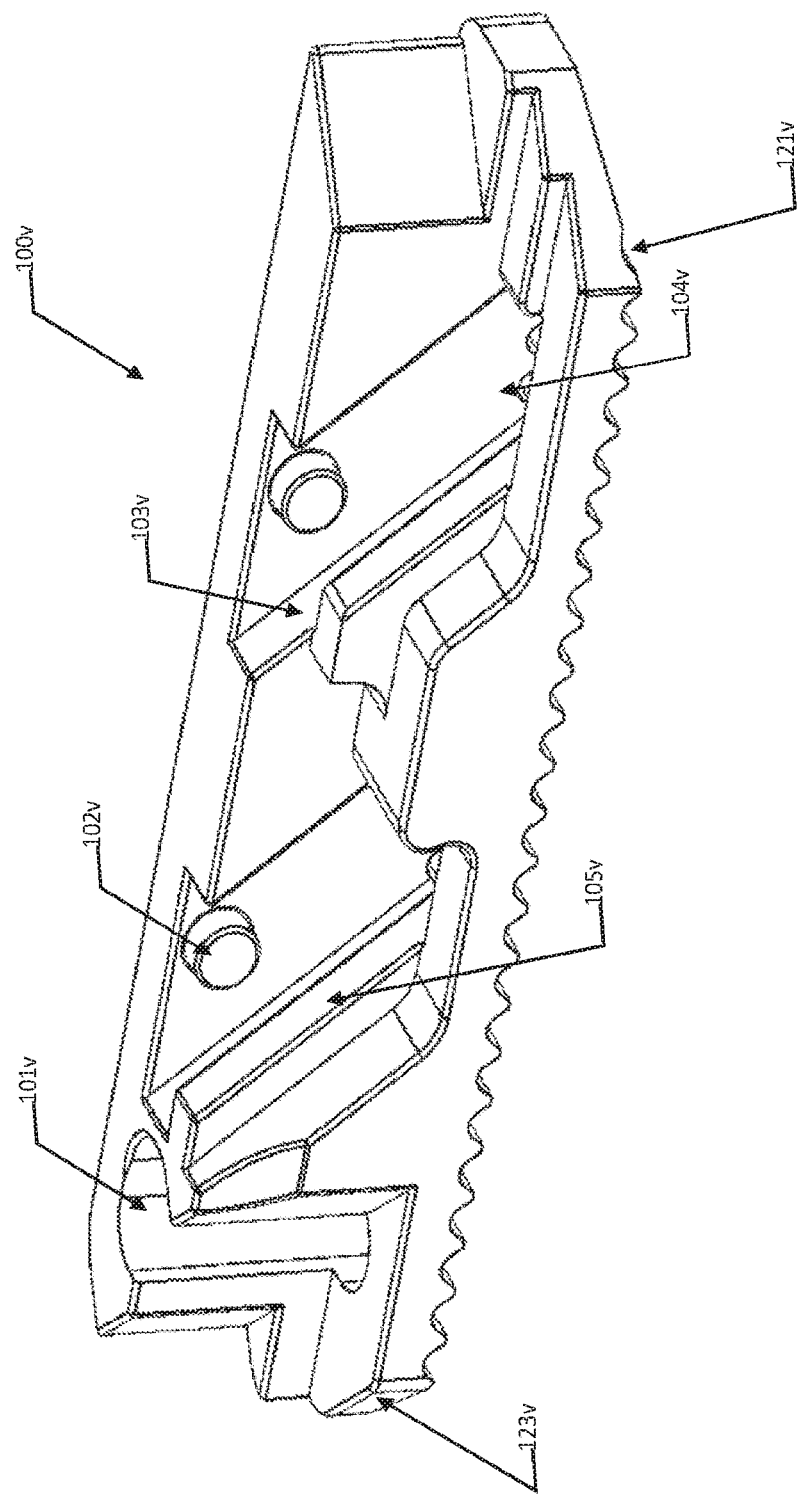

FIG. 86 depicts a perspective view of an exemplary endplate of the eighteenth expandable fusion device.

Figure 87A:
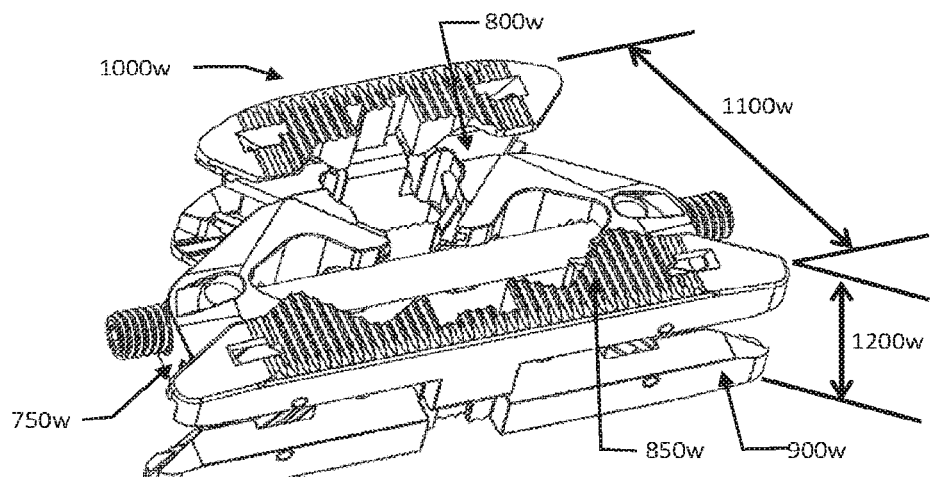

FIG. 87A depicts a perspective view of an exemplary nineteenth expandable fusion device in its expanded state.

Figure 87B:
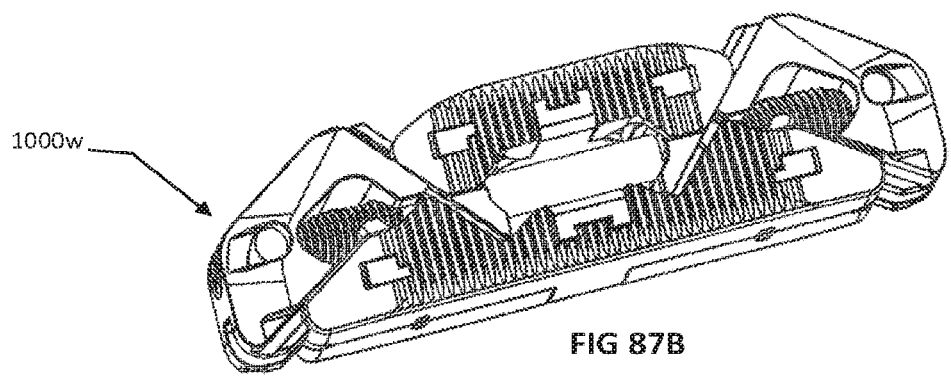

FIG. 87B depicts a perspective view of an exemplary nineteenth expandable fusion device in its collapsed state.

Figure 87C:
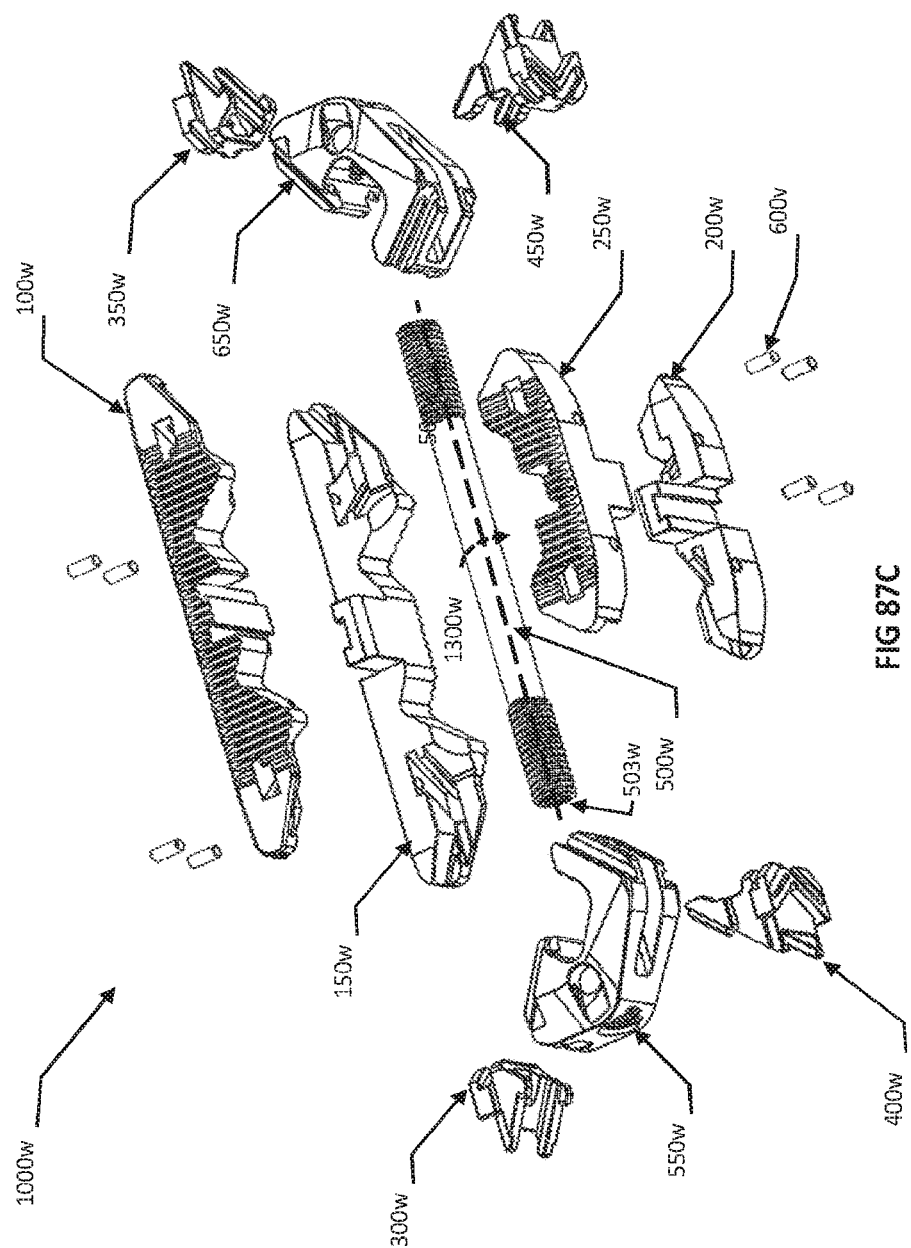

FIG. 87C depicts a perspective view of an exemplary nineteenth expandable fusion device in an exploded state.

FIG. 88 depicts a perspective view of an exemplary actuator of the nineteenth expandable fusion device.

Figure 89A:
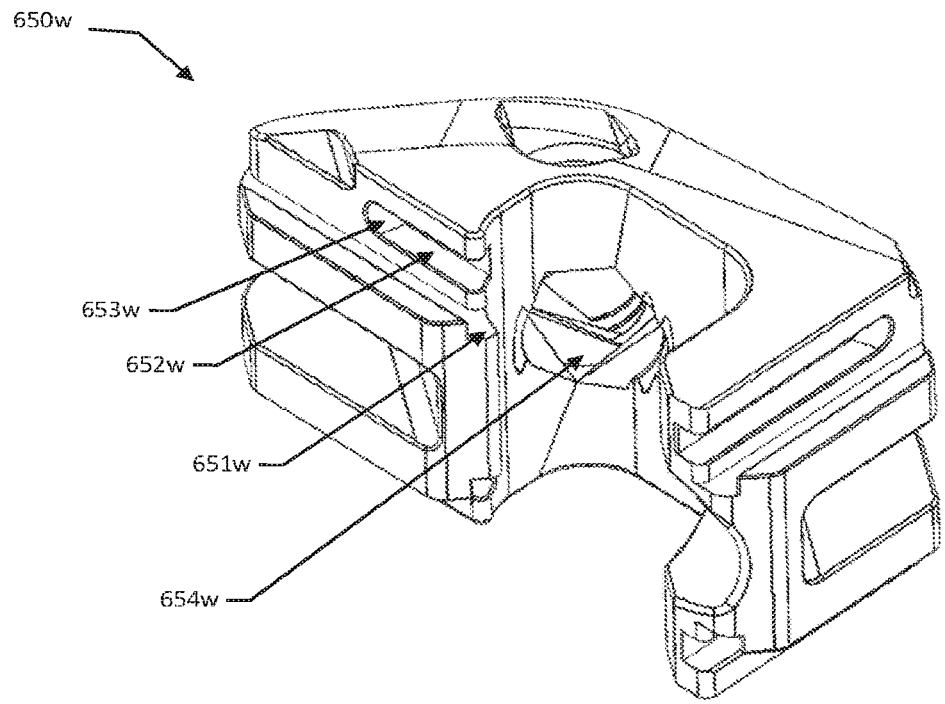

FIG. 89A depicts a perspective view of an exemplary distal wedge of an exemplary nineteenth expandable fusion device.

Figure 89B:
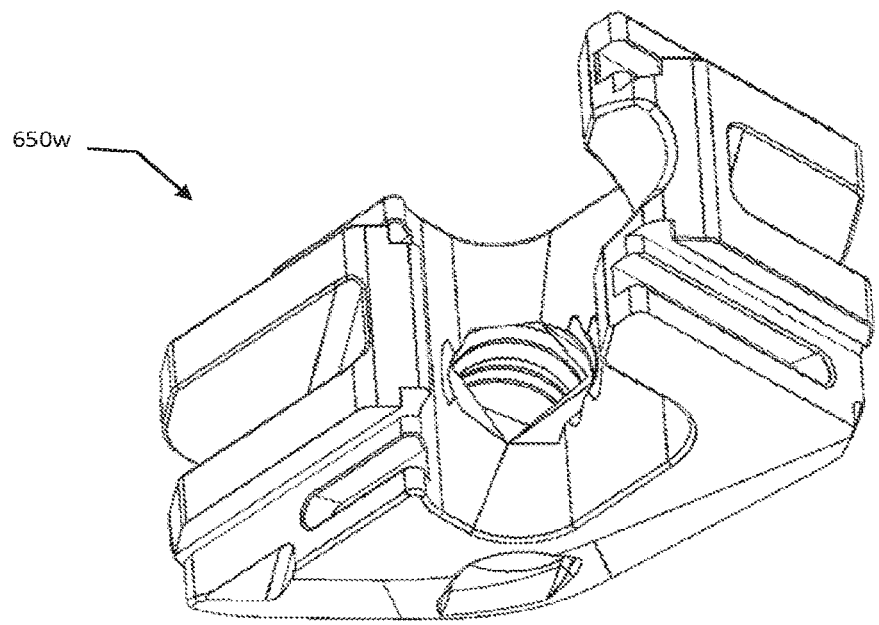

FIG. 89B depicts a perspective view of an exemplary distal wedge of an exemplary nineteenth expandable fusion device.

Figure 90A:
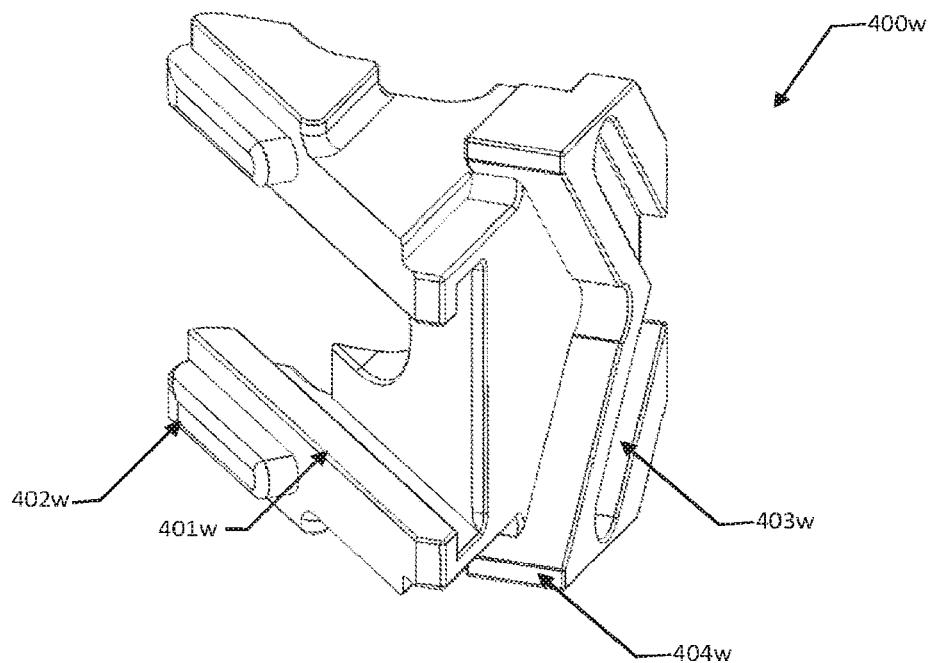

FIG. 90A depicts a perspective view of an exemplary first ramp of an exemplary nineteenth expandable fusion device.

Figure 90B:
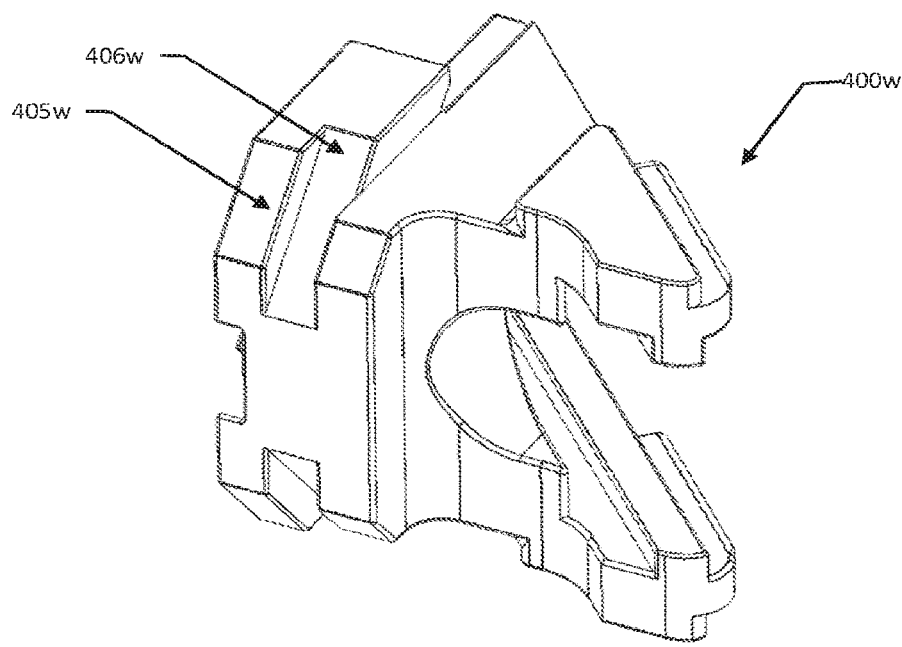

FIG. 90B depicts a perspective view of an exemplary first ramp of an exemplary nineteenth expandable fusion device.

Figure 91A:
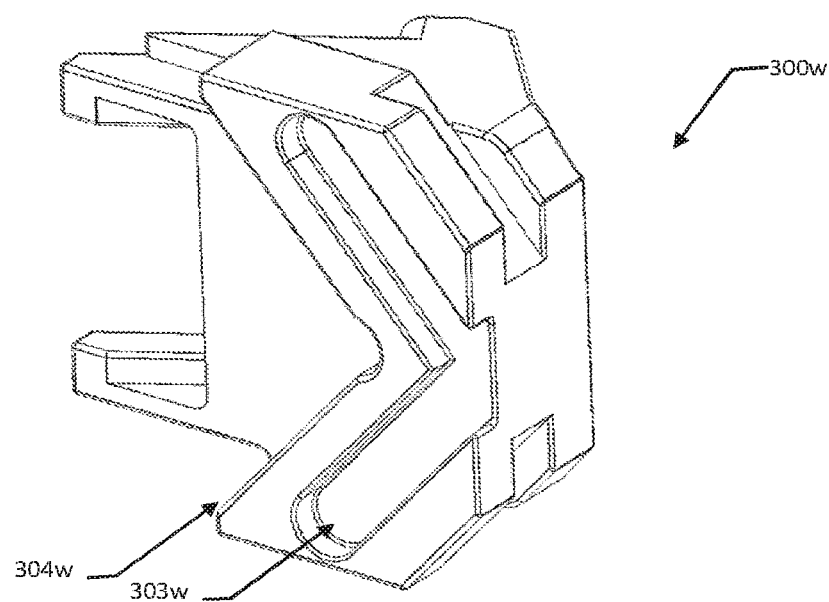

FIG. 91A depicts a perspective view of an exemplary second ramp of an exemplary nineteenth expandable fusion device.

Figure 91B:
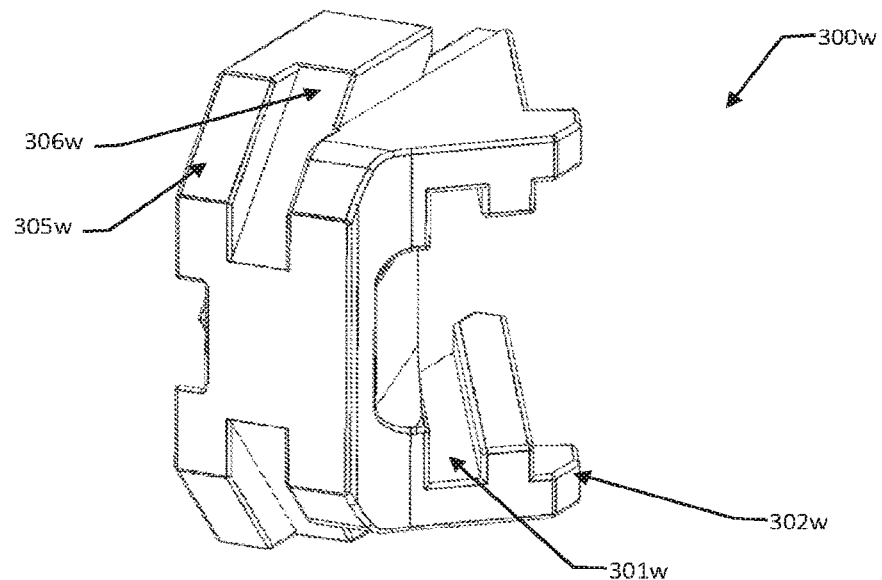

FIG. 91B depicts a perspective view of an exemplary second ramp of an exemplary nineteenth expandable fusion device.

Figure 92A:
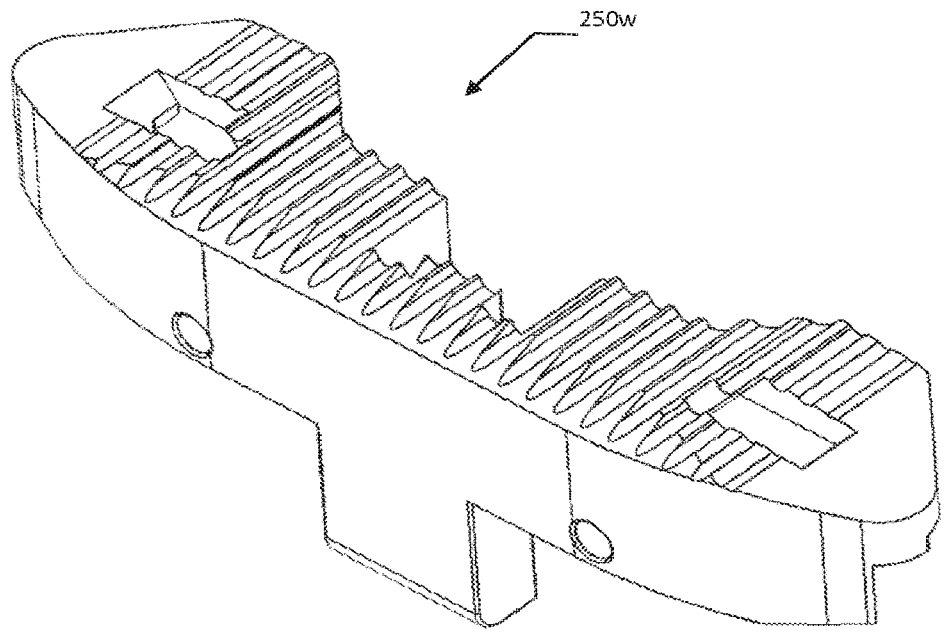

FIG. 92A depicts a perspective view of an exemplary first endplate of an exemplary nineteenth expandable fusion device.

Figure 92B:
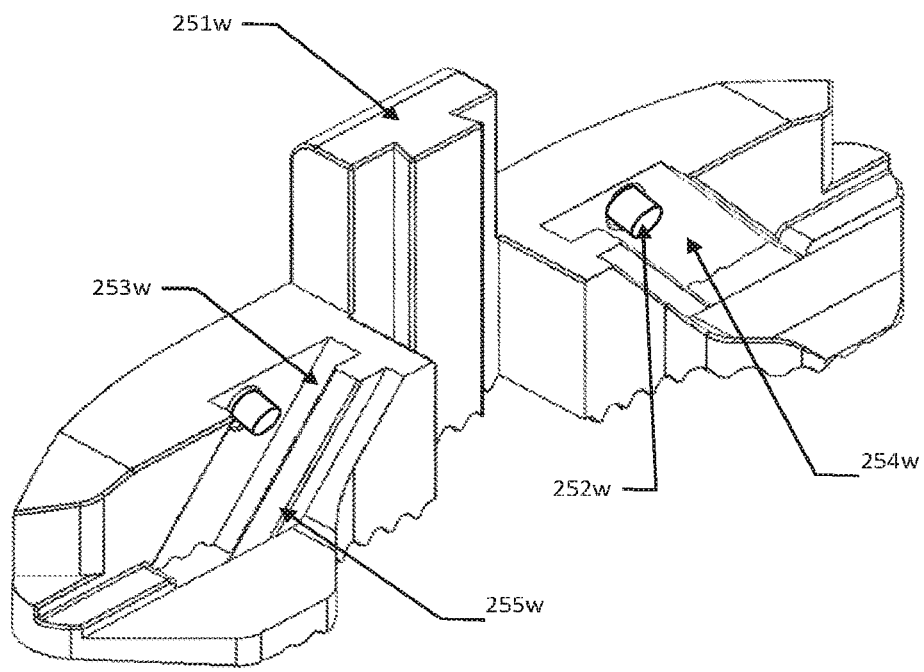

FIG. 92B depicts a perspective view of an exemplary first endplate of an exemplary nineteenth expandable fusion device.

Figure 93A:
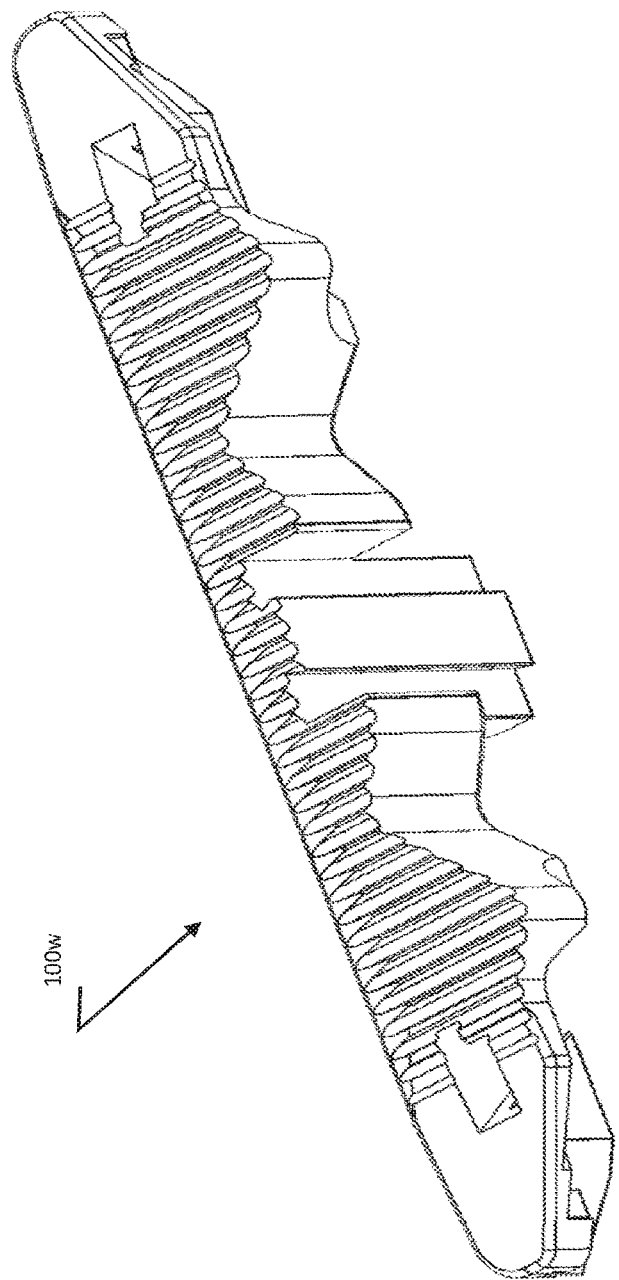

FIG. 93A depicts a perspective view of an exemplary second endplate of an exemplary nineteenth expandable fusion device.

Figure 93B:
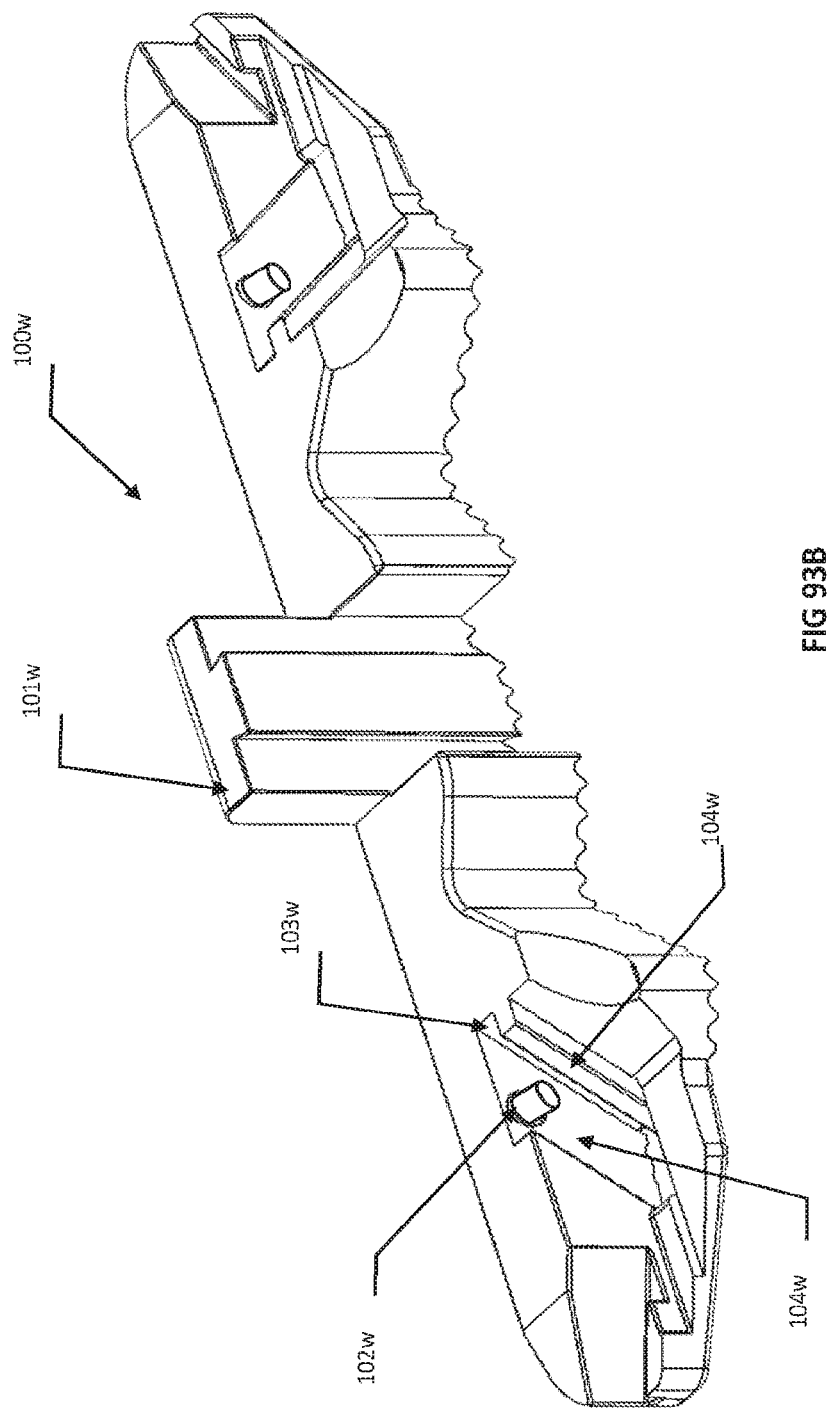

FIG. 93B depicts a perspective view of an exemplary second endplate of an exemplary nineteenth expandable fusion device.

Figure 94A:
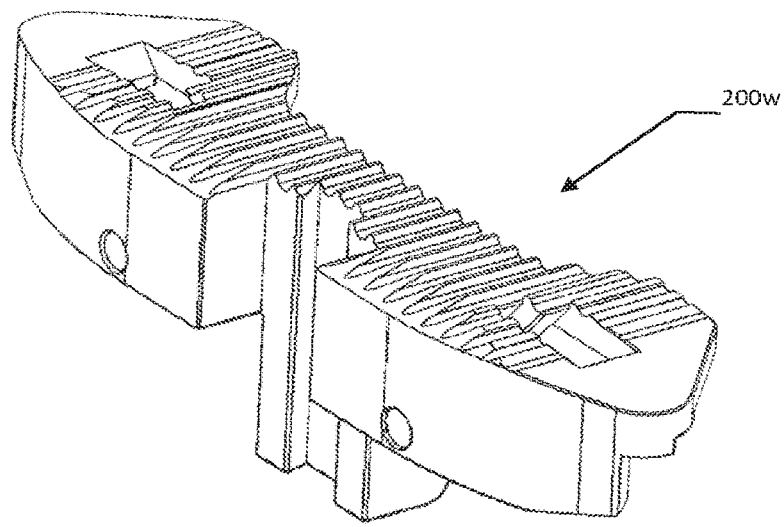

FIG. 94A depicts a perspective view of an exemplary third endplate of an exemplary nineteenth expandable fusion device.

Figure 94B:
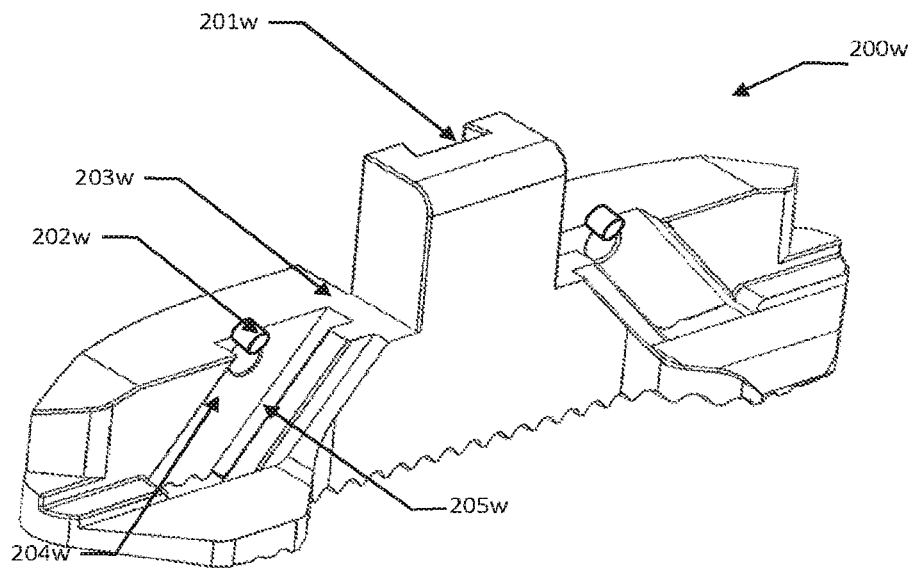

FIG. 94B depicts a perspective view of an exemplary third endplate of an exemplary nineteenth expandable fusion device.

FIG. 95A depicts a perspective view of an exemplary fourth endplate of an exemplary nineteenth expandable fusion device.

FIG. 95B depicts a perspective view of an exemplary fourth endplate of an exemplary nineteenth expandable fusion device.

Figure 96A:
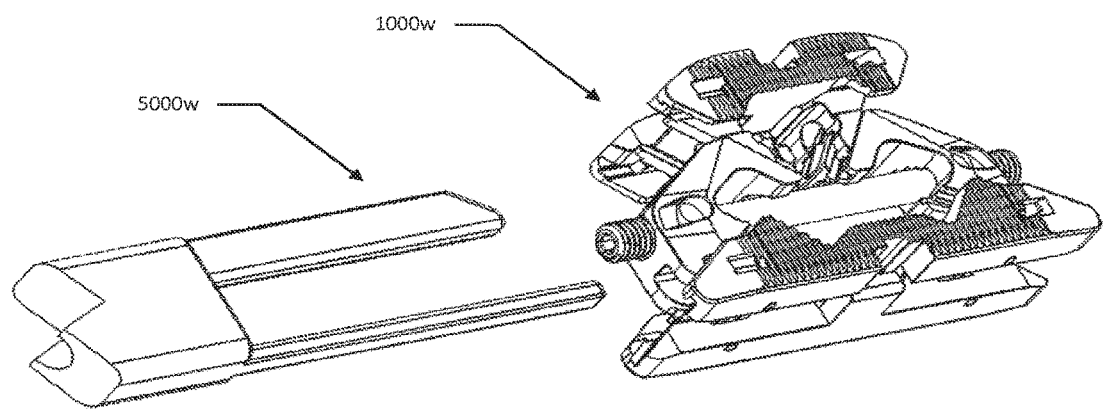

FIG. 96A depicts a perspective view of an exemplary nineteenth expandable fusion device and an exemplary separated inserter tool.

Figure 96B:
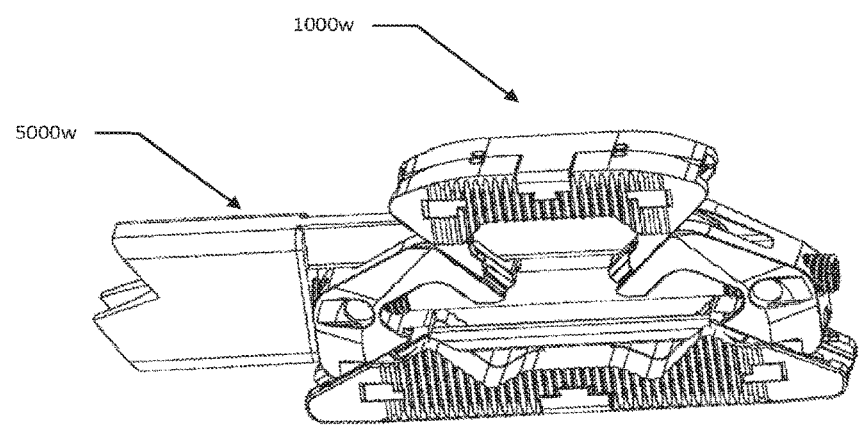

FIG. 96B depicts a perspective view of an exemplary nineteenth expandable fusion device and an exemplary adjoined inserter tool.

Figure 97:
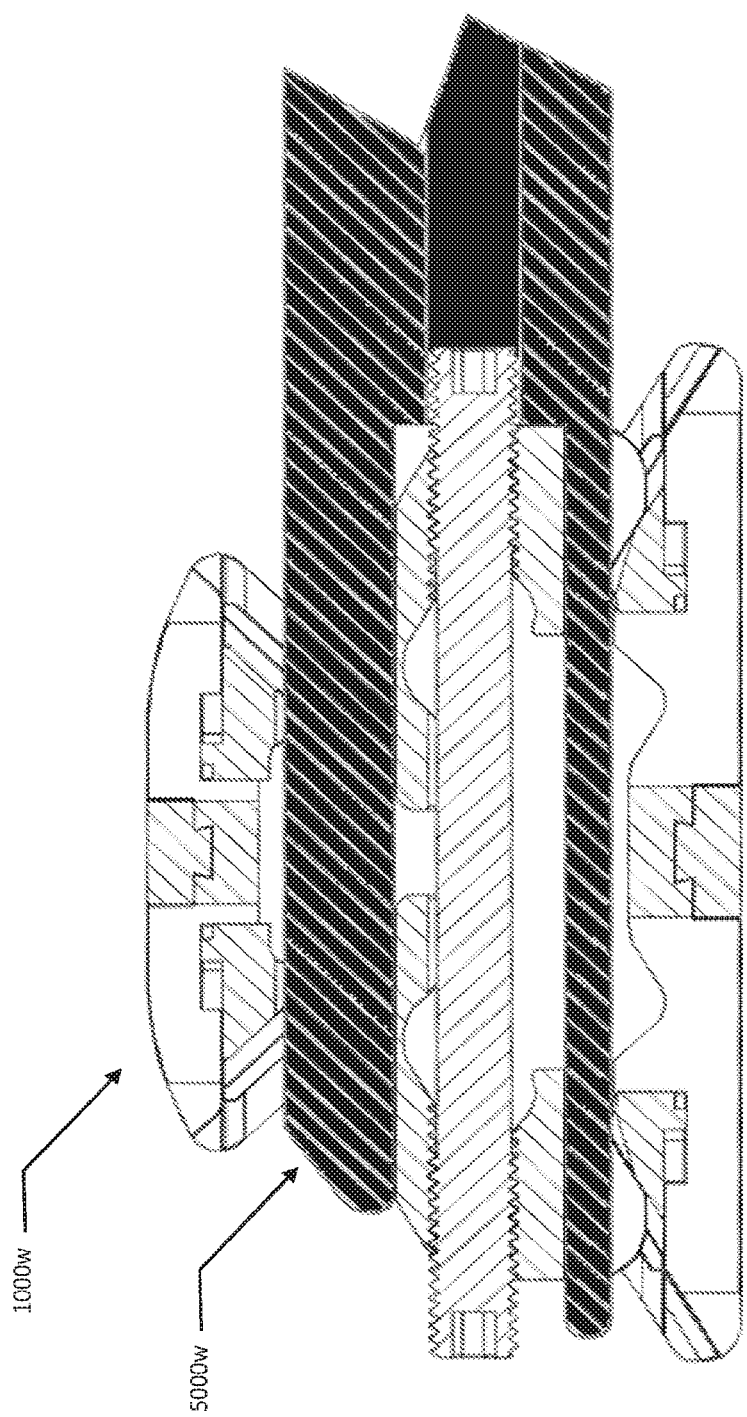

FIG. 97 depicts a cross sectioned view of an exemplary nineteenth expandable fusion device and an exemplary adjoined inserter tool.

Figure 98A:
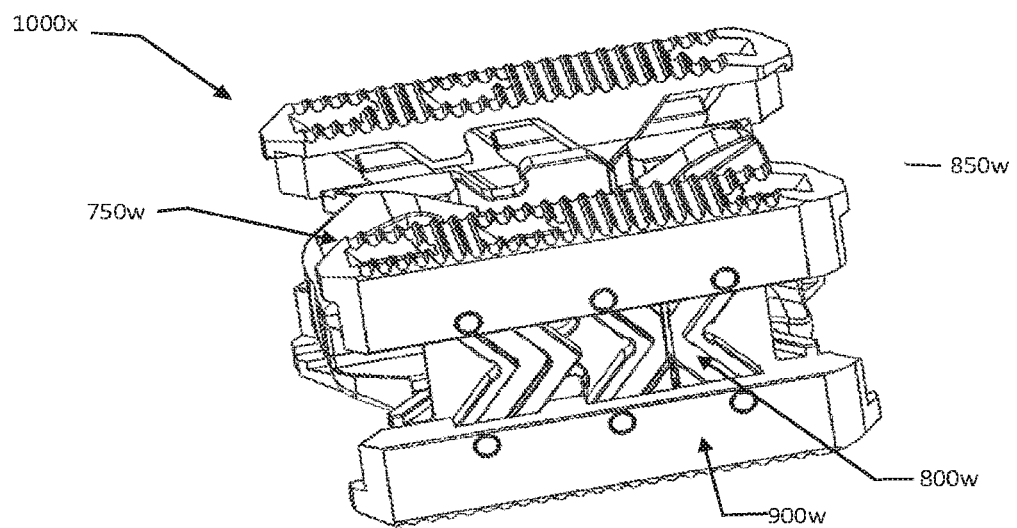

FIG. 98A depicts a perspective view of an exemplary twentieth expandable fusion device in its collapsed state.

Figure 98B:
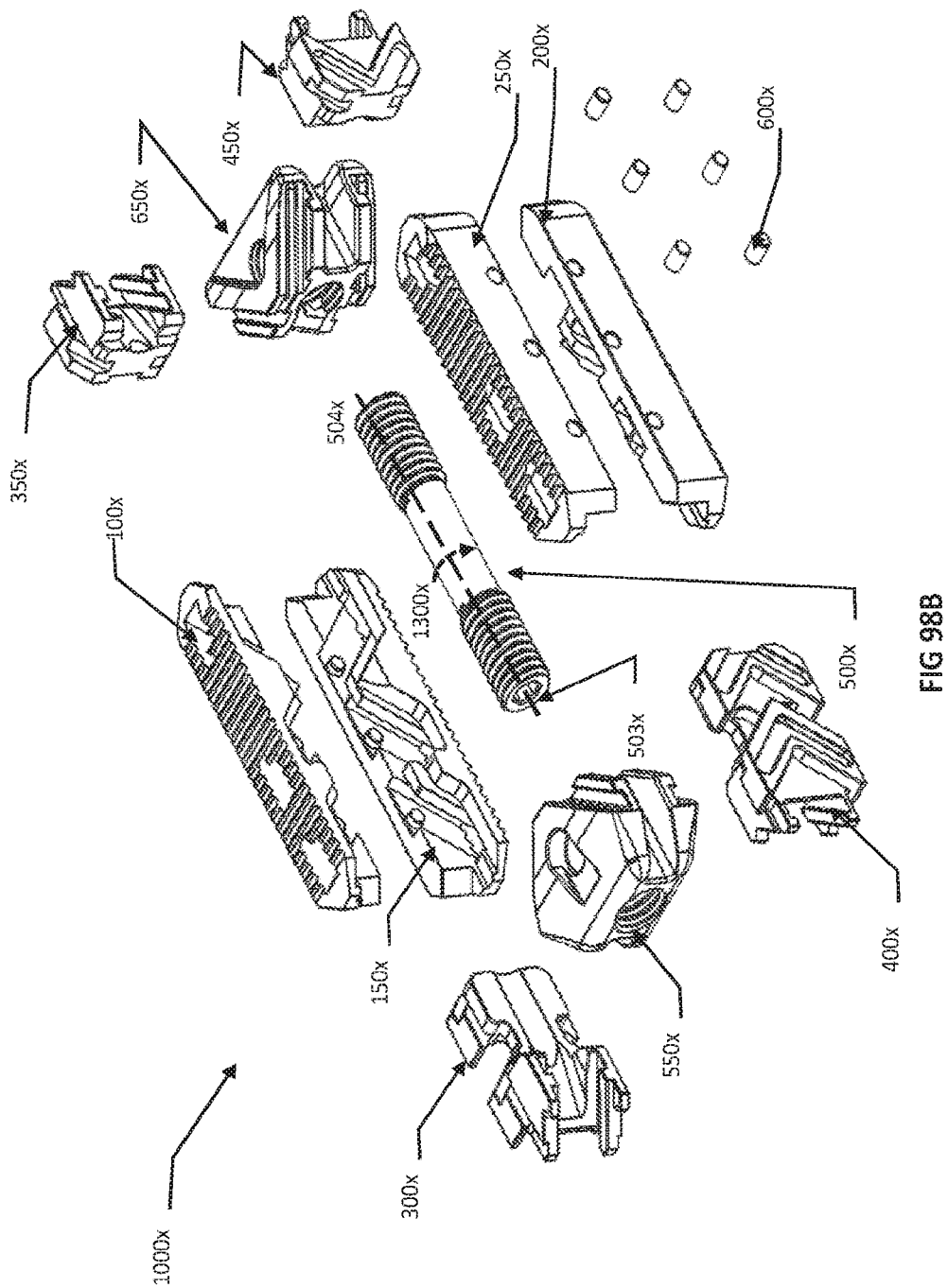

FIG. 98B depicts a perspective view of an exemplary twentieth expandable fusion device in an exploded state.

Figure 99:
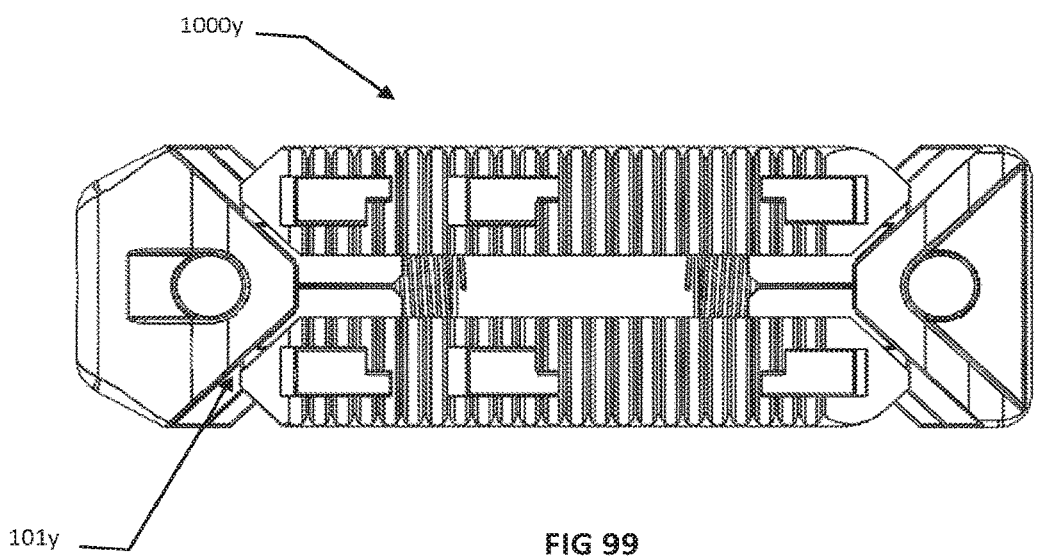

FIG. 99 depicts a top view of an exemplary twenty-first expandable fusion device.

DETAILED DESCRIPTION

The following description of the various embodiments is merely exemplary in nature and is in no way intended to limit the teachings, their applications, or uses. While the following description is directed generally towards embodiments of the expandable fusion device and method for its implantation between two adjacent lumbar vertebrae using a lateral, posterior and transforaminal approaches to spine, it would be appreciated that similar mechanisms and arrangements of the same are also used in treatment of cervical, thoracic and sacral spine segments, utilizing other surgical approaches including but not limited to transpedicular, transiliac, anterior and anterior-lateral approaches and configured to interface with respective anatomies and approach angles. Similarly, while the following description is directed generally towards embodiments of the expandable fusion device in which an actuator draws wedges together to cause expansion, it would be appreciated that in other embodiments the same functionality can easily be achieved through actuator forcing the wedges apart. A spinal fusion is typically employed to eliminate pain caused by the motion of degenerated disk material. Upon successful fusion, a fusion device becomes permanently fixed within the intervertebral disc space.

First Expandable Fusion Device

Figure 1:
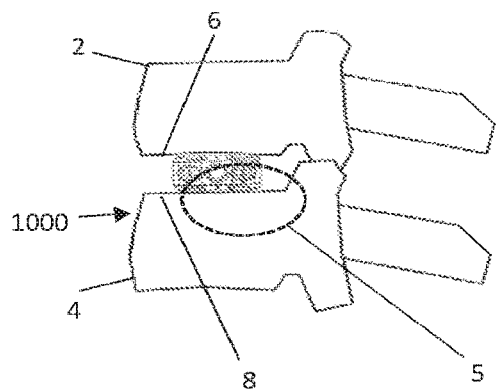
FIG. 1 depicts an exemplary first expandable fusion device implanted between two vertebral bodies in initial collapsed state.

An exemplary embodiment of a first expandable fusion device 1000 is shown, per FIG. 1, in an initial collapsed state implanted between endplates 6 and 8 of adjacent vertebral bodies 2 and 4 through a surgical corridor 5. Implanting the first expandable fusion device 1000 in the initial collapsed state reduces the impaction force and the size of the surgical corridor 5 required for implantation. Per FIG. 2, the first expandable fusion device 1000 is shown in an expanded state (expanded in both width and height) implanted between adjacent vertebral bodies 2 and 4 through the surgical corridor 5 and engaging the endplates 6 and 8. The first expandable fusion device 1000 expands in height from about 8 mm to about 13 mm or more preferably from 8 mm to 16 mm or most preferably from 7 mm to 14 mm and in width from about 10 mm to about 18 mm and more preferably from about 11 mm to about 20 mm and more preferably from about 14 mm to about 24 mm or most preferably from about 15 mm to about 26 mm. The first expandable fusion device 1000 will preferably be longer than it is wide in its initial collapsed state and the endplates will preferably be longer than they are wide. Expanding the fusion device 1000 while implanted between the vertebral bodies 2 and 4 allows an increase in the width of the fusion device 1000 and the spacing or contact area (or foot-print) between the fusion device 1000 and the endplates 6 and 8 beyond that, which would otherwise be allowed by the surgical corridor 5 as well as application of distraction forces to the endplates 6 and 8 in order to preferably increase and maintain the distance and/or angle between the vertebral bodies 2 and 4, by increasing and maintaining the height of the implant and/or the angular orientation of its components.

The components of the first expandable fusion device 1000 may be made out of a variety of materials including but not limited to metals and alloys (e. g. Commercially Pure Titanium, Titanium alloys including Ti-6Al-4V based allows, Cobalt alloys including CoCrMo alloys, Stainless steel, Tantalum and its alloys, Platinum and its alloys, etc.), polymers (e. g. PEEK, PEKK, PEKEK, PEI, PET, PETG, UHMWPE, PPSU, Acetal, Polyacetal, etc. including carbon fiber reinforced varieties and other varieties filled, for example, with Carbon Fiber, Carbon nano-tubes, Graphene, Barium Sulfate or Hydroxyapatite), ceramics (e. g. Aluminum Oxide, Zirconium oxide, Silicon nitride, diamond-like carbon, etc. as well as various metalized ceramics an metal-ceramic composites). Optionally, in any embodiment, the components of the fusion device 1000 are manufactured out of a Titanium alloy (including but not limited to Ti-6Al-4V alloys) or a Cobalt alloy including but not limited to CoCrMo alloys. Optionally, in any embodiment, manufacturing some of the threaded components of the fusion device 1000 out of a CoCr-based alloy allows for increased strength, reduced size, and other performance considerations.

Optionally, in any embodiment, bone allograft, bone autograft, xenogaft, demineralized bone matrix product, synthetic bone substitute, bone morphogenic agents, or other bone growth inducing material are introduced within and/or around the fusion device 1000 to further promote and facilitate the intervertebral fusion. In one embodiment, the fusion device 1000 is preferably packed or injected with bone graft, demineralized bone matrix product, synthetic bone substitute, bone morphogenic agents, or other bone growth inducing material after it has been expanded, but in other embodiments, the graft material may also be introduced into the space within or around the fusion device 1000 prior to implantation or after the implantation but prior to expansion.

Figure 3:
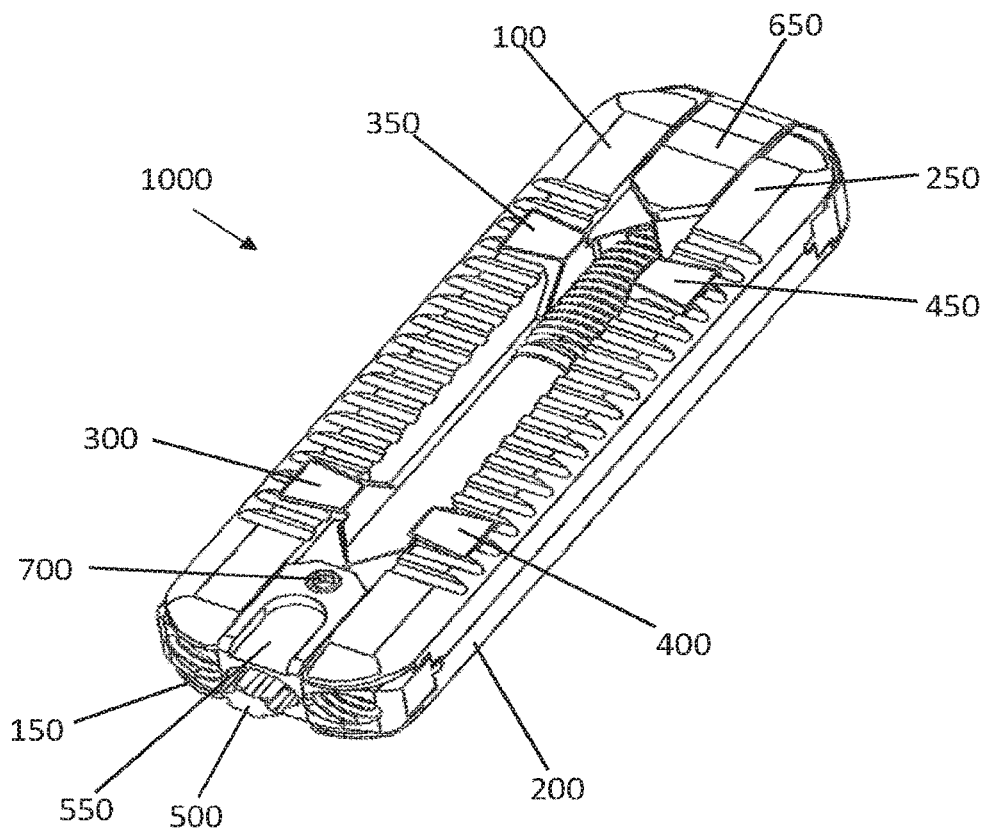
FIG. 3 depicts a perspective view of an exemplary first expandable fusion device in its initial collapsed state.
Figure 4:
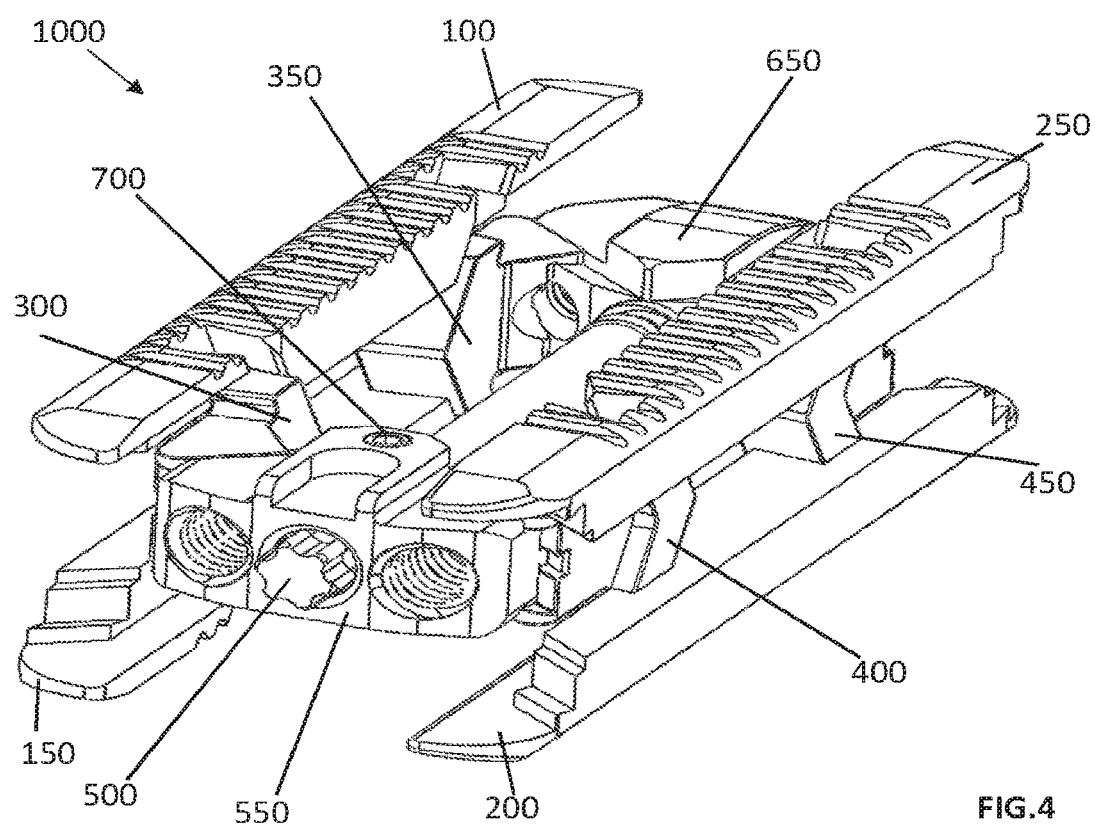
FIG. 4 depicts a perspective view of an exemplary first expandable fusion device in its fully expanded state.
Figure 5:
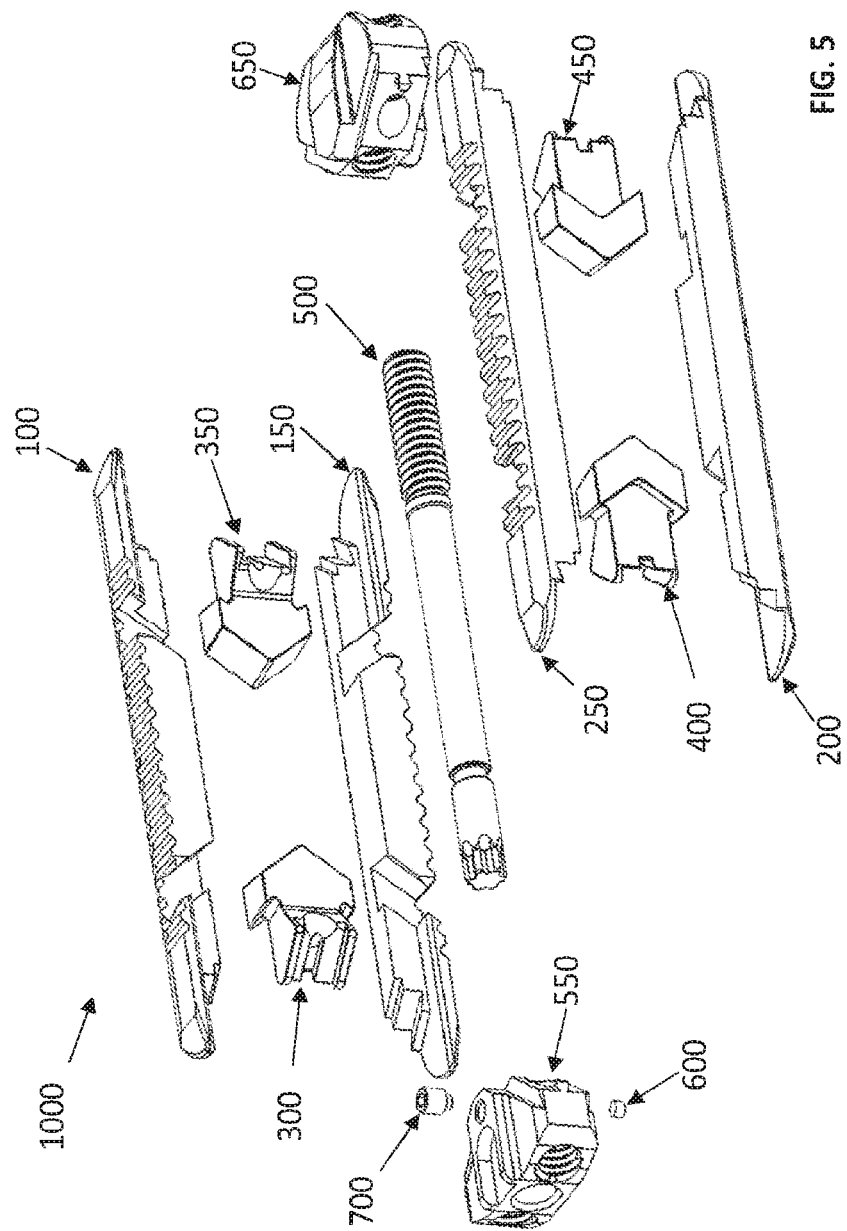
FIG. 5 depicts an exploded view of an exemplary first expandable fusion device.

With reference to FIGS. 3-5, an exemplary fusion device 1000 is shown. FIG. 3 shows the fully collapsed state of the fusion device 1000. FIG. 4 shows an expanded state of the fusion device 1000. FIG. 5 shows an exploded view of the fusion device 1000. Optionally, in any embodiment, the fusion device 1000 includes a first endplate 100, a second endplate 150, a third endplate 200, a fourth endplate 250, a proximal wedge 550, a distal wedge 650, an actuator 500, a first ramp 300, a second ramp 350, a third ramp 400, a fourth ramp 450, a retaining pin 600 (best seen in FIG. 5) and a retaining set screw 700. Optionally, in any embodiment, the first endplate 100, the second endplate 150, the third endplate 200, and the fourth endplate 250 are substantially identical, but although all four have the same set of features, the specific size and angular orientation of these features do not have to be identical in all embodiments or within any particular embodiment. Optionally, in any embodiment, the first ramp 300, the second ramp 350, the third ramp 400 and the fourth ramp 450 are substantially identical (it should be noted that the ramps, even while identical in an embodiment, may or need to be suitably rotated or mirrored to be assembled into arrangements shown in FIGS. 3-5), but although all four have the same set of features, the specific size and angular orientation of these features do not have to be identical in all embodiments or within any particular embodiment. Furthermore, the effects of the endplates, the ramps and the wedges having their ramped surfaces inclined at different angles on the expansion characteristics of the fusion device 1000 is illustrated in further detail below.

As will be discussed in more detail below, the actuator 500 functions, to pull the proximal wedge 550 and distal wedge 650 together forcing the first ramp 300 away from the third ramp 400 and also forcing the second ramp 350 away from the fourth ramp 450, which causes the endplates 100 and 150 to be forced away from the endplates 250 and 200 (resulting in width expansion of the fusion device 1000). Optionally, in any embodiment, only after the width expansion is substantially complete, the first ramp 300 and the second ramp 350 are pulled toward each other and the third ramp 400 and the fourth ramp 450 are pulled toward each other. The movement of the first ramp 300 and the second ramp 350 toward each other forces the first endplate 100 away from the second endplate 150 and the movement of the third ramp 400 toward the fourth ramp 450 forces the third endplate 200 away from the fourth endplate 250 (resulting in height expansion). The retaining pin 600 and the retaining set screw 700 act in an embodiment to resist the tension in the actuator 500 and maintaining the linear position of the proximal wedge 550 relative to the actuator 500. Optionally, in any embodiment, a sub-assembly comprising the actuator, the proximal wedge, the distal wedge, and the four ramps are collectively referred to as the actuator assembly.

Optionally, in any embodiment, the ramps 300 and 350 and the ramps 400 and 450 only start moving toward each other after the width expansion has substantially taken place and the ramps 300 and 400 have substantially reached the limit of their travel relative to the proximal wedge 550 and the ramps 350 and 450 have substantially reached the limit of their travel relative to the distal wedge 650. Optionally, in any embodiment, this delay in height expansion is achieved through the endplates 100, 150, 200, 250 being slidably engaged with proximal wedge 550 and the distal wedge 650 through an initial portion of width expansion process. During the width expansion process, as the wedges 550 and 650 move toward each other, they eventually disengage from endplates 100, 150, 200, 250 and allow them to expand in height as will be discussed below. Optionally, in any embodiment, the delay in height expansion is further accomplished by means of an inserter instrument constraining the height expansion until the width expansion has substantially taken place as will be discussed below.

When fully assembled, the first expandable fusion device 1000 is most preferably, a stable assembly of components that are all detained within the assembly throughout its full range of motion by means of "dove-tailed" articulations, the use of fasteners such as, for example, pins, balls, screws, and set screws. Optionally, in any embodiment, the fasteners are affixed in one component and travel in a mating feature (such as a track) of another component thereby limiting the range of motion of the first component to the amount permissible by the track feature thereby preventing the components from disassembly.

With reference to FIGS. 6A-6F, FIGS. 6A and 6B show side and end views respectively of the fusion device 1000 in an initial fully collapsed state, FIGS. 6C and 6D show side and end views respectively of the fusion device 1000 in a fully expanded width state and FIGS. 6E and 6F show side and end views respectively of the fusion device 1000 in fully expanded width and height state.

FIGS. 7A-7C illustrate a mechanism for delaying the height expansion until width expansion is partially or substantially complete. In FIG. 7A, the fusion device 1000 is shown in an initial collapsed state and demonstrates, as an example, the engagement of the proximal wedge 550 with mating features of the endplates 100 and 150, in this state, drawing the proximal wedge 550 and the distal wedge 650 together results in width expansion but not in height expansion of the fusion device 1000. Optionally, in any embodiment, per FIG. 7A, the engagement between the proximal wedge and the endplates prevents height expansion. Once width expansion occurs to a sufficient extent for the wedges to disengage from the mating features on the endplates (shown in FIG. 7B), the further drawing of the proximal wedge 550 and the distal wedge 650 together may result in either height only expansion (shown in FIG. 7C) or in simultaneous height and width expansion. Optionally, in any embodiment, FIG. 7B, the disengagement of the proximal wedge from the endplates allows height expansion. Optionally, in any embodiment, starting width is preferably 14 mm and the height expansion starts when the width reaches about 20 mm. Optionally, in any embodiment, the height expansion may start when full maximum or substantial (as discussed above) width is achieved. The delay in height expansion is achieved because in order for height expansion to take place, the pairs of ramps on either side of the fusion device 1000 have to translate toward each other relative to the endplates with which they are engaged. This cannot occur while the ramped surfaces of the wedges are simultaneously engaged with both the endplates and the ramps since the endplates are rigid and span the distance between the proximal wedge 550 and the distal wedge 650 and thereby only allow the width expansion until the state shown in FIG. 3C is reached, at which point the wedges are still engaged with the ramps but are no longer engaged with the endplates and drawing the wedges together from this point onward allows the ramps to move toward each other relative to the endplates resulting in height expansion. Detailed description of the components and their features is provided below.

Although the following discussion relates to the first endplate 100, it should be understood that it also equally applies to the second endplate 150, the third endplate 200 and the fourth endplate 250 as the first endplate 100 is substantially identical to the second endplate 150, the third endplate 200 and the fourth endplate 250 in this embodiment (note that the endplates, even while identical in an embodiment, may or need to be suitably rotated or mirrored to be assembled into arrangements shown above in the assemblies shown in FIGS. 3-5). The endplates 100 and 250 are collectively referred to as the upper endplate and the endplates 150 and 200 are collectively referred to as the lower endplate. It should also be understood that while the words "substantially identical" refer to the endplates 100, 150, 200 and 250 having the same or similar set of features, all of which features serving the same or similar function in each of the endplates 100, 150, 200 and 250 as described below, the specific size and angular orientation of these features may or may not be identical between the endplates 100, 150, 200 and 250 within any particular embodiment.

Figure 8A:
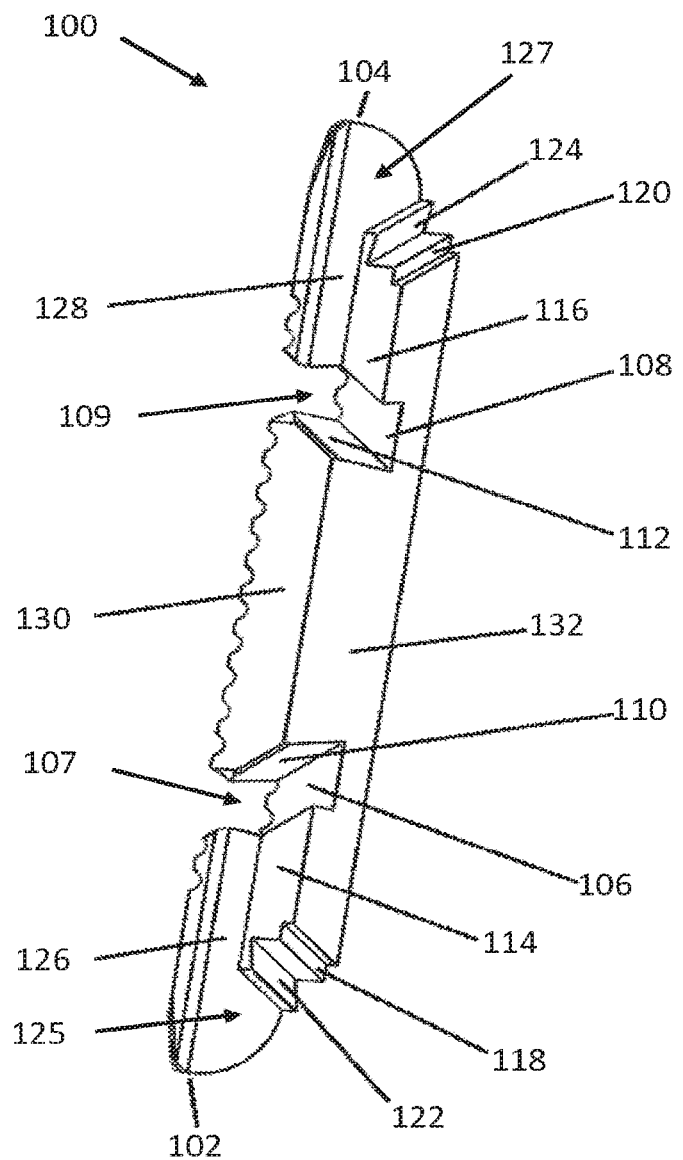
FIG. 8A depicts a bottom view of an exemplary endplate.
Figure 8B:
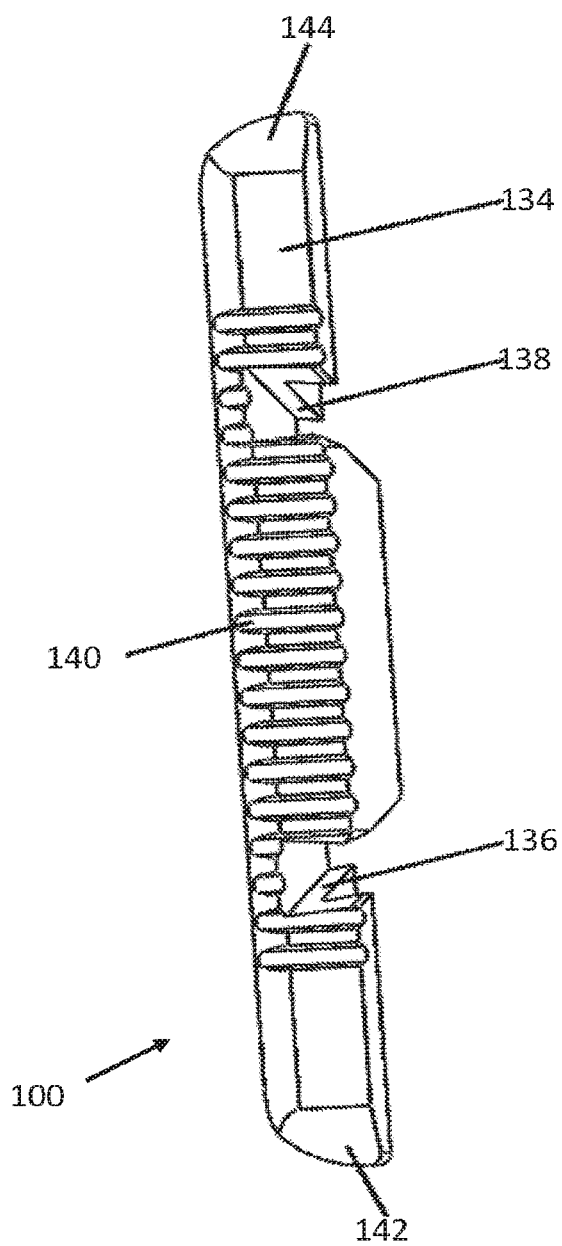
FIG. 8B depicts a top view of an exemplary endplate.

Turning now to FIGS. 8A and 8B showing respectively the bottom and the top views of the endplate 100. Optionally, in any embodiment, the first endplate 100 has a first end 102 and a second end 104. In the illustrated embodiment, the first endplate 100 further comprises an upper surface 134 connecting the first end 102 and the second end 104, and a lower surface 132 connecting the first end 102 and the second end 104. Optionally, in any embodiment, the first endplate 100 further comprises two tapered slots, a first tapered slot 107 proximate the first end 102, extending from the lower surface 132 toward the upper surface 134 and a second tapered slot 109 proximate the second end 104, extending from the lower surface 132 toward the upper surface 134. Optionally, in any embodiment, the slopes or shapes of the tapered slots 107 and 109 are equal or differ from each other.

The first tapered slot 107 comprises a bottom surface 106, which is substantially parallel to the long axis in an embodiment, but may also be angled or curved in the plane transverse to the long axis in other embodiments, a tapered surface 110 generally transverse to the bottom surface 106 and a tapered surface 136 opposite of the tapered surface 110 and generally transverse to the bottom surface 106, whereas the tapered surfaces 110 and 136 taper toward each other from bottom surface 106 and toward the inward surface 130. The second tapered slot 109 comprises a bottom surface 108, which is substantially parallel to the long axis in an embodiment, but may also be angled or curved in the plane transverse to the long axis in other embodiments, a tapered surface 138 generally transverse to the bottom surface 108 and a tapered surface 112 opposite of the tapered surface 138 and generally transverse to the bottom surface 108, whereas the tapered surfaces 138 and 112 taper toward each other from bottom surface 108 and toward the inward surface 130.

Endplate 100 further optionally comprises a first relief 125 forming a planar surface 126 and a second relief 127 forming a planar surface 128. The first relief 125 extending from the first end 102 to the first tapered slot 107 and defined by the planar surface 126 substantially parallel to the lower surface 132 and a first relief surface 114 substantially planar and parallel to the inward surface 130. The second relief 127 extending from the second end 104 to the second tapered slot 109 and defined by a planar surface 128 substantially parallel to the lower surface 132 and a second relief surface 116 substantially planar and parallel to the inward surface 130. Optionally, in any embodiment, the endplate 100 includes a first chamfer 142 proximate the first end 102 and the second chamfer 144 proximate the second end 104. Chamfers 142 and 144 preferably facilitate introduction and removal of fusion device 1000 between the adjacent vertebral bodies 2 and 4 by reducing the height of the endplate 100 at first end 102 and the second end 104 thereby providing a tapered leading and trailing edges.

Optionally, in any embodiment, the endplate 100 further optionally comprises ramped grooves 122 and 118 proximate the first end 102 and ramped grooves 124 and 120 proximate the second end 104. The ramped grooves 122, 118 and 124, 120 are configured to engage the mating ramped geometry of the proximal wedge 550 and the distal wedge 650 to cause the initial expansion of the fusion device 1000 to be limited to width expansion and to prevent the fusion device 1000 from expanding in width and height simultaneously. The slopes of the ramped grooves 122, 118, 124 and 120 are configured to match those of the wedges 550 and 650. Ramped grooves 124 and 122 are configured to mate with the geometry of the trapezoidal (or in other embodiments T-shaped, Y-shaped, etc.) projections of the wedges 550 and 650. The ramped grooves 118 and 120 are preferably each formed by two surfaces, one parallel to the bottom surface 132, and one perpendicular to it. The ramped grooves 118 and 120 are configured to mate with the protuberances of the projections of the wedges 550 and 650.

Turning now to FIGS. 9A-9E. It should be understood that although in the illustrative embodiment, the slots 107 and 109 have trapezoidal cross-sections, they can optionally have but are not limited to the following, T-shaped cross-section (shown in FIG. 9A), L-Shaped cross-section (shown in FIG. 9B), Y-shaped cross-section (shown in FIG. 9C), F-shaped cross-section (shown in FIG. 9D) or generally any cross-section that preferably results in the slots 107 and 109 being narrower at the inward surface 130 than they are at the bottom surfaces 106 and 108 or at any point in between the inward surface 130 and the bottom surfaces 106 and 108. Optionally, in any embodiment, while the shapes described above are preferable when retention of the ramp 300 in the endplate 100 is desired by means of "dove-tailed", tapered, T-shaped or otherwise slot geometry, a non-tapered, generally rectilinear cross-section (shown in FIG. 9E) of the slots 107 and 109 are beneficial for example when an additional fastener (e. g. pin or set screw) are used to retain the ramp 300 in the slots 107 or 109 to only allow translation in one dimension (while rotation in one or more planes may also be allowed). It should also be understood that although the various alternative geometries of the endplates are presented here as discrete embodiments, these alternative embodiments have optional features which may be substituted or mixed/matched with any other embodiment in the specification. It should also be understood that substituting any of the aforementioned optional alternative features in the endplate component may or will necessitate the mating components (e. g. the endplates, the ramps and the wedges) to use the inverse or complementary geometry of those features for proper engagement and that the shape of that inverse or complementary geometry would follow inevitably from the optional alternative feature geometry described above.

Figure 10A:
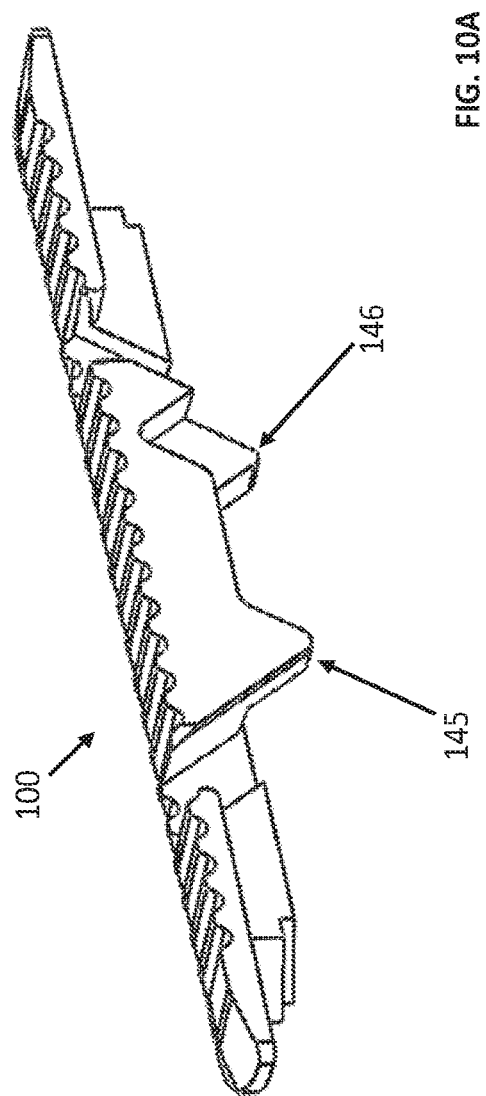
FIG. 10A depicts a perspective top view of an exemplary endplate.
Figure 10B:
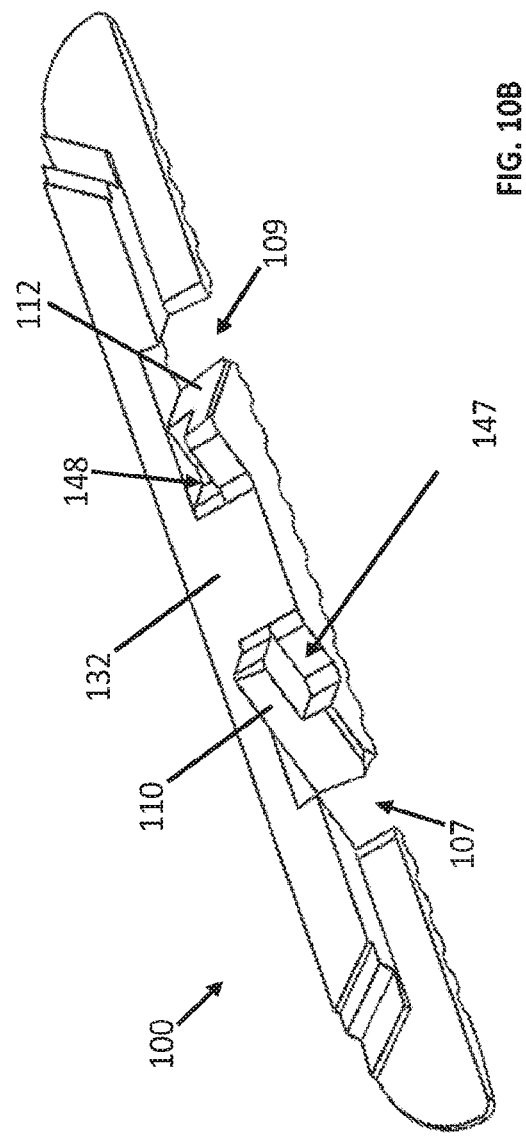
FIG. 10B depicts a bottom view of an exemplary endplate.

FIGS. 10A-10D3 show alternative embodiments of the endplate 100. FIGS. 10A and 10B show an exemplary endplate 100 in which the lower surface 132 further includes a projection 145 sharing the tapered surface 110 with the first tapered slot 107 and a projection 146 sharing the tapered surface 112 with the second tapered slot 109. In the embodiment of FIGS. 10A and 10B, the lower surface 132 further includes a recess 147 configured to accept the projection 146 of another endplate and a recess 148 configured to accept the projection 145 of another endplate. The purpose of the projections 145 and 146 and the recesses 147 and 148 is to increase the contact area and provide additional stability between the endplates 100, 150, 200, 250 and the ramps 300, 350, 400, 450 when the fusion device 1000 approaches maximum height expansion state (shown in FIG. 10C below). In embodiments without the projections 145 and 146, as the fusion device 1000 expands in height, the contact area between the endplates and the ramps steadily decreases as the ramps translate through the tapered slots of the endplates to produce expansion. The projections 145 and 146 compensate for this loss of contact area thereby improving the stability of the fusion device 1000 assembly. It should be understood that the same embodiments discussed above and shown in to FIGS. 9A, 9B, 9C, 9D would equally apply to the embodiments shown in FIGS. 10A and 10B. Optionally, in any embodiment, some of the areas where the projections 145 and 146 generate additional contact area between the endplates and the ramps. Furthermore, Optionally, in any embodiment, the projections 145 and 146 and the mating recesses 147 and 148 though pictured as generally triangular in an embodiment, may have other shapes that accomplish the same goal of increasing the contact area between the endplates 100, 150, 200, 250 and the ramps 300, 350, 400, 450 as the fusion device 1000 approaches maximum height expansion state. FIG. 10C shows a fully expanded state of an exemplary fusion device 1000 that includes the projections 145 and 146 as well as the mating recesses 147 and 148 on the endplates. Some of the areas where the projections generate additional contact area between the endplates and the ramps are indicated and labeled. FIGS. 10D1-10D3 show an exemplary fusion device 1000 in which the endplate 100 includes a protrusion 143 on its proximal end. The protrusion 143 further includes an aperture 149 configured to accept a bone fastener 730. The angle between the central axis of the aperture 149 and the long axis of the endplate 100 may have any value between 0 and 90 degrees but most preferably between 0 and 45 degrees and generally (but not necessarily in embodiments where the proximal portion of the bone fastener 730 (i. e. the "head" of the fastener 730) in contact with the protrusion 143 is substantially greater than that of the main body of the bone fastener 730 contacting bone (i. e. the shank of the fastener 730) and where the main body is substantially smaller than the aperture 149) defines the trajectory of the bone fastener 730, shown assembled with the fusion device 1000 in FIG. 10D3. It should be understood that although the various alternative geometries of the endplates are presented here as discrete embodiments, these alternative embodiments have optional features which may be substituted or mixed/matched with any other embodiment in the specification. It should also be understood that substituting any of the aforementioned optional alternative features in the endplate component may or will necessitate the mating components (e g. the endplates, the ramps and the wedges) to use the inverse or complementary geometry of and to those features for proper engagement and that the shape of that inverse or complementary geometry would follow inevitably from the optional alternative feature geometry described above.

Figure 12A:
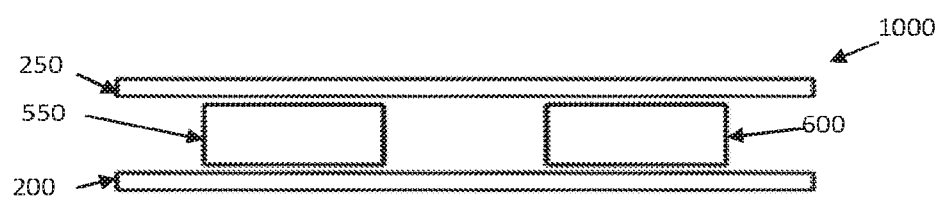
FIG. 12A depicts side view of an exemplary first expandable fusion device with all planar endplates.
Figure 12B:
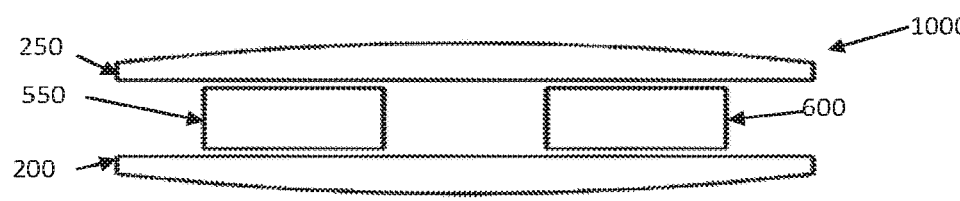
FIG. 12B depicts side view of an exemplary first expandable fusion device with all domed endplates.
Figure 12C:
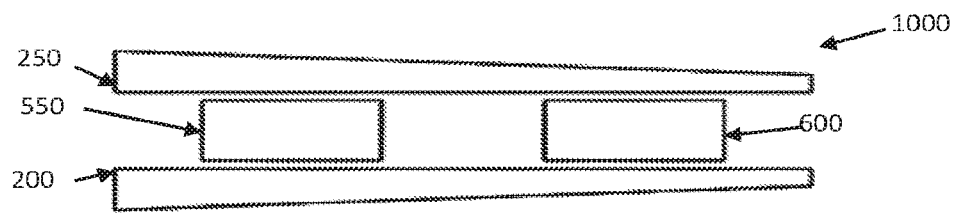
FIG. 12C depicts side view of an exemplary first expandable fusion device with all planar and ramped endplates.
Figure 12D:
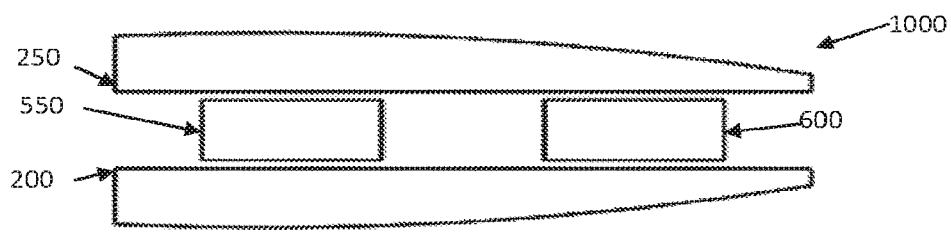
FIG. 12D depicts end view of an exemplary first expandable fusion device with all planar and domed endplates.

As illustrated in FIGS. 11A-12D, Optionally, in any embodiment, per FIGS. 11A, 11D, and 12A, the upper surface 134 of the first endplate 100 is generally planar to allow the upper surface 134 of the first endplate 100 to engage with the adjacent vertebral body 2. Alternatively, the upper surface 134 are curved in one or more planes (shown in FIGS. 11B, 11C, 11F, 11H, and 12B) to allow for a greater degree of engagement with the adjacent vertebral body 2. Optionally, in any embodiment, the upper surface 134 are generally planar but include a generally straight ramped surface (shown in FIGS. 11G and 12C) or a curved ramped surface (shown in FIGS. 11E, 11I and 12D). The ramped surface allows for engagement with the adjacent vertebral body 2 in a lordotic fashion as shown for example in FIG. 11E and/or for example in a coronally tapered fashion as shown for example in FIGS. 12C and 12D. Optionally, in any embodiment, an arrangement of non-ramped endplates of different heights as well as ramped and non-ramped endplates of different heights also results in a geometry suitable for lordotic engagement with the endplates, which are seen illustrated in FIGS. 11D, 11F, 11H, and 11I). It should be understood that since the FIGS. 11A-11I and FIGS. 12A-12D show the device 1000 in two different projections 90 degrees from each other, the ramped quality of the surface 134 is described as "lordotic" for FIGS. 11A-11I and as "tapered" for FIGS. 12A-12D. It is further contemplated that although in one embodiment, all endplates in the fusion device 1000 have the same length, in other embodiments, some or all of the endplates may have different lengths to better accommodate the target anatomy. FIGS. 13A and 13C show a fully collapsed and fully expanded views of an exemplary fusion device 1000 in which all endplates have the same length and FIGS. 13B and 13D show an exemplary fusion device 1000 in which two of the endplates have shorter length than the other two, which is seen as advantageous in lateral approach applications as well as in some posterior approach applications. Optionally, in any embodiment, the upper surface 134 includes texturing 140 to aid in gripping the adjacent vertebral bodies. Although In the illustrated embodiment, the texturing 140 comprises series of parallel grooves running transversely to the long axis of the endplate 100, including but is not limited to the following, the texturing includes teeth, ridges, areas of high surface roughness, metallic or ceramic coatings with relatively high surface roughness, friction increasing elements, keels, spikes, or gripping or purchasing projections. Optionally, in any embodiment, one or more of the endplates are shorter, longer, narrower, or wider than others. It should be understood that although the various alternative geometries of the endplates are presented here as discrete embodiments, these alternative embodiments have optional features which may be substituted or mixed/matched with any other embodiment in the specification. It should also be understood that substituting any of the aforementioned optional alternative features in the endplate component may or will necessitate the mating components (e. g. the endplates, the ramps and the wedges) to use the inverse and/or complementary geometry of/to those features for proper contemplated engagement between the various components of the fusion device 1000 and between those components and the surrounding anatomy and that the shape of that inverse and/or complementary geometry would follow inevitably from the optional alternative feature geometry described above.

Figure 2:
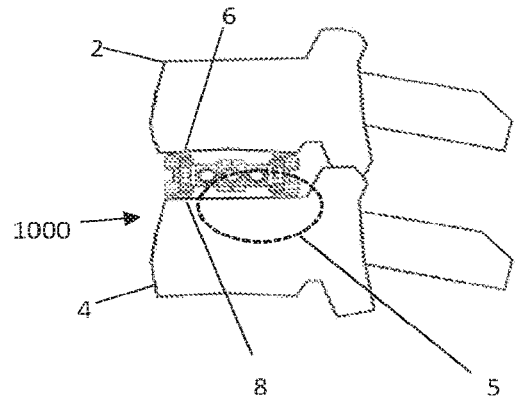
FIG. 2 depicts an exemplary first expandable fusion device implanted between two vertebral bodies in fully expanded state.
Figure 14A:
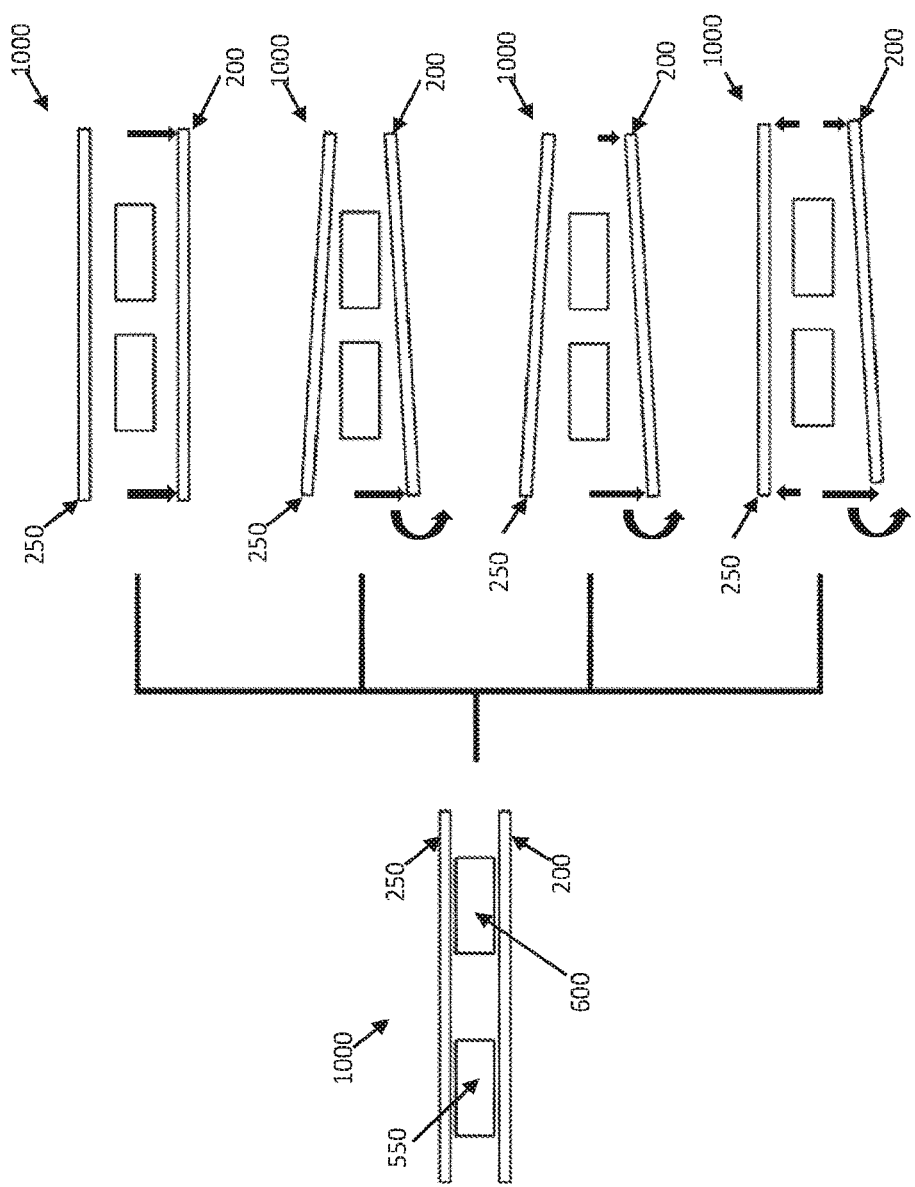
FIG. 14A depicts side views of the height expansion of an exemplary first expandable fusion device.

The effect of varying the slopes and/or the orientations of the tapered slots 107 and 109 or the amount of travel allowed between the ramps and the tapered slots 107 and 109 are seen illustrated in FIGS. 14A-14B2. FIG. 14A shows the effects of varying the slopes and/or the orientation of the slots 107 and 109 on each of the four endplates viewed from the side where the top of the device 1000 is represented by the endplate 250 and the bottom of the device is represented by the endplate 200. Varying the slopes of the slots 107 and 109 or limiting the allowable travel between the ramps and the slots 107 and 109 within each of the endplates may result, but is not limited to the first ends 102 and the second ends 104 expanding evenly on both top and bottom of the fusion device 1000, expanding unevenly on both top and bottom, expanding evenly on top and unevenly on bottom or expanding evenly on bottom and unevenly on top of the fusion device 1000. FIGS. 14B1 and 14B2 show a respectively the initial fully collapsed and an expanded view of an exemplary fusion device 1000 configured to expand unevenly at its proximal and distal ends, leading to an expanded state in which the endplates are tapering at an angle. The embodiment of FIGS. 14B1 and 14B2 employs an alternative embodiment of the ramp 300 (discussed in detail below) suitable for uneven expansion between one end of the endplate and the other end of the endplate by means of allowing the tapered slots 107 and 109 to make contact with circular surfaces instead of the flat ramped surfaces of other embodiments, which in turn allows the long axes of the endplates to be at an angle to the long axes of the ramps. The embodiment of FIGS. 14B1 and 14B2 further employs a mechanism, described in detail below, which independently limits the amount of travel between the ramp and the tapered slot 107 and the ramp and the tapered slot 109, which allows, for example, the proximal end of the endplate to reach the end of its height expansion and therefore stop expanding before the distal end of the endplate does, resulting in the distal end of the endplate continuing expanding after the proximal end has stopped expanding thereby achieving greater height expansion than the proximal end at the fully expanded state.

Figure 15A:
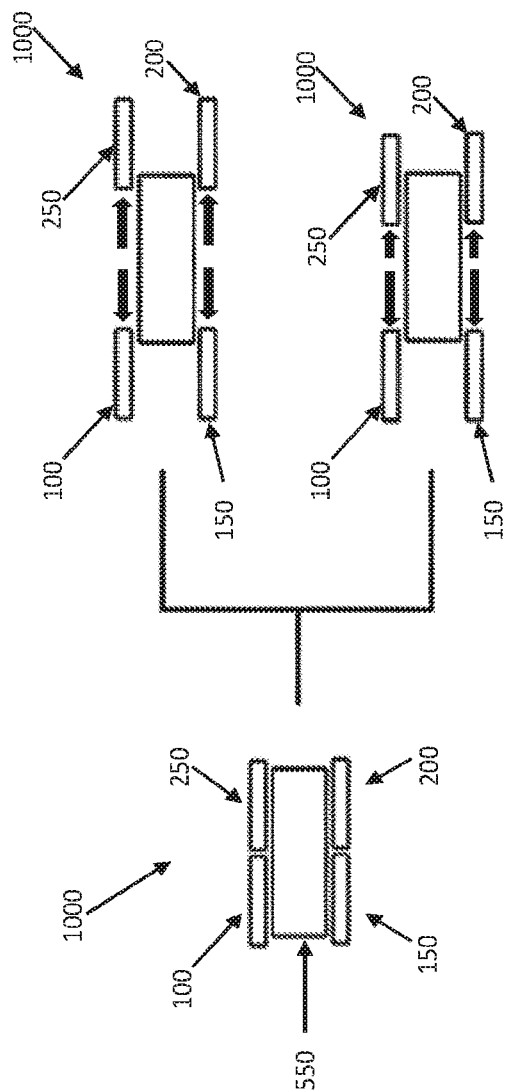
FIG. 15A depicts side views of the width expansion of an exemplary first expandable fusion device.
Figure 15D:
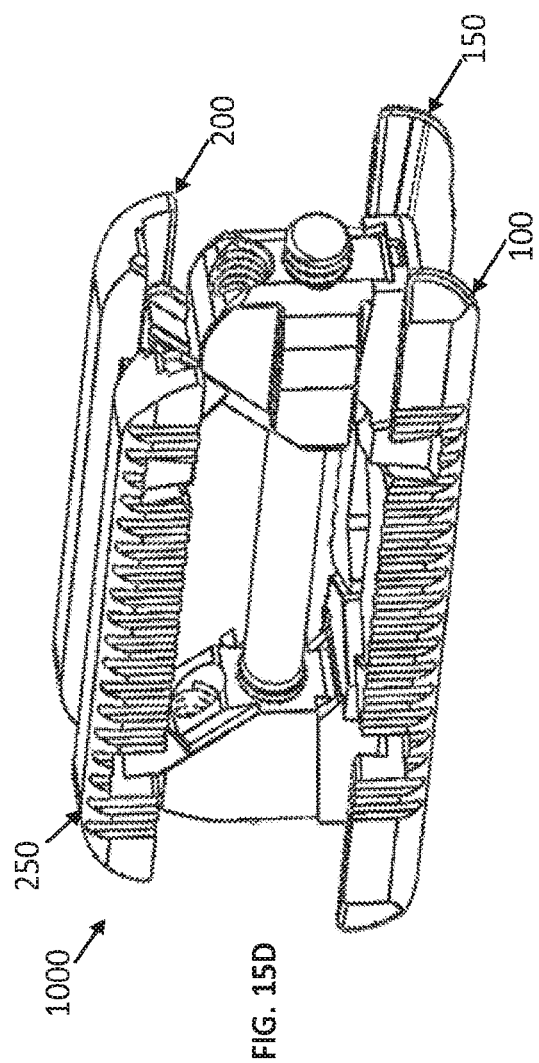
FIG. 15D depicts a perspective view of a fully expanded state of an exemplary first expandable fusion device with different length endplates designed to achieve more width expansion on one side than on the other.
Figure 16:
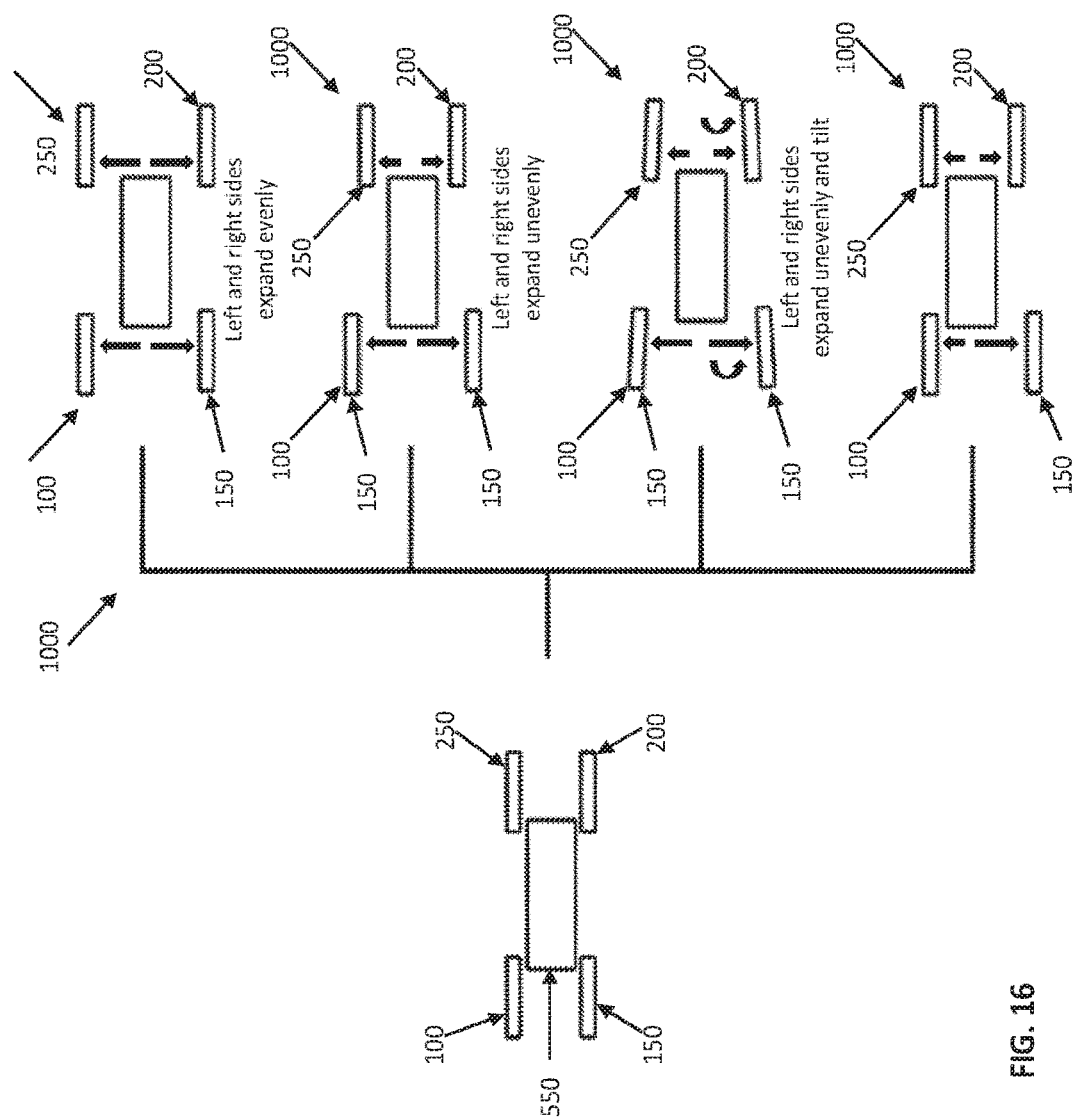
FIG. 16 depicts end views of the height expansion of an exemplary first expandable fusion device.

Turning now to FIGS. 15A-15G, the effects of varying the slope and/or orientation of the ramped grooves 122, 118, 124 and 120 of the endplate 100 as well as the slopes and/or orientations of the complementary mating features of the ramps and the wedges are shown. FIG. 15A shows an end view of the fusion device 1000, where the top of the device 1000 is represented by the endplates 100 and 250 and the bottom of the device is represented by the endplates 150 and 200. FIG. 15A shows an embodiment in which both sides of the fusion device 1000 expand evenly and an embodiment in which left and right sides expand unevenly. FIGS. 15B, 15C and 15D show an exemplary fusion device 1000 in which the left and right sides of the fusion device 1000 expand unevenly due to the variation of the slopes of the mating ramped features of the endplates, the wedges and the ramps. FIG. 15B shows the top view of the collapsed state of the embodiment, FIG. 15C shows the top view of the expanded state of the embodiment and schematically indicates the amounts of width expansion achieved in each direction, which are unequal. FIG. 15D shows a perspective view of the expanded state of the embodiment and allows a better view of the difference in the slopes of the ramped surfaces between the two sides of the fusion device 1000. FIG. 15E further shows an exemplary distal wedge 650 used in the assembly 1000 shown in FIG. 15D. FIG. 15F further shows an exemplary proximal wedge 550 used in the assembly 1000 shown in FIG. 15D. FIG. 15G further shows an exemplary ramp 300 used in the assembly 1000 shown in FIG. 15D. Turning now to FIG. 16, which shows the end views of four embodiments of the fusion device 1000 illustrating the effects of varying the slopes of the slots 107 and 109 between the endplates but keeping them the same within each individual endplate, which may result but is not limited to all four endplates expanding at the same rate, all four endplates expanding at different rates, any three endplates expanding at the same rate, while the fourth expands at a different rate, any two endplates expanding at one rate, while the other two expand at a different rate. Furthermore, curving the slots 107 and 109 in the plane transverse to the long axis of any of the endplates will preferably cause those endplates to tilt during expansion as shown in FIG. 16. It should be understood that although the various alternative geometries of the endplates, the wedges, and the ramps are presented here as discrete embodiments, these alternative embodiments have optional features which may be substituted or mixed/matched with any other embodiment in the specification. It should also be understood that substituting any of the aforementioned optional alternative features in one component may or will necessitate the mating components (e.g. the endplates, the ramps and/or the wedges) to use the inverse and/or complementary geometry of those features for proper contemplated engagement between all of the various components of the fusion device 1000 and between those components and the surrounding anatomy and that the shape of that inverse and/or complementary geometry would follow inevitably from the optional alternative feature geometry described above.

Although the following discussion relates to the first ramp 300, it should be understood that it also equally applies to the second ramp 350, the third ramp 400 and the fourth ramp 450 as the first ramp 300 is substantially identical to the second ramp 350, the third ramp 400 and the fourth ramp 450 in embodiments of the present disclosure (note that the ramps, even while identical in an embodiment, may or need to be suitably rotated to be assembled into arrangements shown above in the assemblies shown in FIGS. 3-5). It should also be understood that while the words "substantially identical" refer to the ramps 300, 350, 400 and 450 having the same set of features, all of which features serving the same or similar function in each of the ramps 100, 150, 200 and 250 as described below, the specific size and angular orientation of these features may or may not be identical between the ramps 300, 350, 400 and 450 within any particular embodiment.

Figure 17A:
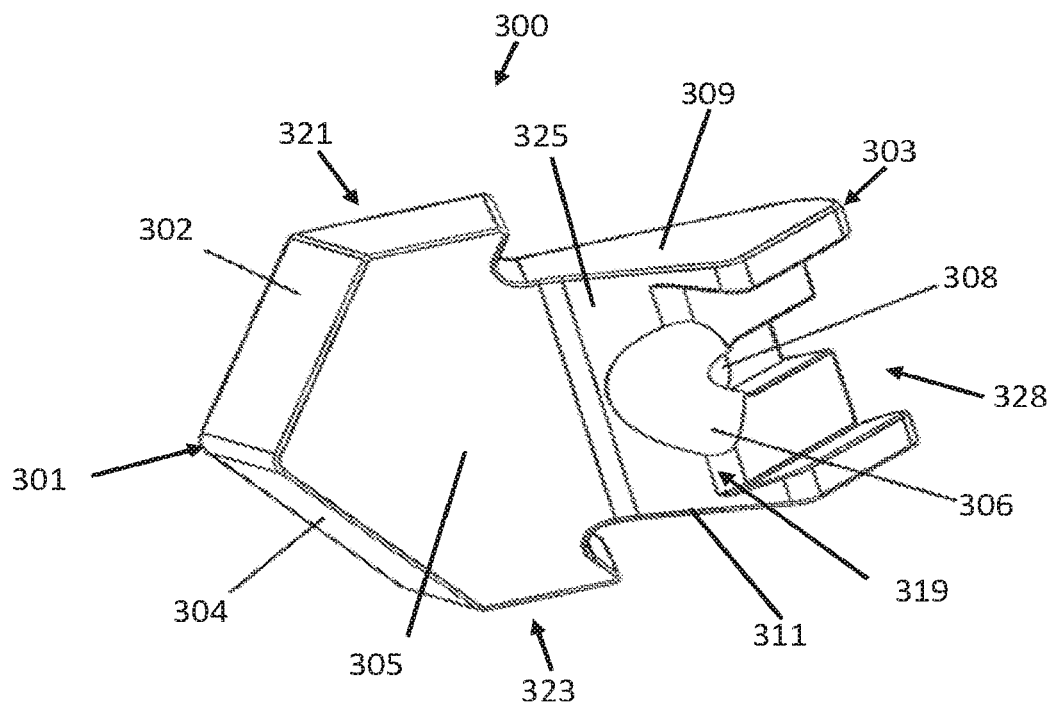
FIG. 17A depicts an inside perspective view of an exemplary ramp.
Figure 17B:
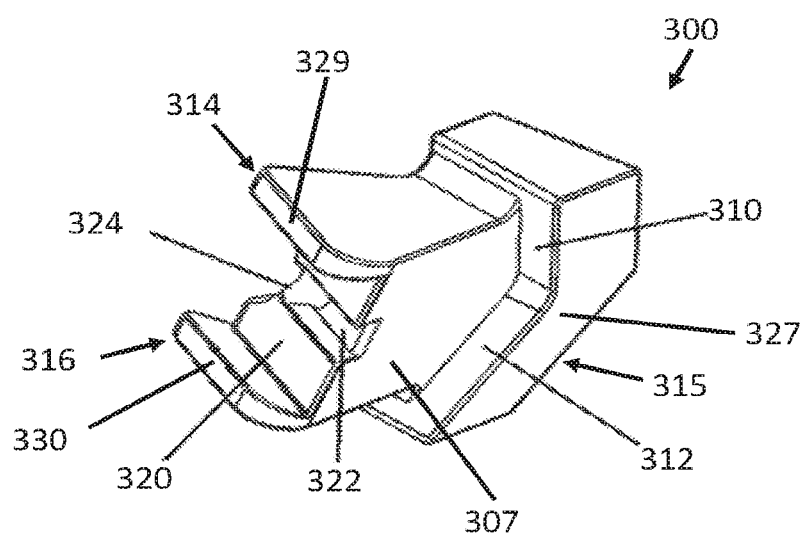
FIG. 17B depicts an outside perspective view of an exemplary ramp.

Turning now to FIGS. 17A and 17B, in an embodiment, the first ramp 300 has a first end 301 and a second end 303. In the illustrated embodiment, the first ramp 300 further comprises an inner surface 305 connecting the first end 301 and the second end 303, and an outer surface 307 (best seen in FIG. 17B) connecting the first end 301 and the second end 303. The first ramp 300 further comprises an upper surface 309 connecting the first end 301 and the second end 303, and a lower surface 311 connecting the first end 301 and the second end 303, the two surfaces 309 and 311 being preferably but not necessarily parallel to each other. The first ramp 300 further comprises a protuberance 315 further comprising an upper branch 321 extending preferably but not necessarily past the outer surface 307 and the lower surface 311, and a lower branch 323 extending preferably but not necessarily past the outer surface 307 and the lower surface 311. The upper branch 321 comprises a first ramped surface 302 and a second ramped surface 310, which extend from the inner surface 305 and taper outward in the direction of outer surface 327, giving the upper branch 321 a generally trapezoidal cross-section. The lower branch 323 comprises a first ramped surface 304 and a second ramped surface 312 which extend from the inner surface 305 and taper outward in the direction of the outer surface 327, giving the lower branch 323 a generally trapezoidal cross-section. The branches 321 and 323 are contemplated to slidably engage the tapered slots 107 and 109 in the end plates. The mating cross-sections of the branches 321 and 323 and the tapered slots 107 and 109 are contemplated to be configured to only allow translation in one dimension, either in a straight or a curved line (though some embodiments may allow rotation in one or more planes).

Figure 18B:
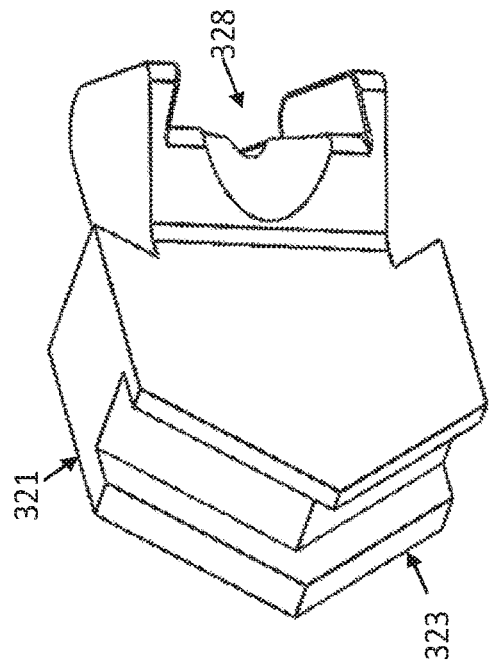
FIG. 18B depicts an inside perspective view of an exemplary ramp with C-shaped branches.
Figure 18A:
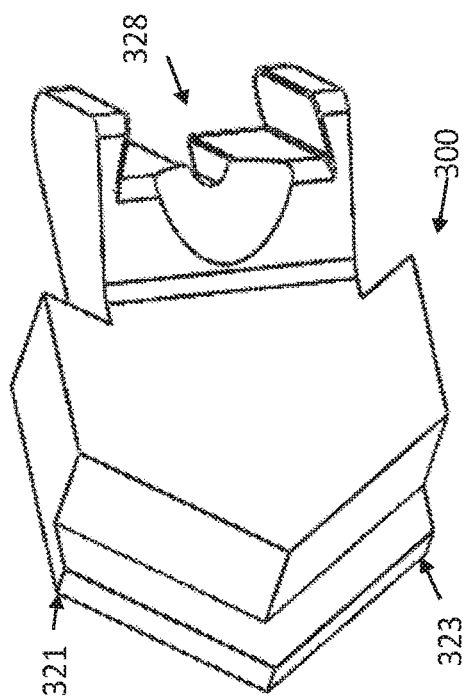
FIG. 18A depicts an inside perspective view of an exemplary ramp with L-shaped branches.
Figure 18C:
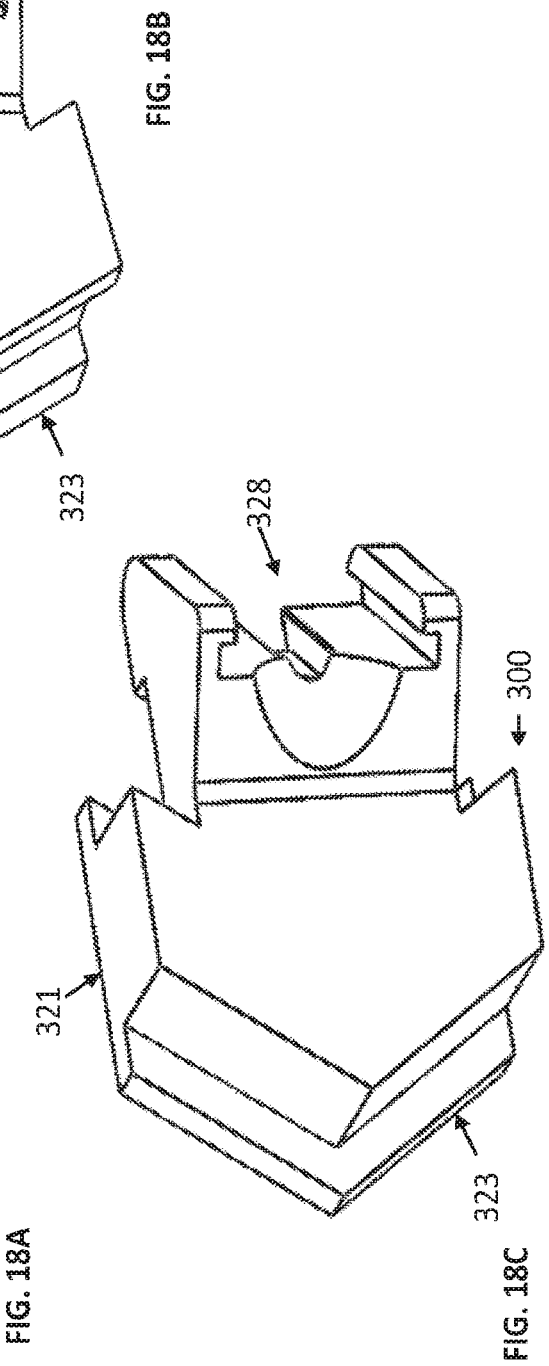
FIG. 18C depicts an inside perspective view of an exemplary ramp with T-shaped branches and T-shaped channel.

As a rest be seen in FIG. 17A, the inner surface 305 includes a projection 319 forming a ramped surface 320 and a surface 325 that preferably form angles greater than 90 degrees with the inner surface 305, as FIG. 17A shows. The projection 319 includes a first branch 314 and a second branch 316 and a groove 322. The groove 322 extends from the outer surface 307, along the ramped surface 320 and toward the inner surface 305. The groove 322 does not extend through the surface 325 instead terminating in a surface 324. As will be discussed below, the purpose of the channel 322 and the surface 324 is to limit the motion of the proximal wedge 550 and the distal wedge 650 with respect to the ramp 300 by causing a mating feature on the ramp 300 to bottom out on the surface 324. The channel 322 may further include a blind bore 308 which is coincident with the surface 324. The purpose of the bore 308 is to optionally accept a mating pin to limit the amount of width expansion allowable. The branch 314 extends from the ramped surface 320 to a surface 329 and the branch 316 extends from the ramped surface 320 to a surface 330. The projection 319 further includes a relief 306 whose axis is substantially parallel to the long axis. The relief 306 is configured to mate with the actuator 500 and allow the ramps to be in closer proximity to each other than would otherwise be possible without the relief 306. The relief 306 has any cross-section suitable to accomplish the function described above, for example a generally rectilinear cross-section or more preferably a partially polygonal cross-section or most preferably a circular cross-section. The ramped surface 320 and the branches 314 and 316 form a tapered channel 328, which has a generally trapezoidal cross-section. It should be understood that although in the illustrative embodiment, the tapered channel 328 has a trapezoidal cross-section, the cross section may comprise, is not limited to, a T-shaped cross-section (shown in FIG. 18C), a Y-Shaped cross-section (shown in FIGS. 18D and 18E), an L-shaped cross-section (not shown), an F-shaped cross-section (not shown) or generally any cross-section that preferably results in the tapered channel 328 being narrower at a surface 329 than it is at the ramped surface 320 or at any point in between the surface 329 and the ramped surface 327. Optionally, in any embodiment, the slope of the ramped surface 320 may or may not be the same between the ramps 350, 400, 450, 500 in the end plates.

It should be understood that although in the illustrative embodiment, the branches 321 and 323 have trapezoidal cross-section, they can have but are not limited to the following, T-shaped cross-section. Y-Shaped cross-section. L-shaped cross-section or generally any cross-section that preferably results in the branches 321 and 323 being narrower at the inner surface 305 than they are at the outer surface 327 or at any point in between the inner surface 305 and the outer surface 327. FIGS. 18A, 18B, 18C, 18D, 18E show a number of cross-sections that the branches 321 and 323 may take. Any embodiment described herein may optionally have these cross-sections in their branches. L-shaped (FIG. 18A), U-shaped (FIG. 18B) and T-shaped (FIG. 18C) cross-sections may be particularly preferable due to manufacturability considerations, but the Y-shaped cross-section (FIG. 18D) and an "Inside-T" shaped cross-section (FIG. 18E) are also possible. Optionally, in any embodiment, the slopes of the branches 321 and 323 are equal or differ from each other. Since the branches 321 and 323 are intended to mate with slots 107 and 109, the effects of varying their slopes is the same as discussed above for the slots 107 and 109 in the endplate 100. Likewise, the effects of varying the slope of the ramped surface 320 between each of the four ramps on the expansion characteristics of the device 1000 has been described above and are seen above in FIGS. 15A-15G, but to add to the description of these figures and in light of the detailed description of the ramp 300 specification provided here, it should be mentioned that since the slope of the ramped surface 320 controls the width expansion of the device 1000, varying its slope in each of the ramps (as well as varying the mating slopes of the ramps in the wedges in complementary fashion) may result in but is not limited to all four endplates expanding at the same rate, the endplates on the right side expanding faster than the endplates on the left side and the endplates on the left side expanding faster than the endplates on the right side or one, some or all of the endplates expanding faster than the others. It should be understood that although the various alternative geometries of the ramps may be presented here as discrete embodiments, these alternative embodiments have optional features which may be substituted or mixed/matched with any other embodiment in the specification. It should also be understood that substituting any of the aforementioned optional alternative features in the ramp component will necessitate the mating components (e. g. the endplates, the wedges and/or the actuator) to use the inverse or complementary geometry of those features for proper engagement and that the shape of that inverse or complementary geometry would follow inevitably from the optional alternative feature geometry described above.

Figure 19A:
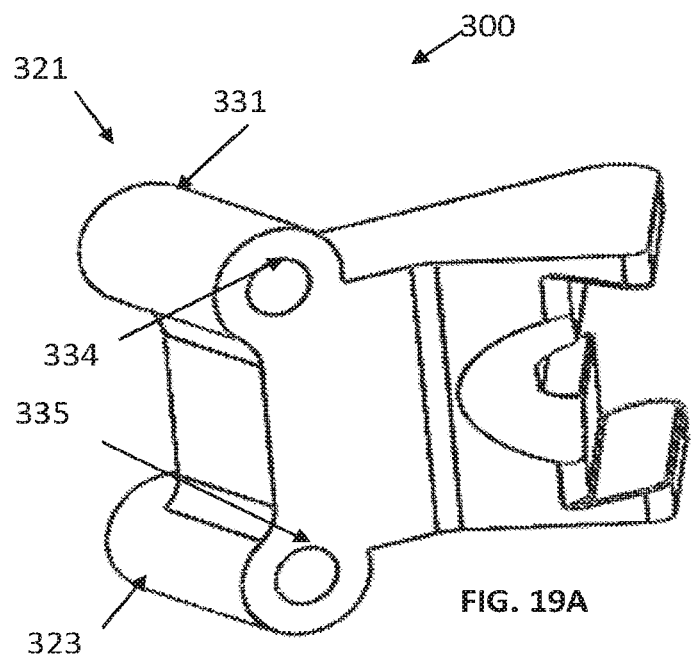
FIG. 19A depicts an inside perspective view of an exemplary ramp with cylindrical branches of rectilinear cross-section.
Figure 19B:
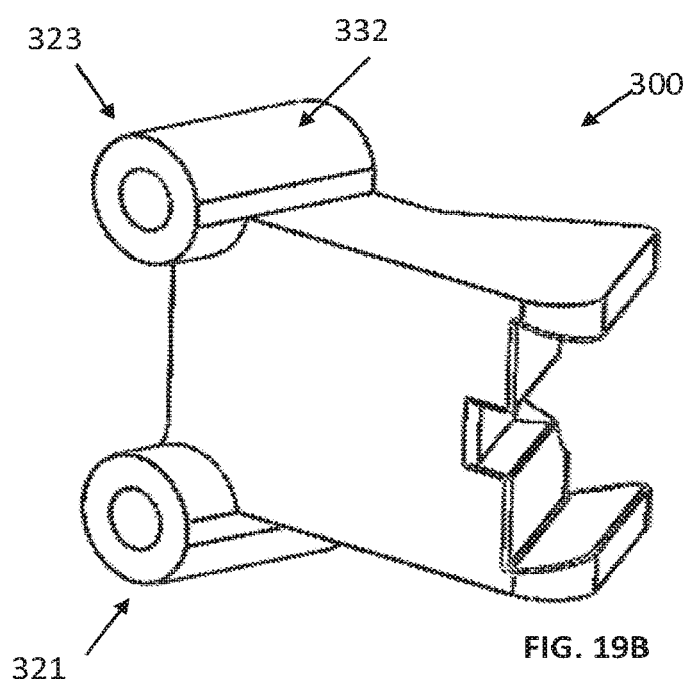
FIG. 19B depicts an outside perspective view of an exemplary ramp with cylindrical branches of rectilinear cross-section.
Figure 19C:
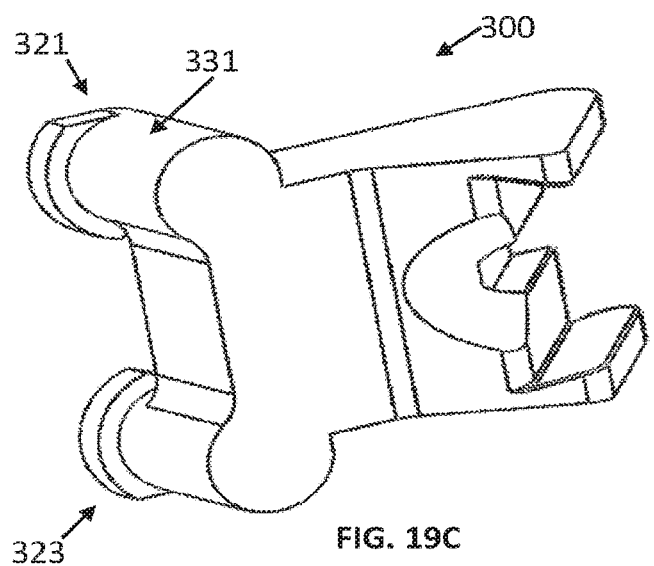
FIG. 19C depicts an inside perspective view of an exemplary ramp with cylindrical branches of L-shaped cross-section.
Figure 19D:
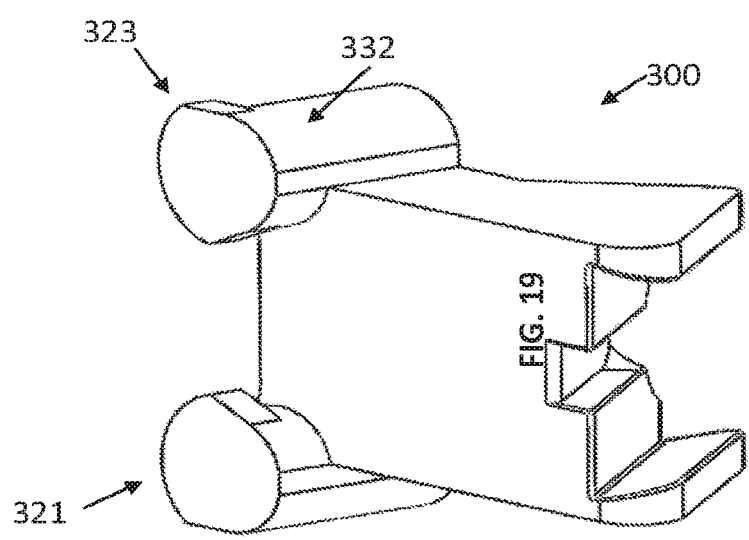
FIG. 19D depicts an outside perspective view of an exemplary ramp with cylindrical branches of L-shaped cross-section.
Figure 19E:
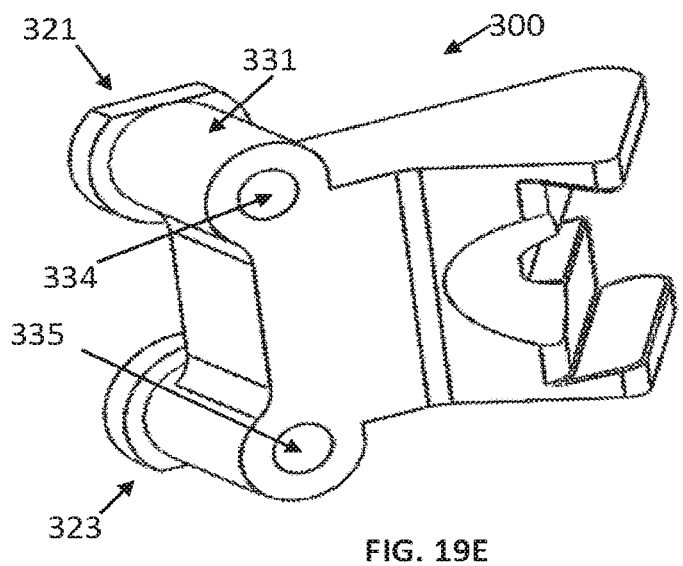
FIG. 19E depicts an inside perspective view of an exemplary ramp with cylindrical branches of T-shaped cross-section.
Figure 19F:
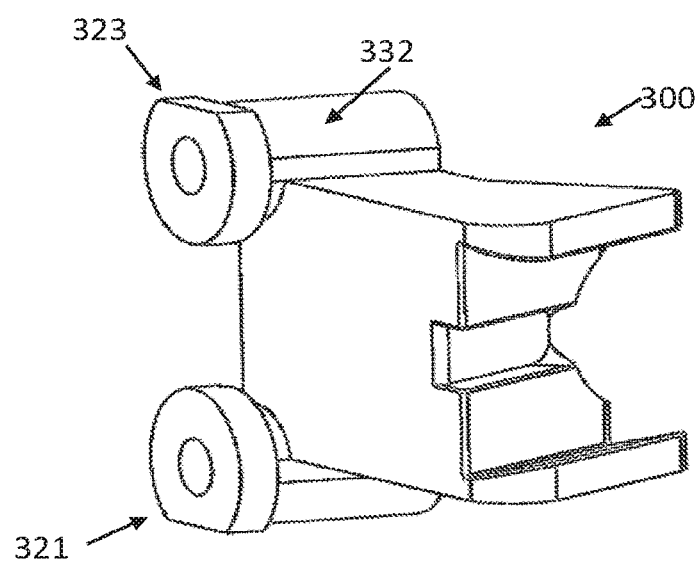
FIG. 19F depicts an outside perspective view of an exemplary ramp with cylindrical branches of T-shaped cross-section.

Turning now to FIGS. 19A-19H2, where the FIGS. 19A and 19B show an alternative embodiment of the ramp 300 in which the branches 321 and 323 comprise generally cylindrical (in other contemplated embodiments—conical) protrusions 331 and 332 respectively with their central axes generally perpendicular to the long axis of the ramp 300. Optionally, in any embodiment, the protrusions 331 and 332 further include apertures 334 and 335 respectively. The apertures 334 and 335 have their central axes coincident with the central axes of the protrusions 331 and 332 and said apertures are configured to engage a fastener 740, which in an embodiment is a pin (but in other embodiments is a screw) configured to engage the apertures 334 and 335 as well as a track 127A (best seen in FIG. 19H2) extending into the bottom surface 108 of the endplate 100 and a corresponding track (not shown) extending into the bottom surface 106 of the endplate 100. The fasteners 740 when engaged into the corresponding tracks in the endplate 100 are intended to equally or preferentially limit the amount of translation allowed between the ramp 300 and the ramped slots 107 and 109 in the endplate 100. It should be understood that although in the illustrative embodiment, the protrusions 331 and 332 have generally rectangular cross-sections through their central axes, or cross sections including but not limited to, L-shaped cross-section (shown in FIGS. 19C and 19D), T-Shaped cross-section (shown in FIGS. 19E and 19F), trapezoidal cross-section (not shown) or generally any cross-section that preferably results in the protrusions 331 and 332 being narrower at the inner surface 305 than they are at the outer surface 327 or at any point in between the inner surface 305 and the outer surface 327. The articulation between these embodiments of the ramp 300 and the endplate 100 is intended to allow the ramp 300 to translate in the ramped slots 107 and/or 109 of the endplate 100 in only one dimension and to rotate within said slots in only one plane.

FIGS. 19G1-19G3 show section views of the assembly of an embodiment of articulation of an exemplary endplate 100 and an exemplary ramp 300 in which the ramp 300 is translationally limited within the ramped slot of the endplate 100 at one angle formed between the long axes of the ramp 300 and the endplate 100 while being allowed to pass (for example and preferably during assembly of the fusion device 1000) at another angle (preferably outside the functional and/or useful range of an exemplary fusion device 1000) between the long axes of the ramp 300 and the endplate 100 due to a T-slot 149 being a blind slot and not breaking through the bottom surface 132 of the endplate 100. FIGS. 19H1 and 19H2 show a portion of an exemplary fusion device 1000 including an embodiment of articulation between the ramp 300 and the endplate 100 in which the ramped slot 109 of the endplate 100 has a generally T-shaped cross-section and in which the protrusion 331 of the ramp 300 has a generally T-shaped cross-section. The protrusion 331 further includes the aperture 334 generally concentric with it, where the aperture 334 is configured to accept the fastener 740, which in this embodiment comprises a pin. The ramped slot 107 of the endplate 100 further comprises a track recessed into its bottom surface and configured to engage the fastener 740 with the purpose of limiting the translational travel of the ramp 300 inside the slot 107 of the endplate 100. FIG. 19H1 shows the side view of the assembled articulation and FIG. 19H2 shows the exploded view of the articulation. Both the embodiments of FIGS. 19G1-19G3 and FIGS. 19H1-19H2 are contemplated as useful for, but not limited to, producing uneven expansion of the distal and proximal ends of the fusion device 1000 shown in FIGS. 14B1 and 14B2 above. It should be understood that although the various alternative geometries of the ramps are presented here as discrete embodiments, these alternative embodiments have optional features which may be substituted or mixed/matched with any other embodiments in the specification. It should also be understood that substituting any of the aforementioned optional alternative features in one component may or will necessitate the mating components (e. g. the endplates, the wedges and/or the actuator) to use the inverse and/or complementary geometry of those features for proper intended engagement between both the various components of the fusion device 1000 and between those components and the surrounding anatomy and that the shape of that inverse and/or complementary geometry would follow inevitably from the optional alternative feature geometries described above.

Figure 21B:
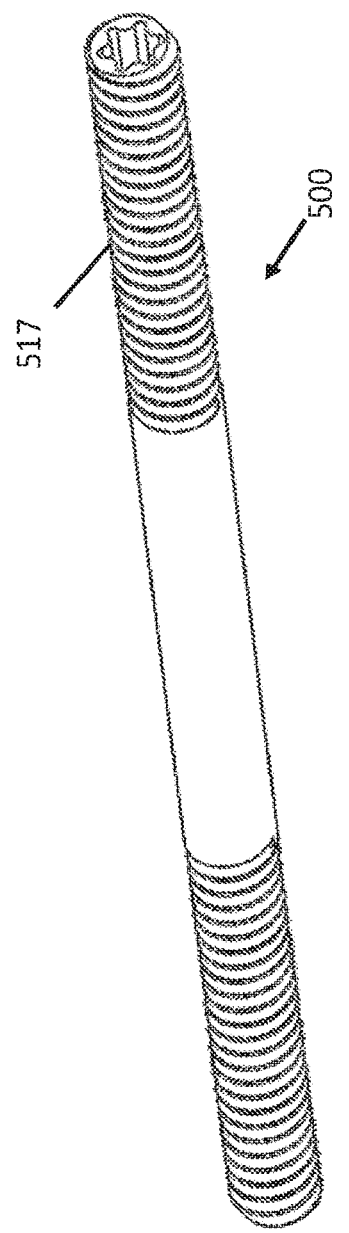
FIG. 21B depicts a perspective view of an exemplary actuator.
Figure 25:
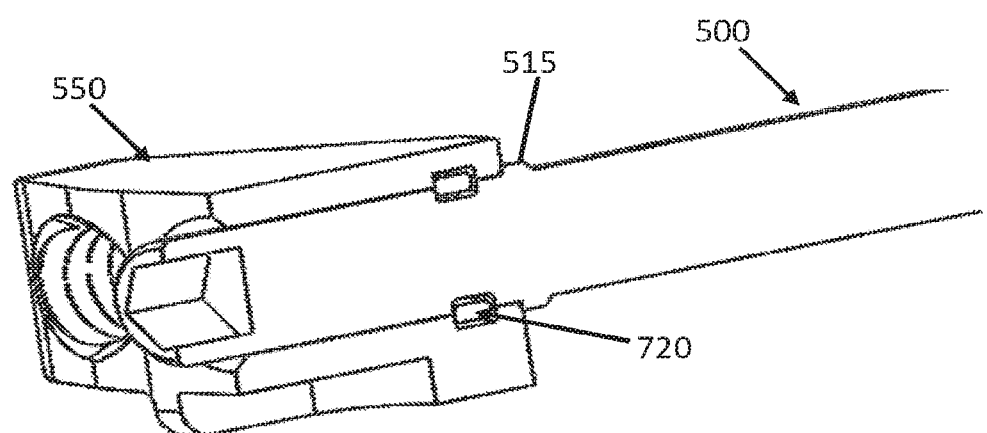
FIG. 25 depicts a section view of articulation between an exemplary proximal wedge, an exemplary actuator, and an exemplary retaining c-clip.

Turning now to FIG. 20. The actuator 500 comprises a proximal end 504, a distal end 502, and a cylindrical surface 506 connecting the proximal end 504 and the distal end 502. Optionally, in any embodiment, the actuator 500 further comprises a drive feature 512 proximate the proximal end 504 and a thread 508 proximate the distal end 502. The cylindrical surface 506 includes a groove 514 circumferentially disposed around the actuator proximate the drive feature 512 and a ridge 510 circumferentially disposed around the actuator proximate the thread 508. The ridge 510 is contemplated to serve as a depth stop to limit the linear travel of the actuator 500 by making contact with the distal wedge 650 at the end of allowable travel range. Although in an embodiment, the drive feature 512 is shown as an hexalobular protrusion (external hexalobe drive). Optionally, in any embodiment, the drive feature 512 may be but is not limited to, internal hexalobe, external hexagon, internal hexagon, external cruciform, internal cruciform or any other shape. Optionally, in any embodiment shown in FIG. 21A, the drive feature 512 is a hexagonal recess (internal hexagon drive). Additionally, in the embodiment shown in FIG. 21A, the cylindrical surface 506 of the actuator 500 further includes a ridge 515 circumferentially disposed around the actuator proximate the proximal end 504, but distal to the groove 514. The ridge 515 is configured to bottom out on the second end 560 of the proximal wedge 550 and is contemplated to provide resistance to the actuator 500 pushing through the central aperture 568 and subjecting the retaining pin 600, the retaining set screw 700, a retaining c-clip 720 or some other actuator retention means to high loads. FIG. 25 shows a section view of a sub-assembly including the proximal wedge 550, the actuator 500, and the retaining c-clip 720 and demonstrates the location and function of the ridge 515. Optionally, in any embodiment shown in FIG. 21B, the actuator 500 comprises an additional thread 517 proximate the proximal end 504. The thread 517 is comprised of a helical groove of opposite direction to that of the thread 508 (i. e. if the thread 508 is right-handed, then the thread 517 is left-handed). The effect of addition of the opposing direction thread 517 is that the actuator 500 would thread into the distal wedge 650 in a for example clock-wise fashion while threading into the proximal wedge 550 in, for example, a counter-clock-wise fashion, which causes the actuator 500 to draw the wedges together while also translating relative to both wedges when torsionally actuated. The extent of travel of the actuator 500 relative to each of the wedges is contemplated as being controlled either by means of thread lengths in which case the run-out of the threads would bottom out on the respective wedges or by means of dedicated ridges (e. g. 510 and 515) circumferentially disposed around the actuator and configured to bottom out on the respective wedges thereby limiting translation of the actuator. It should be understood that although the various alternative geometries of the actuators are presented here as discrete embodiments, these alternative embodiments have optional features which may be substituted or mixed/matched with any other embodiment in the specification. It should also be understood that substituting any of the aforementioned optional alternative features in the actuator component will necessitate the mating components (such as the wedges, the ramps or any auxiliary instrumentation intended to engage the actuator 500) to use the inverse or complementary geometry of those features for proper engagement and that the shape of that inverse geometry would follow inevitably from the optional alternative feature geometry described above.

Figure 22:
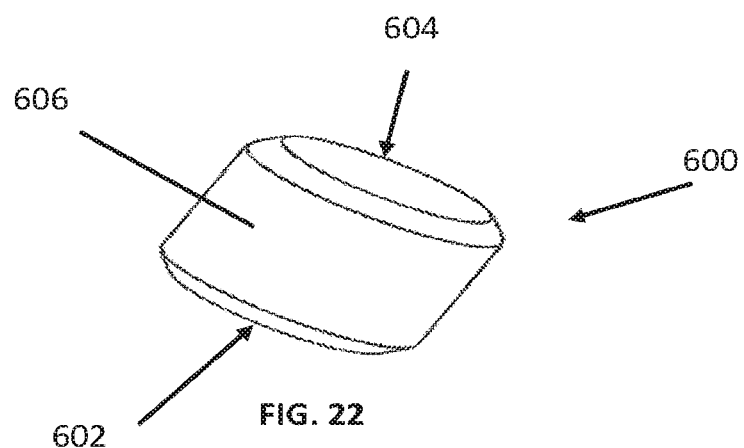
FIG. 22 depicts a perspective view of an exemplary retaining pin.
Figure 23:
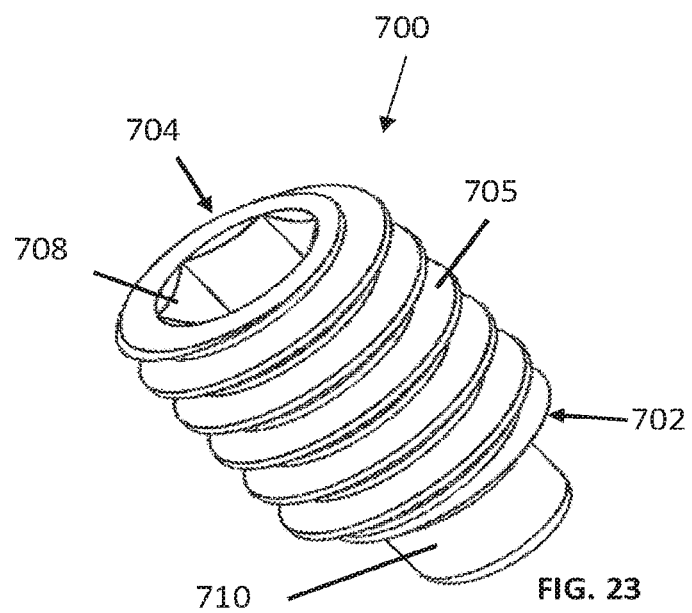
FIG. 23 depicts a perspective view of an exemplary retaining set screw.
Figure 24:
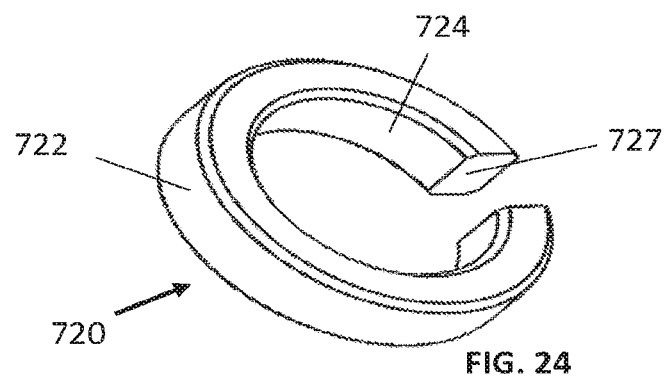
FIG. 24 depicts a perspective view of an exemplary retaining c-clip.

With respect to FIG. 22, the retaining pin 600 comprises a first end 604, a second end 602, and a cylindrical surface 606 connecting the ends 604 and 602, whereas the cylindrical surface 606 may have any diameter and any length suitable for a particular application, mating feature or component. With respect to FIG. 23, the retaining set screw 700 comprises a first end 704, a second end 702, and a threaded surface 705 connecting the ends 704 and 702. The retaining set screw 700 further comprises a drive feature proximate the first end 704 and a cylindrical protrusion 710 extending from the second end 702. With respect to FIG. 24, the retaining c-clip 720 comprises an inner diameter 724, an outer diameter 722, and a split 725 interrupting both the inner diameter 722 and the outer diameter 724.

Referring further to FIGS. 26A-26B, in an exemplary embodiment, the proximal wedge 550 comprises a first end 562, a second end 560, an upper surface 590 connecting the first end 562 and the second end 560, and a lower surface 552 connecting the first end 562 and the second end 560. The proximal wedge further comprises a first ramped surface 580 and a second ramped surface 582 located proximate the second end 560. The first ramped surface 580 includes a first projection 564 extending from the first ramped surface 580 towards a surface 565 and having a generally trapezoidal cross-section. The second ramped surface 582 includes a second projection 566 extending from the second ramped surface 582 toward a surface 567 and having a generally trapezoidal cross-section. Optionally, in any embodiment, the first projection 564 includes a protuberance 574 and the second projection 566 includes a protuberance 575. The projections 564 and 566 are contemplated to be configured to slidably engage the tapered channel 328 of the ramp 300 in the endplates in such a way that the ramp 300 only translates relative to the proximal wedge 550 in one dimension—back and forth in either in a straight or a curved line (Optionally, in any embodiment, rotation in one plane may also be allowed between the ramps and the wedge 550). Optionally, in any embodiment, the protuberances 574 and 575 are configured to engage the groove 322 on the ramp 300 in the endplates and limit the extent of translation between the ramp 300 and the wedge 550 by making contact with the surface 324 at the limit of allowable travel. Optionally, in any embodiment, the upper surface 590 further includes a projection 554 extending from the upper surface 590. The projection 554 includes a channel 599 extending through the first end 562 but not through the second end 560. It should be understood that the channel 599 is intended as a mating feature for auxiliary instrumentation used in introduction, expansion of the device 1000 and/or graft delivery into the device 1000 and may be configured, shaped and located in other ways so long as it is accessible from the first end 562. The proximal wedge 550 further comprises a central aperture 568 (e. g. as shown in FIG. 19), and side apertures 570 and 572 (e. g. as shown in FIG. 26B). Optionally, in any embodiment, the central aperture 568 includes an undercut 571 and both of the side-apertures 570 and 572 are threaded. The central aperture 568 is configured to engage and retain the actuator 500 by means of the retaining set screw 700 engaged in a threaded hole 586 and extending into the groove 514 of the actuator 500 and/or the retaining pin 600 engaged in a bore 584 and extending into the groove 514 of the actuator 500 or the retaining c-clip 720 (see FIG. 24) engaged simultaneously in the undercut 571 and the groove 514 of the actuator 500 (shown in FIG. 25) or any other retaining mechanism allowing the actuator 500 to rotate inside the central aperture 568, but substantially preventing the actuator 500 from translating along the axis of the central aperture 568.

Figure 27A:
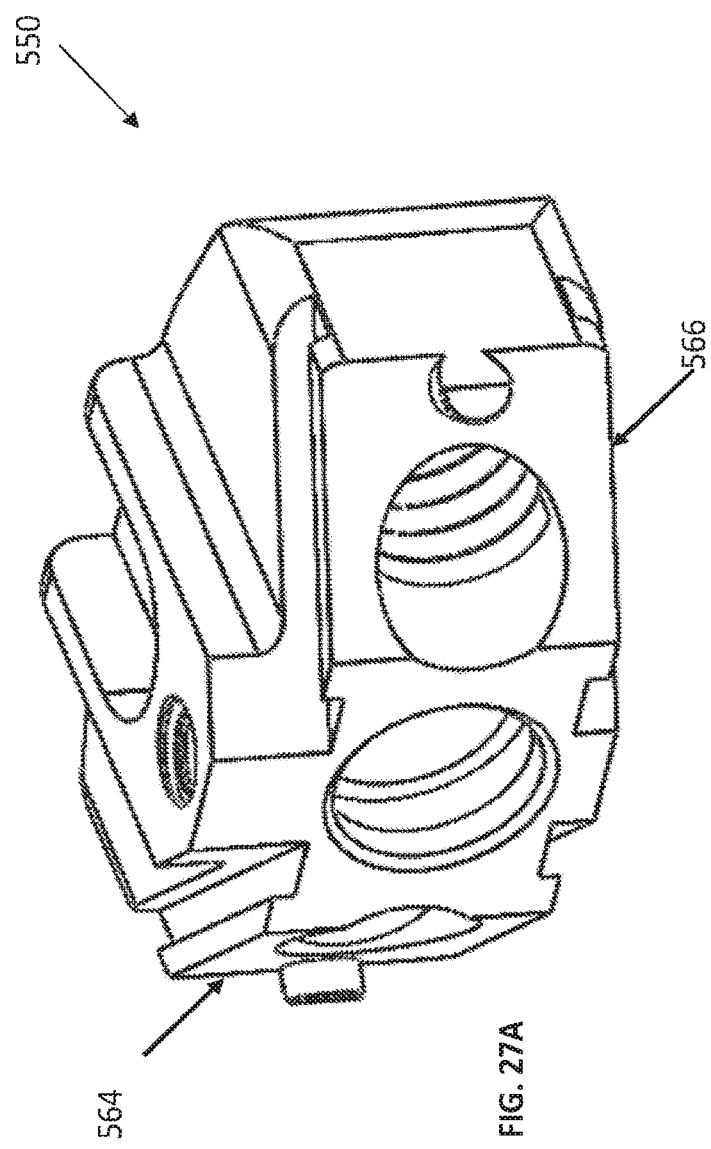
FIG. 27A depicts a perspective view of an exemplary proximal wedge with T-shaped projections.

It should be understood that although in the illustrative embodiment, the first projection 564 and the second projection 566 have trapezoidal cross-sections, or a cross section including but not limited to T-shaped cross-section, Y-Shaped cross-section (not shown), or generally any cross-section that preferably results in the projections 564 and 566 being narrower at the ramped surfaces 580 and 582 than they are at the surfaces 565 and 567. Similarly, any embodiment may optionally have the cross-sections described above. FIG. 27A shows an embodiment with the projections 564 and 566 having T-shaped cross-sections, which may be particularly preferable due to manufacturability and performance considerations.

Side apertures 570 and 572 are intended as a mating features for auxiliary instrumentation used in introduction and/or expansion of the device 1000 and/or graft delivery into the device 1000 and may be configured, shaped and located in other ways so long as they are accessible from the first end 562. As an example, there may be one or two side apertures, one, both or none of the side apertures may be threaded, one or both of the side apertures may be non-circular. Additionally, the central aperture 568 is intended to mate with the actuator and may or may not be in the geometric center of the proximal wedge 550, and may or may not be threaded. As an example, FIG. 27B shows an exemplary proximal wedge 550 in which the central aperture is threaded with a left-handed thread (but may in other embodiments be threaded with a right-handed thread), one of the side apertures is threaded and one of the side apertures has a generally rectangular or preferably, a generally square shape, which is seen as advantageous for graft delivery into the fusion device 1000 because it may provide a greater cross-sectional area for graft material to travel through as compared to a circular opening of similar external dimensions. Other optional instrument attachment features are also contemplated including but not limited to embodiments of the proximal wedge 550 shown in FIGS. 27B, 27C, and 27D. For example, an embodiment shown in FIG. 27B does not include the projection 554 and instead includes a projection 587 and a projection 588 extending from the upper surface and forming a channel 591 and a projection 589 and a projection 590 extending from the lower surface 552 and forming a channel 592. FIG. 27C shows the embodiment from FIG. 27B which includes a groove 592 extending from the projection 587 to the projection 589. Optionally, in any embodiment, another groove (not shown) of similar dimensions may extend from the projection 589 to the projection 590. It is further contemplated that these grooves would serve as engagement features for auxiliary instrumentation. The embodiment of FIG. 27C further includes both side apertures being circular and threaded and the central aperture being unthreaded. FIG. 27D shows the embodiment from FIG. 27C which further includes stepped recesses 593 and 594 on the sides of the proximal wedge 550 with the deeper portions of the stepped recesses 593 and 594 located proximate the second end 560. Optionally, in any embodiment, the stepped recesses 593 and 594 would serve as engagement features for auxiliary instrumentation. The embodiment of FIG. 27D further includes one of the side apertures being circular and threaded, one aperture being generally rectangular or preferably, generally square in shape and the central aperture being unthreaded. Auxiliary instrumentation is discussed in detail below. Optionally, in any embodiment, the slopes of the ramped surfaces 580 and 582 (and the slopes of the ramped surfaces 680 and 682 discussed below) are equal or differ from each other. Since the branches of the ramped surfaces 580, 582 (as well as 680, 682 discussed below) of the wedges are intended to mate with the ramped surfaces 320 of the ramps 300, 350, 400, 450, the effects of varying their slopes is the same as discussed above for the ramped surfaces 320 in the ramp 300. It should be understood that although the various alternative geometries of the proximal wedges are presented here as discrete embodiments, these alternative embodiments have optional features which may be substituted or mixed/matched with any other embodiment in the specification. It should also be understood that substituting any of the aforementioned optional alternative features in the proximal wedge component will necessitate the mating components (e. g. the endplates, the ramps, the actuator and the distal wedge) to use the inverse or complementary geometry to those features for proper engagement and that the shape of that inverse geometry would follow inevitably from the optional alternative feature geometry described above.

Figure 28A:
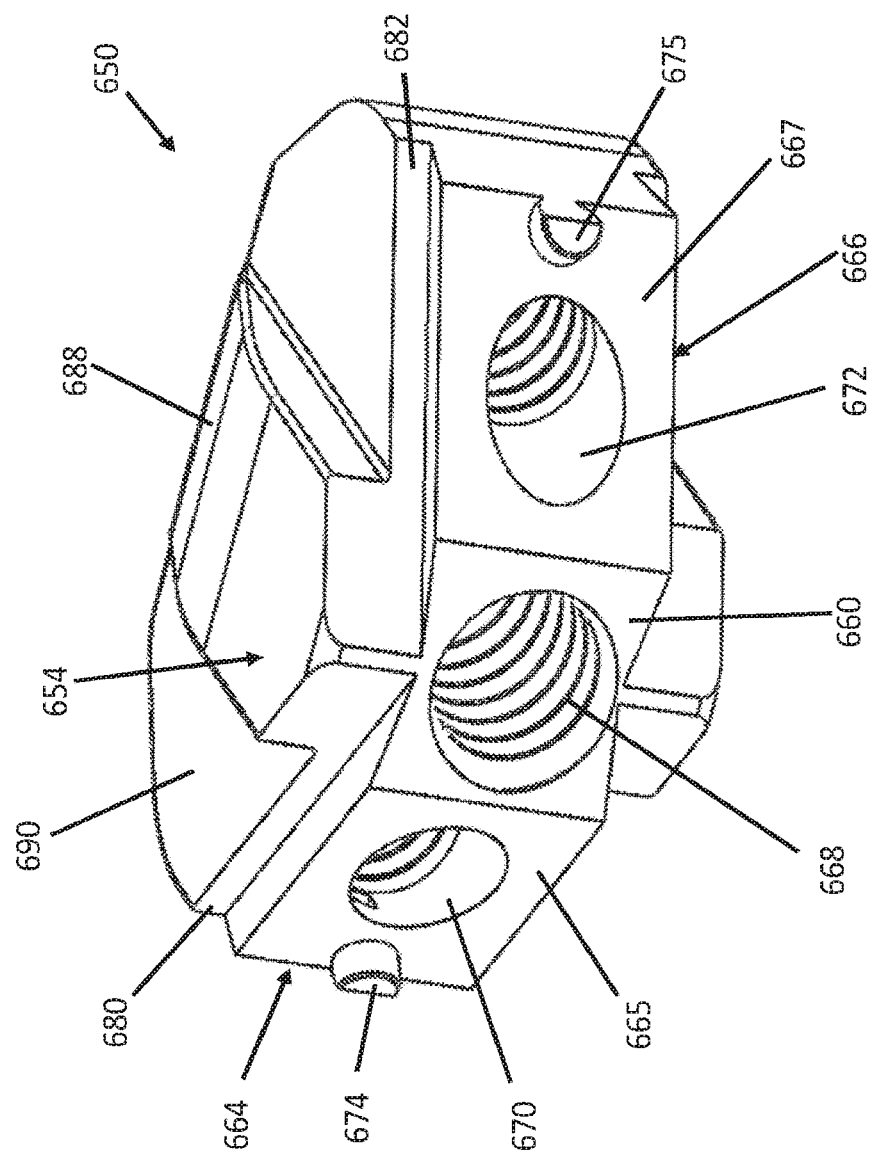
FIG. 28A depicts a front perspective view of an exemplary distal wedge.
Figure 29A:
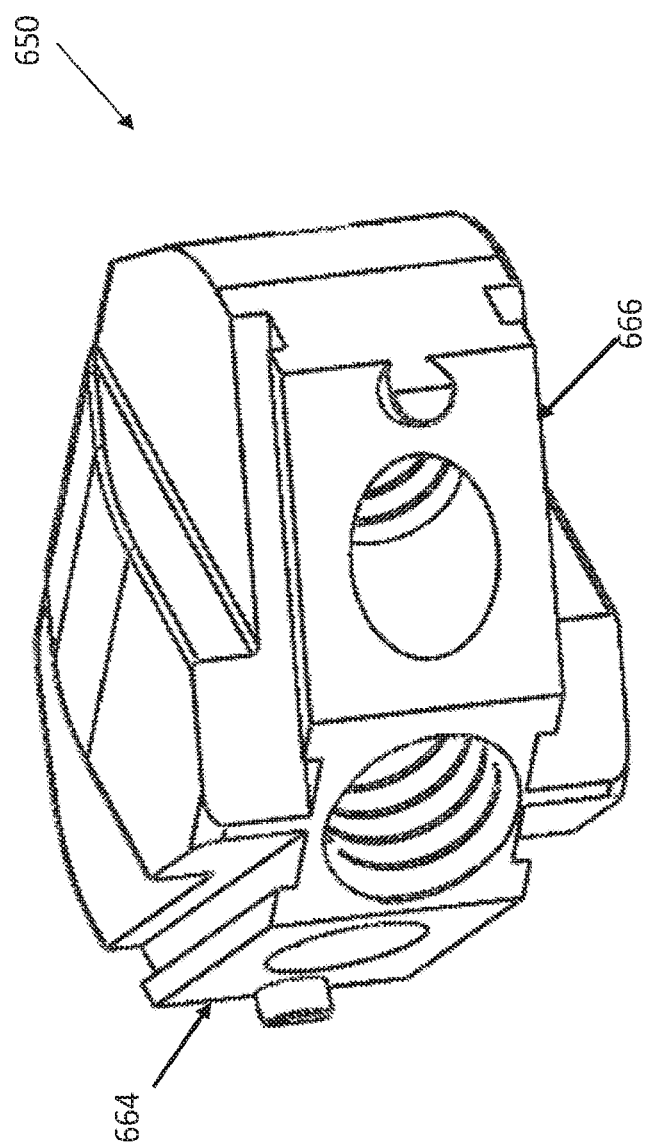
FIG. 29A depicts a front perspective view of an exemplary distal wedge with T-shaped projections.
Figure 29B:
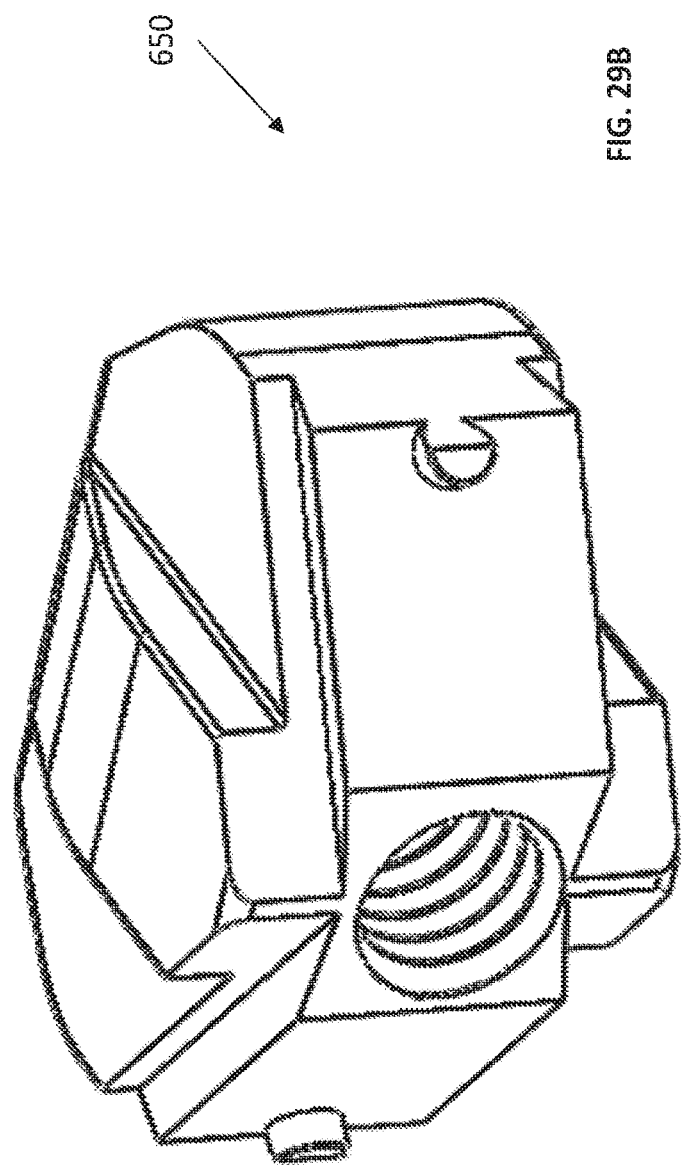
FIG. 29B depicts a front perspective view of an exemplary distal wedge with T-shaped projections and without side apertures.

Turning now to FIGS. 28A and 28B, in an exemplary embodiment, the distal wedge 650 comprises a first end 662, a second end 660, an upper surface 690 connecting the first end 662 and the second end 660, and a lower surface 652 connecting the first end 662 and the second end 660. The proximal wedge further comprises a planar first ramped surface 680 and a planar second ramped surface 682 located proximate the second end 660. The first ramped surface 680 includes a first projection 664 extending from the first ramped surface 680 toward a surface 665 and having a generally trapezoidal cross-section. The second ramped surface 682 includes a second projection 666 extending from the second ramped surface 682 toward a surface 667 and having a generally trapezoidal cross-section. Optionally, in any embodiment, the first projection 664 includes a protuberance 674 and the second projection 666 includes a protuberance 675. The projections 664 and 666 are contemplated to be configured to slidably engage the tapered channel 328 of the ramp 300 in the end plates in such a way that the ramp 300 only translates relative to the proximal wedge 650 in one dimension—back and forth in either in a straight or a curved line. Optionally, in any embodiment, the protuberances 674 and 675 are configured to engage the groove 322 on the ramp 300 and limit the extent of translation between the ramp 300 and the wedge 650 by making contact with the surface 324 at the limit of allowable travel. Optionally, in any embodiment, in an embodiment, the upper surface 690 further includes a projection 654 extending from the upper surface 690 and a projection 655 extending from the lower surface 652. The projections 654 and 655 further include chamfers 688 and 689 configured to facilitate introduction of the device 1000 between and initial distraction of the adjacent vertebrae 2 and 4. The distal wedge 650 further comprises a central aperture 668, and side apertures 670 and 672. The central aperture 668 is fully threaded and both of the side-apertures 670 and 672 are threaded. The central aperture 668 is configured to engage the actuator 500. Side apertures are intended as a mating features for auxiliary instrumentation used in introduction and/or expansion of the device 1000 and/or graft delivery into the device 1000 and may be configured, shaped and located in other ways. Optionally, in any embodiment, there may be one or two side apertures, one, both or none of the side apertures 670 and 672 may be threaded and one or both of the side apertures 670 and 672 may be non-circular. FIG. 29A shows, as an example, an exemplary distal wedge 650 which does not include the side apertures. It should be understood that although in the illustrative embodiment, the first projection 664 and the second projection 666 have trapezoidal cross-sections, they or any other embodiment disclosed herein may optionally have but are not limited to the following, T-shaped cross-section, Y-Shaped cross-section, L-shaped cross-section or generally any cross-section that preferably results in the projections 664 and 666 being narrower at the ramped surfaces 680 and 682 than they are at the surfaces 665 and 667. FIG. 29B shows an exemplary distal wedge 650 with the projections 664 and 666 having T-shaped cross-sections, which may be particularly preferable due to manufacturability and performance considerations. Optionally, in any embodiment, the slopes of the ramped surfaces 580 and 582, and the slopes of the ramped surfaces 680 and 682 are equal or differ from each other. Since the branches of the ramped surfaces 580, 582, 680, 682 of the wedges are intended to mate with the ramped surfaces 320 of the ramps 300, 350, 400, 450, the effects of varying their slopes is the same as discussed above for the ramped surfaces 320 in the ramp 300. It should be understood that although the various alternative geometries of the distal wedges are presented here as discrete embodiments, these alternative embodiments have optional features which may be substituted or mixed/matched with any other embodiment in the specification. It should also be understood that substituting any of the aforementioned optional alternative features in the distal wedge component will necessitate the mating components (e. g. the endplates, the ramps, the actuator and the proximal wedge) to use the inverse or complementary geometry to those features for proper engagement and that the shape of that inverse geometry would follow inevitably from the optional alternative feature geometry described above.

Figure 30:
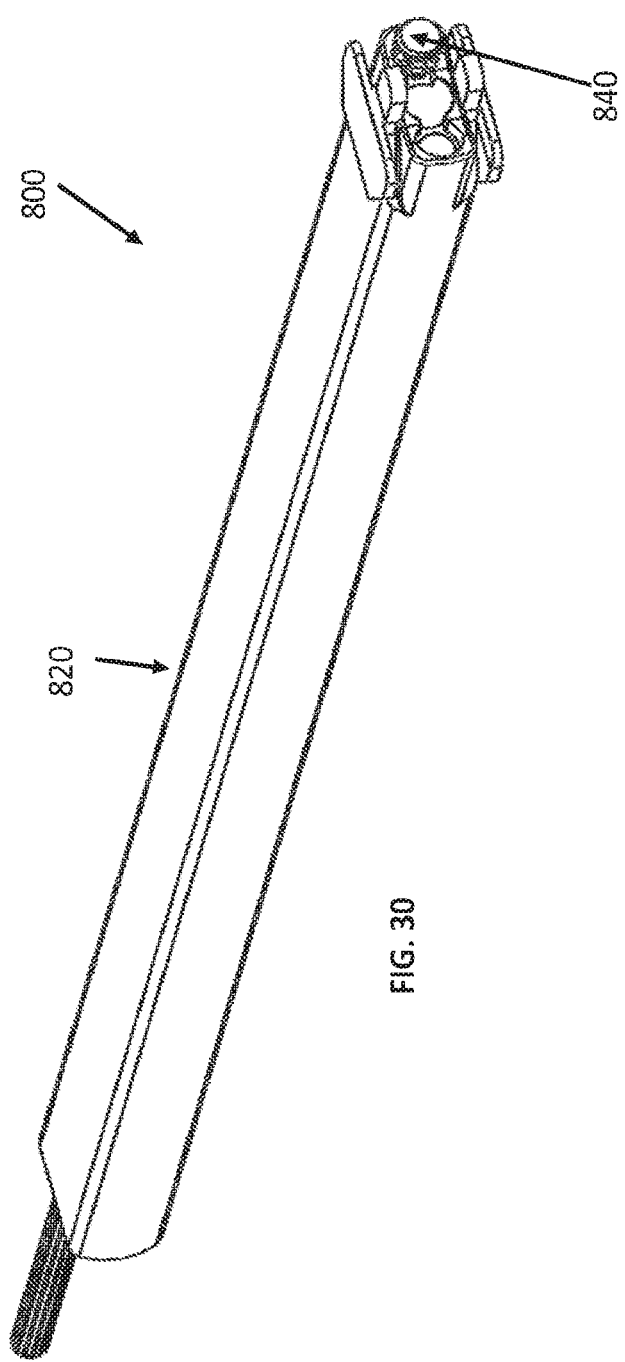
FIG. 30 depicts a perspective view of an exemplary inserter instrument.
Figure 31:
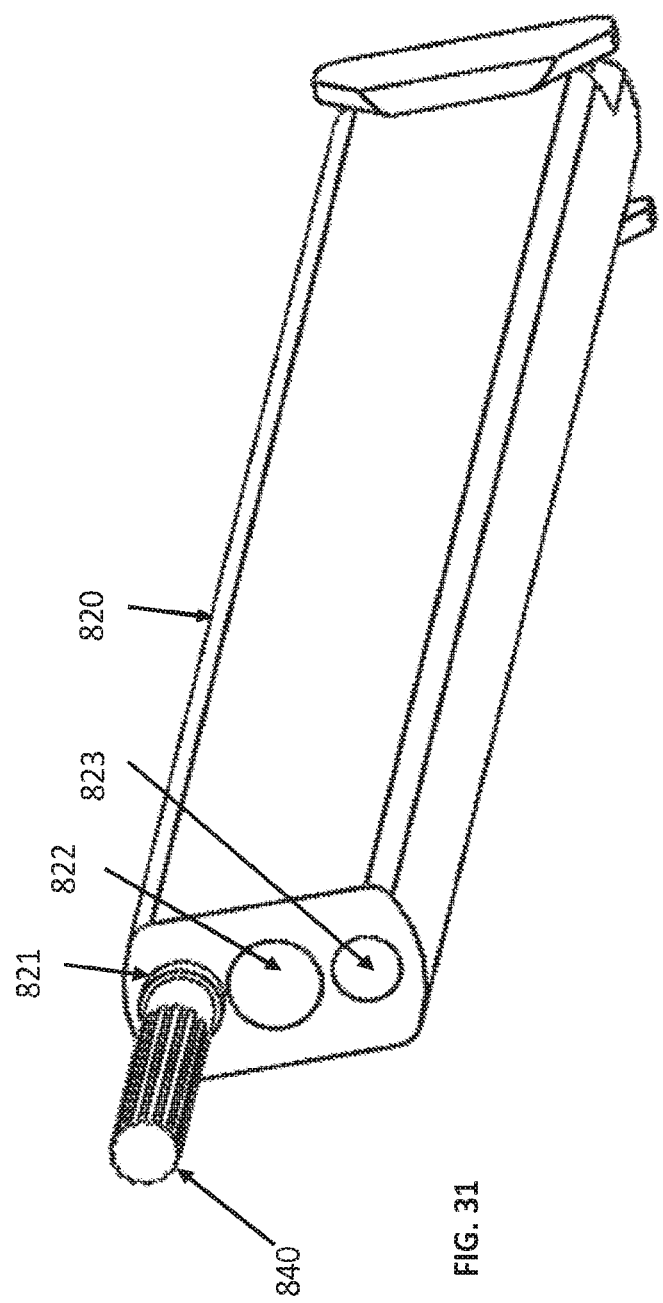
FIG. 31 depicts a perspective view of an exemplary inserter instrument.
Figure 32:
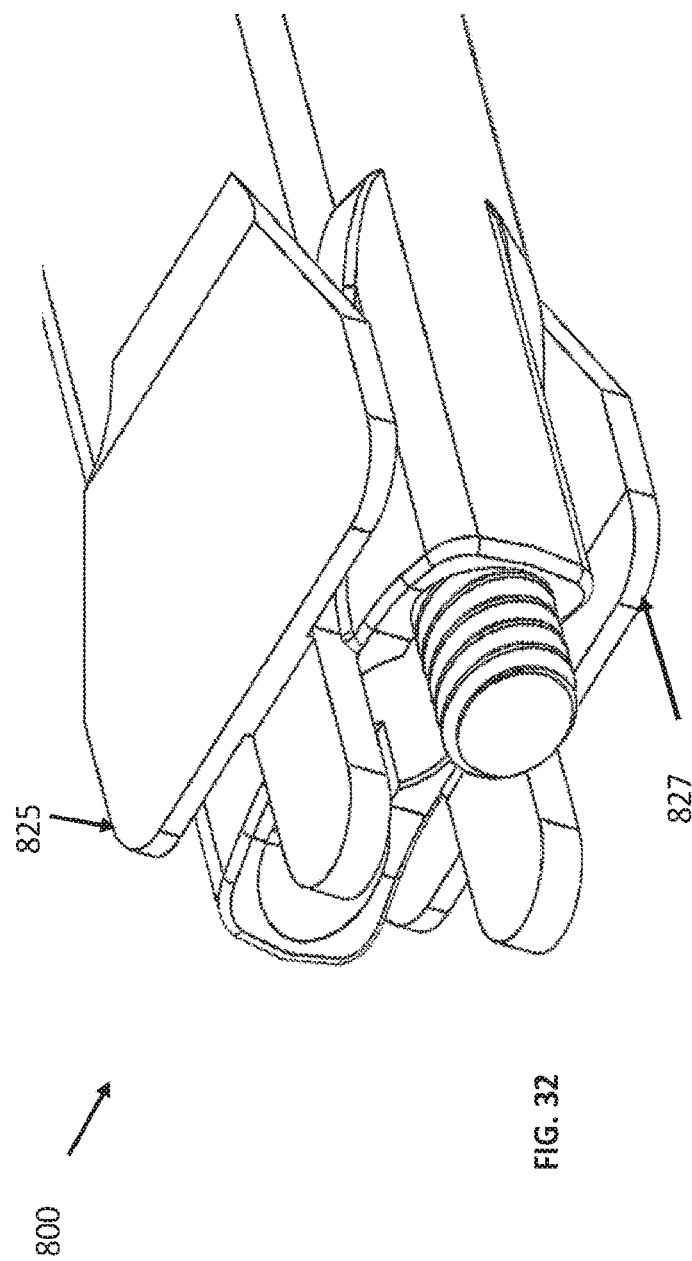
FIG. 32 depicts a detailed perspective view of the distal end of an exemplary inserter instrument.
Figure 33:
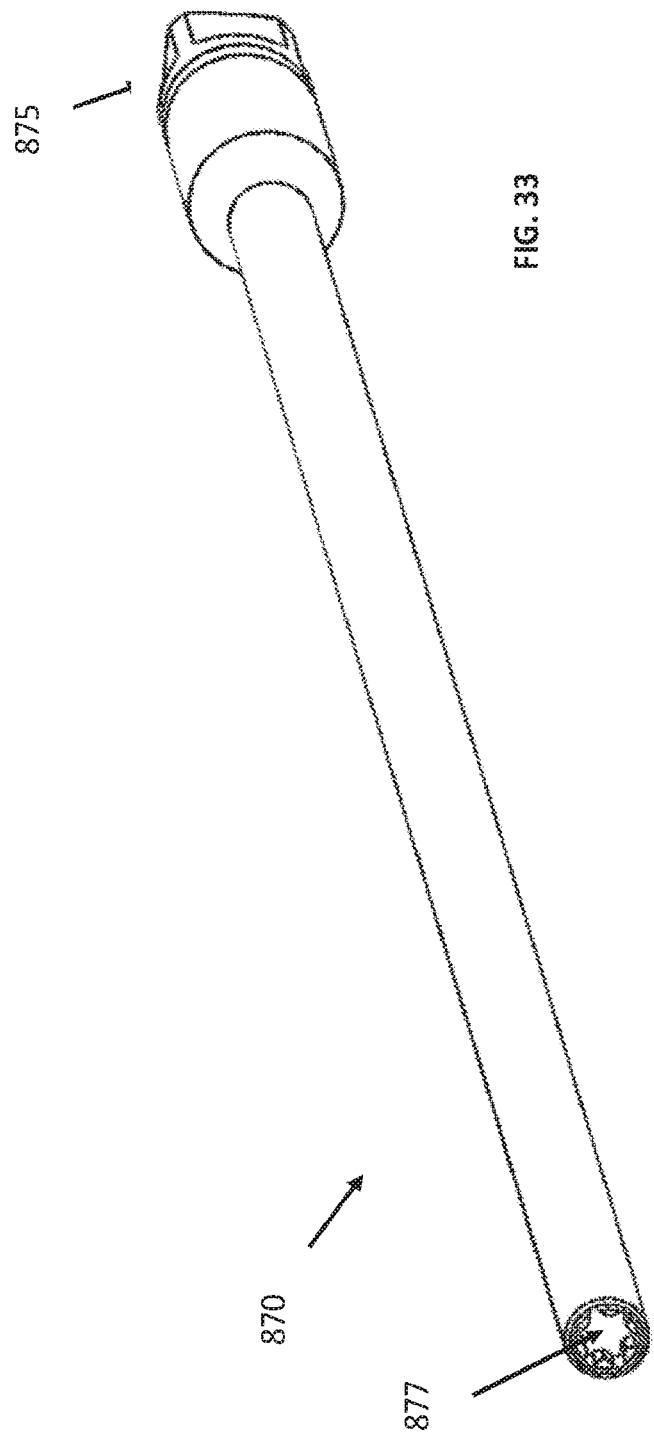
FIG. 33 depicts a perspective view of an exemplary expansion driver instrument.
Figure 34:
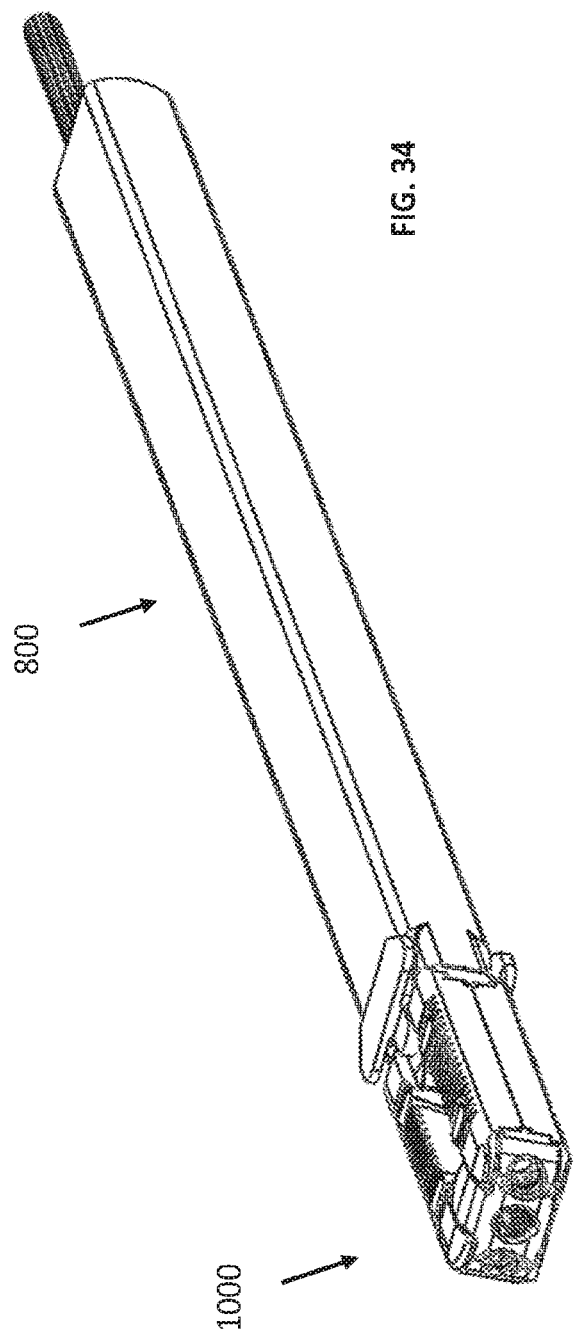
FIG. 34 depicts a perspective view of an exemplary first expandable fusion device attached to an exemplary inserter instrument.
Figure 35:
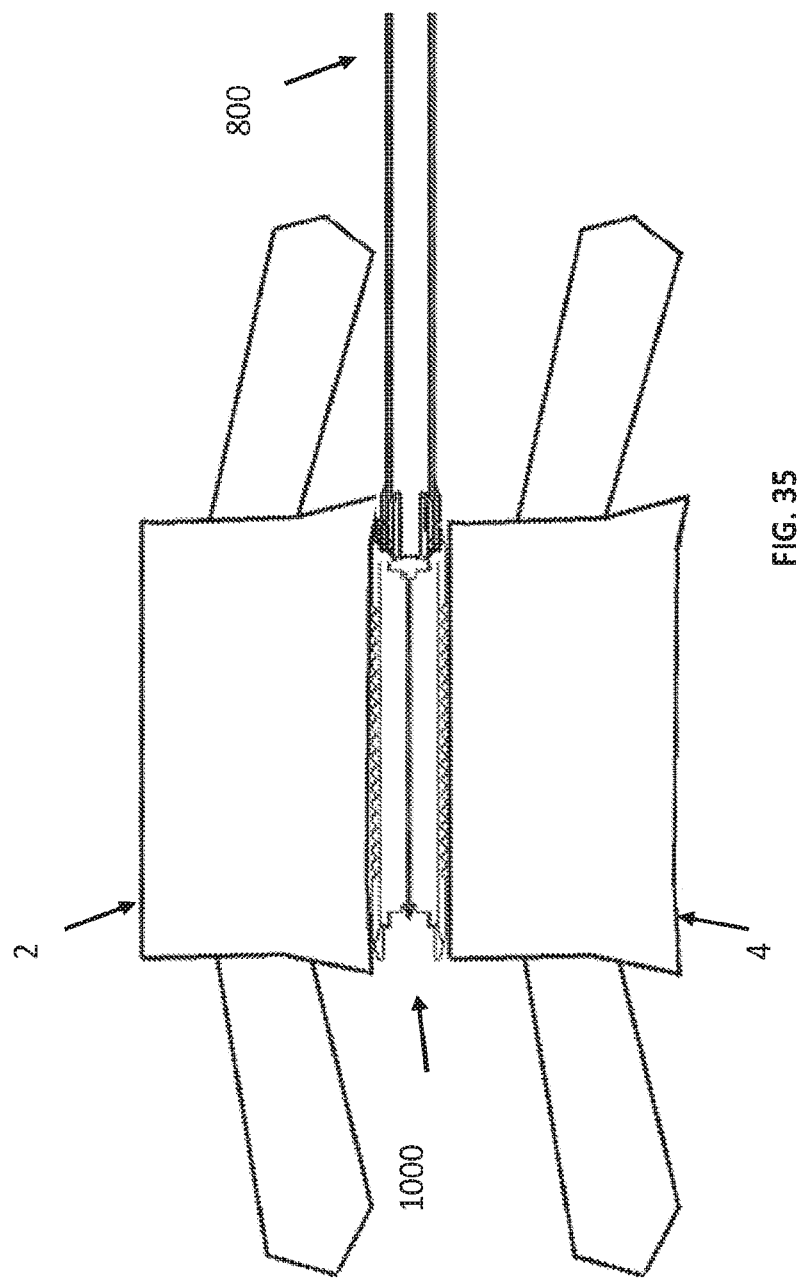
FIG. 35 depicts an exemplary first expandable fusion device implanted between two vertebral bodies in an initial collapsed state while having an exemplary inserter instrument attached to it.
Figure 36:
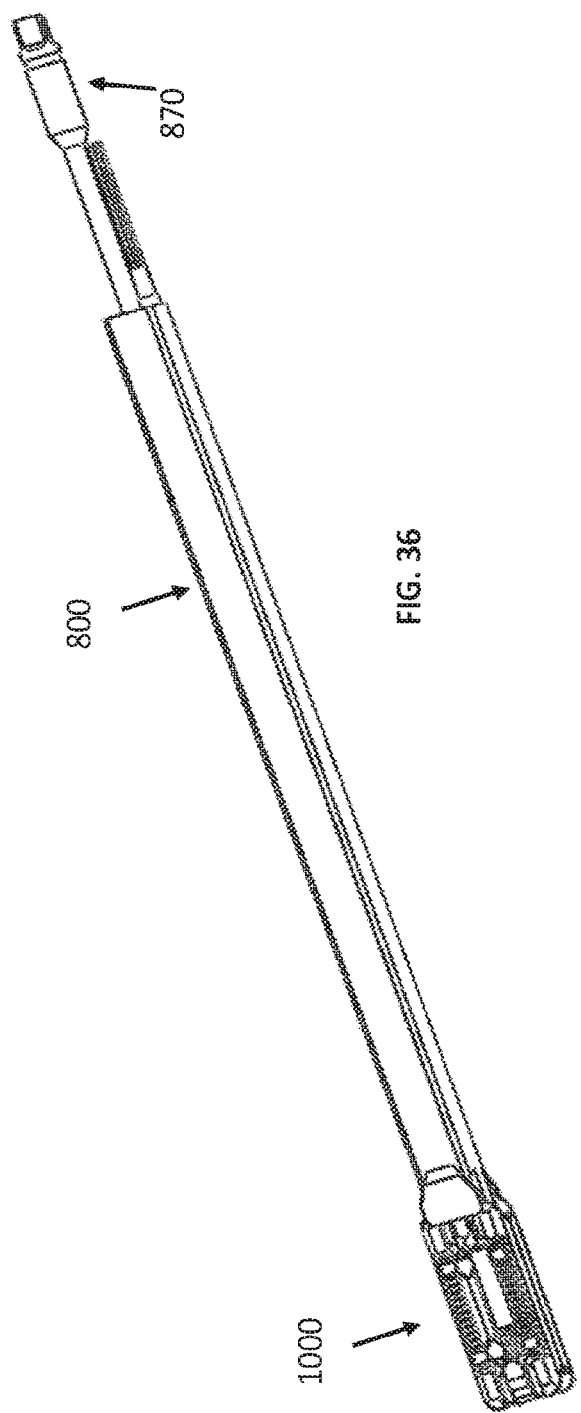
FIG. 36 depicts a perspective view of an exemplary first expandable fusion device attached to an exemplary inserter instrument with an exemplary expansion driver instrument.
Figure 37:
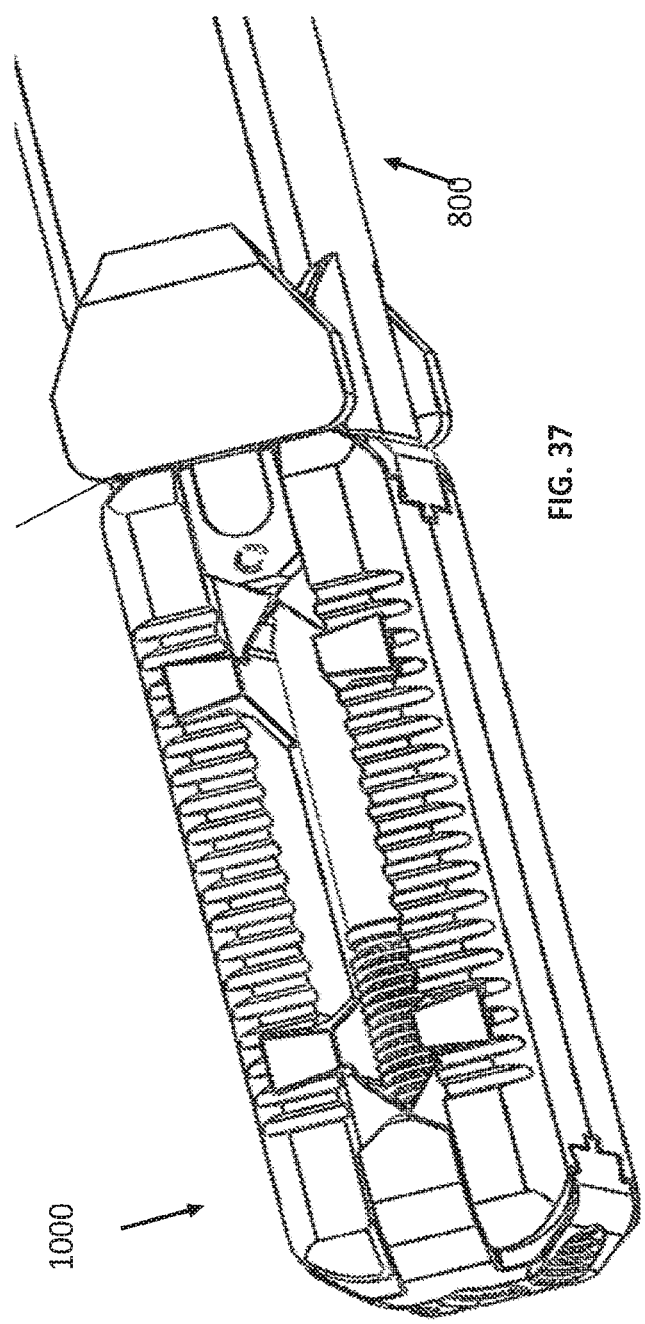
FIG. 37 depicts a detailed perspective view of an exemplary first expandable fusion device attached to an exemplary inserter instrument.
Figure 38:
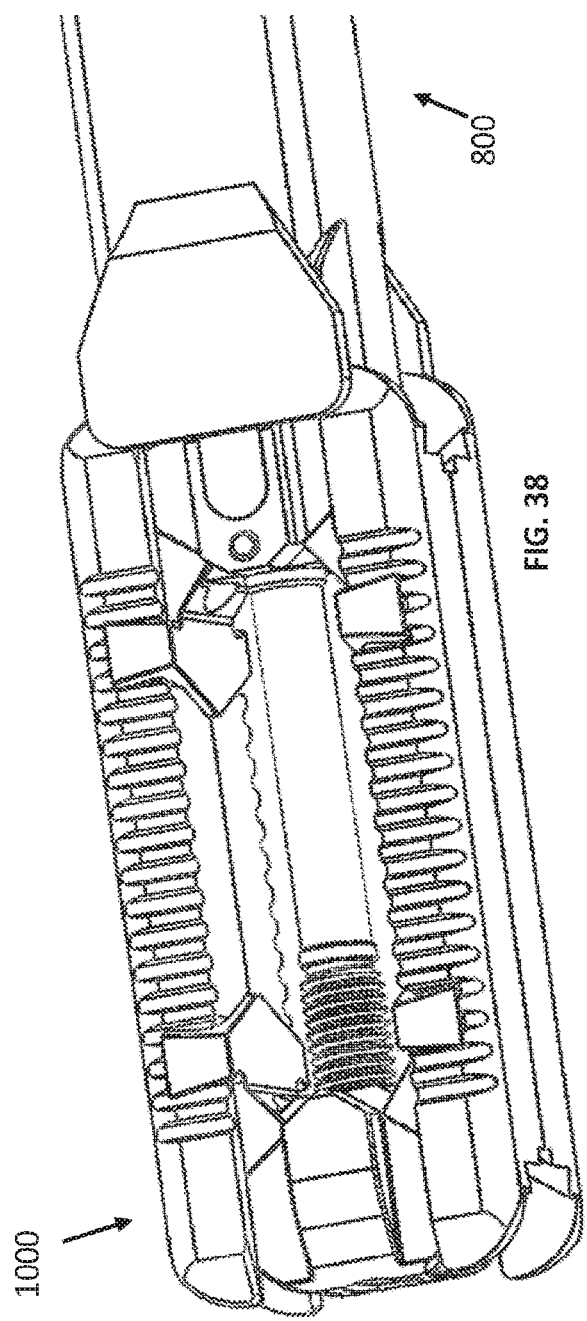
FIG. 38 depicts a detailed perspective view of an exemplary first expandable fusion device in a partially width expanded state attached to an exemplary inserter instrument.
Figure 39:
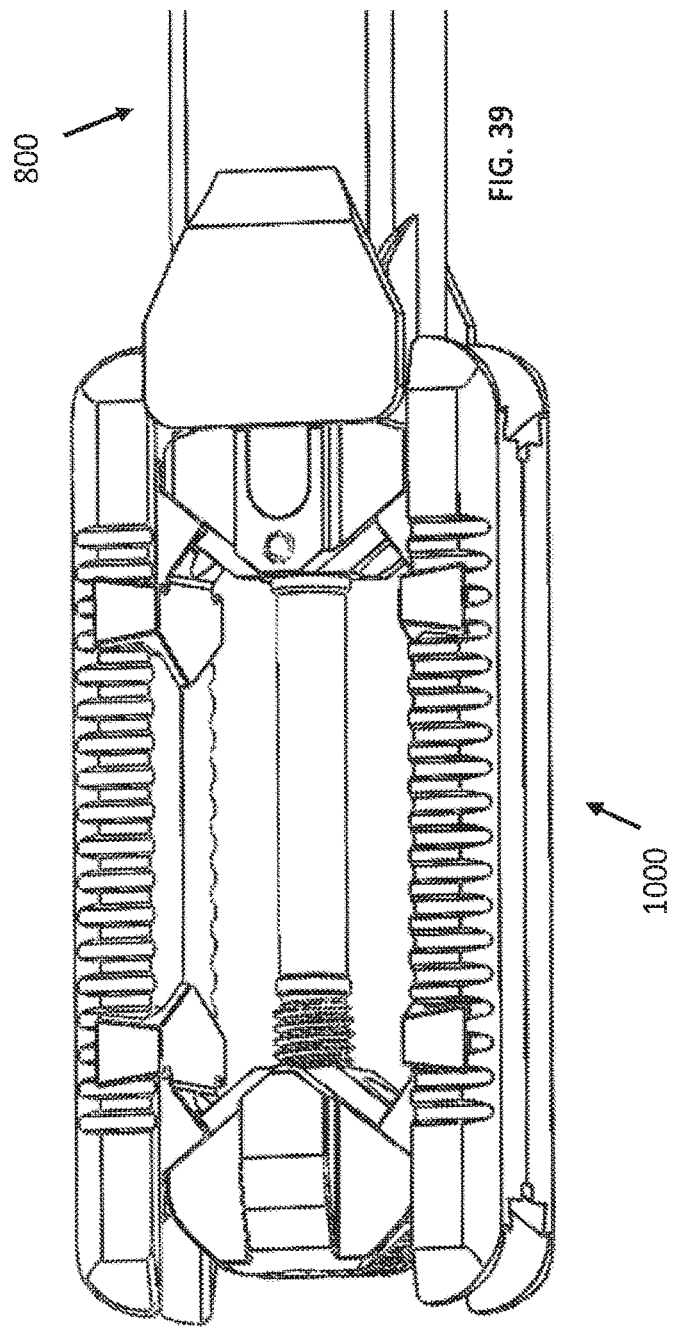
FIG. 39 depicts a detailed perspective view of an exemplary first expandable fusion device in a fully width expanded state attached to an exemplary inserter instrument.
Figure 40:
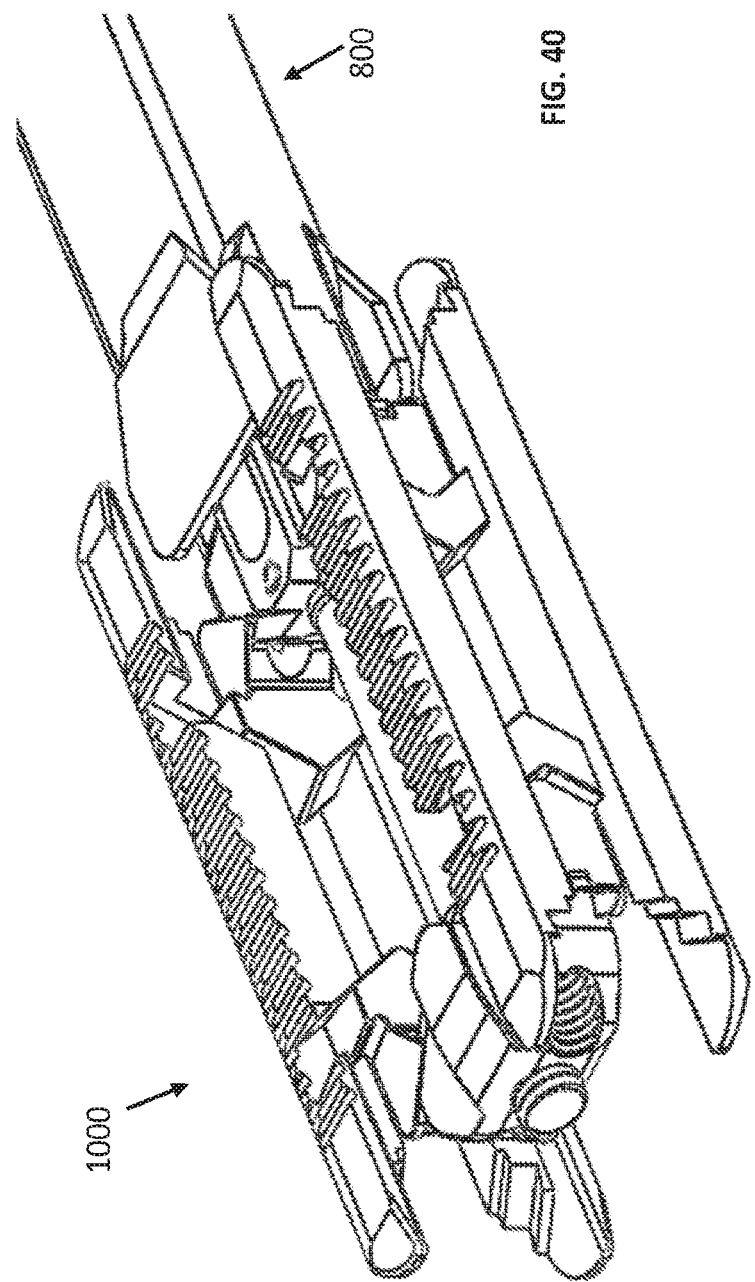
FIG. 40 depicts a detailed perspective view of an exemplary first expandable fusion device in a fully width and height expanded state attached to an exemplary inserter instrument.
Figure 41:
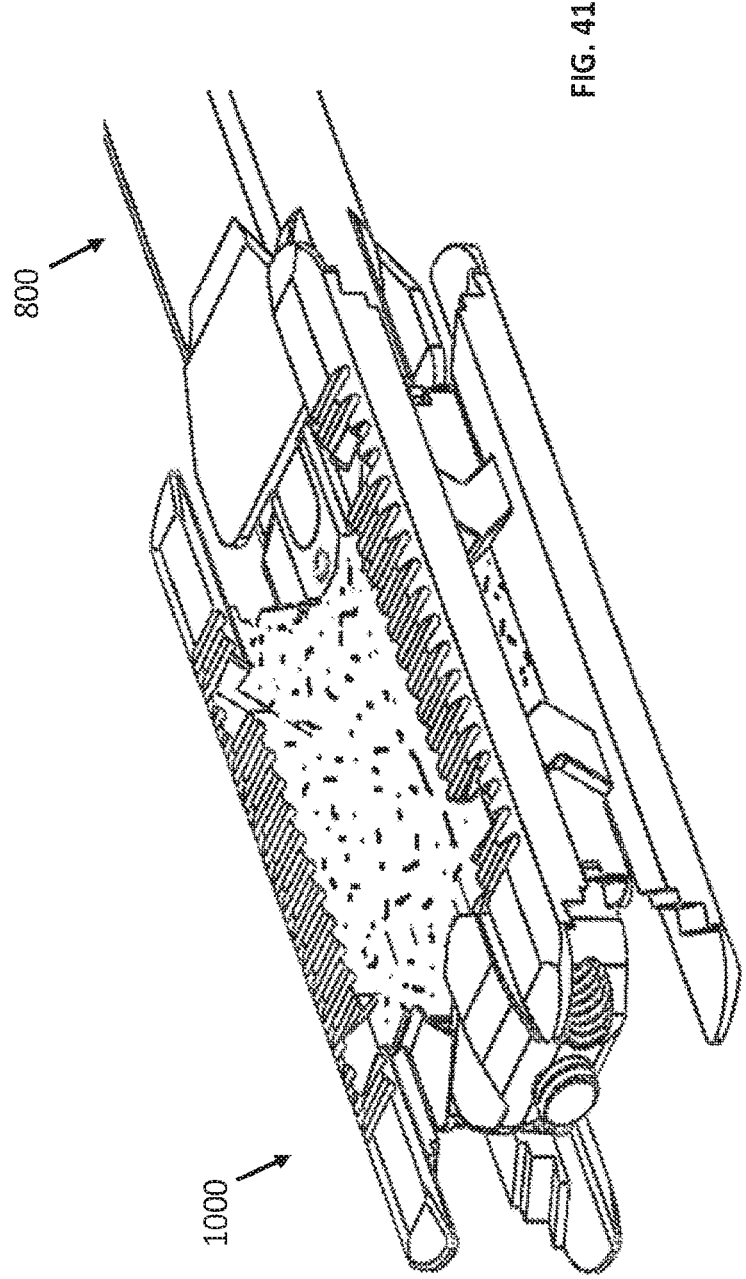
FIG. 41 depicts a perspective view of an exemplary first expandable fusion device in a fully width and height expanded state filled with graft material and attached to an exemplary inserter instrument.
Figure 42:
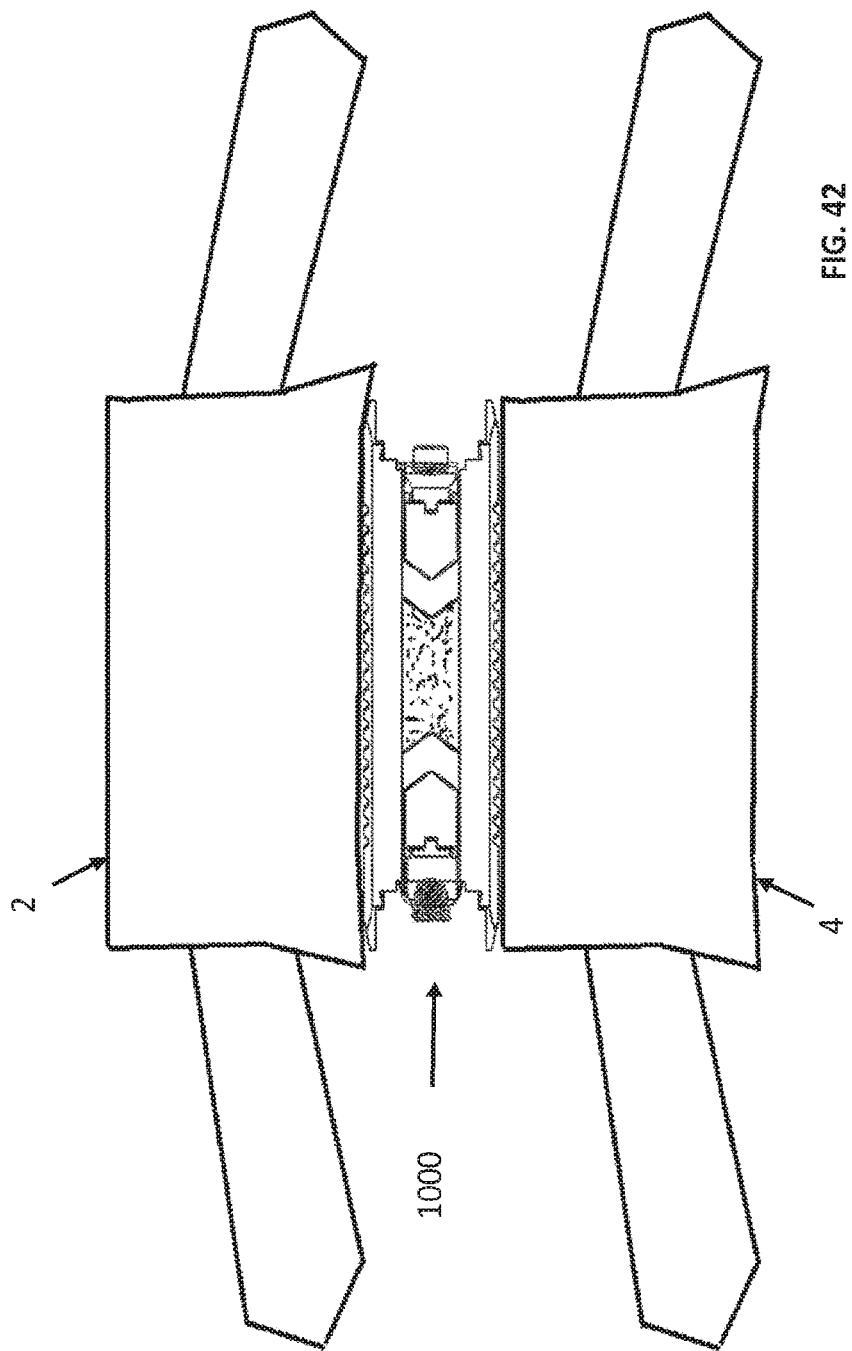
FIG. 42 depicts an exemplary first expandable fusion device implanted between two vertebral bodies in a fully expanded state and filled with graft material.

Turning now to method of implantation of the fusion device 1000 between two adjacent vertebral bodies 2 and 4. FIGS. 30, 31, and 32 show an embodiment of an inserter 800 configured to be reversibly attached to the fusion device 1000, allow the fusion device 1000 to be implanted between the adjacent vertebral bodies 2 and 4 and facilitate graft delivery into the fusion device 1000. Optionally, in any embodiment, the inserter 800 comprises an elongate main body 820 of a generally rectangular shape but may be other shapes in other embodiment, most preferably having a cross-section that is substantially the same as the transverse cross-section of the fusion device 1000 in the initial collapsed state. The inserter 800 further comprises a threaded shaft 840 slidably disposed in the main body. The main body 820 further comprises a distal end configured to mate with the proximal wedge 550 of the fusion device 1000 and includes three apertures running throughout the entire length of the main body 820. The first aperture 821 allows the threaded shaft 840 to access one of the threaded side-apertures of the proximal wedge 550 allowing the reversible attachment of the inserter 800 to the fusion device 1000 by means of threading the threaded shaft 840 into the proximal wedge 550. The second aperture 822 allows an expansion driver 870 to access the drive feature 512 of the actuator 500. The expansion driver 870 is shown in FIG. 33 and comprises a distal end including a drive feature 877 compatible with the drive feature 512 of the actuator 500 and a proximal end including an attachment feature 875 for a torque handle, a torque-limiting handle or a torque indicating handle used to actuate the actuator 500 and achieve expansion of the fusion device 1000. The third aperture 823 allows access to a side aperture of the proximal wedge 550 for the purpose of delivering a therapeutic agent such as bone graft or bone growth inducing material into the fusion device 1000 post expansion. The distal end of the main body 820 further comprises flat planar plates forming ledges 825 and 827 intended to prevent height expansion of the fusion device 1000 until the width expansion is substantially complete. Once the inserter 800 is attached to the fusion device 1000 by means of threading the threaded shaft 840 into the proximal wedge 550 (see FIG. 34), the fusion device 1000 are implanted between the adjacent vertebral bodies 2 and 4 (see FIG. 35). Once the initial implanted position of the fusion device 1000 is found to be satisfactory, the expansion driver 870 is slidably introduced into the second aperture 822 in the inserter 800 and the drive feature 877 is engaged with the drive feature 512 of the actuator 500 (see FIG. 36). Applying torque to the expansion driver 870 now results in expansion of the fusion device 1000. FIG. 37 shows the inserter 800 attached to the fusion device 1000 in fully collapsed state and the ledge 825 partially covering the endplates thereby preventing height expansion but allowing the width expansion of the fusion device 1000. The ledge 825 in FIG. 37 is shown covering a portion of the endplates and preventing height expansion of the fusion device 1000. FIG. 38 shows the inserter 800 attached to the fusion device 1000 in a state of partial width expansion and the ledge 825 partially covering the endplates thereby preventing height expansion but allowing further width expansion of the fusion device 1000. FIG. 39 shows the inserter 800 attached to the fusion device 1000 in a state of full width expansion and the ledge 825 no longer covering the endplates thereby allowing height expansion of the fusion device 1000. FIG. 40 shows the inserter 800 attached to the fusion device 1000 in a state of full width and height expansion. Bone graft or bone growth inducing material (graft material) is then introduced, delivered or injected into the fusion device 1000 through the third aperture 823 of the inserter 800. Optionally, in any embodiment, graft material may be pre-packed into the third aperture 823 prior to attaching the inserter 800 and tamped through the third aperture 823 and into the fusion device 1000 using an elongated tamp (not shown) configured to fit through the third aperture 823 once the fusion device 1000 is implanted and expanded. It is further contemplated that graft material may be delivered into the proximal opening of the third aperture 823 by means including but not limited to a syringe, a funnel, a thread-actuated graft delivery device or a grip-operated graft delivery device after the device 1000 has been expanded. The elongated tamp is then used to push any graft material remaining inside the third aperture 823 into the fusion device 1000. It is further contemplated that graft material are introduced into the fusion device 1000 after it has been expanded and after the inserter instrument has been detached, the graft are introduced through any of the available apertures in the proximal wedge 550 or through the gaps between the first vertebral endplate 6 and the proximal wedge 550 or through the gap between the second vertebral endplate 8 and the proximal wedge 550 or both at the same time. FIG. 41 shows the fusion device 1000 in fully expanded state filled with bone graft material and still attached to the inserter 800. FIG. 42 shows the fusion device 1000 between the two adjacent vertebral bodies 2 and 4 in fully expanded state filled with bone graft and detached from the inserter 800. The implantation of the fusion device 1000 is then complete and the surgical wound may then be closed.

Figure 43:
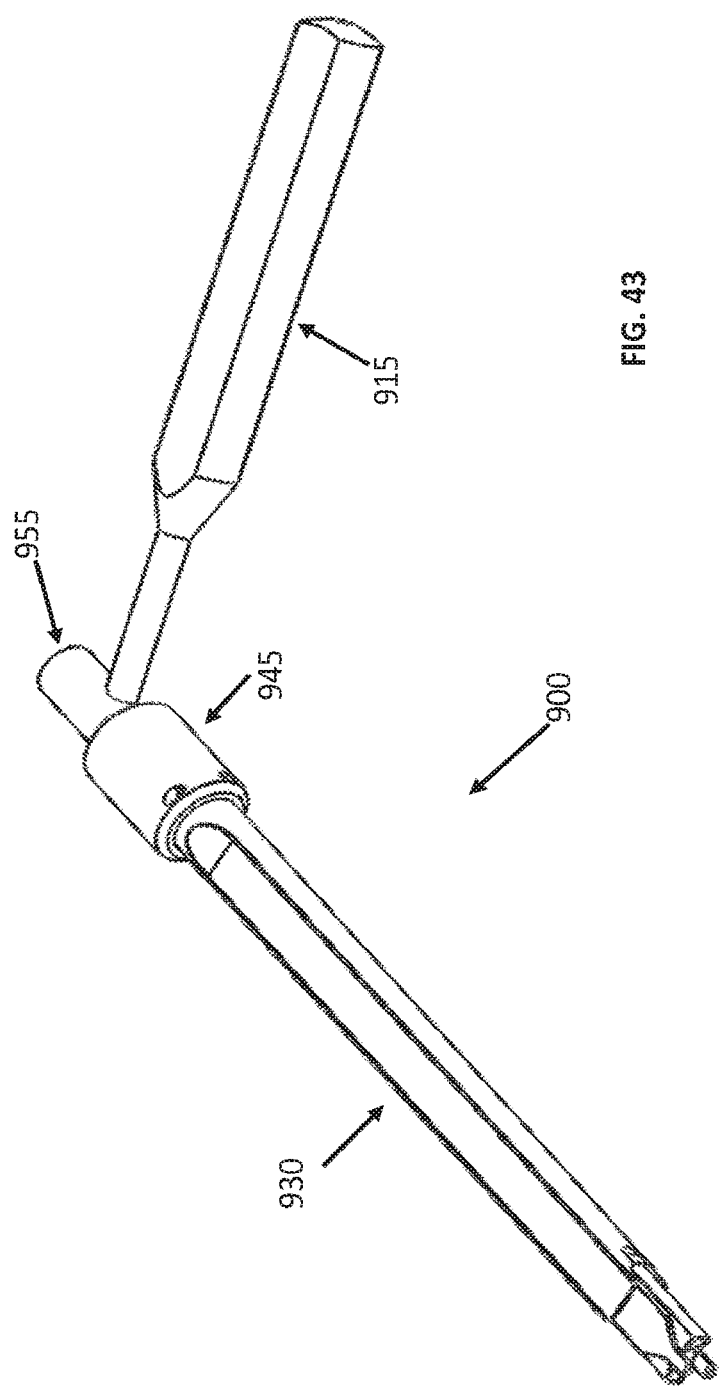
FIG. 43 depicts an exemplary inserter instrument.
Figure 44:
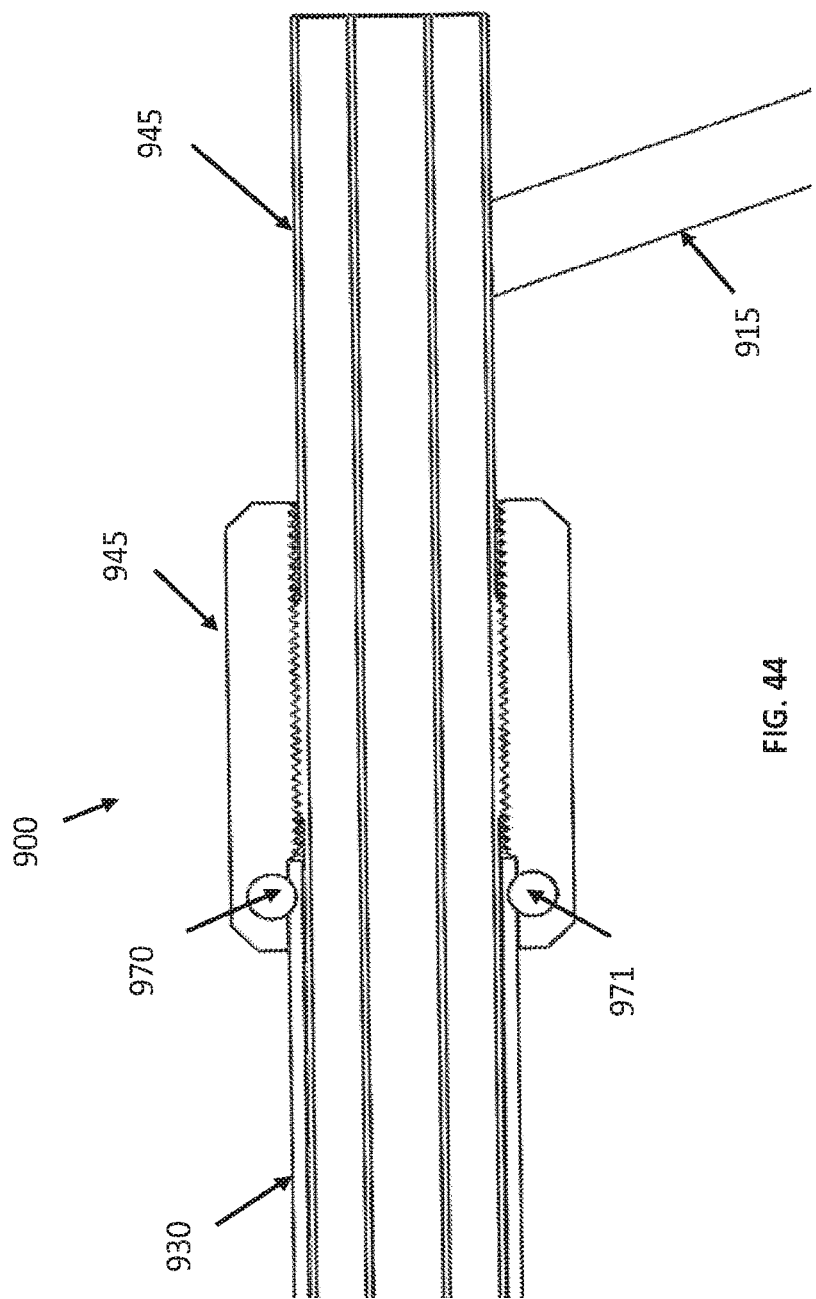
FIG. 44 depicts a detailed section view of an exemplary actuation mechanism of an exemplary inserter instrument.
Figure 45:
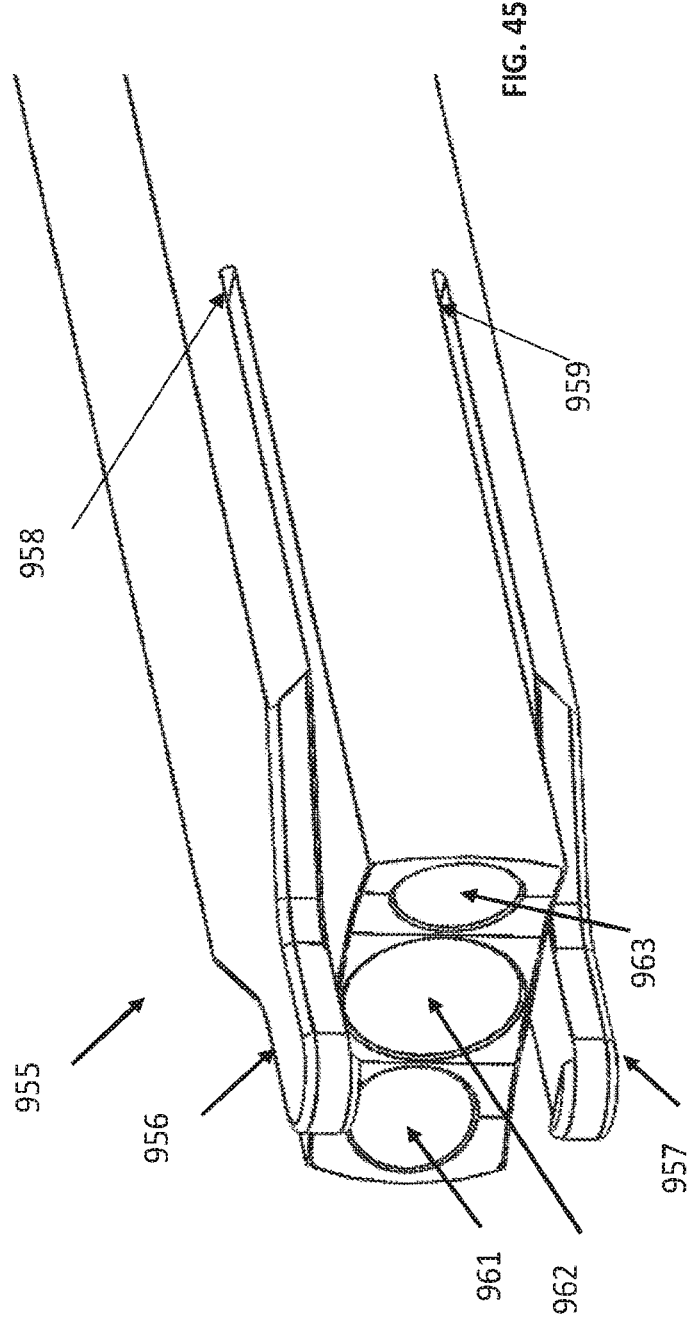
FIG. 45 depicts a detailed view of the distal end of the main shaft of an exemplary inserter instrument.
Figure 46:
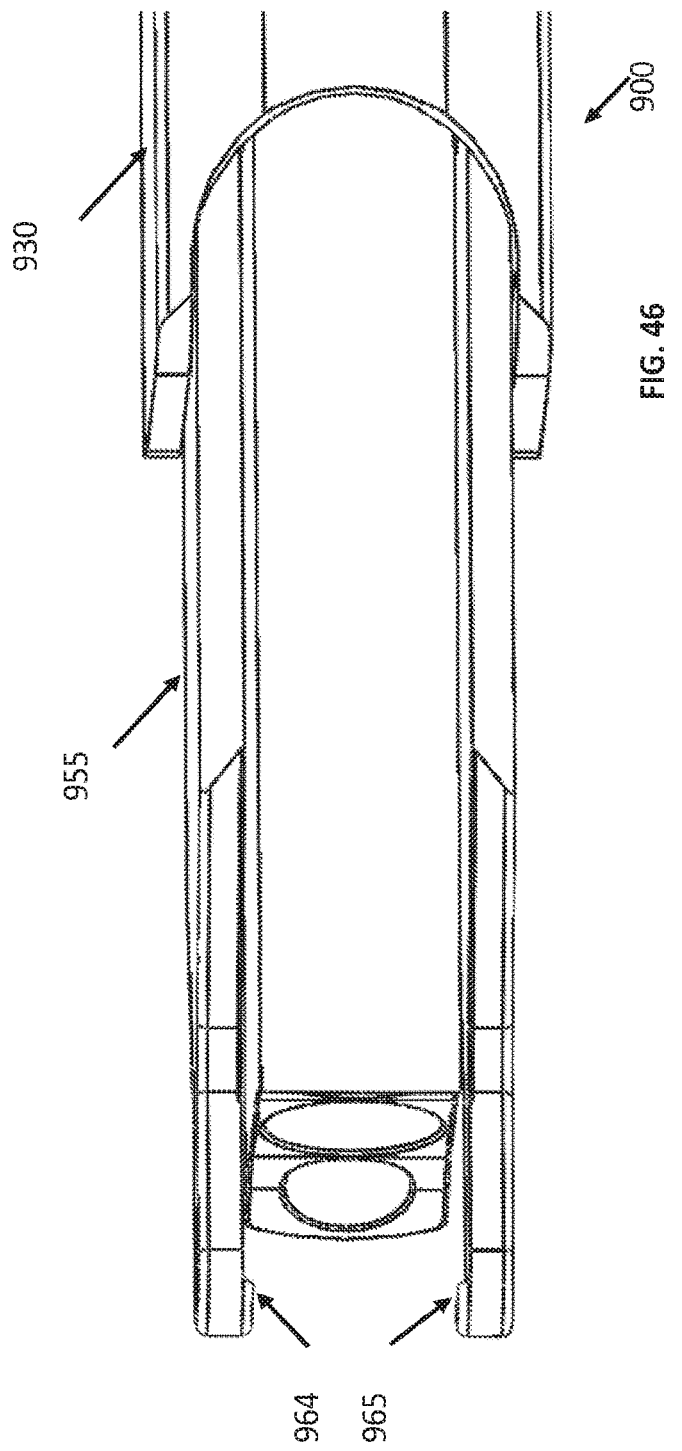
FIG. 46 depicts a detailed view of the distal end of an exemplary inserter instrument.
Figure 47:
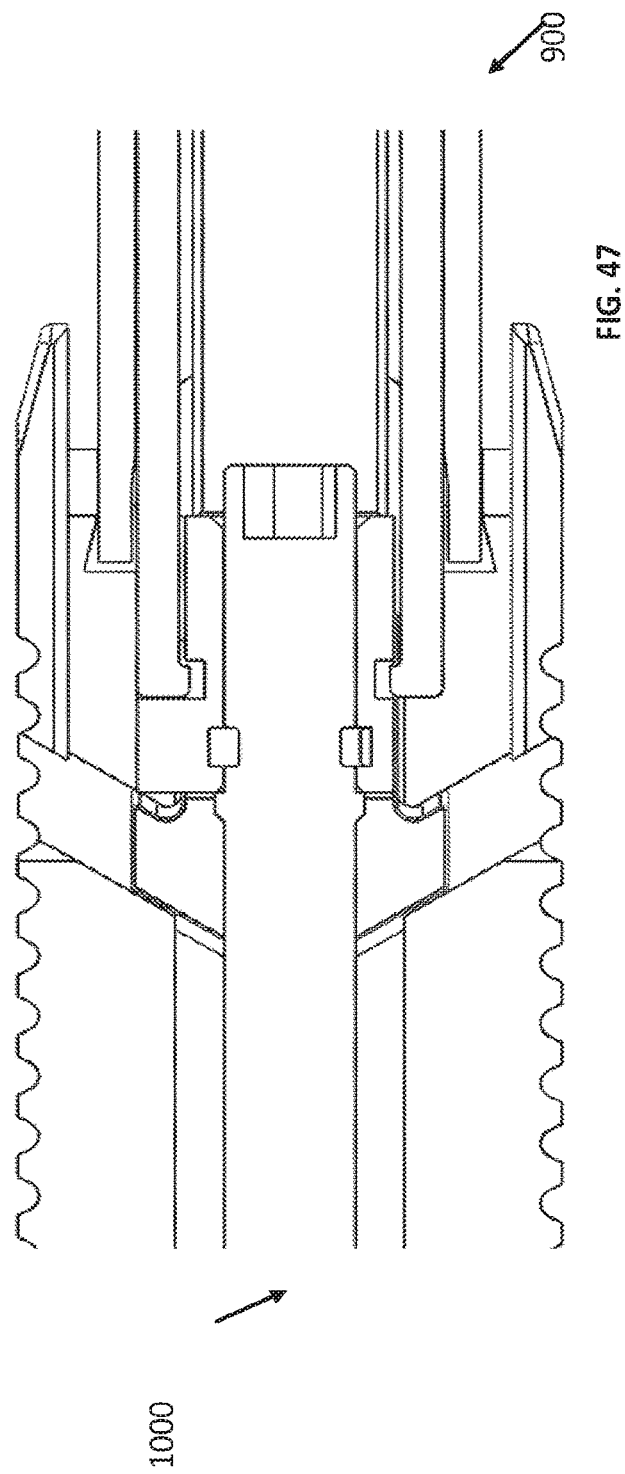
FIG. 47 depicts a detailed section view of the articulation between an exemplary first expandable fusion device and an exemplary inserter instrument.
Figure 48:
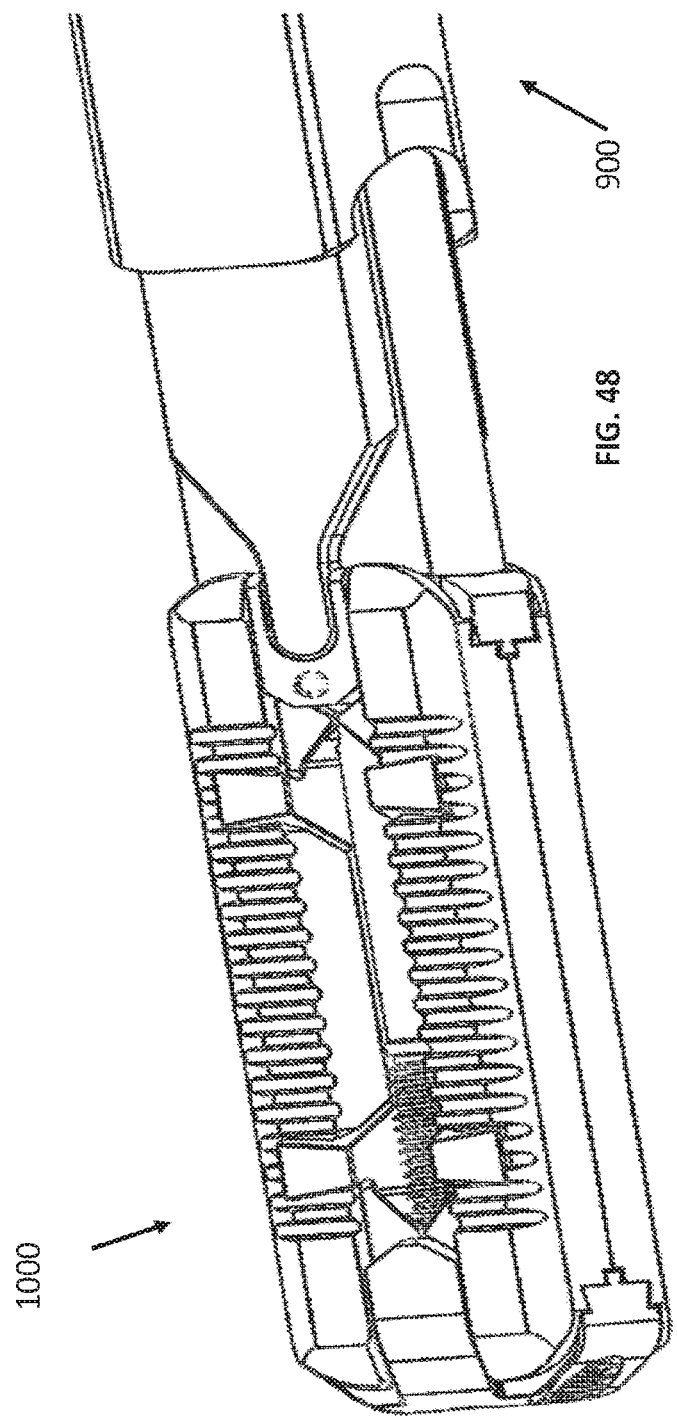
FIG. 48 depicts a detailed perspective view of an exemplary first expandable fusion device in an initial collapsed state attached to an exemplary inserter instrument in an unlocked state.
Figure 49:
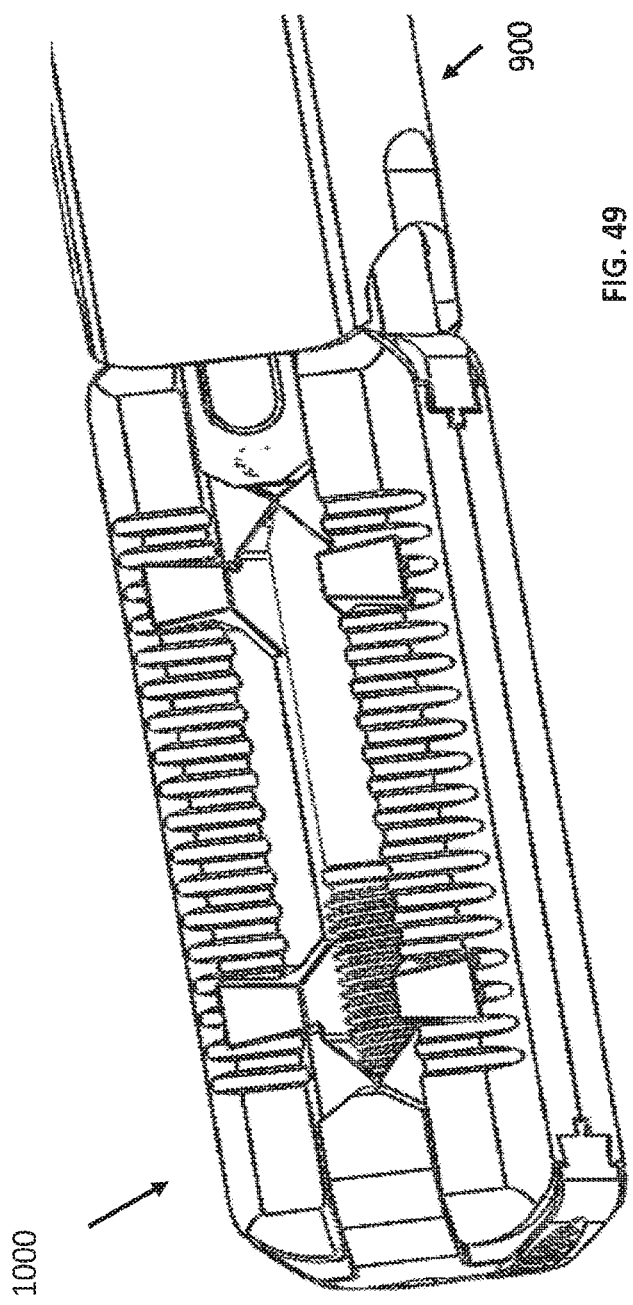
FIG. 49 depicts a detailed perspective view of an exemplary first expandable fusion device in an initial collapsed state attached to an exemplary inserter instrument in a locked state.
Figure 50:
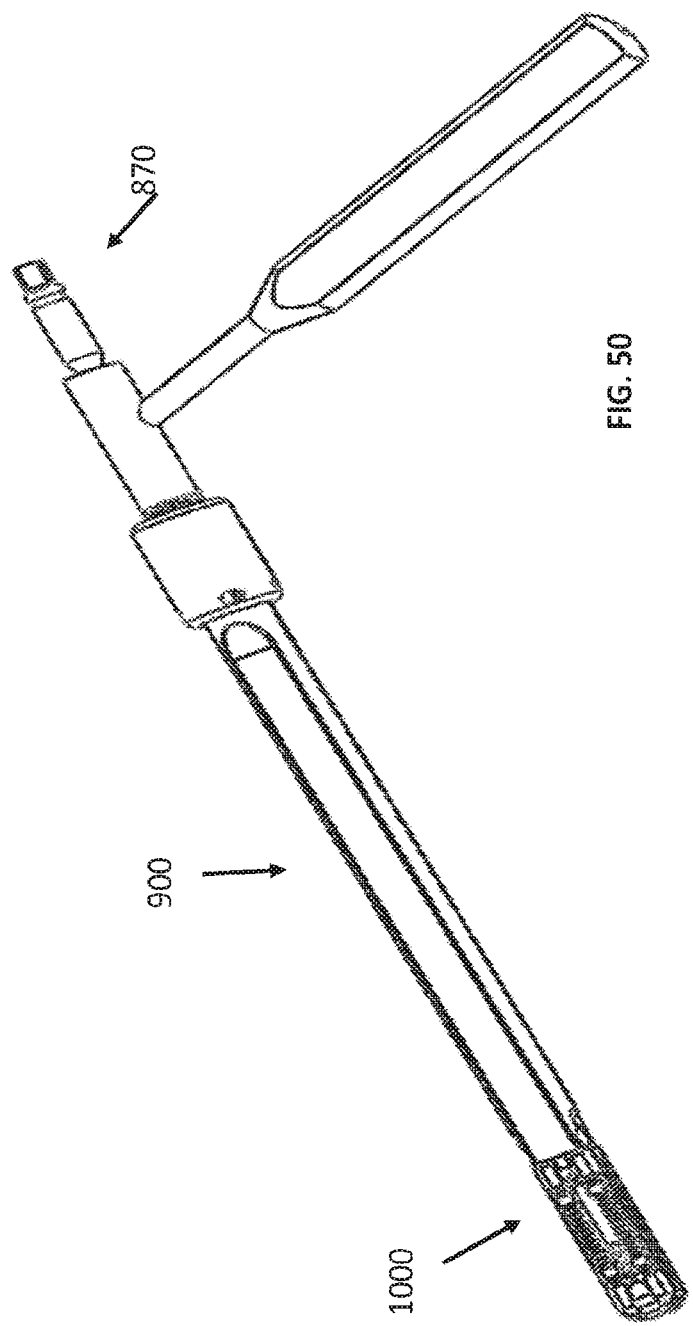
FIG. 50 depicts a perspective view of an exemplary first expandable fusion device attached to an exemplary inserter instrument with an exemplary expansion driver instrument.
Figure 51:
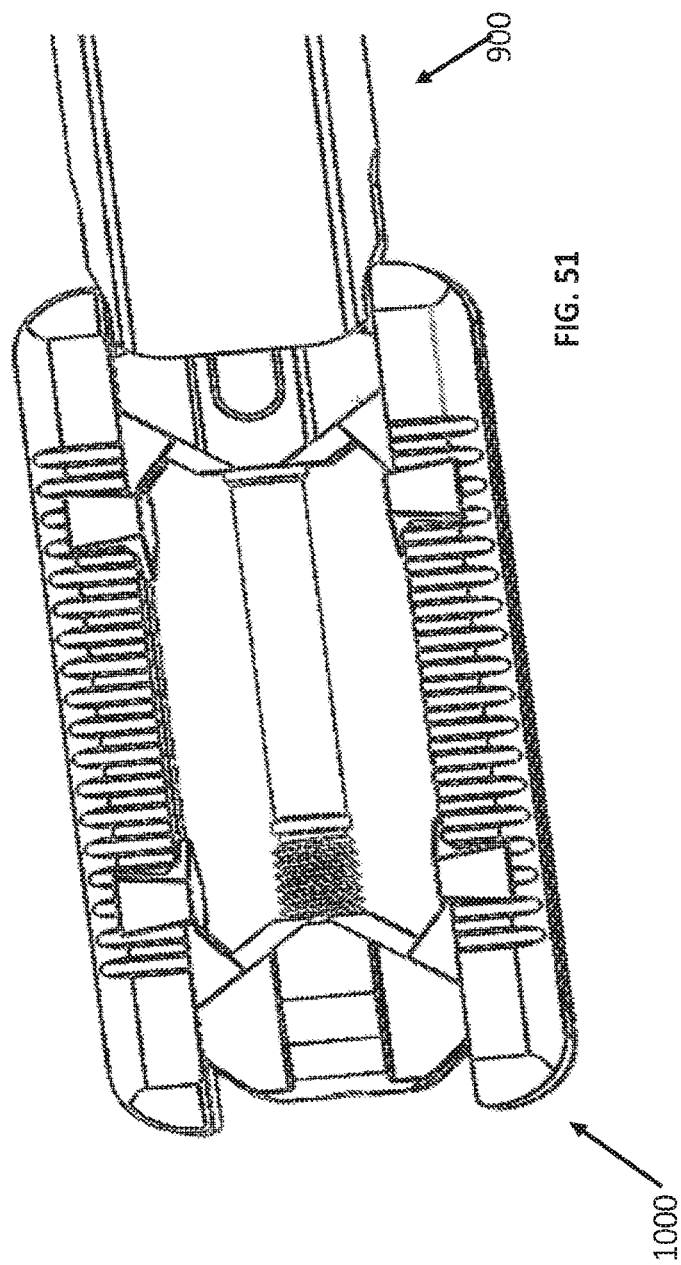
FIG. 51 depicts a perspective view of an exemplary first expandable fusion device in a fully width expanded state attached to an exemplary inserter instrument.

FIG. 43 shows an exemplary inserter instrument. An inserter 900 comprises a main shaft 955, a sleeve 930, a wheel 945, a handle 915, and pins 970 and 971. The main shaft 955 further comprises a distal end configured to mate with the proximal wedge 550 of the fusion device 1000 and an external thread located proximate the proximal end. A detailed section view of the threaded articulation of the inserter is seen in FIG. 44. As shown in FIGS. 45 and 46, the main shaft further includes three apertures running throughout the entire length of the main shaft 955. The second aperture 961 allows an expansion driver 870 to access the drive feature 512 of the actuator 500. The first aperture 961 and the third aperture 963 allow access to the side apertures of the proximal wedge 550 for the purpose of delivering bone graft or bone growth inducing material into the fusion device 1000 post expansion. The distal end of the main shaft 955 further comprises a first tang 956 including a distal protrusion 964 and a second tang 957 including a distal protrusion 965. The tangs 956 and 957 are partially separated from the main bulk of the main shaft 955 by the slits 958 and 959, which give the tangs flexibility. Distal ends of the tangs are configured to engage mating features of an exemplary proximal wedge 550; this articulation is shown in a section view in FIG. 47. The sleeve 930 is configured to slide over the main shaft 955 and are advanced distally or proximally along the main shaft 955 by means of turning the wheel 945 which is threadably engaged with the main shaft 955 and rotationally engaged with the sleeve 930 by means of the pins 970 and 971, which results in an articulation whereby the wheel 945 rotates relative to the sleeve 930 but not translate relative to it. The handle 915 is rigidly attached to the proximal end of the main shaft 955. When the sleeve 930 is in its proximal-most position (shown in FIG. 48), the tangs 956 and 957 are allowed to elastically deform away from each other to engage the mating features on the proximal wedge 550 of the fusion device 1000, and when the sleeve 930 is in its distal-most position (shown in FIG. 49), it prevents the tangs 956 and 957 from elastically deforming away from each other, resulting in a positive engagement between the proximal wedge 550 of the fusion device 1000 and the inserter 900. Furthermore, in its distal-most state the sleeve 930 and specifically its distal end carries out the same function in the inserter 900 as the ledges 825 and 827 do in the inserter 800, this function being preventing the fusion device 1000 from expanding in height until the width expansion has been substantially complete. Once the inserter 900 is attached to the fusion device 1000, the fusion device 1000 is implanted between the adjacent vertebral bodies 2 and 4. Once the initial implanted position of the fusion device 1000 is found to be satisfactory, the expansion driver 870 is introduced into the second aperture 962 in the inserter 900 and the drive feature 877 is engaged with the drive feature 512 of the actuator 500 (see FIG. 50). Applying torque to the expansion driver 870 now results in expansion of the fusion device 1000 first in width (see FIG. 51) and then in both width and height (see FIG. 52). The delivery of the bone graft material through the inserter 900 and into the fusion device 1000 may now be accomplished through one or both of the apertures 961 and 963 in the way discussed above. FIG. 53 shows the fusion device 1000 in fully expanded state filled with bone graft material and still attached to the inserter 900. The inserter 900 may then be detached from the fusion device 1000, the implantation of the fusion device 1000 is then complete, and the surgical wound may then be closed.

Second Expandable Fusion Device

Figure 54B:
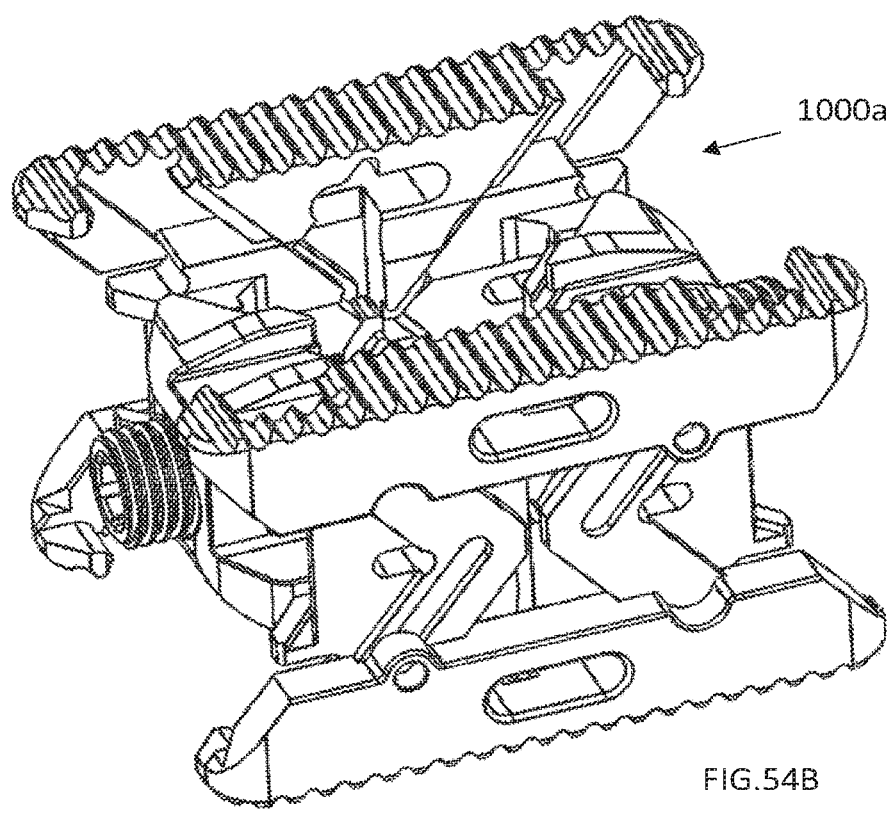
FIG. 54B depicts a perspective view of an exemplary second expandable fusion device of FIG. 54A in a fully expanded state.

Turning now to FIGS. 54A-54C, which show an exemplary second expandable fusion device 1000a. FIG. 54A shows an exemplary second expandable fusion device 1000a in a fully collapsed state, FIG. 54B shows an exemplary second expandable fusion device 1000a in a fully expanded state and FIG. 54C shows an exploded view of an exemplary second expandable fusion device 1000a. Optionally, in any embodiment, the second expandable fusion device 1000a comprises an embodiment 300a of the first ramp 300 (as well as the ramps 350a, 400a and 450a, which are all identical in this embodiment, and the ramp 400a is used to indicate the reference numbers for the ramp 300a in FIG. 54C) is the same as the exemplary embodiment of the first ramp 300 with the following exceptions: the outer surface 327 includes ramped slot 335a that is parallel to the ramped surfaces of the branch 323, the branches 321 and 323 have generally C-shaped cross-sections, the surfaces 329 and 330 include protrusions 337a and 338a, the channel 328 has a generally T-shaped cross-section and does not include the groove 322 present in previously discussed embodiments of the ramp 300.

The second expandable fusion device 1000a further comprises an embodiment 100a of the first endplate 100 (as well as the endplates 150a, 200a and 250a, which are all identical in this embodiment, but may need to be suitably aligned in order to be assembled into the arrangement of the second expandable fusion device 1000a) in which the ramped slots 107 and 109 have C-shaped cross-sections configured to mate with the ramp 300a, the top surface 132 includes a protrusion 145a proximate the slot 109 and a recess 146a proximate the ramped slot 107, whereas the protrusion 145a and the recess 146a have complementary shapes so that when two endplates are suitably rotated, the protrusion 145a of one nests in the recess 146a of the other allowing the bottom surface of the top endplate and the top surface of the bottom endplate to touch. The outward facing surface of the protrusion 145a further includes a divot 147a (shown in FIG. 54C on the endplate 200a) that is generally aligned with the long axis of the ramped slots 335a of the ramp 300a when assembled but doesn't go all the way through to the other side of the endplate. Divot 147a may have spherical, cylindrical (as shown) or any other shape. The purpose of the divot is to create an area of thinned material between the bottom of the divot and the inward surface of the ramped slot 109, which allows to deform (peen) the bottom of the divot and create protruding dimple 148a on the inward facing surface of slot 109 of the endplate. The peening step is performed as the last step in assembly process when the components are assembled and are in a fully collapsed state and is performed by means of a punch or a pointed or rounded tool applying load to the bottom surface of the divot by means of impaction, pressing, or other means. As described above, the peening produces the dimple 148a on the inward facing surfaces of the endplates, which in the assembled device state—lines up with and engages the ramped recesses of the ramps, capturing them and preventing dis-assembly of the second expandable fusion device 1000a by hyper-expansion. Optionally, in any embodiment, the divots are replaced with thru-openings in the endplates and the function of the peened dimples are performed by pins pressed through the end endplate openings and engaging the ramped slots of the ramps. The endplate 100a does not include tapered grooves 122, 118, 124 and 120 present in previously discussed embodiments of the endplate 100, but instead includes ramped surfaces 121a and 123a (shown in FIG. 54C on the endplate 200a), which perform generally the same function as the grooves 122, 118, 124 and 120, which is to prevent height expansion from taking place until the device is sufficiently expanded in width. This is accomplished through the ramped surfaces 121a and 123a being in contact with mating ramped surfaces of the wedges throughout most of the width expansion process and while they are in contact with the wedges, the ramps on the opposing sides of each endplate are only able to move along the direction of the ramped surfaces of the wedges and the ramped surfaces 121a and 123a, while remaining static relative to one another, whereas to achieve height expansion the opposing ramps need to be able to move toward each other along the long axis of the device. Once the width expansion is substantially completed and once the ramped surfaces 121a and 123a no longer contact the wedges, the ramps are allowed to move toward each other resulting in height expansion. The top surface 132 further includes a protrusion 115a proximate the ramped slot 107 and the inward surface 130 includes a recess 117a proximate the slot 109, whereas the protrusion 115a and the recess 117a have complementary shapes so that when two endplates are suitably rotated, the protrusion 115a of one nests in the recess 117a of the other allowing the opposing top and bottom surfaces of the two endplates to touch. Protrusion 115a is configured to mate with the ramp 300a as an extension of the ramped surfaces of the ramped slot 107. The purpose of the protrusion 115a is to increase device stability at the upper limits of allowed height expansion by maintaining a large contact area between the ramp and the endplate. The endplate 100a further includes an opening 119a extending from the inner surface to the outer surface. This feature is optional and is contemplated to allow graft material to exit the interior of the device and fill the space surrounding it. The endplate 100a further includes a relief 149a whose axis is substantially parallel to the long axis. The relief 149a is configured to mate with the actuator 500a and allow the endplates to be in closer proximity to each other than would otherwise be possible without the relief 149a.

The second expandable fusion device 1000a further comprises an embodiment 500a of the actuator 500. The actuator 500a comprises a proximal end 504a, a distal end 502a and a cylindrical surface 506a connecting the proximal end 504a and the distal end 502a. Optionally, in any embodiment, the actuator 500a further comprises a drive feature 512a on the proximal end 504a, a thread 517a proximate the proximal end 504a, and a thread 508a proximate the distal end 502a. The thread 508a is comprised of a helical groove of opposite direction to that of the thread 508 (e. g. if the thread 508a is right-handed, then the thread 517a is left-handed or vice versa). This embodiment further includes a second drive feature on the distal end (not shown). This second drive feature is deemed useful in the event of a revision surgery where the revision approach is not the same as the approach used during the original surgery.

Figure 55A:
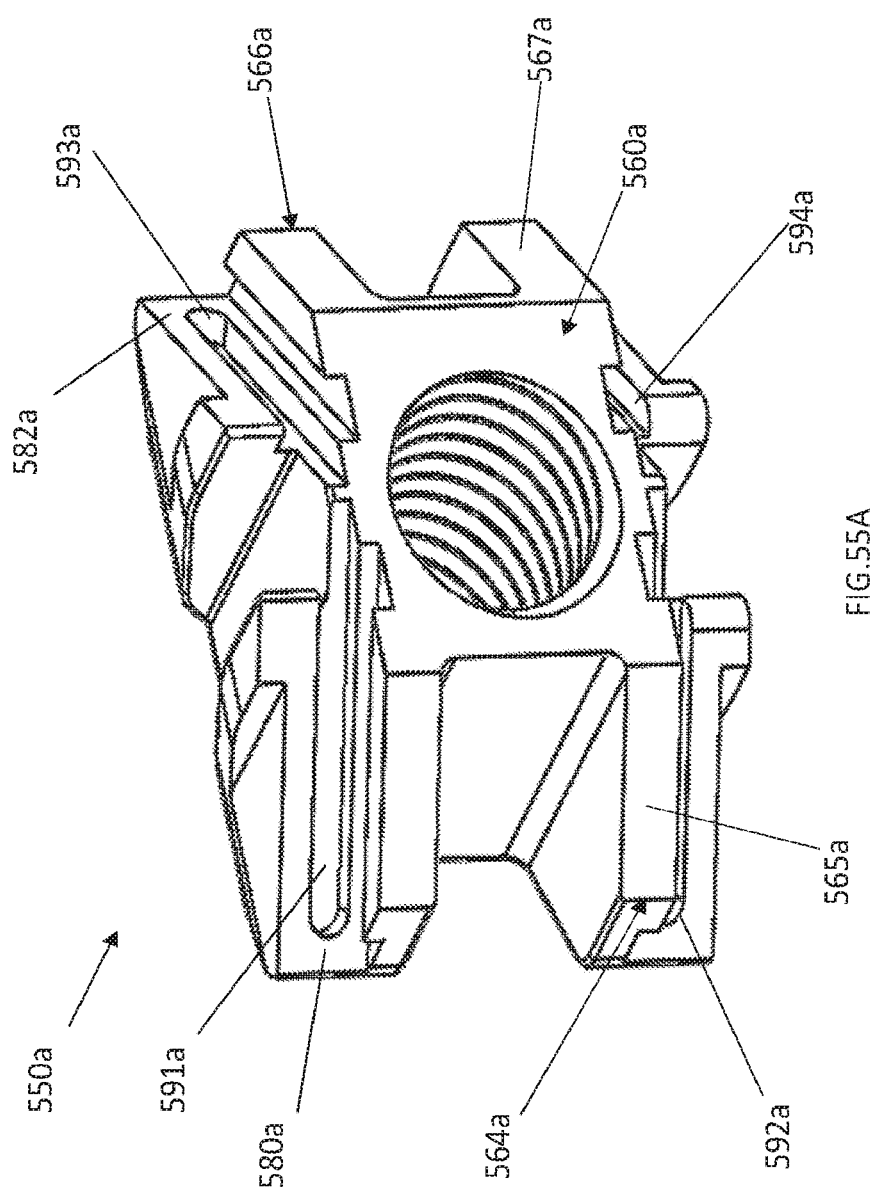
FIG. 55A depicts a front view of an exemplary proximal wedge, used in an exemplary second expandable fusion device of FIGS. 54A-54C.

The second expandable fusion device 1000a further comprises an embodiment 550a of the proximal wedge 550. The proximal wedge 550a is shown in front and rear perspective views in FIG. 55A and FIG. 55B respectively. The proximal wedge 550a comprises a first end 562a, a second end 560a, an upper surface 590a connecting the first end 562a and the second end 560a and a lower surface 552 connecting the first end 562a and the second end 560a. The proximal wedge further comprises a first ramped surface 580a and a second ramped surface 582a located proximate the second end 560a. The first ramped surface 580a includes a first ramped recessed track 591a proximate the upper surface and a second ramped recessed track 592a proximate the lower surface. The first ramped surface 580a further includes a projection 564a extending from the first ramped surface 580a towards a surface 565a and having a generally T-shaped cross-section. The projection 564a results in the ramped surface 580a to be split into an upper portion and a lower portion. The second ramped surface 582a includes a first ramped recessed track 593a proximate the upper surface and a second ramped recessed track 594a proximate the lower surface. The second ramped surface 582 includes a projection 566 extending from the second ramped surface 582a toward a surface 567 and having a generally T-shaped cross-section. The projection 566a results in the ramped surface 582a to be split into an upper portion and a lower portion. The ramped recessed tracks 591a, 592a, 593a, and 594a do not break through the side surfaces of the wedge 550a and function to limit the travel of the ramps relative to the proximal wedge by functioning as a depth stop for the protrusions 337a and 338a of the ramp 300a to bottom out on. The upper surface 590a further includes a projection 554a extending from the upper surface 590a. The lower surface 552a further includes a projection 555 extending from the lower surface 552a. The projections 554a and 555a include channels 599a and 598a extending through the first end 562a and the second end 560a. It should be understood that the channels 599a and 598a are intended as a mating features for auxiliary instrumentation used in introduction, expansion of the second expandable fusion device 1000a and/or graft delivery into the second expandable fusion device 1000a and may be configured, shaped and located in other ways so long as they are accessible from the first end 562a. The proximal wedge 550a further comprises a threaded central aperture 568a and generally rectangular apertures 570a and 572a which break through the respective sides of the proximal wedge 550a. The proximal wedge 550a further includes a partial bore 597a extending from the first end 562a to some depth toward, but not all the way to the second end 560a and about centering on the major diameter of the threaded central aperture 568a interrupting its threads. The partial bore 597a allows to access the proximal end of the threaded actuator after the device has been expanded and to deform the first threads on it using a punch, awl, or an automatic punch tool. This is done to prevent or reduce the chances of the actuator unthreading post-operatively resulting in the device losing height.

The second expandable fusion device 1000a further comprises an embodiment 650a of the distal wedge 650 (best seen in exploded view in FIG. 54C) n this embodiment, the proximal wedge 650a is identical to the proximal wedge 550a with the exception that the distal wedge 650a includes a central aperture that is threaded in the direction opposite to that of the proximal wedge. For example, if the central aperture of the proximal wedge 550a has a left-handed thread, then the central aperture of the distal wedge 650a has a right-handed thread. Optionally, in any embodiment, having all the insertion features present on the proximal wedge also being present on the distal wedge along with the actuator having a second drive feature on the distal end (as discussed above) is useful in the event of a revision surgery where the revision approach is not the same as the approach used during the original surgery. Optionally, in any embodiment, the distal wedge may have a more bulleted distal end to facilitate initial implantation.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the device second expandable fusion device utilizes some or any of the actuator embodiments, height and width expansion features, configurations and embodiments as well as the endplate stabilization features and embodiments described here.

Third Expandable Fusion Device

Figure 56A:
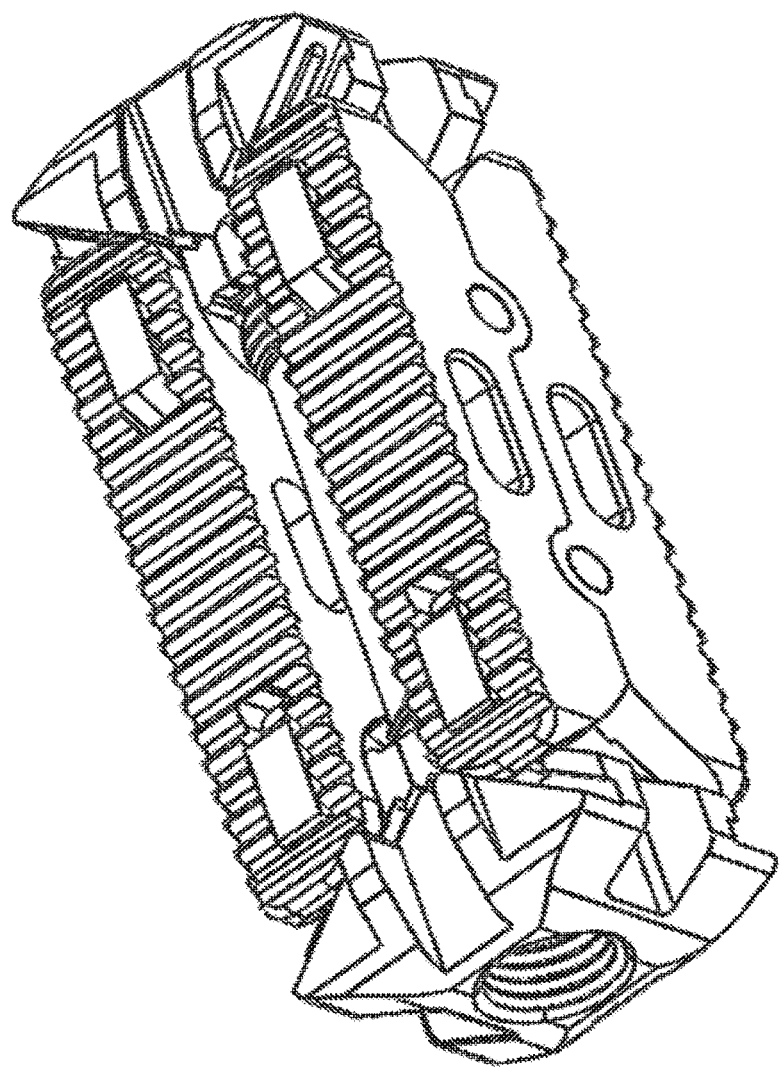
Figure 56C:
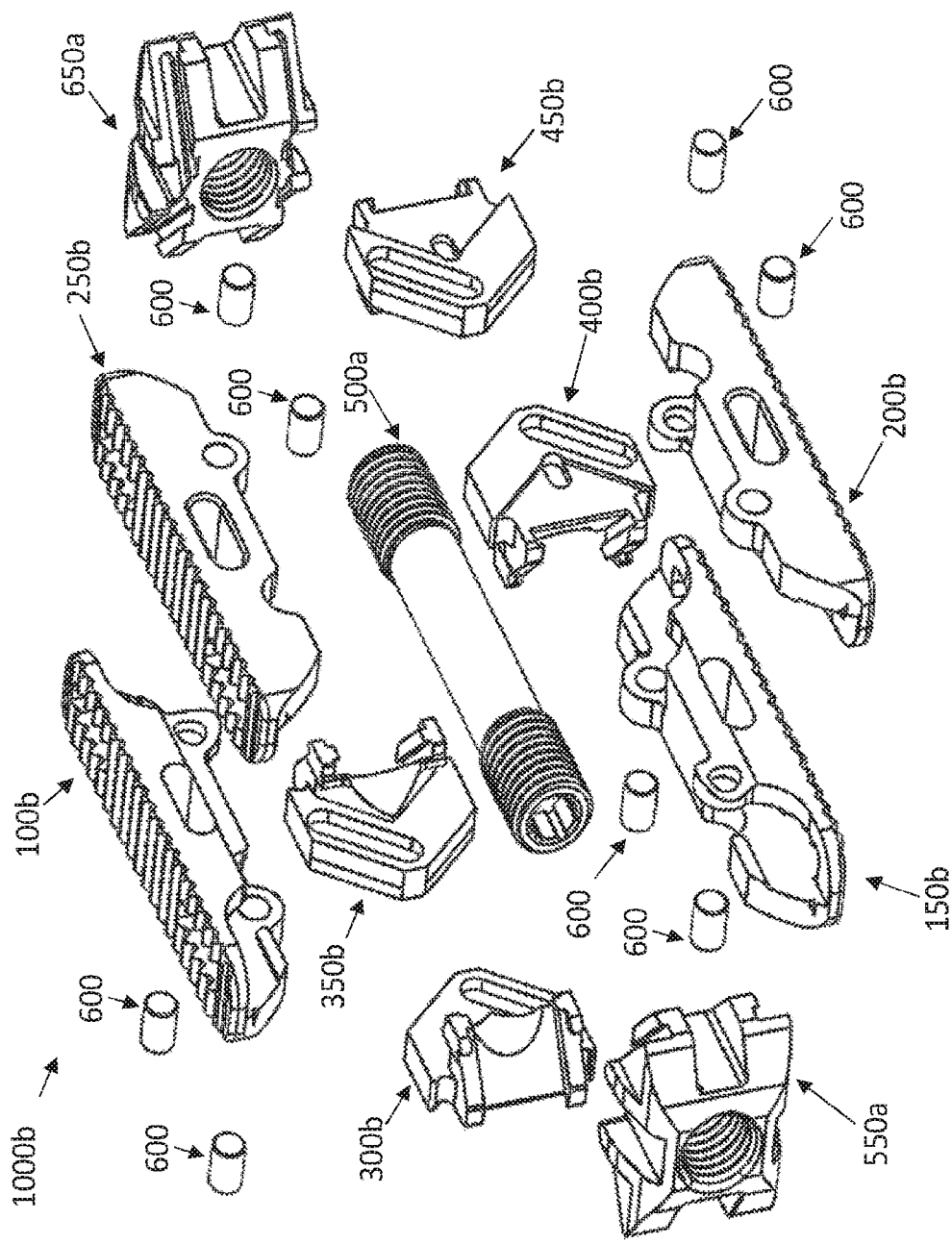

Turning now to FIGS. 56A-56C, which show an exemplary third expandable fusion device 1000b. FIG. 56A shows an exemplary third expandable fusion device 1000b in a fully collapsed state, FIG. 56B shows an exemplary third expandable fusion device 1000b in a fully expanded state and FIG. 56C shows an exploded view of an exemplary third expandable fusion device 1000b. The third expandable fusion device 1000b has similar functionality as the previously discussed embodiments in that it is configured transition from the initial collapsed state (shown in FIG. 56A) to the final expanded state (shown in FIG. 56B), but the expansion is accomplished using a modified mechanism where ramped slots of the ramp 300b are configured to accept pins 600 inserted through the mating openings in the endplates 100b. Since the endplates 100b contain no ramped surfaces, the height expansion is accomplished by the pins 600 traveling along the ramped slots and by the various curved surfaces of the endplates making tangent contact with the ramped surfaces of the ramps. Disassembly by hyper-expansion is prevented by means of the pins 600 bottoming out in the ramped slots of the ramps 300b at the limit of allowed travel. The third expandable fusion device 1000b comprises an embodiment 300b of the first ramp 300 (as well as the ramps 350, 400 and 450, which are all identical in this embodiment) shown in complementary views in FIGS. 57A and 57B has a first end 301b and a second end 303b. The first ramp 300b further comprises an inner surface 305b connecting the first end 301b and the second end 303b, and an outer surface 307b (best seen in FIG. 57B) connecting the first end 301b and the second end 303b. The first ramp 300b further comprises an upper surface 309b connecting the first end 301b and the second end 303b, and a lower surface 311b connecting the first end 301b and the second end 303b, the two surfaces 309b and 311b being preferably parallel to each other. The first ramp 300b further comprises a protuberance 315b further comprising an upper branch 321b extending preferably past the outer surface 307b and the upper surface 309b, and a lower branch 323b extending preferably past the outer surface 307b and the lower surface 311b. The upper branch 321b comprises an upper end surface 341b, a first ramped surface 302b and preferably a second ramped surface 310b. The lower branch 323b comprises a lower end surface 343b, a first ramped surface 304b and preferably a second ramped surface 312b. The inner surface 305b includes a projection 319b forming a ramped surface 320b. The projection 319b includes a first branch 314b and a second branch 316b. The first branch 314b extends from the ramped surface 320b to a surface 329b and the second branch 316b extends from the ramped surface 320b to a surface 330b. The ramped surface 320b and the branches 314b and 316b form a channel 328b having a generally T-shaped cross-section, which is formed due to the branches 314b and 316b including respective projections extending along and being parallel to the ramped surfaces 329b and 330b respectively and extending toward each other. The first branch 314b further includes a projection 348b and the second branch 316b further includes a projection 349b. The projection 319b further includes a relief 306b whose axis is substantially parallel to the long axis. The relief 306b is configured to mate with the actuator 500a and allow the ramps to be in closer proximity to each other than would otherwise be possible without the relief 306b. The relief 306b has any cross-section suitable to accomplish the function described above, for example a generally rectilinear cross-section. The ramp 300b further comprises a first ramped slot 337b recessed into the inner surface 305b and extending from midplane of the ramp 300b toward the upper branch 321b but not breaking through the upper end surface 341b, and a second ramped slot 338b recessed into the outer surface 327b and extending from the midplane of the ramp 300b toward the branch 323b, but not breaking through the lower end surface 343b. The ramp 300b further comprises a first ramped relief 341b extending from the midplane of the ramp 300b and toward the branch 321b and disposed between the inner surface 305b and the inner margin of the projection 319b and a second ramped relief 342b extending from the midplane of the ramp 300b and toward the branch 323b and disposed between the inner surface 305b and the inner margin of the projection 319b. The slope of the ramped reliefs may or may not be parallel to the respective ramped slots and the purpose of the ramped reliefs is to clear parts of the endplate during height expansion.

Figure 58:
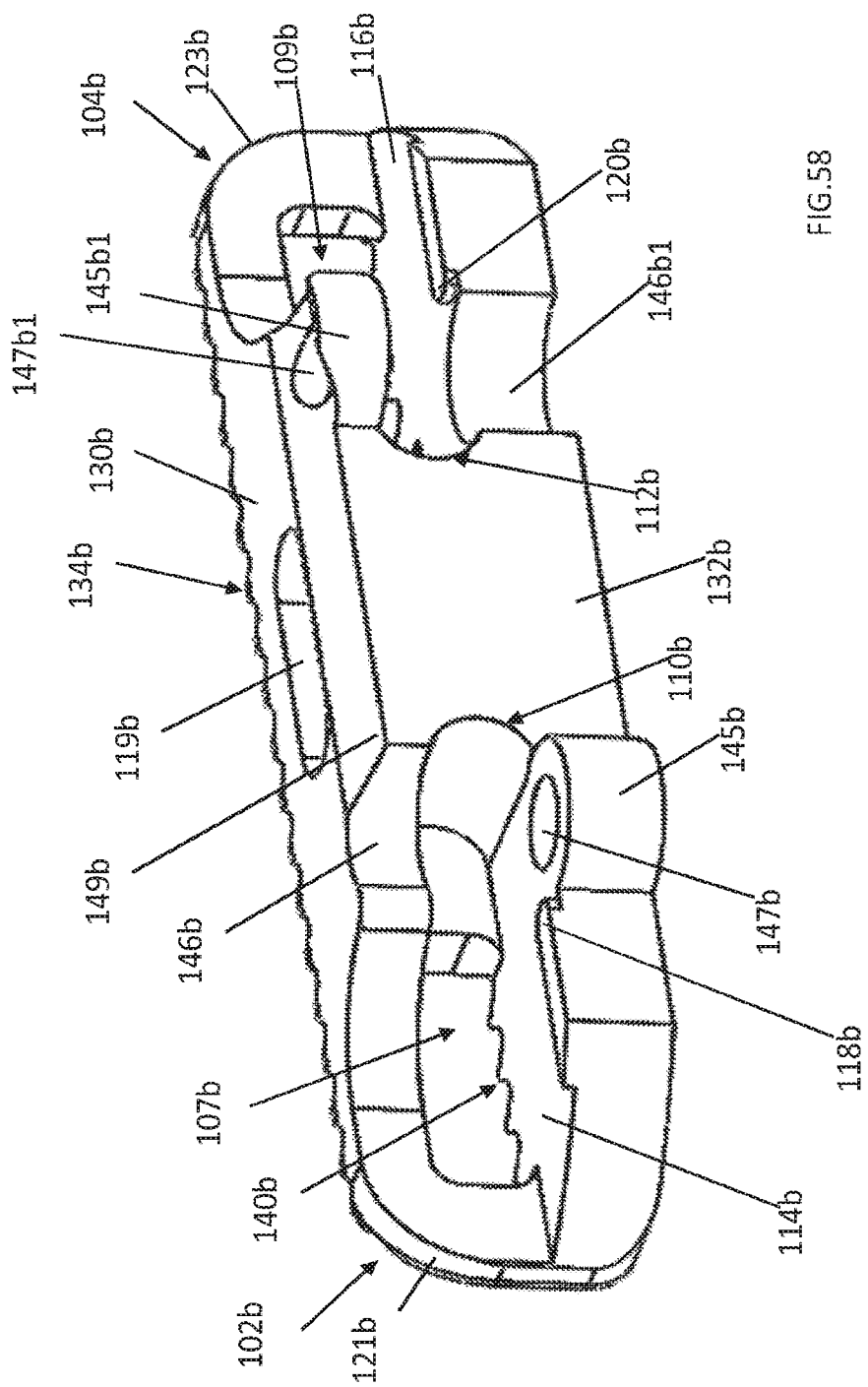

The third expandable fusion device 1000b further comprises an embodiment 100b (best seen in FIG. 58) of the first endplate 100 (as well as the endplates 150, 200 and 250, which are all identical in this embodiment) which comprises a first end 102b and a second end 104b. The first endplate 100b further comprises an upper surface 134b connecting the first end 102b and the second end 104b, and a lower surface 132b connecting the first end 102b and the second end 104b. The first endplate 100b further comprises a first elongated opening 107b proximate the first end 102b and a second elongated opening 109b proximate the second end 104*b*. The elongated openings 107*b* and 109*b* extend from the lower surface 132*b* through the upper surface 140*b* in the direction perpendicular to the long axis. The first endplate 100*b* further comprises a first elongated recess 110*b* extending from the first end 102*b* and past the first elongated opening 107*b* and a second elongated recess 112*b* extending from the second end 104*b* and past the second elongated opening 109*b*. The elongated recesses 110*b* and 112*b* extend from the bottom surface 132*b* toward but not through the upper surface 140*b* in the direction perpendicular to the long axis and forming a first inward face 114*b* and a second inward face 116*b* respectively.

The bottom surface 132*b* includes a first protrusion 145*b* proximate the opening 107*b*, a second protrusion 145*b*1 proximate the opening 109*b*, a first recess 146*b* proximate the first opening 107*b* and a second recess 146*b*1 proximate the second opening 109*b*. Whereas the protrusions 145*b* and 145*b*1 and the recesses 146*b* and 146*b*1 have complementary shapes so that when two endplates are collapsed against each other, the protrusion 145*b* of one nests in the recess 146*b*1 of the other and the protrusion 145*b*1 of one nests in the recess 146*b* of the other, while allowing the respective top and bottom surfaces of the two endplates to touch and the inner surfaces 130*b* of the two endplates to be aligned. The centers of the protrusions are configured to generally align with the ramped slots of the ramp 300*b* when assembled. The protrusions 145*b* and 145*b*1 further include thru openings 147*b* and 147*b*1 respectively, configured to accept pins that would engage the ramped slots of the ramp 300*b* The inner surface 130*b* further includes a relief 149*b* whose axis is substantially parallel to the long axis. The relief 149*a* is configured to mate with the actuator 500*b* and allow the endplates to be in closer proximity to each other than would otherwise be possible without the relief 149*b*. The inner surface 130*b* further includes an opening 119*b* extending from inward facing surface to the outward facing surface. This feature is optional and is contemplated to allow graft material to exit the interior of the device and fill the space surrounding it. The first inward face 114*b* and the second inward face 116*b* further include a first protrusion 118*b* and a second protrusion 120*b* respectively. The protrusions are rounded on the surfaces facing each other. The rounded sections of the protrusions 114*b* and 116*b* are configured to make tangent contact with the ramped surfaces 310*b* and 312*b* of the ramp 300*b* to increase the contact area between the endplates and the ramps. The corners formed by at least the first end 102*b* and the inward surface 130*b* and by the second end 104*b* and the inward surface 130*b* include rounded surfaces 121*b* and 123*b* respectively. The purpose of these rounded surfaces is to help prevent height expansion from taking place until the device is sufficiently expanded in width. This is accomplished through the rounded surfaces 121*b* and 123*b* being in tangent contact with mating ramped surfaces of the wedges throughout most of the width expansion process and while they are in tangent contact with the wedges, the ramps 300*b* on the opposing sides of each endplate 100*b* are only able to move along the direction of the ramped surfaces of the wedges 550*b* and 650*b* as these ramped surfaces make tangent contact with rounded surfaces 121*a* and 123*a*, while the ramps 300*b* remain static relative to one another, whereas to achieve height expansion the opposing ramps need to be able to move toward each other along the long axis of the device. Once the width expansion is substantially completed and once the rounded surfaces 121*a* and 123*a* no longer tangentially contact the wedges, the ramps are allowed to move toward each other resulting in height expansion. The upper surface 134*b* includes texturing 140*b* to aid in gripping the adjacent vertebral bodies. Although In the illustrated embodiment, the texturing 140*b* comprises series of parallel grooves running transversely to the long axis of the endplate 100*b*, including but is not limited to teeth, ridges, areas of high surface roughness, metallic or ceramic coatings with relatively high surface roughness, friction increasing elements, keels, spikes, or gripping or purchasing projections. Optionally, in any embodiment, one or more of the endplates may be shorter, longer, narrower, or wider than others.

The third expandable fusion device 1000*b* further comprises the proximal wedge 550*a*, the distal wedge 650*a*, the actuator 500*a* and pins 600.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the third expandable fusion device 1000*b* may utilize some or any of the actuator embodiments, height and width expansion features, configurations and embodiments as well as the endplate stabilization features and embodiments described here.

Fourth Expandable Fusion Device

Turning now to FIGS. 59A-59C, which show an exemplary fourth expandable fusion device 1000*c*. FIG. 59A shows an exemplary fourth expandable fusion device 1000*c* in a fully collapsed state, FIG. 59B shows an exemplary fourth expandable fusion device 1000*c* in a fully expanded state and FIG. 59C shows a top view of an exemplary fourth expandable fusion device 1000*b*. The fourth expandable fusion device 1000*c* is identical to the previously described third expandable fusion device 1000*b* except that in the third expandable fusion device 1000*c*, the endplates include nested interlocking stabilization features (best seen in FIG. 59D) allowing to improve stability, ensure proper alignment and reduce "slop" between top and bottom end-plates on either side of the device and facilitate even device expansion. Opposing endplates (FIG. 59D for example shows the opposing endplates 100*c* and 150*c*) on top and bottom of the fourth expandable fusion device 1000*c* include projections 111*c*1 and 111*c*2 directed toward each other as well as mating recesses 113*c*1 and 113*c*2 extending the length of the projections and through upper surfaces of the endplates. The recesses further contain a dovetailed track 103*c*2 on one endplate and a dovetailed projection 103*c*1 on the opposing endplate (best seen in FIG. 59C) so that the mating endplates only move in one dimension relative to each other, towards or away from each other along the long axis of the dovetailed track. Whereas the projections 111*c*1 and 111*c*2 and the recesses 113*c*1 and 113*c*2 have complementary shapes so that when two endplates are suitably rotated, the projection 111*c*1 of one nests in the recess 113*c*2 of the other and the recess 113*c*1 of one accepts the projection 111*c*2 of the other, while allowing the lower surfaces of the two endplates to touch and the inner and outer surfaces of the two endplates to be aligned. It should be understood that although the stabilization features of this embodiment have been shown here to slidably interconnect upper and lower endplate portions, the same arrangement is also be used to slidably interconnect the upper pairs or lower pairs of the endplate portions, or to slidably interconnect both the upper pairs, the lower pairs and the upper and lower endplate portions.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the fourth expandable fusion device 1000c may utilize some or any of the actuator embodiments, height and width expansion features, configurations and embodiments as well as the endplate stabilization features and embodiments described here.

Fifth Expandable Fusion Device

Turning now to FIGS. 60A-60C, which show an exemplary fifth expandable fusion device 1000d. FIG. 60A shows an exemplary fifth expandable fusion device 1000d in a fully expanded state and FIG. 60B shows a side view of an exemplary fifth expandable fusion device 1000d in a fully expanded state. The fifth expandable fusion device 1000d is identical to the previously described fourth expandable fusion device 1000c except that in the fifth expandable fusion device 1000d, the endplates contain nested interlocking stabilization features, in which the projections 111c1 and 111c2 described above in relation to the device 1000c, also include curved protrusions 111d3 and 111d4 respectively, and the recesses 113c1 and 113c2 described above in relation to the device 1000c, also include curved reliefs 113d3 and 113d4 respectively, which are configured to accept the curved protrusions 111d3 and 111d4 in a nesting fashion. The curved protrusions are configured to tangentially contact the ramped surfaces of the ramps 300b thereby providing additional contact points between the ramps and the endplates and resulting in improved device stability at the upper limits of allowable height expansion. The endplates of the fifth expandable fusion device 1000d contain no ramped surfaces and rely on the pin components to transmit expansion force between the ramps and the endplates, which may lead to undesired motion (or slop) between these components due to low contact area. Adding curved features (such as the curved protrusions 111d3 and 111d4) to the endplates allows to approximate a continuous contact surface between the ramps and the endplates thereby improving stability as mentioned above.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the fifth expandable fusion device 1000d may utilize some or any of the actuator embodiments, height and width expansion features, configurations and embodiments as well as the endplate stabilization features and embodiments described here.

Sixth Expandable Fusion Device

Turning now to FIGS. 61A-61B, which show an exemplary sixth expandable fusion device 1000e. FIG. 61A shows an exemplary sixth expandable fusion device 1000e in a fully expanded state and FIG. 61B shows an exploded view of an exemplary sixth expandable fusion device 1000e. The sixth expandable fusion device 1000e comprises an embodiment 100e of the first endplate 100 (as well as the endplates 150, 200 and 250, whereas the endplates 100e and 150e are identical and the endplates 250e and 200e are mirrors of the endplates 100e and 150e), which is identical to the endplate 100 with the following exceptions. In the endplate 100e, the slots 107 and 109 have a generally C-shaped cross-sections and have equal slopes inclined in the same direction, whereas both the slots 107 and 109 start at the upper surface 134 and slope toward the second end 104, the bottom surface 132 includes a protrusion 145e proximate the slot 109 and a recess 146e proximate the slot 107, whereas the protrusion 145e and the recess 146e have complementary shapes so that when top and bottom endplates are collapsed against each other, the protrusion 145a of one nests in the recess 146e of the other allowing the respective top and bottom surfaces of the opposing endplates to touch. The protrusion 145e further includes an opening 147e (shown in FIG. 61B on the endplate 150a) that is generally aligned with the ramped slots 335e of the ramp 300e when assembled and is configured to accept the pin 600, which then engage the ramped slots in the ramp 300e.

The endplate 100e does not include tapered grooves 122, 118, 124 and 120 present in previously discussed embodiments of the endplate 100, but instead includes ramped surfaces 121e and 123e, which perform generally the same function as the grooves 122, 118, 124 and 120, which is to prevent height expansion from taking place until the device is sufficiently expanded in width. This is accomplished through the ramped surfaces 121e and 123e being in contact with mating ramped surfaces of the wedges throughout most of the width expansion process and while they are in contact with the wedges, the ramps on the opposing sides of each endplate are only able to move along the direction of the ramped surfaces of the wedges and the ramped surfaces 121e and 123e, while remaining static relative to one another, whereas to achieve height expansion the opposing ramps need to be able to move toward each other along the long axis of the device. Once the width expansion is substantially completed and once the ramped surfaces 121e and 123e no longer contact the wedges, the ramps are allowed to move toward each other resulting in height expansion. The endplate 100e further includes an opening 119e extending from the upper surface through to the lower surface in the direction perpendicular to the long axis. The purpose of the opening 119e is to be engaged by mating protuberances 315e of the ramp 350e or 450e. The endplate 100a further includes a rectilinear relief 149e spanning the distance between the slots 107 and 109. The purpose of the relief 149e is to allow the ramps 300e and 400e to mate properly with the endplates.

The sixth expandable fusion device 1000e further comprises a distal ramp 350e and a distal ramp 450e, which are identical and will henceforth be referred to as the distal ramp 350e The sixth expandable fusion device 1000e further comprises a proximal ramp 300e and a proximal ramp 400e, which are identical and will henceforth be referred to as the proximal ramp 300e. The distal ramp 350 is the same as the ramp 300b described above with the following exceptions: the distal ramp 350e does not include the protuberance 315b or the ramped slots present in the ramp 300b and instead includes a protuberance 315e, which extends past the upper surface 309b, past the lower surface 311b and past the outer surface 307b and has an elongated shape extending generally in the direction normal to the upper and lower surfaces. The proximal ramp 300e is the same as the ramp 300b described above with the following exceptions: in the proximal ramp 300e, the ramped slot 337b is recessed into the outer surface 327b as opposed to the inner surface 305b as it is in the previously described ramp 300b, this results in both the ramped slots 337b and 338b being on the same side of the proximal ramp 300e, and merging together at the mid-plane. The proximal ramp 300e does not include the ramped reliefs 341b and 342b, the branches 323b and 321b of the protrusion 315b have generally C-Shaped cross-sections, and the proximal ramp 300e further includes a protrusion 315e1 connected to the tip of the proximal ramp 300e by an isthmus 315e2 and forming a first end 301e of the proximal ramp 300e. The protrusion 315e1 is identical to the protrusion 315b including having the two ramped slots 338e and 337e which are both recessed into the outer surface 327e coplanar with the outer surface 327b. The tip of the protrusion 315e1 forming the first end 301e is truncated to be shorter than that of the protrusion 315b.

The sixth expandable fusion device 1000e further comprises the actuator 500a, the proximal wedge 550a, the distal wedge 650a and the pins 600 configured to press into the mating openings of the endplates and to engage the ramped slots 338b, 337b, 338e and 337e of the proximal ramps to provide stability and prevent device disassembly due to hyper-expansion, by bottoming out in the ramped slots at the end of maximum allowed travel and height expansion. As in other embodiments of the fusion device, after the sixth expandable fusion device 1000e has substantially reached the maximum width expansion, further drawing the wedges together causes the proximal ramps and distal ramps to move toward each other. The proximal ramps are engaged with the ramped slots of the endplates and effect height expansion by moving relative to the endplates in both the direction of the long axis of the device and the direction of height expansion and along the angle of the mated ramped surfaces of the endplates and the proximal ramps, whereas the distal ramps only move relative to the endplates in the direction of the height expansion. Optionally, in any embodiment, replacing the ramps 350e and 450e with the ramps 350a and 450a, as well as adding mating ramped slot to the endplates to provide mating geometry for the ramps 350a and 450a would result in an embodiment with desirable characteristics including improved endplate stability and easier and more uniform height expansion.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the sixth expandable fusion device 1000e may utilize some or any of the actuator embodiments, height and width expansion features, configurations and embodiments as well as the endplate stabilization features and embodiments described here.

Seventh Expandable Fusion Device

Turning now to FIGS. 62A-62B, which show an exemplary seventh expandable fusion device 1000f. FIG. 62A shows an exemplary seventh expandable fusion device 1000f in a fully expanded state and FIG. 62B shows an exploded view of an exemplary seventh expandable fusion device 1000f. In this embodiment, the ramps in the front end of the seventh expandable fusion device 1000f engage the rear ramped surfaces of the endplates and the ramps on the rear of the device engage the front ramped surfaces on the endplates, causing the device to expand in height as the front and rear ramps are forced together when the actuator is actuated. The seventh expandable fusion device 1000f comprises an embodiment 100f of the first endplate 100 (as well as the endplates 150, 200 and 250, whereas the endplates 100f and 250f are identical and the endplates 150f and 200f are mirrors of the endplates 100f and 250f) in which the slots 107 and 109 have "sideways T"-shaped cross-sections, have equal slopes and are inclined in the opposing directions, whereas the slot 107f extends through the inner surface 132f and the slot 109f extends through the outer surface 134f.

The endplate 100f does not include tapered grooves 122, 118, 124 and 120 present in previously discussed embodiments of the endplate 100, but instead includes rounded surfaces 1211 proximate the first end 102 and rounded surfaces 1231 proximate the second end 104, which perform generally the same function as the grooves 122, 118, 124 and 120, which is to prevent height expansion from taking place until the device is sufficiently expanded in width. This is accomplished through the rounded surfaces 1211 and 1231 being in tangent contact with mating ramped surfaces of the wedges throughout most of the width expansion process and while they are in contact with the wedges, the ramps on the opposing sides of each endplate are only able to move along the direction of the ramped surfaces of the wedges as they maintain tangent contact with the rounded surfaces 1211f and 123f, while remaining static relative to one another, whereas to achieve height expansion the opposing ramps need to be able to move toward each other along the long axis of the device. Once the width expansion is substantially completed and once the rounded surfaces 1211f and 123f lose their tangent contact with the wedges, the ramps are allowed to move toward each other resulting in height expansion. Optionally, in any embodiment, the rounded surfaces 1211f and 123f are also ramped planar surfaces generally parallel to the ramped surfaces of the wedges to achieve the same height expansion-limiting effect as described above.

The endplate 100f further includes a rectilinear relief 149f spanning the distance between the slot 107f and the second end 104 and a corresponding relief on the other side that is the same and is not seen spanning the distance between the slot 109 and the first end 102. The purpose of the reliefs is to allow the ramps 300f and 350f to mate properly with the endplates. The endplate 100f further includes reliefs 149f3 in both the inner surface 132f and the outer surface 134f, whose axes are substantially parallel to the long axis. The reliefs 149f3 are configured to mate with the actuator 500a and allow the endplates to be in closer proximity to each other than would otherwise be possible without the relief 149*f*3. The reason for there being two reliefs 149*f*3 is that since, as discussed above, the endplate 100*f* is identical to the endplate 250 and the endplate 150*f* is identical to the endplate 200*f*, depending on whether the endplate 100*f* is assembled in the seventh expandable fusion device 1000*f* in the left or the right position, the inner surface 132*f* of the endplate 100*f* may form either an inner or an outer margin of the assembled device. With this in mind, the endplate 100*f* includes two reliefs 149*f*3 in order to keep the left and right endplate components identical in this embodiment, even though only one of the reliefs 149*f*3 actually contacts the actuator 500*a* in any given endplate in any given assembly.

The seventh expandable fusion device 1000*f* further comprises a proximal outside ramp 300*f* and a distal outside ramp 450*f*, which are identical and will henceforth be referred to as the outside ramp 300*f*1. The fusion device 1000*e* further comprises a proximal inside ramp 400*f* and a distal inside ramp 350*f*, which are identical and will henceforth be referred to as the inside ramp 350*f*1. Here the ramps are described as inside and outside based on whether their ramped surfaces make contact with the inner or the outer slots in the endplates. The inside ramp 350*f* is the same as the ramp 300*b* described above with the following exceptions: the inside ramp 350*f* does not include the ramped slots 337*b* and 338*b* or the ramped reliefs 341*b* and 342*b* present in the ramp 300*b*, the branches 321*f* and 323*f* have sideways-T-shaped cross-sections configured to mate with similarly shaped slots 107*f* and 109*f* of the endplates. The inside ramp 350*f* is longer than the ramp 300*b* and has a truncated tip proximate the first end 301*b*. The inside ramp 350*f* is configured to engage the inward facing slots of the endplates and to allow the outside ramp 300*f* to clear the outer surfaces of the outside ramp 350*f* while itself engaging the outward facing slots of the endplates.

The outside ramp 300*f* is the same as the ramp 300*b* described above with the following exceptions: the inside ramp 300*f* does not include the ramped slots present in the ramp 300*b*, the branches 321*f* and 323*f* have sideways-T-shaped cross-sections configured to mate with similarly shaped slots 107*f* and 109*f* of the endplates. The inside ramp 350*f* is longer than the ramp 300*b* and has a truncated tip proximate the first end. Furthermore, the protuberance 315*f* of the outside ramp 300*f* protrudes past both the outer surface 307*f* and the inner surface 305*f* as opposed to the protuberance 315*b* of the ramp 300*b* which only protrudes past the outer surface 307*b*. The outside ramp 300*f* is configured to engage the outward facing slots of the endplates and to allow the inside ramp 350*f* to clear the inner surfaces of the outside ramp 300*f* while itself engaging the inward facing slots of the endplates.

The seventh expandable fusion device 1000*f* further comprises the actuator 500*a*, the proximal wedge 550*a*, and the distal wedge 650*a*. As in other embodiments of the fusion device, after the device 1000*e* has substantially reached the maximum width expansion, further drawing the wedges together causes the proximal ramps and distal ramps to move toward each other. The proximal ramps are engaged with the ramped slots of the endplates and effect height expansion by moving relative to the endplates in both the direction of the long axis of the device and the direction of height expansion and along the angle of the mated ramped surfaces of the endplates and the proximal ramps. Disassembly of the seventh expandable fusion device 1000*f* through hyper expansion are prevented using a variety of methods described in other embodiments above as well as those that will be obvious to one skilled in the art. One additional contemplated method for achieving this is to assemble the device in the state of height expansion that is greater than desired maximum allowable height, then reduce the height slightly once the device is fully assembled and then deform the threads of the actuator 500*a* in such a way so as to no longer allow the seventh expandable fusion device 1000*f* to return to its initial hyper-expanded state required for assembly or disassembly of components.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the seventh expandable fusion device 1000*f* may utilize some or any of the actuator embodiments, height and width expansion features, configurations and embodiments as well as the endplate stabilization features and embodiments described here.

Eighth Expandable Fusion Device

Turning now to FIGS. 63A-63D, which show an exemplary eighth expandable fusion device 1000*g* in which each of the endplates comprise a front portion and a rear portion, the front portion and the rear portion further include mating cut-outs and circular openings which allow the portions to be pivotably connected with a pin (or with an integral cylindrical protrusion on one of the portions engaging a mating hole in the other portion). The pin may be pressed or welded or machined as a protrusion into one portion, inserted into the other portion and its free end swaged to prevent disassembly. The ramps include cylindrical protrusions that engage the ramped slots in the wedges, which allow the ramps to both translate and rotate relative to the wedges. The slots also limit how far the ramps translate relative to the wedges, including a contemplated configuration in which no translation is allowed and the ramps are only able to rotate relative to the wedges. Such configuration is achieved by adjusting the length of the slots so that at the initial collapsed state, the ramps only pivot or rotate relative to their respective wedges as the width expansion occurs. The eighth expandable fusion device 1000*g* functions in a fashion identical to the fusion device 1000*a*, with the following exceptions. The ramps of the eighth expandable fusion device 1000*g* are able to both translate and rotate relative to the wedges, this combined with the fact that each of the endplates is comprised of two pivotably connected portions results in the eighth expandable fusion device 1000*g* being able to expand in width by both translating opposing endplates away from each other, and by allowing the endplates to articulate in to a generally diamond-shaped or square configuration in a width expanded state.

The eighth expandable fusion device 1000*g* comprises an embodiment 100*g* of the first endplate 100 (as well as the endplates 150, 200 and 250, whereas the compound endplates 100*g*, 250*g*, 150*g* and 200*g* are all identical but rotated relative to each other for proper assembly). The compound endplate 100*g* is identical to the endplate 100*a* described above with the following exceptions. The compound endplate 100*g* comprises two portions 100*g*1 and 100*g*2 pivotably connected with pin 600 through the center of the compound endplate 100g. Each of the portions 100g1 and 100g2 contain complementary reliefs 149g1 and 149g2 and circular openings 119g1 and 119g2, which when concentrically aligned allow the upper surfaces and the lower surfaces of the portions 100gi and 100g2 to be aligned in a generally co-planar fashion and allowed to pivot around the axis of the openings 119g1 and 119g2.

The eighth expandable fusion device 1000g further comprises an embodiment 300g of the ramp 300 (as well as the ramps 350, 400 and 450, whereas the ramps 300g, 350g, 400g and 450g are all identical in this embodiment but are rotated relative to each other for proper assembly). The ramp 300g is identical to the ramp 300a described above with the following exceptions. The branches 316g and 314g form a channel 328g having a generally rectangular cross-section as opposed to the channel 328a of the ramp 300a having a T-shaped cross-section. The surfaces 330a and 329a do not include protrusions 349a and 348a as they do in the ramp 300a. The branches 316g and 314g further include ramped surfaces 330g1 and 329g1 in addition to the ramped surfaces 330a and 329a of the ramp 300a, whereas the surfaces 330g1 and 329g1 are at an angle to the surfaces 330a and 329a. The branches 316g and 314g further include cylindrical protrusions 349g and 348g respectively. Whereas the cylindrical protrusions share the same central axis and are tangent to the surfaces 330a, 329a, 316g and 314g. The purpose of the protrusions 349g and 348g is to translationally and pivotably engage the mating slots of the wedges.

The eighth expandable fusion device 1000g further comprises an embodiment 550g of the distal wedge 550. The distal wedge 550g (shown in detail in FIG. 64) is identical to the distal wedge 550a with the following exceptions. The distal wedge 550g does not include ramped recessed tracks 591a, 592a, 593a and 594a, but does include protrusions 564g and 566g which include ramped recessed tracks 591g and 593g respectively formed in the upper surfaces of the protrusions 564g and 566g, and further include ramped recessed tracks 592g and 594g respectively formed in the lower surfaces of the protrusions 564g and 566g. The protrusions 555g and 554g include ramped surfaces 596g, 597g, which are configured to allow the endplates to move relative to the wedges once the eighth expandable fusion device 1000g is fully expanded in width. Channel 598g of the proximal wedge does not break through the protrusion 555g.

The eighth expandable fusion device 1000g further comprises an embodiment 650g of the distal wedge 650. In this embodiment, the proximal wedge 650g is identical to the proximal wedge 550g with the exception that the distal wedge 650a includes a central aperture that is threaded in the direction opposite to that of the proximal wedge. For example, if the central aperture of the proximal wedge 550g has a left-handed thread, then the central aperture of the distal wedge 650g has a right-handed thread. Optionally, in any embodiment, having all the insertion features present on the proximal wedge also being present on the distal wedge along with the actuator having a second drive feature on the distal end (as discussed above) is useful in the event of a revision surgery where the revision approach is not the same as the approach used during the original surgery. Optionally, in any embodiment, the distal wedge may have a more bulleted distal end to facilitate initial implantation.

The eighth expandable fusion device 1000g further comprises the actuator 500a and the pins 600.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the eighth expandable fusion device 1000g may utilize some or any of the actuator embodiments, height and width expansion features, configurations and embodiments as well as the endplate stabilization features and embodiments described here.

Ninth Expandable Fusion Device

Turning now to FIGS. 65A-65E, which show an exemplary ninth expandable fusion device 1000h. FIG. 65A shows an initial collapsed state of an exemplary ninth expandable fusion device 1000h, FIG. 65B shows a fully expanded state of an exemplary ninth expandable fusion device 1000h, FIG. 65C shows a partially assembled view of an exemplary ninth expandable fusion device 1000h in a collapsed state, FIG. 65D shows a partially assembled view of an exemplary ninth expandable fusion device 1000h is a state of full linear width expansion and FIG. 65E shows a partially assembled view of an exemplary ninth expandable fusion device 1000h in a state of full linear and angular expansion. In the ninth expandable fusion device 1000h each of the endplates comprise a front portion and a rear portion, the front portion and the rear portion further include mating cut-outs and circular openings which allow the portions to be pivotably connected with a pin (or with an integral cylindrical protrusion on one of the portions engaging a mating hole in the other portion). The pin may be pressed or welded or machined as a protrusion into one portion, inserted into the other portion and its free end swaged to prevent disassembly. The ramps include cylindrical protrusions that engage the ramped slots in the wedges, which allow the ramps to both translate and rotate relative to the wedges. The slots also limit how far the ramps translate relative to the wedges. The ninth expandable fusion device 1000h functions in a fashion identical to the third expandable fusion device 1000b, with the following exceptions. The ramps of the ninth expandable fusion device 1000h are able to both translate and rotate relative to the wedges, this combined with the fact that each of the endplates is comprised of two pivotably connected portions results in the ninth expandable fusion device 1000h being able to expand in width by both translating opposing endplates away from each other, and by allowing the endplates to articulate in to a generally diamond-shaped or square configuration in a width expanded state.

The ninth expandable fusion device 1000h comprises an embodiment 100h of the first endplate 100 (as well as the endplates 150, 200 and 250, whereas the compound endplates 100h, 250h, 150h and 200h are all identical but rotated relative to each other for proper assembly). The compound endplate 100h is identical to the endplate 100b described above including having the rounded surfaces 121b and 123b with the exception that it comprises two portions that are pivotably connected exactly as described above for the endplate 100g.

The ninth expandable fusion device 1000h further comprises an embodiment 300h of the ramp 300 (as well as the ramps 350, 400 and 450, whereas the ramps 300*h*, 350*h*. 400*h* and 450*h* are all identical in this embodiment but are rotated relative to each other for proper assembly). The ramp 300*h* is identical to the ramp 300*b* described above with some exceptions. The ramp 300*h* differs from the ramp 300*b* in exactly the same ways that the ramp 300*g* described above differs from the ramp 300*a* described above including having the cylindrical protrusions 349*g* (best seen in FIG. 65C) and 348*g* (shown in figures pertaining to the discussion of the device 1000*g*). It should be understood that if in the initial collapsed state of the ninth expandable fusion device 1000*h*, the rounded surfaces 121*b* and 123*b* of the endplates 100*h* are concentric or near concentric with the cylindrical protrusions 349*g* and 348*g* of the ramp 300*h* (this articulation is best seen in FIGS. 65C, 65D and 65E), the ninth expandable fusion device 1000*h* will be able to expand in width both linearly and angularly starting immediately at the initial collapsed state due to the fact that in this scenario, both the ramp and the endplate portions will be able to rotate relative to the wedges around a common axis. Whereas if the rounded surfaces 121*b* and 123*b* of the endplates 100*h* are not concentric or with the cylindrical protrusions 349*g* and 348*g* of the ramp 300*h*, the ninth expandable fusion device 1000*h* will start width expansion in a linear fashion and only be able to expand angularly after the contact is lost between the rounded surfaces of the endplates and the wedges. This is because for the rounded surfaces of the endplates and the cylindrical protrusions of the ramps are not coaxial, but still maintain simultaneous tangent contact with the ramped surfaces of the wedges and are therefore unable to rotate relative to the wedges until the ninth expandable fusion device 1000*h* is sufficiently expanded in width where the rounded surfaces lose contact with the ramped surfaces of the wedges.

The ninth expandable fusion device 1000*h* further comprises the proximal wedge 550*g*, the distal wedge 650*g*, the actuator 500*a*, and the pins 600.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the ninth expandable fusion device 1000*h* may utilize some or any of the actuator embodiments, height and width expansion features, configurations and embodiments as well as the endplate stabilization features and embodiments described here.

Tenth Expandable Fusion Device

Turning now to FIG. 66A, which shows an exemplary tenth expandable fusion device 1000*k* in a fully expanded state, whereas the tenth expandable fusion device 1000*k* comprises an upper endplate 100*k* comprising two portions 100*k*1 and 100*k*2 connected together into a single component by a series of angled deformable struts 100*k*3 and further comprising a lower endplate 200*k* comprising two portions 200*k*1 and 200*k*2 connected together into a single component by a series of angled deformable struts 200*k*3. The portions 100*k*1, 100*k*2 and 200*k*1 and 200*k*2 may be identical to any of the embodiments of the endplates 100, 150, 200, and 250 described above. The angled deformable struts 100*k*3 and 200*k*3 are chevron or V-shaped in this embodiment but are of any other suitable shape including U-Shaped, W-shaped, and Z-Shaped etc. The struts are configured to deform upon width expansion of the device with the angles between the surfaces of the struts increasing through the width expansion process from some initial angle at the initial collapsed state (shown in FIG. 66B) to a larger angle at a full width expanded state (shown in FIG. 66C). With the exception of the two portions of the upper and lower endplates being integrally connected by angled deformable struts, the components comprising the tenth expandable fusion device 1000*k* are identical to any of their embodiments described above. During the width expansion step, the series of angled deformable struts connecting the portions comprising the upper and lower endplates are plastically deformed by the action of the actuator and the wedges to permanently bring the upper and the lower endplates from the initial collapsed state (shown in FIG. 66D) into a width expanded state.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the tenth expandable fusion device 1000*k* may utilize some or any of the actuator embodiments, height and width expansion features, configurations and embodiments as well as the endplate stabilization features and embodiments described here.

Eleventh Expandable Fusion Device

Turning now to FIG. 67A, which shows an exemplary eleventh expandable fusion device 1000*m* in a fully expanded state, whereas the eleventh expandable fusion device 1000*m* comprises an endplate complex 100*m* (shown in FIG. 67B) comprising upper portions 100*m*1 and 100*m*2 and lower portions 200*m*1 and 200*m*2. Whereas all four portions are integrally connected together by series of angled (or, in other embodiments, curved) deformable struts, whereas the two upper portions are connected together by angled deformable struts 250*m*1 and the two lower portions are connected together by angled deformable struts 250*m*1 and whereas the upper portions are connected to the lower portions by angled deformable struts 250*m*2. The portions 100*m*1, 100*m*2 and 200*m*1 and 200*m*2 may be identical to any of the embodiments of the endplates 100, 150, 200 and 250 described above. The angled deformable struts 250*m*1 and 250*m*2 are chevron or V-shaped in this embodiment but are of any other suitable shape including U-Shaped, W-shaped, and Z-Shaped etc. The struts 250*m*1 are configured to deform with width expansion and the struts 250*m*2 are configured to deform with height expansion of the device with the angles between the surfaces of the struts increasing through the expansion process from some initial angle at the initial collapsed state (shown in FIG. 67C) to a larger angle at a full width expanded state (shown in FIG. 67D) and at a full width and height expanded state. With the exception of the portions of the endplates being integrally connected by angled deformable struts into the endplate complex 100*m*, the components comprising the eleventh expandable fusion device 1000*m* are identical to any of their embodiments described above. During the device expansion, the series of angled deformable struts connecting the portions comprising the endplate complex are plastically deformed by the action of the actuator, the wedges and the ramps to permanently bring the endplate complex 100*m* from the initial collapsed state into a width expanded state and then into a width and height expanded state.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the eleventh expandable fusion device 1000*m* may utilize some or any of the actuator embodiments, height and width expansion features, configurations and embodiments as well as the endplate stabilization features and embodiments described here.

Twelfth Expandable Fusion Device

Turning now to FIGS. 68-72C, which show an exemplary twelfth expandable fusion device 1000*n* and its components. FIG. 68 shows an initial collapsed state of an exemplary twelfth expandable fusion device 1000*n*, which is identical to an third expandable fusion device 1000*b* described above with the exceptions described below. The twelfth expandable fusion device 1000*n* comprises a proximal wedge 550*n*, which is identical to the proximal wedge 550*a* with the following exceptions. The proximal wedge 550*n* (shown in FIGS. 69A and 69B) includes side apertures 570*n* and 572*n* that are generally circular in cross-section, do not break through the side walls of the wedge (although in other embodiments they may break out), and angle toward the midline of the proximal wedge 550*n*. The proximal wedge 550*n* further includes a stepped central aperture 568*n*, which further includes a through hole 568*n*1 and a blind bore 568*n*2 proximate the first end 562*n*, whereas the blind bore 568*n*2 includes a threaded section proximate the first end 562. The proximal wedge 550*n* does not include channels 598*a* and 599*a*, which are present in the proximal wedge 550*a*.

The twelfth expandable fusion device 1000*n* further comprises a distal wedge 650*n* (shown in FIGS. 70A and 70B), which is identical to the proximal wedge 550*n* with the following exceptions. The distal wedge 650*n* does not include a central aperture and instead includes a threaded blind bore 668*n* through the second end 660*n*, which is generally aligned with the central aperture 568*n* of the proximal wedge 550*n*. The distal wedge 650*n* further includes a relief groove 662*n*1 proximate the first end 662*n* intended to compensate for the thickness of a tension member looped around the wedge and engaging the side apertures.

The twelfth expandable fusion device 1000*n* further includes a flexible tension member 715*n*, looped through the side apertures 670*n* and 672*n* of the distal wedge 650, whereas the free ends of the tension member 715*n* further pass through the side apertures 570*n* and 572*n* and extending out of the first end 562*n* of the proximal wedge 550*n*, whereas these free ends may then be tied or clamped or otherwise detained or coupled to an actuator of an inserter/tensioner tool (not shown). The flexible tension member 715*n* may comprise a suture, tape, fiber rope, monofilament or a bundle of either of the above and may be made out of one or more of the following: polymers (e. g. UHMWPE, PET, Nylon, PEEK, Kevlar, etc.), metals (e. g. Titanium, Titanium alloys, Stainless steel, CoCrMo, etc.) or any other fiber such as for example, silk, carbon fiber, etc.

The twelfth expandable fusion device 1000*n* further comprises a set screw 700*n* (best seen in FIG. 71), which is identical to the set screw 700 described above with the following exceptions, the drive feature 708*n* (which may be a hexagon, hexalobe, trilobe, square, double-square, etc.) goes all the way through the set screw and the set screw 700*n* is relatively larger than the set screw 700 so as to suitably function as described below. The set screw 700*n* is threaded into the threaded portion of the bore 568*n*2 of the proximal wedge 550*n* and is configured to (when actuated or tightened) make contact with the flexible tension member 715*n* as it passes through the side openings 570*n* and 572*n* of the proximal wedge 550*n* at the pinch points indicated in FIG. 72C. The thru drive feature of the set screw 700*n* is configured to pass a threaded shaft 840*n* (first seen in FIG. 71, which shows the twelfth expandable fusion device 1000*n* in a fully collapsed state engaged with the threaded shaft 840*n* of a tensioner instrument) of a tensioner instrument (not shown in its entirety) and allow it to access the threaded hole 668*n* of the distal wedge (best seen in FIG. 72A, which shows a section view of the twelfth expandable fusion device 1000*n* in a fully collapsed state engaged with the threaded shaft 840*n* of the tensioner instrument) and further allows graft material to be delivered through it and into the interior of the device 1000*n* after the device is expanded (seen in a section view of the twelfth expandable fusion device 1000*n* in FIG. 72B), the threaded shaft 840*n* withdrawn and the set screw 700*n* is actuated or tightened to lock the flexible tension member 715*n* by contacting it at the pinch points indicated in a section view of the twelfth expandable fusion device 1000*n* in FIG. 72C and thereby causing the flexible tension member 715*n* to hold the tension generated by the vertebral bodies applying compressive force to the endplates and thereby allowing the twelfth expandable fusion device 1000*n* to remain in its expanded state.

Unlike the fusion third expandable fusion device 1000*b*, the twelfth expandable fusion device 1000*n* does not comprise the actuator 500*a*, instead, the functionality of the threaded (or more generally—linear) actuator 500*a* of effecting the expansion of the fusion device 1000*n* and keeping the twelfth expandable fusion device 1000*n* at the desired state of expansion is split between the threaded shaft 840*n* of the tensioner instrument (not shown here in its entirety), which threads into the distal wedge 650*n* and has linear tension applied to it by the tensioner instrument while the body of said tensioner instrument simultaneously bears on the proximal wedge 550*n* to cause the proximal and distal wedges 550*n* and 650*n* to move toward each other causing the twelfth expandable fusion device 1000*n* to expand in a manner described above for other embodiments of the device, and the flexible tension member 715*n* which, being attached to the tensioner instrument during the device expansion allows to keep the twelfth expandable fusion device 1000*n* in the desired state of expansion by means of tightening the set screw 700*n* It should be understood that the tension member 715*n* may also be locked by means other than the set screw 700*n*, including tying the ends of the tension member into a knot or employing other means of preventing loss of tension or slippage of the tension member such as those widely understood, known and utilized in the designs of suture anchors and buttons used in orthopedic surgery. The ends of the tension member 715*n* may need to be trimmed off following the expansion and locking step.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the twelfth expandable fusion device 1000*n* may utilize some or any of the actuator embodiments, height and width expansion features, configurations and embodiments as well as the endplate stabilization features and embodiments described here.

Thirteenth Expandable Fusion Device

With reference to FIGS. 73A-74B, FIGS. 73A, 73B, 73C and 73D show respectively an initial collapsed state, a fully width expanded state, a fully height expanded state and an exploded view of an exemplary thirteenth expandable fusion device fusion device 1000*p* comprising the endplates 100*a*, 150*a*, 200*a* and 250*a* (which are all identical in this embodiment), ramps 300*p*, 350*p*, 400*p* and 450*p* (which are all identical in this embodiment), proximal wedge 550*p*, distal wedge 650*p* (distal and proximal wedges are identical in this embodiment) and the actuator 500*a*. The thirteenth expandable fusion device fusion device 1000*p* is identical to the second expandable fusion device fusion device 1000*a* described above with the following exceptions. The ramp 300*p* is identical to the ramp 300*a* described above with the exception that surfaces 320*p*, 329*p* and 330*p* are not ramped but are generally transverse (they are either perpendicular as shown or angled to the long axis depending on whether the mating surfaces of the particular embodiment of the wedges are perpendicular or angled with respect to the long axis of the device) to the long axis of the thirteenth expandable fusion device fusion device 1000*p*. The distal wedge 650*p* is identical to the distal wedge 650*a* described above with the following exceptions. It should be noted that above, the distal wedge 650*a* was described simply as identical to the proximal wedge 550*a*, whereas the proximal wedge 550*a* was described in detail. The surfaces 680*p* and 682*p* are not ramped with respect to each other as the corresponding surfaces of the wedge 650*a* are, but are instead generally parallel and generally transverse (Optionally, in any embodiment, they are either perpendicular as shown or angled with respect to the long axis of the device) to the long axis of the thirteenth expandable fusion device fusion device 1000*p* The surfaces 680*p* and 682 further include slots 691*p* and 692*p* respectively, which break through one side of the wedge, but not the other side of the wedge and serve the purpose of limiting the translation of the ramps relative to the wedge on the side where the slots don't break through the side wall of the wedge 650*p*. To limit the translation of the ramps relative to the wedge on the other side of the wedge, the opening of the slots may be plastically deformed or "swaged" after the device is assembled to prevent disassembly. Furthermore, the upper and lower surfaces 652*p* and 690*p* of the distal wedge 650*p* do not include projections or channels as they do in wedge 650*a*. Distal wedge 650*p* is identical to the proximal wedge 550*p*.

Since the mating sliding surfaces of the ramps and their respective mating wedges are generally collectively parallel and transverse (perpendicular as shown or could be angled) to the long axis of the thirteenth expandable fusion device fusion device 1000*p*, this arrangement causes the thirteenth expandable fusion device fusion device 1000*p* to not be able to expand in width when the actuator 500*a* is actuated. Instead, when the actuator 500*a* is actuated, the device 1000*p* only expands in height, which is different from the way all of the previously described embodiments behave. Since the mating sliding surfaces of the ramps and the wedges are collectively parallel and are transverse to the long axis, the thirteenth expandable fusion device fusion device 1000*p* are expanded in width by means of application of external force, for example, by means of an inserter/expander instrument. As such, the articulations between the ramps and the wedges no longer act as an expansion mechanism, but simply keep the device's components in proper alignment while preventing disassembly at the upper limit of width expansion affected by the instrument. The width expansion is now independent from the height expansion, which is beneficial in some applications. FIGS. 74A and 74B show the thirteenth expandable fusion device fusion device 1000*p* assembled with inserter-expander instrument 840*p* in respectively the initial collapsed state and in the fully width expanded state. The inserter-expander instrument 840*p* (not shown in its entirety) comprises a pair of front wedges 840*p*1 and a pair of rear wedges 840*p*2, which are drawn together or forced apart using a screw-operated, grip-operated or any other mechanism (not shown). The inserter-expander instrument is engaged with the thirteenth expandable fusion device fusion device 1000*p* in a fully width expanded state of the device; the device is then collapsed back to its initial state for insertion. Once inserted into the disc-space, the front wedges and the rear wedges of the instrument are drawn together causing the thirteenth expandable fusion device fusion device 1000*p* to expand in width up an expansion width at which, the front wedges no longer make contact with the device 1000*p* (state best seen in FIG. 74B) and are withdrawn. Once that happens, the device is expanded in height. This arrangement means that in order for the instrument 840*p* to be disengaged from the thirteenth expandable fusion device fusion device 1000*p*, the device has to be sufficiently expanded in width to allow the front wedge to be withdrawn. Optionally, in any embodiment, multiple different front wedge widths may be supplied to the end-user to allow them to make a determination of what target expansion width is best suited for a particular application. It should be noted that having the width expansion operated by two opposing wedges does not allow to decrease the width from wider to narrower state without a dove-tail, hook or otherwise articulation between the front and rear wedges and the device, which would allow the instrument to exert both tension and compression onto the device and thereby allow the instrument to both expand and collapse the width of the device. This functionality will be explored in embodiments below. It should also be mentioned at this point that all expansion mechanisms and configurations described above with the exception of the device 1000*p* are configured (albeit with various degrees of practicality) to allow the device expansion in both width and height to be reversed by reversing the actuation direction, this is so because all of the ramped articulations described above except in the thirteenth expandable fusion device fusion device 1000*p* have both the front-facing and rear-facing ramped contact surfaces allowing these articulations to take both tensile and compressive forces resulting in the ability to both expand and collapse those devices by actuating the actuators in a "forward" and "reverse" directions respectively.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the thirteenth expandable fusion device fusion device 1000*p* may utilize some or any of the actuator embodiments, height and width expansion features, configurations and embodiments as well as the endplate stabilization features and embodiments described here.

Fourteenth Expandable Fusion Device

With reference to FIGS. 75A-75E, FIGS. 75A, 75B, 75C, 75D and 75E show respectively an initial collapsed state, a fully width expanded state, a fully height expanded state, the fully width and height expanded state and an exploded view of an exemplary fourteenth expandable fusion device 1000*r* comprising the endplates 100*r*, 150*r*, 200*r* and 250*r* (which are all identical in this embodiment), ramps 300*r*, 350*r*, 400*r* and 450*r* (which are all identical in this embodiment), proximal wedge 550*p*, distal wedge 650*p* (distal and proximal wedges are identical in this embodiment) and the actuator 500*a*. The fourteenth expandable fusion device 1000*r* is identical to the thirteenth expandable fusion device 1000*p* described above with the following exceptions. The endplate 100*r* has a first end 102*r* and a second end 104*r*. The first endplate 100*r* further comprises an upper surface 134*r*, a lower surface 132*r* and an inner surface 130*r* connecting the first end and the second end. As in all other embodiment described here, the upper surface includes surface features increasing the roughness of the surface. The inner surface includes a cylindrical relief 149*r* whose axis is parallel to the long axis. The first endplate 100 further comprises a first ramped surface 110*r* proximate the first end and a second ramped surface 112*r* proximate the second end. The ramped surfaces 110*r* and 112*r* further include dovetailed ramped slots 107*r* and 109*r* respectively. As discussed above, although in this embodiment, the slots are dovetailed and have generally trapezoidal cross-sections, they may also have T-shaped, Y-shaped, or any other suitable cross-section that would allow the mating articulations to possess both the leading and trailing contact surfaces. The endplate 100*r* further includes an opening 119*r* extending through the side surfaces in the direction transverse to the long axis. Relief 149*r*. The edges formed by intersection of the ramped surfaces 110*r* and 112*r* and the inner surface 130*r* include chamfers 121*r* and 123*r* configured to mate with the inserter-expander instrument 840*p* described above.

The ramp 300*r* is identical to the ramp 300*p* described above with the following exceptions. The branches 321*r* and 323*r* do not have U-shaped cross-sections as the corresponding features of the ramp 300*p* do, instead the branches 321*r* and 323*r* include ramped surfaces 302*r* and 304*r* respectively, whereas these ramped surfaces include dovetailed fins 302*r*1 and 304*r*1 respectively. The dovetailed fins are configured to mate with the dovetailed ramped slots of the endplates. The ramp 300*r* does not include a recessed slot present in the ramp 300*p*. The fourteenth expandable fusion device 1000*r* has similar functionality to the thirteenth expandable fusion device 1000*p* described above including the reliance on external expander instrument for width expansion.

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the fourteenth expandable fusion device 1000*r* may utilize some or any of the actuator embodiments, height and width expansion features, configurations and embodiments as well as the endplate stabilization features and embodiments described here.

Fifteenth Expandable Fusion Device

With reference to FIGS. 76A-76D, FIGS. 76A, 76B, 76C and 76D show respectively an initial collapsed state, a fully width expanded state and a fully height expanded state and an exploded view of an exemplary fifteenth expandable fusion device 1000*s* comprising endplates 100*r*, 150*r*, 200*r* and 250*r* (which are all identical in this embodiment), ramps 300*s*, 350*s*, 400*s* and 450*s* (which are all identical in this embodiment), proximal wedge 550*s*, distal wedge 650*s* (distal and proximal wedges are identical in this embodiment) and the actuator 500*a*. The fifteenth expandable fusion device 1000*s* is identical to the fourteenth expandable fusion device 1000*r* described above with the following exceptions. The proximal wedge 550*s* is identical to the proximal wedge 550*a* described above with the following exceptions, the upper and lower surfaces of the wedge 550*s* include no projections or channels as they do in the wedge 550*a* and the opposing ramped surfaces of the wedge 550*s* have larger included angle "A" between them than they do in the wedge 550. This angle is best seen in FIG. 76A and is contemplated as being greater than 100 degrees and less than 179 degrees and more preferably greater than 140 degrees and most preferably greater than 160 degrees (150 degree angle is shown for illustrative purposes). The ramp 300*s* is identical to the ramp 300*r* with the following exceptions: the surfaces 330*s*, 320*s* and 329*s* are not perpendicular to the long axis as they are in the ramp 300*r*, but are instead ramped at an angle equal to half of the angle "A" discussed above relative to the long axis, this is best seen in FIG. 76A. The ramp 300*s* further includes ramped undercuts 337*s*1 and 337*s*2, which are configured to mate with an expander instrument and may have either a rectangular section or L-shaped, T-shaped or dovetailed section. The endplate 100*s* is identical to the endplate 100*r* described above with the exception that the endplate 100*s* also includes ramped undercuts 147*s*1 and 147*s*2, which are configured to mate with an expander instrument and may have either a rectangular section or L-shaped, T-shaped or dovetailed section. Undercuts 337*s*1, 337*s*2, 147*s*1 and 147*s*2 when having rectangular sections, serve the purpose of preventing the device from expanding in height while the width expansion is affected by the expander instrument. When these undercuts have L-shaped, dovetailed or similar sections, they serve an additional purpose of allowing the expander instrument to both increase and decrease the width of the device by reversing the direction of actuation. As discussed above, this is because, the L-shaped, T-shaped, dovetailed, etc. sections contain both the front and rear contact surfaces allowing to capture the mating components and allow tension or compression to be applied to the interface.

The significance and usefulness of the large included angle "A" between the ramped surfaces of the wedges is not obvious and requires an additional clarification. Functionality and clinical utility of many of the embodiments of the expandable fusion device described here (e. g. 1000*a*, 1000*b*, 1000*c*, 1000*d*, 1000*e*, etc.) rely on the fact that complete or significant width expansion has to occur before the height expansion is initiated. This is achieved through the endplates maintaining sliding contact with mating surfaces of the wedges during width expansion step and when configured in the ways described above, this contact while maintained prevents the ramps from moving closer to each other (which would be necessary to affect height expansion). In the course of width expansion, this contact between the endplates and the wedges is eventually lost and the height expansion is allowed to start. However, the fifteenth expandable fusion device 1000*s* does not include such delay mechanism, and both the width and height expansion appear to be able to occur simultaneously by turning the actuator. If we imagine an alternative fifteenth expandable fusion device 1000*s*1 (not shown), which is identical to the fifteenth expandable fusion device 1000*s* except that its angle "A" is relatively small (e. g. around 90 degrees) and imagine this alternate fifteenth expandable fusion device 1000*s*1 in a state of expansion where the width of the device is less than at the state of full width expansion and where the device is at least somewhat expanded in height. If we now keep the actuator static, which it generally would be while not actuated (i. e. due to thread friction), and apply compression to the device endplates, such as the adjacent vertebral endplates would apply in clinical use, the alternate fifteenth expandable fusion device 1000*s*1 will tend to collapse in height and simultaneously expand in width until either the full width expansion or the full collapse of height is reached (whichever happens first based on the initial extent of height and width expansion). This happens because in any device state where full width expansion is not yet reached, for each position of the actuator relative to the wedges and consequently—for every separation distance between the proximal and the distal wedges, there exists a range of expansion states that are achievable. In other words, in this situation, the alternate fifteenth expandable fusion device 1000*s*1 is not at equilibrium and its height expansion are "converted" into width expansion by the following mechanism of action. In such a state, when compression is applied to the endplates in the height direction, the ramp components see a force urging them apart generated by inclined surfaces involved in height expansion, since the actuator remains static, the ramps only move apart by sliding relative to the wedges into a state of greater width expansion thereby increasing the distance between the ramps and decreasing the height of the device. In a similar height-only or a width-only expansion mechanism, this reversal of expansion is prevented due to the friction in the threads of the actuator, which has to do with the "locking" property of threads used. Locking threads are characterized by a low "helical angle", which for example prevents an average screw from being axially pushed into a mating thread without applying any torque (it should be noted that no amount of pure axial force will cause a locking thread to follow a helical path into a mating thread). This is in contrast to a non-locking (or overhauling) thread such as one used in a cork-screw, which are forced to twist into a work-piece through application of pure axial force. But in this case, since the actuator does not move, and the dis-equilibrium is intrinsic to the mechanism, the locking property of the actuator threads cannot prevent the loss of height. Similar to the threads having their mechanical efficiency controlled by angle of the thread helix (with low helical angles imparting a locking property to the threads), the ramps or "inclined planes" (of which a wedge mechanism is an adaptation) are also known to possess mechanical efficiency (or advantage), which is expressed as the length of the incline divided by its rise or more simply—by the included angle of the wedge. The larger the included angle, the less mechanical advantage the wedge mechanism has. Furthermore, for any wedge mechanism and materials used (and friction generated), there exists some maximum included angle at which the wedge will cease acting as a wedge in that attempting to push such a wedge between two objects will not cause these objects to be forced apart no matter how high the applied load is due to frictional forces, loads and material strength.

Bringing this back to the fifteenth expandable fusion device 1000*s*, because the proximal and distal wedges 550*s* and 650*s* utilize a high angle "A", they do not function as a width expansion mechanism and instead function as a locking mechanism preventing the fifteenth expandable fusion device 1000*s* from spontaneously losing height and gaining width. This means that if in the initial collapsed state, the actuator 500 is turned, the fifteenth expandable fusion device 1000*s* will only expand in height and not in width and no reasonable compressive force acting in the height direction will cause the device to lose height and gain width as discussed above. The fifteenth expandable fusion device 1000*s* relies on an external inserter-expander instrument 840*s* (seen in FIGS. 77A and 77B) to affect the width expansion.

The inserter-expander instrument 840*s* (not shown in its entirety) comprises a pair of front wedges 840*s*1 and a pair of rear wedges 840*s*2, which are drawn together or forced apart using a screw-operated, grip-operated or any other mechanism (not shown). The instrument 840*s* is configured to simultaneously actuate (here: turn) the actuator in the forward or reverse direction and translate the front and the rear wedges together or apart. Turning the actuator in the process of width expansion does not cause or substantially contribute to width expansion itself (due to high angles "A" of the wedges and the resulting near-zero mechanical efficiency of these wedges), but simply allows the proximal and the distal wedges to move toward each other providing room for the width expansion to be effected by the forces supplied by the instrument 840*s*. The inserter-expander instrument is engaged with the fifteenth expandable fusion device 1000*s* in a fully width expanded state of the device, the device is then collapsed back to its initial state for insertion into the disc space (best seen in FIG. 77A). Once inserted into the disc-space, the front wedges and the rear wedges of the instrument are drawn together causing the fifteenth expandable fusion device 1000s to expand in width up to an expansion width at which, the front wedges no longer make contact with the device 1000p (state best seen in FIG. 77B) and are withdrawn. Once that happens, the device is expanded in height. This arrangement means that in order for the instrument 840s to be disengaged from the device 1000p, the device has to be sufficiently expanded in width to allow the front wedge to be withdrawn. Optionally, in any embodiment, multiple different front wedge widths may be supplied to the end-user to allow them to make a determination of what target expansion width is best suited for a particular application. It should be noted that having the width expansion operated by two opposing wedges does not allow to decrease the width from wider to narrower state unless a dove-tail, hook, L-shaped or otherwise articulation between the front and rear wedges and the device is used, which would allow the instrument to exert both tension and compression onto the device and thereby allow the instrument to both expand and collapse the width of the device as discussed above).

It should also be understood that although the various alternative geometries of the various components are presented here as discrete embodiments, these alternative embodiments have optional features which may be substituted or mixed/matched with any other embodiment in the specification. It should also be understood that substituting any of the aforementioned optional alternative features in any of the components may or will necessitate the mating components to use the inverse or complementary geometry of those features for proper engagement and that the shape of that inverse or complementary geometry would follow inevitably from the optional alternative feature geometry described above and from the detailed description of the embodiments described as utilizing that geometry. As an example, the fifteenth expandable fusion device 1000s may utilize some or any of the actuator embodiments, height and width expansion features, configurations and embodiments as well as the endplate stabilization features and embodiments (such as shown for example in embodiments 1000c and 1000d) described here.

Sixteenth Expandable Fusion Device

With reference to FIGS. 78, 79A and 79B, FIG. 78 shows the initial collapsed state of an expandable device 1000t, FIG. 79A shows the initial collapsed state of an exemplary sixteenth expandable fusion device 1000t with expander instrument attached and FIG. 79B shows a width-expanded state of the device 1000t with expander instrument attached. The sixteenth expandable fusion device 1000t comprises endplates 100t, 150t (best seen in FIG. 79B). 200t and 250t (which are all identical in this embodiment), ramps 300s, 350s, 400s and 450s (which are all identical in this embodiment), proximal wedge 550s, distal wedge 650s (distal and proximal wedges are identical in this embodiment) and the actuator 500a. The sixteenth expandable fusion device 1000t is identical to the device 1000s described above with the following exceptions. The endplate 100t includes a ramped slot 107t2 formed in the upper surface 134t. This ramped slot is configured to engage the inserter-expander instrument 840t (best seen in FIGS. 79A and 79B).

The inserter-expander instrument 840t (not shown in its entirety) comprises a pair of front bifurcated ramps 840t1 which are pushed or pulled while the main body of the instrument (not shown) is attached to and bears against the proximal wedge. The instrument 840t is configured to simultaneously actuate (here: turn) the actuator in the forward or reverse direction and translate the bifurcated ramps forward or backward depending on actuation direction. Turning the actuator in the process of width expansion does not cause or substantially contribute to width expansion itself (due to high angles "A" of the wedges and the resulting near-zero mechanical efficiency of these wedges), but simply allows the proximal and the distal wedges to move toward each other providing room for the width expansion to be effected by the forces supplied by the instrument 840t. The inserter-expander instrument is engaged with the sixteenth expandable fusion device 1000t in a fully width expanded state of the device, the device is then collapsed back to its initial state for insertion into the disc space (best seen in FIG. 79A). Once inserted into the disc-space, the bifurcated ramps of the instrument are pulled toward the proximate end of the device with the main body of the instrument bearing against the proximal wedge and simultaneously turning the actuator. This causes the sixteenth expandable fusion device 1000t to expand in width up to an expansion width at which, the bifurcated ramps no longer make contact with the sixteenth expandable fusion device 1000t (state best seen in FIG. 79B) and are withdrawn. Once that happens, the device is expanded in height. This arrangement means that in order for the instrument 840t to be disengaged from the sixteenth expandable fusion device 1000t, the device has to be sufficiently expanded in width to allow the front wedge to be withdrawn. Optionally, in any embodiment, multiple different front wedge widths may be supplied to the end-user to allow them to make a determination of what target expansion width is best suited for a particular application. Due to the fact that the bifurcated ramps of the instrument have both front and rear contact surfaces with the endplates, the width expansion process is reversible in that if actuating the instrument in one direction will cause the device to expand in width, then reversing the direction of actuation will cause the device to collapse in width.

Seventeenth Expandable Fusion Device

Now with reference to FIG. 80. FIG. 80 shows a diagram of general width expansion functionality of an exemplary seventeenth expandable fusion device 1000u, which is identical to the thirteenth expandable fusion device 1000p described above with certain exceptions described below. The seventeenth expandable fusion device 1000u is a modification of the thirteenth expandable fusion device 1000p where the generally parallel articulating surfaces between the proximal wedge and its two mating ramps and between the distal wedge and its two mating ramps are inclined with respect to the long axis of the device and possesses a desirable property of allowing the device to expand in width in a non-rectilinear fashion, causing the width expanded states of the device to have a general shape of a parallelogram instead of a rectangle produced by for example the thirteenth expandable fusion device 1000p. This is useful for some surgical approaches where the approach axis is angled with respect to standard anatomical planes such as a transforaminal (or TLIF) approach.

Eighteenth Expandable Fusion Device

Provided herein, per FIGS. 81A-86, is an eighteenth expandable fusion device 1000v for implantation between two adjacent vertebrae. Optionally, in any embodiment, per FIG. 81A the device 1000v comprises: an actuator 500v comprising a drive feature 503v and an longitudinal axis 504v; a wedge assembly 750v coupled to the actuator 500v; a ramp assembly 800v slidably coupled with the wedge assembly 750v; an upper endplate assembly 850v slidably coupled with the ramp assembly 800v; and a lower endplate assembly 900v slidably coupled with the ramp assembly 800v.

Optionally, in any embodiment, per FIG. 81B, the device 1000v has a width 1100v comprising an external width of at least one of the upper endplate assembly 850v and the lower endplate assembly 900v. Optionally, in any embodiment, the device has a height 1200v comprising an external distance between the upper endplate assembly 800v and the lower endplate assembly 900v.

Optionally, in any embodiment, per FIG. 81C, actuation of the drive feature 503v by a first number of actuations in a first actuation direction 1300v increases the width 1100v without increasing the height 1200v. Optionally, in any embodiment, actuation of the drive feature 503v by a second number of actuations beyond the first number of actuations in the first actuation direction 1300v increases at least one of the height 1200v and the width 1100v. Optionally, in any embodiment, actuation of the drive feature 503v by a second number of actuations beyond the first number of actuations in the first actuation direction 1300v increases both the height 1200v and the width 1100v, wherein actuation of the drive feature 503v by a third number of actuations beyond the second number of actuations in the first actuation direction 1300v increases the height 1200v without increasing the width 1100v. Optionally, in any embodiment, actuation of the drive feature 503v by a second number of actuations beyond the first number of actuations in the first actuation direction 1300v increases neither the height 1200v nor the width 1100v, wherein actuation of the drive feature 503v by a third number of actuations beyond the second number of actuations in the first actuation direction 1300v increases the height 1200v without increasing the width 1100v. Optionally, in any embodiment, the width 1100v of the device 1000v reaches an apex once the drive feature 503v is actuated by at least the first number of actuations. Optionally, in any embodiment, the height 1200v of the device 1000v reaches an apex once the drive feature 503v is actuated by at least the first and second number of actuations.

Optionally, in any embodiment, actuation of the drive feature 503v by a second number of actuations beyond the first number of actuations in the first actuation direction 1300v increases both the height 1200v and the width 1100v. Optionally, in any embodiment, actuation of the drive feature 503v by a second number of actuations beyond the first number of actuations in the first actuation direction increases the height 1200v without increasing the width 1100v.

Optionally, in any embodiment, actuation of the drive feature 503v in the first actuation direction 1300v by at least the first number of actuations increases the height 1200v of the device 1000v by about 30% to about 400%. Optionally, in any embodiment, actuation of the drive feature 503v in the first actuation direction 1300v by at least the first and the second number of actuations increases the width 1100v of the device 1200v by about 14% to about 150%.

Optionally, in any embodiment, per FIG. 82, the actuator 500v comprises a cylindrically shaped elongate shaft with a distal end and a proximal end. Optionally, in any embodiment, at least a portion of the distal end comprises a first thread feature 501v. Optionally, in any embodiment, at least a portion of the proximal end comprises a second thread feature 502v, and wherein the proximal end comprises the drive feature 503v. Optionally, in any embodiment, at least one of the first thread feature 501v and the second thread feature 502v comprise a thread disposed externally around the actuator 500v. Optionally, in any embodiment, the first thread feature 501v and the second thread feature 502v have opposing threading directions. Optionally, in any embodiment, the first thread feature 501v and the second thread feature 502v have the same threading direction. Optionally, in any embodiment, at least one of the first thread feature 501v and the second thread feature 502v comprises a right-handed threading. Optionally, in any embodiment, at least one of the first thread feature 501v and the second thread feature 502v comprises a left-handed threading. Optionally, in any embodiment, the drive feature 503v comprises a recessed region configured to receive a driving instrument. Optionally, in any embodiment, the recessed region comprises a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess or any other shaped recess. Optionally, in any embodiment, the driving feature comprises a protuberance extending therefrom and configured to be coupled to a driving instrument. Optionally, in any embodiment, the protuberance comprises a hex, a hexalobular, or a square protuberance or any other shaped protuberance. Optionally, in any embodiment, the drive feature 503v is coincident with the longitudinal axis 504v.

Optionally, in any embodiment, per FIG. 81C, the wedge assembly comprises a distal wedge 650v and a proximal wedge 550v. Optionally, in any embodiment, actuation of the drive feature in the first direction converges the distal wedge 650v and the proximal wedge 550v toward one another. Optionally, in any embodiment, per FIG. 83A, the distal wedge 650v is an isosceles trapezoid prism comprising a distal face and a proximal face. Optionally, in any embodiment, the distal wedge 650v comprises a third thread feature 654v. Optionally, in any embodiment, the third thread feature 654v extends from the distal face of the distal wedge 650v, to the proximal face of the distal wedge 650v. Optionally, in any embodiment, the distal wedge 650v further comprises one or more features configured for temporary attachment to an inserter tool. Optionally, in any embodiment, the third thread feature 654v is threadably coupled to the second thread feature 502v of the actuator 500v. Optionally, in any embodiment, the distal wedge 650v further comprises first slot 651v and second slot 652v. Optionally, in any embodiment, the first slot 651v comprises an upper left first slot 651v, an upper right first slot 651v, a lower left first slot 651v, and a lower right first slot 651v. Optionally, in any embodiment, the upper left first slot 651v and the upper right first slot 651v, and the lower left first slot 651v and a lower right first slot 651v have mirrored symmetry about a sagittal plane of the distal wedge 650v. Optionally, in any embodiment, the upper left first slot 651v and the lower left first slot 651v, and the upper right first slot 651v and a lower right first slot 651v have mirrored symmetry about a transverse plane of the distal wedge 650v. Optionally, in any embodiment, the medial plane of each of the upper left first slot 651v, the upper right first slot 651v, the lower left first slot 651v, and the lower right first slot 651v are oriented at the transverse angle from the sagittal plane of the distal wedge 650v. Optionally, in any embodiment, at least one of the third thread feature 654v and the fourth thread feature 554v in the distal wedge 650v and the proximal wedge 550v, respectively, comprise a thread locking feature configured to prevent actuation of at least one of the third first feature 501v and the second thread feature 502v of the actuator 500v in a direction opposite the first actuation direction 1300v. Optionally, in any embodiment, the thread locking feature comprises a deformable insert, a deformable thread, a distorted thread, a flexible lip, or any combination thereof. Optionally, in any embodiment, the thread locking feature comprises a bore within at least one of the distal wedge 650v and the proximal wedge 550ν configured to provide access to the third thread feature 654ν or the fourth thread feature 554ν, and/or which is configured to receive an insert such as a pin, a screw, a dowel, a nut, or any combination thereof to prevent actuation of the actuator 500ν.

Optionally, in any embodiment, the second slot 652ν comprises an upper left second slot 652ν, an upper right second slot 652ν, a lower left second slot 652ν, and a lower right second slot 652ν. Optionally, in any embodiment, the upper left second slot 652ν and the upper right second slot 652ν, and the lower left second slot 652ν and a lower right second slot 652ν have mirrored symmetry about a sagittal plane of the distal wedge 650ν. Optionally, in any embodiment, the upper left second slot 652ν and the lower left second slot 652ν, and the upper right second slot 652ν and a lower right second slot 652ν have mirrored symmetry about a transverse plane of the distal wedge 650ν. Optionally, in any embodiment, the medial plane of the upper left second slot 652ν, the upper right second slot 652ν, the lower left second slot 652ν, and the lower right second slot 652ν are oriented at the transverse angle from the sagittal plane of the distal wedge 650ν.

Optionally, in any embodiment, per FIG. 83B, the proximal wedge 550ν has an isosceles trapezoid prism shape comprising a distal face and a proximal face. Optionally, in any embodiment, the proximal wedge 550ν comprises a fourth thread feature 554ν. Optionally, in any embodiment, the fourth thread feature 554ν extends from the distal face of the proximal wedge 550ν, to the proximal face of the proximal wedge 550ν. Optionally, in any embodiment, the proximal wedge 550ν further comprises one or more features configured for temporary attachment to an inserter tool. Optionally, in any embodiment, the fourth thread feature 554ν is threadably coupled to the first thread feature 501ν of the actuator 500ν. Optionally, in any embodiment, the third thread feature 654ν comprises a thread disposed internally within the distal wedge 650ν. Optionally, in any embodiment, the fourth thread feature 554ν comprises a thread disposed internally within the proximal wedge 650ν. Optionally, in any embodiment, the third thread feature 654ν and the fourth thread feature 554ν have opposing threading directions. Optionally, in any embodiment, the third thread feature 654ν and the fourth thread feature 554ν have the same threading direction. Optionally, in any embodiment, at least one of the third thread feature 654ν and the fourth thread feature 554ν comprises a right-handed threading. Optionally, in any embodiment, at least one of the third thread feature 654ν and the fourth thread feature 554ν comprises a left-handed threading.

Optionally, in any embodiment, per FIG. 81C, the ramp assembly 800ν comprises a first proximal ramp 300ν, a second proximal ramp 400ν, a first distal ramp 350ν, and a second distal ramp 450ν.

Optionally, in any embodiment, per FIGS. 84A and 84B, the second distal ramp 400ν comprises a rectangular prism divided into two lobes. Optionally, in any embodiment, the second distal ramp 400ν comprises a first ridge 401ν, a first protrusion 402ν, a v-slot 403ν, a third protrusion 404ν, a third ridge 405ν, and a third slot 406ν. Optionally, in any embodiment, the first ridge 401ν comprises two first ridges 401ν. Optionally, in any embodiment, the first ridge 401ν is located on the proximal end of the second distal ramp 400ν. Optionally, in any embodiment, the medial plane of the first ridge 401ν lies at the traverse angle from the medial face of the second distal ramp 400ν. Optionally, in any embodiment, the first protrusion 402ν comprises two first protrusions 402ν. Optionally, in any embodiment, the first protrusion 402ν is located on the mesial proximal corners of the second distal ramp 400ν. Optionally, in any embodiment, the v-slot 403ν comprise two v-slots 403ν. Optionally, in any embodiment, the v-slot 403ν is located on the mesial plane of the second distal ramp 400ν. Optionally, in any embodiment, the apex of the v-slot 403ν is oriented towards the distal end of the second distal ramp 400ν. Optionally, in any embodiment, the protrusion 404ν comprises two protrusions 404ν. Optionally, in any embodiment, the protrusion 404ν is located on the lower face of the distal ramp 400ν. Optionally, in any embodiment, the third ridge 405ν comprises two the third ridges 405ν. Optionally, in any embodiment, the third ridge 405ν is located on the upper surface of the second distal ramp 400ν. Optionally, in any embodiment, the medial plane of the third ridge 405ν is parallel to the mesial face of the second distal ramp 400ν. Optionally, in any embodiment, the third slot 406ν comprises two third slot 406ν comprises two the two third slots 406ν. Optionally, in any embodiment, the third slot 406ν is located on the upper surface of the second distal ramp 400ν Optionally, in any embodiment, the medial plane of the third slot 406ν is parallel to the mesial face of the distal ramp 400ν. Optionally, in any embodiment, the first distal ramp 300ν is a mirrored equivalent of the second distal ramp 400ν. Optionally, in any embodiment, the first distal ramp 350ν comprises a second ridge 351ν. Optionally, in any embodiment, the second ridge 351ν comprises two second ridges 351ν. Optionally, in any embodiment, the second ridge 351ν is located on the lateral side of the first distal ramp 350ν. Optionally, in any embodiment, the first distal ramp 350ν comprises a second protrusion 352ν. Optionally, in any embodiment, the second protrusion 352ν comprises two second protrusions 352ν. Optionally, in any embodiment, the second protrusion 352ν is located on the lateral proximal end of the first distal ramp 350ν. Optionally, in any embodiment, the medial plane of the second protrusion 352ν is perpendicular to the medial plane of the second ridge 351ν. Optionally, in any embodiment, the first distal ramp 350ν comprises a tongue 353ν. Optionally, in any embodiment, the tongue 353ν extends from the bottom of the distal ramp 350ν to the top of the distal ramp 350ν along the lateral proximal edge of the distal ramp 350ν. Optionally, in any embodiment, the second distal ramp 450ν is a mirrored equivalent of the first distal ramp 350ν.

Optionally, in any embodiment, the upper endplate assembly comprises a first endplate 100ν and a second endplate 250ν. Optionally, in any embodiment, the lower endplate assembly comprises a third endplate 150ν and a fourth endplate 200ν.

Optionally, in any embodiment, at least one of the first endplate 100ν and the second endplate 250ν, the third endplate 150ν and the fourth endplate 200ν, the first proximal ramp 300ν and the second proximal ramp 400ν, and the first distal ramp 350ν and the second distal ramp 450ν have mirrored equivalence. Optionally, in any embodiment, at least one of the second endplate 250ν and the fourth endplate 200ν is larger than at least one of the first endplate 100ν and the third endplate 150ν. Optionally, in any embodiment, at least one of the exterior faces of the first end plate 100ν, the second endplate 250ν, the third endplate 150ν, and the fourth endplate 200ν comprise a texture configured to grip the vertebrae. Optionally, in any embodiment, the texturing comprises a tooth, a ridge, a roughened area, a metallic coating, a ceramic coating, a keel, a spike, a projection, a groove, or any combination thereof.

Optionally, in any embodiment, per FIGS. 81A and 81C, the slideable coupling between at least one of the wedge assembly 750v and the ramp assembly 800v, the ramp assembly 800v and the upper endplate assembly 850v, and the ramp assembly 800v and the lower endplate assembly 900v is at a transverse angle from the longitudinal axis 504v. Optionally, in any embodiment, the transverse angle is about 0 degrees to about 90 degrees.

Optionally, in any embodiment, the slideable coupling between at least one of the wedge assembly 750v and the ramp assembly 800v, the ramp assembly 800v and the upper endplate assembly 850v, and the ramp assembly 800v and the lower endplate assembly 900v comprises a protrusion and a slot. Optionally, in any embodiment, the protrusion extends from at least one of the wedge assembly 750v the ramp assembly 800v, the upper endplate assembly 850v, and the lower endplate assembly 900v. Optionally, in any embodiment, the slot is disposed in at least one of the wedge assembly 750v the ramp assembly 800v, the upper endplate assembly 850v, and the lower endplate assembly 900v. Optionally, in any embodiment, the protrusion comprises a pin 600, a ridge, a dimple, a bolt, a screw, a bearing, or any combination thereof. Optionally, in any embodiment, the slot comprises a through slot, a blind slot, a t-slot, a v-slot, a groove, or any combination thereof.

Optionally, in any embodiment, per FIGS. 81A-86B, the slideable coupling between the wedge assembly 750v and the ramp assembly comprises 800v the first slot 651v and the second slot 652v within the distal wedge 650v, the third slot 551v and the fourth slot 552v within the proximal wedge 550v, a first protrusion 402v and a first ridge 401v, within the first proximal ramp 300v and the second proximal ramp 400v, and a second protrusion 352v, a second ridge 351v, and a tongue 353v within the first distal ramp 350v and the second distal ramp 450v. Optionally, in any embodiment, the number of at least one of the first slots 651v, the second slots 652v, the third slots 551v, the fourth slots 552v, the first protrusions 402v, the first ridges 401v, the second protrusions 352v, and the second ridges 351v is about 1, 2, 3, 4 or more.

Optionally, in any embodiment, the slideable coupling between the proximal wedge 550v and the first proximal ramp 300v or the second proximal ramp 400v comprises a slideable coupling between the third slot 551v and the first ridge 401v, and a slideable coupling between the fourth slot 552v and the first protrusion 402v.

Optionally, in any embodiment, the slideable coupling between the distal wedge 650v and the first distal ramp 350v or the second distal ramp 450v comprises a slideable coupling between a first slot 651v and a second ridge 351v, a slideable coupling between a second slot 652v and a second protrusion 352v, or any combination thereof.

Optionally, in any embodiment, the second slot 652v within distal wedge 650v comprises a first stop 653v to prevent the first protrusion 402v from exiting the second slot 652v in one direction. Optionally, in any embodiment, the fourth slot 552v within the proximal wedge 550v comprises a second stop 553v to prevent the first protrusion 402v from exiting the second slot 652v in one direction.

Optionally, in any embodiment, the slideable coupling between the ramp assembly 800v and the upper endplate assembly 850v or the lower endplate assembly 900v comprises a tongue 353v within at least one of first distal ramp 350 and the second distal ramp 450, and a v-slot 403v, a third protrusion 404v, a third ridge 405v, and a third slot 406v within at least one of first proximal ramp 300 and the second proximal ramp 400, and a dovetail slot 101v, a fourth protrusion 102v, a fourth slot 104v, a fifth slot 103v and a fourth ridge 105v within at least one of the first endplate 100v, the second endplate 250v, the third endplate 150v and the fourth endplate 200v.

Optionally, in any embodiment, the slideable coupling between the first distal ramp 350v or the second distal ramp 450v and the first end plate 100v, the second endplate 250v, the third endplate 150v, or the fourth endplate 200v comprises a slideable coupling between the dovetail slot 101v and the tongue 353v.

Optionally, in any embodiment, the slideable coupling between the first proximal ramp 300v or the second proximal ramp 400v and the first end plate 100v, the second endplate 250v, the third endplate 150v, or the fourth endplate 200v comprises a slideable coupling between the v-slot 403v and the fourth protrusion 102v, a slideable coupling between the third protrusion 404v and the fourth slot 104v, a slideable coupling between the third ridge 405v and the fifth slot 103v, a slideable coupling between the third slot 406v and the fourth ridge 105v, or any combination thereof.

Optionally, in any embodiment, the fourth protrusion 102v comprises a feature of the first end plate 100v, the second endplate 250v, the third endplate 150v, or the fourth endplate 200v. Optionally, in any embodiment, the fourth protrusion 102v comprises a separate component that is firmly inserted into the first end plate 100v, the second endplate 250v, the third endplate 150v, or the fourth endplate 200v. Optionally, in any embodiment, the fourth protrusion 102v comprises the pin 600v.

Optionally, in any embodiment, the slideable coupling between the wedge assembly 750v and at least one of the upper endplate assembly 850v and lower endplate assembly 900v comprises a slideable coupling between a distal chamfer 123v and a proximal chamfer 121v in at least one of the first end plate 100v, the second endplate 250v, the third endplate 150v, and the fourth endplate 200v, and a guide surface 621v 521v in at least one of the distal wedge 650v and a proximal wedge 550v. Optionally, in any embodiment, the slideable coupling between the wedge assembly 750v and at least one of the upper endplate assembly 850v and lower endplate assembly 900v prevents the height 1200v of the device from increasing until the width 1100v of the device's 1000v reaches its apex.

Optionally, in any embodiment, at least one of the actuator 500v, the wedge assembly 750v, the ramp assembly 8000v, the upper endplate assembly 850v, and the lower endplate assembly 900v comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Further provided herein, per FIG. 81A, is an expandable fusion system for implantation between two adjacent vertebrae, the system comprising a collapsing tool 5000v and the eighteenth expandable fusion device 1000v. Optionally, in any embodiment, once the actuator 500v is actuated by at least the first number and the second number of actuations in a first actuation direction 1300v, such that the width 1100v and the height 1200v of the device 1000v are at their apex, actuation of the actuator 500v in a direction opposite the first actuation direction 1300v may only reduce the width 1100v, without reducing the height 1200v of the device 1000v. Optionally, in any embodiment, a collapsing tool 5000v may be employed to allow the height 1200v reduction without width 1100v reduction. Optionally, in any embodiment, the collapsing tool 5000v comprises a first prong 5001v and a second prong 5001v, wherein the first prong 5001v is configured to be inserted between the proximal wedge 550v and/or the distal wedge 650v and the first proximal ramp 300v, and wherein the second prong 5002v is configured to be inserted between the proximal wedge 550v and/or the distal wedge 650v and the second proximal ramp 400v. Optionally, in any embodiment, the first prong 5001v and the second prong 5001v have the same length. Optionally, in any embodiment, the first prong 5001v and the second prong 5001v have different lengths. Optionally, in any embodiment, the first prong 5001v and the second prong 5001v have the same thickness. Optionally, in any embodiment, the first prong 5001v and the second prong 5001v have different thicknesses.

Optionally, in any embodiment, the eighteenth expandable fusion device 1000v may further or alternatively include any features, components, or characteristics of any of the previously described expandable fusion device.

The numerical indicators for the components of the exemplary eighteenth expandable fusion device are compiled in Table 1, below.

TABLE 1

| | |
|---|---|
| 100v | First endplate |
| 101v | Dovetail slot |
| 102v | Fourth protrusion |
| 103v | Fourth slot |
| 104v | Fifth slot |
| 105v | Fourth ridge |
| 150v | Third endplate |
| 200v | Fourth endplate |
| 250v | Second endplate |
| 300v | First proximal ramp |
| 350v | First distal ramp |
| 351v | Second protrusion |
| 352v | Second ridge |
| 353v | Tongue |
| 400v | Second proximal ramp |
| 401v | First ridge |
| 402v | First protrusion |
| 403v | V-slot |
| 404v | Third protrusion |
| 405v | Third ridge |
| 406v | Third slot |
| 450v | Second distal ramp |
| 500v | Actuator |
| 501v | First thread feature |
| 502v | Second thread feature |
| 503v | Drive feature |
| 504v | Longitudinal axis |
| 550v | Proximal wedge |
| 551v | Third slot |
| 552v | Fourth slot |
| 553v | Second Stop |
| 554v | Fourth thread feature |
| 600v | Pin |
| 650v | Distal wedge |
| 651v | First slot |
| 652v | Second slot |
| 653v | First Stop |
| 654v | Third thread feature |
| 750v | Wedge assembly |
| 800v | Ramp assembly |
| 850v | Upper endplate assembly |
| 900v | Lower endplate assembly |
| 1000v | Eighteenth Device |
| 1100v | Width |
| 1200v | Height |
| 1300v | Axis of actuation |
| 5000v | Inserter |

Nineteenth Expandable Fusion Device

Provided herein, per FIGS. 87A-94D, is a nineteenth expandable fusion device 1000w for implantation between two adjacent vertebrae. Optionally, in any embodiment, per FIG. 81A the device 1000w comprises: an actuator 500w comprising a drive feature 503w and an longitudinal axis 504v; a wedge assembly 750w coupled to the actuator 500v; a ramp assembly 800w slidably coupled with the wedge assembly 750v; an upper endplate assembly 850w slidably coupled with the ramp assembly 800v; and a lower endplate assembly 900w slidably coupled with the ramp assembly 800w. Optionally, in any embodiment, the upper endplate assembly 850w is further slidably coupled with the lower endplate assembly 900w.

Optionally, in any embodiment, per FIG. 87A, the device 1000w has a width 1100w comprising an external width of at least one of the upper endplate assembly 850w and the lower endplate assembly 900w. Optionally, in any embodiment, the device has a height 1200w comprising an external distance between the upper endplate assembly 800w and the lower endplate assembly 900w.

Optionally, in any embodiment, per FIG. 87C, actuation of the drive feature 503w by a first number of actuations in a first actuation direction 1300w increases the width 1100w without increasing the height 1200w. Optionally, in any embodiment, actuation of the drive feature 503w by a second number of actuations beyond the first number of actuations in the first actuation direction 1300w increases the height 1200w without increasing the width 1100w. Optionally, in any embodiment, actuation of the drive feature 503w by a second number of actuations beyond the first number of actuations in the first actuation direction 1300w increases both the height 1200w and the width 1100w, wherein actuation of the drive feature 503w by a third number of actuations beyond the second number of actuations in the first actuation direction 1300w increases the height 1200w without increasing the width 1100v. Optionally, in any embodiment, actuation of the drive feature 503w by a second number of actuations beyond the first number of actuations in the first actuation direction 1300w increases neither the height 1200w nor the width 1100w, wherein actuation of the drive feature 503w by a third number of actuations beyond the second number of actuations in the first actuation direction 1300w increases the height 1200w without increasing the width 1100w. Optionally, in any embodiment, the width 1100w of the device 1000w reaches an apex once the drive feature 503w is actuated by at least the first number of actuations. Optionally, in any embodiment, the height 1200w of the device 1000w reaches an apex once the drive feature 503w is actuated by at least the first and second number of actuations.

Optionally, in any embodiment, actuation of the drive feature 503w by a second number of actuations beyond the first number of actuations in the first actuation direction 1300w increases both the height 1200w and the width 1100w. Optionally, in any embodiment, actuation of the drive feature 503w by a second number of actuations beyond the first number of actuations in the first actuation direction increases the height 1200w without increasing the width 1100w.

Optionally, in any embodiment, actuation of the drive feature 503w in the first actuation direction 1300w by at least the first number of actuations increases the height 1200w of the device 1000w by about 30% to about 400%. Optionally, in any embodiment, actuation of the drive feature 503w in the first actuation direction 1300w by at least the first and the second number of actuations increases the width 1100w of the device 1200w by about 14% to about 150%.

Optionally, in any embodiment, per FIG. 88, the actuator 500w comprises a cylindrically shaped elongate shaft with a distal end and a proximal end. Optionally, in any embodiment, at least a portion of the distal end of the actuator 500w comprises a first thread feature 501w. Optionally, in any embodiment, at least a portion of the proximal end of the actuator 500w comprises a second thread feature 502w, and wherein the proximal end comprises the drive feature 503w. Optionally, in any embodiment, at least one of the first thread feature 501w and the second thread feature 502w comprise a thread disposed externally around the actuator 500w. Optionally, in any embodiment, the first thread feature 501w and the second thread feature 502w have opposing threading directions. Optionally, in any embodiment, the first thread feature 501w and the second thread feature 502w have the same threading direction. Optionally, in any embodiment, at least one of the first thread feature 501w and the second thread feature 502w comprises a right-handed threading. Optionally, in any embodiment, at least one of the first thread feature 501w and the second thread feature 502w comprises a left-handed threading. Optionally, in any embodiment, the drive feature 503w comprises a recessed region configured to receive a driving instrument. Optionally, in any embodiment, the recessed region comprises a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess. Optionally, in any embodiment, the driving feature comprises a protuberance extending therefrom and configured to be coupled to a driving instrument. Optionally, in any embodiment, the protuberance comprises a hex, a hexalobular, or a square protuberance. Optionally, in any embodiment, the drive feature 503w is coincident with the longitudinal axis 504w.

Optionally, in any embodiment, per FIG. 87C, the wedge assembly comprises a distal wedge 650w and a proximal wedge 550w. Optionally, in any embodiment, actuation of the drive feature in the first direction converges the distal wedge 650w and the proximal wedge 550w toward one another. Optionally, in any embodiment, per FIG. 89A-B, the distal wedge 650w is a crescent-shaped prism comprising a distal end, a proximal end, a top side, and a bottom side. Optionally, in any embodiment, the distal wedge 650w comprises a third thread feature 654w. Optionally, in any embodiment, the third thread feature 654w extends from the distal end of the distal wedge 650w, to the proximal end of the distal wedge 650w. Optionally, in any embodiment, the distal wedge 650w further comprises one or more features configured for temporary attachment to an inserter tool. Optionally, in any embodiment, the third thread feature 654w is threadably coupled to the second thread feature 502w of the actuator 500w. Optionally, in any embodiment, the distal wedge 650w further comprises first slot 651w and second slot 652w. Optionally, in any embodiment, the first slot 651w comprises an upper left first slot 651w, an upper right first slot 651w, a lower left first slot 651w, and a lower right first slot 651w. Optionally, in any embodiment, the upper left first slot 651w and the lower left first slot 651w, and the upper right first slot 651w and a lower right first slot 651w have mirrored symmetry about a transverse plane of the distal wedge 650w. Optionally, in any embodiment, the medial plane of each of the upper left first slot 651w, the upper right first slot 651w, the lower left first slot 651w, and the lower right first slot 651w are oriented at the transverse angle from the sagittal plane of the distal wedge 650w. Optionally, in any embodiment, the second slot 652w comprises an upper left second slot 652w, an upper right second slot 652w, a lower left second slot 652w, and a lower right second slot 652w. Optionally, in any embodiment, the upper left second slot 652w and the lower left second slot 652w, and the upper right second slot 652w and a lower right second slot 652w have mirrored symmetry about a transverse plane of the distal wedge 650w. Optionally, in any embodiment, the medial plane of the upper left second slot 652w, the upper right second slot 652w, the lower left second slot 652w, and the lower right second slot 652w are oriented at the transverse angle from the sagittal plane of the distal wedge 650w. Optionally, in any embodiment, the proximal wedge 550w is equivalent to the distal wedge 650w. Optionally, in any embodiment, per FIG. 87C, the sagittal plane of the distal wedge 650w is arranged to be coplanar with the sagittal plane of the proximal wedge 550w Optionally, in any embodiment, per FIG. 87C, the sagittal plane of the distal wedge 650w is arranged to be arranged 180 degrees from the sagittal plane of the proximal wedge 550w.

Optionally, in any embodiment, at least one of the third thread feature 654w and the fourth thread feature 554w in the distal wedge 650w and the proximal wedge 550w, respectively, comprise a thread locking feature configured to prevent actuation of at least one of the third first feature 501w and the second thread feature 502w of the actuator 500w in a direction opposite the first actuation direction 1300w. Optionally, in any embodiment, the thread locking feature comprises a deformable insert, a deformable thread, a distorted thread, a flexible lip, or any combination thereof. Optionally, in any embodiment, the thread locking feature comprises a bore within at least one of the distal wedge 650w and the proximal wedge 550w configured to provide access to the third thread feature 654w or the fourth thread feature 554w, and/or which is configured to receive an insert such as a pin, a screw, a dowel, a nut, or any combination thereof to prevent actuation of the actuator 500w. Optionally, in any embodiment, per FIG. 87C, the ramp assembly 800w comprises a first proximal ramp 300w, a second proximal ramp 400w, a first distal ramp 350w, and a second distal ramp 450w.

Optionally, in any embodiment, per FIGS. 90A and 90B, the second proximal ramp 400w generally comprises a triangular prism. Optionally, in any embodiment, the second proximal ramp 400w comprises a first ridge 401w, a first protrusion 402w, a v-slot 403w, a third protrusion 404w, a third ridge 405w, and a third slot 406w. Optionally, in any embodiment, the first ridge 401w comprises two first ridges 401w. Optionally, in any embodiment, the medial plane of the first ridge 401w lies at the traverse angle from the medial face of the second proximal ramp 400w. Optionally, in any embodiment, the first protrusion 402w comprises two first protrusions 402w. Optionally, in any embodiment, the v-slot 403w is located on the transverse plane of the second proximal ramp 400w. Optionally, in any embodiment, the apex of the v-slot 403w is oriented towards the mesial plane of the device 1000w. Optionally, in any embodiment, the protrusion 404w comprises two protrusions 404w. Optionally, in any embodiment, the protrusion 404w is located on the lower face of the distal ramp 400w. Optionally, in any embodiment, the third ridge 405w comprises two the third ridges 405w. Optionally, in any embodiment, the third ridge 405w is located on the lower surface of the second proximal ramp 400w. Optionally, in any embodiment, the medial plane of the third ridge 405w is parallel to the mesial face of the second proximal ramp 400w. Optionally, in any embodiment, the third slot 406w comprises two third slot 406w comprises two the two third slots 406w. Optionally, in any embodiment, the third slot 406w is located on the upper surface of the second proximal ramp 400w. Optionally, in any embodiment, the medial plane of the third slot 406w is parallel to the mesial face of the distal ramp 400w. Optionally, in any embodiment, the second proximal ramp 300w is equivalent to the first distal ramp 350w.

Optionally, in any embodiment, per FIGS. 91A and 91B, the first proximal ramp 300w generally comprises a triangular prism. Optionally, in any embodiment, the second distal ramp 300w comprises a first ridge 301w, a first protrusion 302w, a v-slot 303w, a third protrusion 304w, a third ridge 305w, and a third slot 306w. Optionally, in any embodiment, the first ridge 301w comprises two first ridges 301w. Optionally, in any embodiment, the medial plane of the first ridge 301w lies at the traverse angle from the medial face of the second distal ramp 300w. Optionally, in any embodiment, the first protrusion 302w comprises two first protrusions 302w Optionally, in any embodiment, the v-slot 303w is located on the transverse plane of the second distal ramp 300w. Optionally, in any embodiment, the apex of the v-slot 303w is oriented towards the mesial plane of the device 1000w. Optionally, in any embodiment, the protrusion 304w comprises two protrusions 304w. Optionally, in any embodiment, the protrusion 304w is located on the lower face of the distal ramp 300w. Optionally, in any embodiment, the third ridge 305w comprises two the third ridges 305w. Optionally, in any embodiment, the third ridge 305w is located on the lower surface of the second distal ramp 300w Optionally, in any embodiment, the medial plane of the third ridge 305w is parallel to the mesial face of the second distal ramp 300w. Optionally, in any embodiment, the third slot 306w comprises two third slot 306w comprises two the two third slots 306w. Optionally, in any embodiment, the third slot 306w is located on the upper surface of the second distal ramp 300w. Optionally, in any embodiment, the medial plane of the third slot 306w is parallel to the mesial face of the distal ramp 300w. Optionally, in any embodiment, the first proximal ramp 300w is equivalent to the second distal ramp 450w.

Optionally, in any embodiment, the upper endplate assembly comprises a first endplate 100w and a second endplate 250w. Optionally, in any embodiment, the lower endplate assembly comprises a third endplate 150w and a fourth endplate 200w.

Optionally, in any embodiment, at least one of the first endplate 100w and the second endplate 250w, the third endplate 150w and the fourth endplate 200w, the first proximal ramp 300w and the second proximal ramp 400w, and the first distal ramp 350w and the second distal ramp 450w have mirrored equivalence. Optionally, in any embodiment, at least one of the second endplate 250w and the fourth endplate 200w is larger than at least one of the first endplate 100w and the third endplate 150w. Optionally, in any embodiment, at least one of the exterior faces of the first end plate 100w, the second endplate 250w, the third endplate 150w, and the fourth endplate 200w comprise a texture configured to grip the vertebrae. Optionally, in any embodiment, the texturing comprises a tooth, a ridge, a roughened area, a metallic coating, a ceramic coating, a keel, a spike, a projection, a groove, or any combination thereof.

Optionally, in any embodiment, per FIGS. 87A and 87C, the slideable coupling between at least one of the wedge assembly 750w and the ramp assembly 800w, the ramp assembly 800w and the upper endplate assembly 850w, and the ramp assembly 800w and the lower endplate assembly 900w is at a transverse angle from the longitudinal axis 504w. Optionally, in any embodiment, the transverse angle is about 0 degrees to about 90 degrees.

Optionally, in any embodiment, the slideable coupling between at least one of the wedge assembly 750w and the ramp assembly 800w, the ramp assembly 800w and the upper endplate assembly 850w, and the ramp assembly 800w and the lower endplate assembly 900w comprises a protrusion and a slot. Optionally, in any embodiment, the protrusion extends from at least one of the wedge assembly 750w the ramp assembly 800w, the upper endplate assembly 850w, and the lower endplate assembly 900w. Optionally, in any embodiment, the slot is disposed in at least one of the wedge assembly 750w the ramp assembly 800w, the upper endplate assembly 850w, and the lower endplate assembly 900w. Optionally, in any embodiment, the protrusion comprises a pin 600, a ridge, a dimple, a bolt, a screw, a bearing, or any combination thereof. Optionally, in any embodiment, the slot comprises a through slot, a blind slot, a t-slot, a v-slot, a groove, or any combination thereof.

Optionally, in any embodiment, per FIGS. 87A-95B, the slideable coupling between the wedge assembly 750w and the ramp assembly comprises 800w the first slot 651w and the second slot 652w within the distal wedge 650w, the third slot 551w and the fourth slot 552w within the proximal wedge 550w, a first protrusion 402w and a first ridge 401w, within the first proximal ramp 300w and the second proximal ramp 400w, and a second protrusion 352w, a second ridge 351w, and a v-slot 353w within the first distal ramp 350w and the second distal ramp 450w. Optionally, in any embodiment, the number of at least one of the first slots 651w, the second slots 652w, the third slots 551w, the fourth slots 552w, the first protrusions 402w, the first ridges 401w, the second protrusions 352w, and the second ridges 351w is about 1, 2, 3, 4 or more.

Optionally, in any embodiment, the slideable coupling between the proximal wedge 550w and the first proximal ramp 300w or the second proximal ramp 400w comprises a slideable coupling between the third slot 551w and the first ridge 401w, and a slideable coupling between the fourth slot 552w and the first protrusion 402w.

Optionally, in any embodiment, the slideable coupling between the distal wedge 650w and the first distal ramp 350w or the second distal ramp 450w comprises a slideable coupling between a first slot 651w and a second ridge 351w, a slideable coupling between a second slot 652w and a second protrusion 352w, or any combination thereof.

Optionally, in any embodiment, the second slot 652w within distal wedge 650w comprises a first stop 653w to prevent the first protrusion 402w from exiting the second slot 652w in one direction. Optionally, in any embodiment, the fourth slot 552w within the proximal wedge 550w comprises a second stop 553w to prevent the first protrusion 402w from exiting the second slot 652w in one direction.

Optionally, in any embodiment, the slideable coupling between the ramp assembly 800w and the upper endplate assembly 850w or the lower endplate assembly 900w comprises a tongue 353w within at least one of first distal ramp 350 and the second distal ramp 450, and a v-slot 403w, a third protrusion 404w, a third ridge 405w, and a third slot 406w within at least one of first proximal ramp 300 and the second proximal ramp 400, and a dovetail slot 101w 151w 201w 251w, a fourth protrusion 102w 152w 202w 252w, a fifth slot 103w 153w 203w 253w, a fourth slot 104w 154w 204w 254w and a fourth ridge 105w 155w 205w 255w within at least one of the first endplate 100w, the second endplate 250w, the third endplate 150w and the fourth endplate 200w.

Optionally, in any embodiment, the slideable coupling between the first distal ramp 350w or the second distal ramp 450w and the first end plate 100w, the second endplate 250w, the third endplate 150w, or the fourth endplate 200w comprises a slideable coupling between the dovetail slot 101w 151w 201w 251w and the tongue 353w.

Optionally, in any embodiment, the slideable coupling between the first proximal ramp 300w or the second proximal ramp 400w and the first end plate 100w, the second endplate 250w, the third endplate 150w, or the fourth endplate 200w comprises a slideable coupling between the v-slot 403w and the fourth protrusion 102w 152w 202w 252w, a slideable coupling between the third protrusion 404w and the fourth slot 104w 154w 204w 254w, a slideable coupling between the third ridge 405w and the fifth slot 103w 153w 203w 253w, a slideable coupling between the third slot 406w and the fourth ridge 105w 155w 205w 255w, or any combination thereof.

Optionally, in any embodiment, the fourth protrusion 102w 152w 202w 252w comprises a feature of the first end plate 100w, the second endplate 250w, the third endplate 150w, or the fourth endplate 200w. Optionally, in any embodiment, the fourth protrusion 102w 152w 202w 252w comprises a separate component that is firmly inserted into the first end plate 100w, the second endplate 250w, the third endplate 150w, or the fourth endplate 200w. Optionally, in any embodiment, the fourth protrusion 102w 152w 202w 252w comprises the pin 600w.

Optionally, in any embodiment, the slideable coupling between the upper endplate assembly 850w and the lower endplate assembly 900w comprises a slideable coupling between a tongue 101w in the first endplate 100w and a groove 151w in the third endplate 150w, and a slideable coupling between a tongue 251w in the second endplate 250w and a groove 201w in the fourth endplate 200w.

Optionally, in any embodiment, the slideable coupling between the wedge assembly 750w and at least one of the upper endplate assembly 850w and lower endplate assembly 900w comprises a slideable coupling between a distal chamfer 123w and a proximal chamfer 121w in at least one of the first end plate 100w, the second endplate 250w, the third endplate 150w, and the fourth endplate 200w, and a guide surface 621w 521w in at least one of the distal wedge 650w and a proximal wedge 550w. Optionally, in any embodiment, the slideable coupling between the wedge assembly 750w and at least one of the upper endplate assembly 850w and lower endplate assembly 900w prevents the height 1200w of the device from increasing until the width 1100w of the device's 1000w reaches its apex.

Optionally, in any embodiment, at least one of the actuator 500w, the wedge assembly 750w, the ramp assembly 8000w, the upper endplate assembly 850w, and the lower endplate assembly 900w comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Optionally, in any embodiment, the nineteenth expandable fusion device 1000W may further or alternatively include any features, components, or characteristics of any of the previously described expandable fusion device.

Further provided herein, per FIGS. 96A to 97, is an expandable fusion system for implantation between two adjacent vertebrae, the system comprising a collapsing tool 5000w and the nineteenth expandable fusion device 1000v. Optionally, in any embodiment, once the actuator 500w is actuated by at least the first number and the second number of actuations in a first actuation direction 1300w such that the width 1100w and the height 1200w of the device 1000w are at their apex, actuation of the actuator 500w in a direction opposite the first actuation direction 1300w may only reduce the width 1100w, without reducing the height 1200w of the device 1000v. Optionally, in any embodiment, a collapsing tool 5000w may be employed to allow the height 1200w reduction without width 1100w reduction. Optionally, in any embodiment, the collapsing tool 5000w comprises a first prong 5001w and a second prong 5001w, wherein the first prong 5001w is configured to be inserted between the proximal wedge 550w and/or the distal wedge 650w and the first proximal ramp 300w, and wherein the second prong 5002w is configured to be inserted between the proximal wedge 550w and/or the distal wedge 650w and the second proximal ramp 400w. Optionally, in any embodiment, the first prong 5001w and the second prong 5001w have the same length. Optionally, in any embodiment, the first prong 5001w and the second prong 5001w have different lengths. Optionally, in any embodiment, the first prong 5001w and the second prong 5001w have the same thickness. Optionally, in any embodiment, the first prong 5001w and the second prong 5001w have different thicknesses.

The numerical indicators for the components of the exemplary nineteenth expandable fusion device are compiled in Table 2, below.

TABLE 2

| | |
|---|---|
| 100w | First endplate |
| 101w | Dovetail slot |
| 102w | Fourth protrusion |
| 103w | Fourth slot |
| 104w | Fifth slot |
| 105w | Fourth ridge |
| 150w | Third endplate |
| 200w | Fourth endplate |
| 250w | Second endplate |
| 300w | First proximal ramp |
| 350w | First distal ramp |
| 351w | Second protrusion |
| 352w | Second ridge |
| 353w | Tongue |
| 400w | Second proximal ramp |
| 401w | First ridge |
| 402w | First protrusion |
| 403w | V-slot |
| 404w | Third protrusion |
| 405w | Third ridge |
| 406w | Third slot |
| 450w | Second distal ramp |
| 500w | Actuator |
| 501w | First thread feature |
| 502w | Second thread feature |
| 503w | Drive feature |
| 504w | Longitudinal axis |
| 550w | Proximal wedge |
| 551w | Third slot |
| 552w | Fourth slot |
| 553w | Second Stop |
| 554w | Fourth thread feature |
| 600w | Pin |
| 650w | Distal wedge |
| 651w | First slot |
| 652w | Second slot |
| 653w | First Stop |
| 654w | Third thread feature |
| 750w | Wedge assembly |
| 800w | Ramp assembly |
| 850w | Upper endplate assembly |
| 900w | Lower endplate assembly |
| 1000w | Eighteenth Device |
| 1100w | Width |
| 1200w | Height |
| 1300w | Axis of actuation |
| 5000w | Inserter |

Twentieth Expandable Fusion Device

Provided herein, per FIGS. 98A-B, is a twentieth expandable fusion device 1000x for implantation between two adjacent vertebrae. Optionally, in any embodiment, per FIG. 95a the device 1000x comprises: an actuator 500x comprising a drive feature 503x and an longitudinal axis 504x; a wedge assembly 750x coupled to the actuator 500x; a ramp assembly 800x slidably coupled with the wedge assembly 750x; an upper endplate assembly 850x slidably coupled with the ramp assembly 800x; and a lower endplate assembly 900x slidably coupled with the ramp assembly 800w.

Optionally, in any embodiment, at least one of the actuator 500w, the wedge assembly 750x, the ramp assembly 8000x, the upper endplate assembly 850x, and the lower endplate assembly 900x comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Optionally, in any embodiment, the twentieth expandable fusion device 1000x can further or alternatively include any features, components, or characteristics of any of the previously described expandable fusion device.

Twenty-First Expandable Fusion Device

Provided herein, per FIG. 99, is a twenty-first expandable fusion device 1000y for implantation between two adjacent vertebrae. Optionally, in any embodiment, per FIG. 95a the device comprises: an actuator comprising a drive feature and an longitudinal axis; a wedge assembly coupled to the actuator; a ramp assembly slidably coupled with the wedge assembly; an upper endplate assembly slidably coupled with the ramp assembly; and a lower endplate assembly slidably coupled with the ramp assembly. Optionally, in any embodiment, the twenty-first expandable fusion device 1000y comprises a gap 101y between at least one of the upper endplate assembly and the lower endplate assembly, and at least one of the proximal wedge and the distal wedge. Optionally, in any embodiment, the gap 101y enables the device 1000y to expand in width and height simultaneously.

Optionally, in any embodiment, at least one of the actuator, the wedge assembly, the ramp assembly, the upper endplate assembly, and the lower endplate assembly comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Optionally, in any embodiment, the lack of a slideable coupling between the wedge assembly and at least one of the upper endplate assembly and lower endplate assembly allows both the height and width of the device 1000y to increase until their relative apexes. Optionally, in any embodiment, the height and width of the 1000y increase at the same rate when the actuator is actuated in a first direction.

Optionally, in any embodiment, actuation of the drive feature by first number of actuations in the first actuation direction increases both the height and the width of the device 1000x at the same rate. Optionally, in any embodiment, actuation of the drive feature by first number of actuations in the first actuation direction increases both the height and the width of the device 1000x at different rates.

Optionally, in any embodiment, the twentieth expandable fusion device 1000x can further or alternatively include any features, components, or characteristics of any of the previously described expandable fusion device.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "longitudinal axis" refers to a theoretical axis in space comprising an axis of revolving symmetry of an object.

As used herein, the term "slidably coupled" refers to a relationship between two or more components whereby the components share at least one degree of freedom.

As used herein, the term "external width" refers to the width between the outermost surfaces of an object.

As used herein, the term "external distance" refers to the distance between the outermost surfaces of an object.

As used herein, the term "apex" refers to the maximum value of a distance, measurement, or parameter.

As used herein, the term "thread feature" refers to one or more helical or spiral protrusions or recesses capable of acting as, or coupling with another thread feature.

I claim:

1. A method for implanting an expandable fusion device between two adjacent vertebrae comprising:
    obtaining an expandable fusion device for implantation between two adjacent vertebrae, the device comprising an actuator comprising a drive feature and a longitudinal axis; a wedge assembly coupled to the actuator;
        a ramp assembly slidably coupled with the wedge assembly;
        an upper endplate assembly slidably coupled with the ramp assembly; and a lower endplate assembly slidably coupled with the ramp assembly;
        wherein, the device has a width comprising an external width of at least one of the upper endplate assembly and the lower endplate assembly;
        wherein, the device has a height comprising an external distance between the upper endplate assembly and the lower endplate assembly;
        wherein, actuation of the drive feature by a first number of actuations in a first actuation direction increases the width without increasing the height; and,
        wherein, actuation of the drive feature by a second number of actuations beyond the first number of actuations in the first actuation direction increases at least one of the height and the width;
    inserting the device, having the width and the height, between two adjacent vertebrae;
    actuating the drive feature by the first number of actuations in the first actuation to increase the width without increasing the height; and,
    actuating the drive feature by the second number of actuations beyond the first number of actuations in the first actuation direction to increase at least one of the height and the width;
    attaching an inserter to the expandable fusion device, the device having the width and the height and comprising the drive feature.

2. The method of claim 1, wherein actuation of the drive feature by the second number of actuations beyond the first number of actuations in the first actuation direction increases both the height and the width.

3. The method of claim 1, wherein actuation of the drive feature by a third number of actuations beyond the first and second number of actuations in the first actuation direction increases the height without increasing the width.

4. The method of claim 1, wherein the width of the device reaches an apex once the drive feature is actuated by at least the first number of actuations.

5. The method of claim 1, wherein the height of the device reaches an apex once the drive feature is actuated by at least the first and second number of actuations.

6. The method of claim 4, wherein actuating the drive feature in the first actuation direction beyond the first number of actuations increases the height of the device by at most about 400%.

7. The method of claim 6, wherein actuating the drive feature in the first actuation direction by at least the first and the second number of actuations increases the width of the device by at most about 150%.

* * * * *